United States Patent
Al-Abed et al.

(10) Patent No.: US 11,471,507 B2
(45) Date of Patent: Oct. 18, 2022

(54) HMGB1 ANTAGONIST

(71) Applicant: THE FEINSTEIN INSTITUTES FOR MEDICAL RESEARCH, Manhasset, NY (US)

(72) Inventors: Yousef Al-Abed, Manhasset, NY (US); Huan Yang, Manhasset, NY (US)

(73) Assignee: THE FEINSTEIN INSTITUTES FOR MEDICAL RESEARCH, Manhasset, NY (US)

( * ) Notice: Subject to any disclaimer, the term of this patent is extended or adjusted under 35 U.S.C. 154(b) by 42 days.

(21) Appl. No.: 16/869,939

(22) Filed: May 8, 2020

(65) Prior Publication Data
US 2020/0352887 A1 Nov. 12, 2020

Related U.S. Application Data

(60) Provisional application No. 62/845,568, filed on May 9, 2019, provisional application No. 62/845,576, filed on May 9, 2019, provisional application No. 62/845,578, filed on May 9, 2019.

(51) Int. Cl.
| | |
|---|---|
| A61K 38/17 | (2006.01) |
| A61K 47/10 | (2017.01) |
| A61K 47/26 | (2006.01) |
| A61K 38/07 | (2006.01) |
| A61K 38/00 | (2006.01) |
| A61K 9/08 | (2006.01) |
| A61P 25/02 | (2006.01) |
| C07K 5/10 | (2006.01) |
| A61K 9/00 | (2006.01) |
| C07K 1/113 | (2006.01) |
| A61K 47/65 | (2017.01) |
| C07K 14/47 | (2006.01) |
| A61K 31/197 | (2006.01) |
| C07K 5/107 | (2006.01) |

(52) U.S. Cl.
CPC ............ *A61K 38/17* (2013.01); *A61K 9/007* (2013.01); *A61K 9/0014* (2013.01); *A61K 9/0019* (2013.01); *A61K 9/0043* (2013.01); *A61K 9/0053* (2013.01); *A61K 31/197* (2013.01); *A61K 38/07* (2013.01); *A61K 47/10* (2013.01); *A61K 47/26* (2013.01); *A61K 47/65* (2017.08); *A61P 25/02* (2018.01); *C07K 1/113* (2013.01); *C07K 5/1016* (2013.01); *C07K 14/4703* (2013.01); *A61K 9/08* (2013.01); *A61K 38/00* (2013.01)

(58) Field of Classification Search
CPC ...... A61K 31/197; A61K 38/00; A61K 38/07; A61K 38/17; A61K 47/10; A61K 47/20; A61K 47/26; A61K 47/65; A61P 25/02; C07K 14/4703; C07K 1/113; C07K 5/10; C07K 5/1016; C07K 5/06069; C07K 5/0819
See application file for complete search history.

(56) References Cited

U.S. PATENT DOCUMENTS

| | | | |
|---|---|---|---|
| 5,602,231 A | 2/1997 | Cotton et al. | |
| 6,664,372 B1* | 12/2003 | Janda | .................... C07C 281/06 435/7.1 |
| 8,563,565 B2 | 10/2013 | Norimine et al. | |
| 9,186,371 B2 | 11/2015 | Taniguchi et al. | |
| 2006/0281686 A1 | 12/2006 | Lopez Areiza et al. | |
| 2007/0155803 A1* | 7/2007 | Bondebjerg | ........ C07K 5/06078 514/357 |
| 2011/0086836 A1 | 4/2011 | Soeberdt et al. | |
| 2018/0344808 A1 | 12/2018 | Tracey et al. | |
| 2019/0055283 A1 | 2/2019 | Ekici et al. | |

FOREIGN PATENT DOCUMENTS

WO    WO 2016/094899 A2    6/2016

OTHER PUBLICATIONS

Martinotti et al., "Emerging roles of HMGB1 protein in immunity, inflammation, and cancer," ImmunoTargets and Therapy, 2015, 4: 101-109. (Year: 2015).*
Yang et al., "MD-2 is required for disulfide HMGB1-dependent TLR4 signaling," J. Ex. Med., 2015, 212(1): 5-14. (Year: 2015).*
Yang et al. "MD-2 is required for disulfide HMGB1-dependent TLR4 signaling" The Journal of Experimental Medicine; Published on Jan. 5, 2015; vol. 212; p. 5-14.
Sun et al. "Folic acid derived-P5779 mimetics regulate DAMP-mediated inflammation through disruption of HMGB1:TLR4:MD-2 axes" PLOS One; Published on Feb. 15, 2018; vol. 13; p. 1-14.
International Search Report dated Jul. 31, 2020, from corresponding International Application No. PCT/US20/32025.
Written Opinion of the International Searching Authority dated Jul. 31, 2020, from corresponding International Application No. PCT/US20/32025.
PubChem CID-136595533 "(2,5-Dioxopyrrol-1-yl) N-(2,5-dihydroxypyrrol-1-yl)-N-(1,3-dioxoisoindol-2-yl)carbamate" Created on Jan. 4, 2019.
PubChem CID-132255576 "(2S)-2-(lmidazole-1-carbonylamino)pentanedioic acid" Created on Jan. 29, 2018.
International Search Report dated Sep. 2, 2020, from corresponding International Application No. PCT/US20/31998.
Written Opinion of the International Searching Authority dated Sep. 2, 2020, from corresponding International Application No. PCT/US20/31998.
PubChem CID-519335 "Methanethioic S-acid" Created on Mar. 27, 2005.

(Continued)

*Primary Examiner* — Julie Ha
(74) *Attorney, Agent, or Firm* — Davidson, Davidson & Kappel, LLC

(57) ABSTRACT

The present invention is related to HMGB1 antagonists and, in particular, HMGB1 tetramer peptidomimetics which have been stabilized with at least one azatide linkage, such as K883. The present invention is also related to pharmaceutical compositions comprising HMGB1 antagonists such as K883.

20 Claims, 21 Drawing Sheets
(19 of 21 Drawing Sheet(s) Filed in Color)
Specification includes a Sequence Listing.

(56) References Cited

OTHER PUBLICATIONS

Heffeter et al. "Anticancer Thiosemicarbazones: Chemical Properties, Interaction with Iron Metabolism, and Resistance Development" Antioxidants & Redox Signaling; vol. 30, No. 8, 2019.
International Search Report dated Sep. 10, 2020, from corresponding International Application No. PCT/US20/31992.
Written Opinion of the International Searching Authority dated Sep. 10, 2020, from corresponding International Application No. PCT/US20/31992.
PubChem CID-67548889 "Methyl (2S)-1-(imidazole-1-carbonyl)pyrrolidine-2-carboxylate" Created on Nov. 30, 2012.
PubChem CID-1089188 "(2s)-1-(1-lmidazolylcarbonyl)pyrrolidine-2-carboxylic acid benzyl ester" Created on Oct. 26, 2006.
International Search Report dated Sep. 16, 2020, from corresponding International Application No. PCT/US20/31988.
Written Opinion of the International Searching Authority dated Sep. 16, 2020, from corresponding International Application No. PCT/US20/31988.
Mohan R. Dasu, PHD et al., "Increased Toll-Like Receptor (TLR) Activation and TLR Ligands in Recently Diagnosed Type 2 Diabetic Subjects", Diabetes Care, vol. 33, No. 4, Apr. 2010.
Shehla Akbar et al., "6-Methoxyflavanone attenuates mechanical allodynia and vulvodynia in the streptozotocin-induced diabetic neuropathic pain", Biomedicine & Pharmacotherapy, vol. 84, p. 962-971, 2016.
Edward Abraham et al., "Cutting Edge: HMG-1 as a Mediator of Acute Lung Inflammation", The Journal of Immunology, vol. 165, p. 2950-2954, 2000.
Kazuhiro Abeyama et al., "The N-terminal domain of thrombomodulin sequesters high-mobility group-B1 protein, a novel anti-inflammatory mechanism", J Clin Invest., vol. 115(5), p. 1267-1274, 2005.
Adhikari, N.K., et al., Critical care and the global burden of critical illness in adults, Lancet, 2010, 376(9749): p. 1339-46.
Ahmed M. Abu El-Asrar, "The Proinflammatory Cytokine High-Mobility Group Box-1 Mediates Retinal Neuropathy Induced by Diabetes", Hindawi Publishing Corporation Mediators of Inflammation, vol. 2014, Article ID 746415, 10 pages, Nov. 2014.
Yohance M. Allette et al., "Identification of a functional interaction of HMGB1 with Receptor for Advanced Glycation End-products in a model of neuropathic pain", Brain Behav Immun., vol. 42, p. 169-177, Nov. 2014.
Ulf Andersson et al., "Extracellular HMGB1 as a therapeutic target in inflammatory diseases" Expert Opinion on Therapeutic Targets, vol. 22, No. 3, 263-277, 2018.
Nilesh M. Agalave et al., "Spinal HMGB1 Induces TLR4-mediated Long-lasting hypersensitivity and glial activation and regulates pain-like behavior in experimental arthritis", Pain 155, p. 1802-1813, 2014.
Derek C. Angus et al., "Circulating high-mobility group box 1 (HMGB1) concentrations are elevated in both uncomplicated pneumonia and pneumonia with severe sepsis" Crit Care Med, vol. 35, No. 4, 2007.
Derek C. Angus, "The Lingering Consequences of Sepsis A Hidden Public Health Disaster?," JAMA, vol. 304, No. 16, p. 1833-1834, Oct. 27, 2010.
Derek C. Angus et al., "Severe Sepsis and Septic Shock", The New England Journal of Medicine, 369:9, p. 840-851, Aug. 29, 2013.
Daniel J Antoine et al., "A Systematic Nomenclature for the Redox States of High Mobility Group Box (HMGB) Proteins", MOL MED 20:135-137, 2014.
Stéphanie Barnay-Verdier, "Emergence of autoantibodies to HMGB1 is associated with survival in patients with septic shock", Intensive Care Med, 37:957-962, 2011.
Lionel Apetoh et al., "Toll-like receptor 4-dependent contribution of the immune system to anticancer chemotherapy and radiotherapy", Nature Medicine, vol. 13, No. 9,, p. 1050-1059, Sep. 2007.

Bernard, G.R., et al., "Efficacy and safety of recombinant human activated protein C for sepsis", N Engl J Med, 344(10): p. 699-709, 2001.
Ralf Baron et al., "Neuropathic pain: diagnosis, pathophysiological mechanisms, and treatment", Lancet Neurol, vol. 9: 807-19, 2010.
Tiziana Bonaldi, "Monocytic cells hyperacetylate chromatin protein HMGB1 to redirect it towards secretion", The EMBO Journal, vol. 22, No. 20, p. 5551-5560, 2003.
Magda Cepkova et al., "Pharmacotherapy of Acute Lung Injury and the Acute Respiratory Distress Syndrome", J Intensive Care Med., 21(3): 119-143, 2006.
Damien Bertheloot et al., "HMGB1, IL-1α, IL-33 and S100 proteins: dual-function alarmins", Cellular & Molecular Immunology, 13, 1-22, 2016.
Marucia Chacur et al., "A new model of sciatic inflammatory neuritis (SIN): induction of unilateral and bilateral mechanical allodynia following acute unilateral peri-sciatic immune activation in rats", Pain, 94:231-244, 2001.
Grace Y. Chen et al., "Sterile inflammation: sensing and reacting to damage", Nat Rev Immunol., 10(12): 826-837, Dec. 2010.
Celeste M. Torio et al., "National Inpatient Hospital Costs: The Most Expensive Conditions by Payer, 2011", Healthcare Cost and Utilization Project, Agency for Healthcare Research and Quality, Rockville MD, Statistical Brief #160, Aug. 2013.
Fernanda M. Consolim-Colombo et al., "Galantamine alleviates inflammation and insulin resistance in patients with metabolic syndrome in a randomized trial", JCI Insight, 2(14), 2017.
Sangeeta S Chavan et al., "HMGB1 Mediates Cognitive Impairment in Sepsis Survivors", Molecular Medicine, 18:930-937, 2012.
Sandra L. Colby et al., "Projections of the Size and Composition of the U.S. Population: 2014 to 2060", U.S. Department of Commerce, Economics and Statistics Administration U.S. Census Bureau, p. 25-1143, p. 1 -13, Mar. 2015.
Centers for Disease Control and Prevention, "National Diabetes Statistics Report: Estimates of Diabetes and Its Burden in the United States", Atlanta, GA: U.S. Department of Health and Human Services, 2014.
The Diabetes Control and Complications Trial and Research Group, "The Effect of Intensive Treatment of Diabetes on the Development and Progression of Long-Term Complications and Insulin-Dependent Diabetes Mellitus", The New England Journal of Medicine, vol. 329, No. 14, Sep. 30, 1993.
Making Health Care Safer. Think sepsis. Time matters. CDC VitalSigns. Aug. 2016 and Control, C.f.D. CDC VitalSigns, cited Aug. 24, 2016, available from: www.cdc.gov/vitalsigns/sepsis/index.html.
Marie-Amélie de Ménorval et al., "Effects of Dimethyl Sulfoxide in Cholesterol-Containing Lipid Membranes: A Comparative Study of Experiments In Silico and with Cells", PLOS One 7(7): e41733, Jul. 25, 2012.
Lien Dejager et al., "Cecal ligation and puncture: the gold standard model for polymicrobial sepsis?", Trends in Microbiology, vol. 19, No. 4, Apr. 2011.
Michael Costigan et al., "Neuropathic Pain: A Maladaptive Response of the Nervous System to Damage", Annu Rev Neurosci., 32: 1-32, 2009.
A. Dray, "Neuropathic pain: emerging treatments", British Journal of Anaesthesia, 101 (1): 48-58, 2008.
Robert H. Dworkin, "Advances in Neuropathic Pain", Neurological Review, Arch Neurol, 60:1524-1534, 2003.
Anne Elixhauser et al., "Septicemia in U.S. Hospitals, 2009", Healthcare Cost and Utilization Project, Agency For Healthcare Research and Quality, Rockville, MD, Oct. 2011.
Meihong Deng et al., "The Endotoxin Delivery Protein HMGB1 Mediates Caspase-11- Dependent Lethality in Sepsis", Immunity, 16; 49(4): 740-753.e7, Oct. 2018.
Jie Fan et al. "Hemorrhagic Shock Induces NAD(P)H Oxidase Activation in Neutrophils: Role of HMGB1-TLR4 Signaling", The Journal of Immunology, 178:6573-6580, 2007.
Polina Feldman et al. "The persistent release of HMGB1 contributes to tactile hyperalgesia in a rodent model of neuropathic pain", Journal of Neuroinflammation, 9:180, 2012.

(56) References Cited

OTHER PUBLICATIONS

Maria Entezari et al., "Inhibition of High-Mobility Group Box 1 Protein (HMGB1) Enhances Bacterial Clearance and Protects against Pseudomonas Aeruginosa Pneumonia in Cystic Fibrosis", Molecular Medicine 18: 477-485, 2012.
Joana Galvao et al., "Unexpected low-dose toxicity of the universal solvent DMSO", The FASEB Journal, vol. 28, 1317-1330, 2014.
Carolin Fleischmann et al., "Assessment of Global Incidence and Mortality of Hospital-treated Sepsis", Am J Respir Crit Care Med, vol. 193, Issue 3, p. 259-272, Feb. 1, 2016.
Sébastien Gibot et al., "High-mobility group box 1 protein plasma concentrations during septic shock", Intensive Care Med, 33:1347-1353, 2007.
Jianjun Gao et al., "Breakthrough: Chloroquine phosphate has shown apparent efficacy in treatment of COVID-19 associated pneumonia in clinical studies", BioScience Trends., 14(1):72-73, 2020.
Kathryn L. Griffin et al., "2-O, 3-O-Desulfated Heparin Inhibits Neutrophil Elastase-Induced HMGB-1 Secretion and Airway Inflammation", American Journal of Respiratory Cell and Molecular Biology, vol. 50 Issue 4, p. 2407-2413, Apr. 2014.
Adam Gordois et al., "The Health Care Costs of Diabetic Peripheral Neuropathy in the U.S.", Diabetes Care, vol. 26, No. 6, Jun. 2003.
Peter M. Grace et al., "Pathological pain and the neuroimmune interface", Nat Rev Immunol.,14(4), p. 217-231, Apr. 2014.
L.-H. Guo et al., "The innate immunity of the central nervous system in chronic pain: The role of Toll-like receptors", Cellular and Molecular Life Sciences, 64:1128-1136, 2007.
W. Guan et al., "Clinical Characteristics of Coronavirus Disease 2019 in China", The New England Journal of Medicine, 382; 18, Apr. 30, 2020.
Weidun Alan Guo et al., "The receptor for advanced glycation end products and acute lung injury/acute respiratory distress syndrome", Intensive Care Med, 38; 1588-1598, 2012.
Satoshi Hagiwara et al., "Effects of hyperglycemia and insulin therapy on high mobility group box 1 in endotoxin-induced acute lung injury in a rat model", Crit Care Med, vol. 36, No. 8, 2008.
Ling Zhang et al., "Receptor for Advanced Glycation End Products Is Subjected to Protein Ectodomain Shedding by Metalloproteinases", The Journal of Biological Chemistry, vol. 283, No. 51, p. 35507-35516, Dec. 19, 2008.
Hatayama K, et al., "Combined effect of anti-high-mobility group box-1 monoclonal antibody and peramivir against influenza A virus-induced pneumonia in mice", Journal of Medical Virology, 91(3):361-9, 2019.
Helena Erlandsson Harris et al., "HMGB1: A multifunctional alarmin driving autoimmune and inflammatory disease", Nature Reviews Rheumatology, vol. 8, Apr. 2012.
Zhenghua He et al., "Intrathecal Lentivirus-mediated Transfer of Interleukin-10 Attenuates Chronic Constriction Injury-induced Neuropathic Pain through Modulation of Spinal High-mobility Group Box 1 in Rats", Pain Physician, 16:E615-E625, 2013.
Margaret S. Herridge et al., "One-Year Outcomes in Survivors of the Acute Respiratory Distress Syndrome", The New England Journal of Medicine, vol. 348, No. 8, Feb. 20, 2003.
Jennifer L. Hanslick et al., "Dimethyl Sulfoxide (DMSO) Produces Widespread Apoptosis in the Developing Central Nervous System", Neurobiol Dis., 34(1): 1-10, Apr. 2009.
X. Q. Hou et al., "Potential role of high-mobility group box 1 protein in the pathogenesis of influenza H5N1 virus infection", Acta virologica 58: 69-75, 2014.
Hulda Sigridur Hreggvidsdóttir et al., "High Mobility Group Box Protein 1 (HMGB1)-Partner Molecule Complexes Enhance Cytokine Production by Signaling Through the Partner Molecule Receptor", MOL MED 18:224-230, 2012.
Chaolin Huang et al., "Clinical features of patients infected with 2019 novel coronavirus in Wuhan, China", Lancet, 395: 497-506, 2020.

Jared M. Huston et al., "Transcutaneous vagus nerve stimulation reduces serum high mobility group box 1 levels and improves survival in murine sepsis", Laboratory Investigations, Crit Care Med, vol. 35, No. 12, 2007.
Wufeng Huang et al., "High-mobility group box 1 impairs airway epithelial barrier function through the activation of the RAGE/ERK pathway", International Journal of Molecular Medicine, 37: 1189-1198, 2016.
Takashi Ito et al., "Thrombomodulin as an intravascular safeguard against inflammatory and thrombotic diseases", Expert Opinion, Ther. Targets, 20(2):151-158, 2016.
Yumiko Imai et al., "Identification of Oxidative Stress and Toll-like Receptor 4 Signaling as a Key Pathway of Acute Lung Injury", Cell, 133, 235-249, Apr. 18, 2008.
Theodore J. Iwashyna et al., "Long-term Cognitive Impairment and Functional Disability Among Survivors of Severe Sepsis", JAMA., 304(16), 1787-1794, Oct. 27, 2010.
Yasir N Jassam et al., "Neuroimmunology of Traumatic Brain Injury: Time for a Paradigm Shift" Neuron, 95(6), 1246-1265, Sep. 13, 2017.
Saad Javed et al.z "Treatment of painful diabetic neuropathy", Therapeutic Advances in Chronic Disease, vol. 6(1) 15-28, 2015.
Elizabeth R. Johnson et al., "Acute Lung Injury: Epidemiology, Pathogenesis, and Treatment", Journal of Aerosol Medicine and Pulmonary Drug Delivery, vol. 23, No. 4, 2010.
David J. Kaczorowski et al., "Innate Immune Mechanisms in Ischemia/Reperfusion", Frontiers in Bioscience E1, 91-98, Jun. 1, 2009.
Chang Jia et al., "Endothelial cell pyroptosis plays an important role in Kawasaki disease via HMGB1/RAGE/cathespin B signaling pathway and NLRP3 inflammasome activation", Cell Death and Disease (2019) 10:778.
Peter Huebener et al., "The HMGB1/RAGE axis triggers neutrophil-mediated injury amplification following necrosis", J Clin Invest., 125(2):539-550, 2015.
Jennifer A Stokes et al., "Toll-like receptor signaling adapter proteins govern spread of neuropathic pain and recovery following nerve injury in male mice", Journal of Neuroinflammation, 10:14, 2013.
Munehiro Kitada et al., "Rodent models of diabetic nephropathy: their utility and limitations", International Journal of Nephrology and Renovascular Disease, 9 279-290, 2016.
Ivana Knezevic et al., "Immunogenicity assessment of monoclonal antibody products: A simulated case study correlating antibody induction with clinical outcomes", Biologicals, 43 (2015) 307-317.
Mary A. Lake, "What we know so far: COVID-19 current clinical knowledge and research", Clinical Medicine vol. 20, No. 2: 124-7, 2020.
Kai Le et al., "SIRT1-regulated HMGB1 release is partially involved in TLR4 signal transduction: A possible anti neuroinflammatory mechanism of resveratrol in neonatal hypoxic-ischemic brain injury", International Immunopharmacology 75 (2019) 105779.
Sodam Kim et al., "Signaling of High Mobility Group Box 1 (HMGB1) through Toll-like Receptor 4 in Macrophages Requires CD14", MOL MED, 19:88-98, 2013.
Ryan M. Levy et al., "Systemic inflammation and remote organ injury following trauma require HMGB1", Am J Physiol Regul Integr Comp Physiol, 293, R1538-R1544, 2007.
Li Fu et al., "Therapeutic effects of antiHMGB1 monoclonal antibody on pilocarpine-induced status epilepticus in mice", Scientific Reports, 7: 1179, 2017.
Kehan Li et al., "Ketamine attenuates sepsis-induced acute lung injury via regulation of HMGB1-RAGE pathways", International Immunopharmacology, 34:114-128, 2016.
Anna M. Leitgeb et al., "Inhibition of merozoite invasion and transient de-sequestration by sevuparin in humans with Plasmodium falciparum malaria", PLoS One 12(12) e0188754, Dec. 15, 2017.
Hwai-Jeng Lin et al., "Coalescence of RAGE in Lipid Rafts in Response to Cytolethal Distending Toxin-Induced Inflammation", Frontiers in Immunology, vol. 10, Article 109, Feb. 2019.
Yan Li et al., "Toll-like receptor 4 signaling contributes to paclitaxel-induced peripheral neuropathy", J Pain, 15(7): 712-725, Jul. 2014.

(56) References Cited

OTHER PUBLICATIONS

Kaifeng Lisa Lin et al., "CCR2+ Monocyte-Derived Dendritic Cells and Exudate Macrophages Produce Influenza-Induced Pulmonary Immune Pathology and Mortality", The Journal of Immunology, 180:2562-2572, 2008.
Tong Liu et al., "Emerging role of Toll-like receptors in the control of pain and itch", Neurosci Bull, 28(2): 131-144, Apr. 1, 2012.
Ming Liu et al., "Simvastatin suppresses vascular inflammation and atherosclerosis in ApoE$^{-/-}$ mice by downregulating the HMGB1-RAGE axis", Acta Pharmacologica Sinica, 34, 830-836, 2013.
Ben Lu et al., "JAK/STAT1 signaling promotes HMGB1 hyperacetylation and nuclear translocation" PNAS, vol. 111, No. 8, 3068-3073, 2014.
Peter Lundbäck et al., "A Novel High Mobility Group Box 1 Neutralizing Chimeric Anitbody Attenuates Drug-Induced Liver Injury and Postinjury Inflammation in Mice", Hepatology, vol. 64, No. 5, 2016.
Michael T. Lotze et al., "High-Mobility Group Box 1 Protein (HMGB1): Nuclear Weapon In The Immune Arsenal", Nature Reviews Immunology, vol. 5, p. 331-342, Apr. 2005.
Takehiko Maeda et al., "HMGB1 as a Potential Therapeutic Target for Neuropathic Pain", Journal of Pharmacological Sciences, 123, 301-305, 2013.
Fei Ma et al., "Disulfide high mobility group box-1 causes bladder pain through bladder Toll-like receptor 4", BMC Physiology, 17:6, 2017.
Melinda Magna et al., "The Role of HMGB1 in the Pathogenesis of Inflammatory and Autoimmune Diseases", Molecular Medicine, 20:138-146, 2014.
Thomas R. Martin et al., "A TRIFfic Perspective on Acute Lung Injury", Cell, vol. 33, p. 208-210, Apr. 18, 2008.
Sara Manti et al., "Induction of High Mobility Group Box-1 in vitro and in vivo by Respiratory Syncytial Virus", Pediatr Res., 83(5): 1049-1056, May 2018.
Eric B Milbrandt et al., "Predicting late anemia in critical illness", Critical Care, vol. 10, No. 1, 2006.
Claudia Monaco et al., "Anti-TNF therapy: past, present and future", International Immunology, vol. 27, No. 1, pp. 55-62, Nov. 2014.
Yoki Nakamura et al., "Neuropathic Pain in Rats with a Partial Sciatic Nerve Ligation Is Alleviated by Intravenous Injection of Monoclonal Antibody to High Mobility Group Box-1", PLOS One, vol. 8, Issue 8, 2013.
Lu Meng et al. "The protective effect of dexmedetomidine on LPS-induced acute lung injury through the HMGB1-mediated TLR4/NF-κB and PI3K/Akt/mTOR pathways" Molecular Immunology 94 (2018) 7-17.
QM Nhu et al., "Novel signaling interactions between proteinase-activated receptor 2 and Toll-like receptors in vitro and in vivo", Mucosal Immunol, 3(1): 29-39, Jan. 2010.
Rebecca Notman et al., "Molecular Basis for Dimethylsulfoxide (DMSO) Action on Lipid Membranes", Journal of the American Chemical Society, 128, 13982-13983, Dec. 2006.
Nobuyuki Nosaka et al., "Anti-high mobility group box-1 monoclonal antibody treatment provides protection against influenza A virus (H1N1)-induced pneumonia in mice", Critical Care, 19;249, 2015.
Michael H. Ossipov et al., "Challenges in the Development of Novel Treatment Strategies for Neuropathic Pain", The Journal of the American Society for Experimental NeuroTherapeutics, vol. 2, 650-661, Oct. 2005.
William Ottestad et al., "Biphasic Release of the Alarmin High Mobility Group Box 1 Protein Early After Trauma Predicts Poor Clinical Outcome", Online Clinical Investigations, vol. 47, No. 8, Aug. 2019.
Sophia I. Pachydaki et al., "Upregulation of RAGE and its ligands in proliferative retinal disease", Experimental Eye Research 82, 807-815, 2006.

Polly E. Parsons et al., "Lower tidal volume ventilation and plasma cytokine markers of inflammation in patients with acute lung injury", Crit Care Med, vol. 33, No. 1, 2005.
Valentin A. Pavlov et al., "Molecular and Functional Neuroscience in Immunity", Annu Rev Immunol, 36: 783-812, Apr. 2018.
Ming-Zhe Qin et al., "Ketamine effect on HMGB1 and TLR4 expression in rats with acute lung injury", Int J Clin Exp Pathol, 8(10):12943-12948, 2015.
Amit Porat et al., "DNA-Mediated Interferon Signature Induction by SLE Serum Occurs in Monocytes Through Two Pathways: A Mechanism to Inhibit Both Pathways", Frontiers in Immunology, vol. 9, Article 2, Dec. 2018.
Shixin Qin et al., "Role of HMGB1 in apoptosis-mediated sepsis lethality", The Journal of Experimental Medicine, vol. 203, No. 7, 1637-1642, Jul. 10, 2006.
Lihua Qu et al., "Glycyrrhizic acid ameliorates LPS-induced acute lung injury by regulating autophagy through the PI3K/AKT/mTOR pathway", Am J Transl Res, 11(4):2042-2055, 2019.
Krishnan Raghavendran et al., "Pharmacotherapy of Acute Lung Injury and Acute Respiratory Distress Syndrome", Curr Med Chem, 15(19): 1911-1924, 2008.
V. Marco Ranieri et al., "Effect of Mechanical Ventilation on Inflammatory Mediators in Patients With Acute Respiratory Distress Syndrome A Randomized Controlled Trial", JAMA, vol. 281, No. 1, Jul. 7, 1999.
Angela Raucci et al., "A soluble form of the receptor for advanced glycation endproducts (RAGE) is produced by proteolytic cleavage of the membrane-bound form by the sheddase a disintegrin and metalloprotease 10 (ADAM10)", The FASEB Journal, vol. 22, p. 3716-3727, Oct. 2008.
Konrad Reinhart et al., "Anti-tumor necrosis factor therapy in sepsis: Update on clinical trials and lessons learned", Crit Care Med, vol. 29, No. 7, 2001.
Daniel Remick et al., "Blockade of Tumor Necrosis Factor Reduces Lipopolysaccharide Lethality, but not the Lethality of Cecal Ligation and Puncture", Shock, vol. 4, No. 2, pp. 89-95, 1995.
Kempaiah Rayavara et al., "Proinflammatory Effects of Respiratory Syncytial Virus—Induced Epithelial HMGB1 on Human Innate Immune Cell Activation", The Journal of Immunology, 201:2753-2766, Oct. 1, 2018.
Hussin A. Rothan et al., "The epidemiology and pathogenesis of coronavirus disease (COVID-19) outbreak", Journal of Autoimmunity 109, 102433, 2020.
Gordon D. Rubenfeld et al., "Incidence and Outcomes of Acute Lung Injury", The New England Journal of Medicine, 353:16, 1685-93, Oct. 20, 2005.
Kenneth E. Remy et al., "Haptoglobin improves shock, lung injury, and survival in canine pneumonia", JCI Insight, 3(18):e123013, 2018.
Gottfried Rudofsky, Jr et al., "Asp299Gly and Thr399Ile Genotypes of the TLR4 Gene Are Associated With a Reduced Prevalence of Diabetic Neuropathy in Patients With Type 2 Diabetes", Diabetes Care, vol. 27, No. 1, p. 179-183, Jan. 2004.
Ari Rouhiainen et al., "Inhibition of Homophilic Interactions and Ligand Binding of the Receptor for Advanced Glycation End Products by Heparin and Heparin-Related Carbohydrate Structures", Medicines, 5, 79, 2018.
A. Parker Ruhl et al., "Health Care Resource Use and Costs of Two-Year Survivors of Acute Lung Injury", AnnalsATS vol. 12, No. 3, p. 392-401, Mar. 2015.
Paola Scaffidi et al., "Release of chromatin protein HMGB1 by necrotic cells triggers inflammation", Nature, vol. 418, pp. 191-195, Jul. 11, 2022.
Gustav Schelling et al., "Health-related quality of life and post-traumatic stress disorder in survivors of the acute respiratory distress syndrome", Critical Care Medicine, Issue: vol. 26(4), pp. 651-659, Apr. 1998.
Hanna Schierbeck et al., "Immunomodulatory Drugs Regulate HMGB1 Release from Activated Human Monocytes", MOL MED 16 (9-10) pp. 343-351, Sep.-Oct. 2010.

(56) References Cited

OTHER PUBLICATIONS

Hanna Schierbeck et al., "Monoclonal Anti-HMGB1 (High Mobility Group Box Chromosomal Protein 1) Antibody Protection in Two Experimental Arthritis Models", MOL MED 17 (9-10) pp. 1039-1044, Sep.-Oct. 2011.
Lokesh Sharma et al., "Partially-desulfated heparin improves survival in Pseudomonas pneumonia by enhancing bacterial clearance and ameliorating lung injury", Journal of Immunotoxicology, 11(3): 260-267, 2014.
Ting Shi et al., "Global, regional, and national disease burden estimates of acute lower respiratory infections due to respiratory syncytial virus in young children in 2015: a systematic review and modelling study", Lancet, vol. 390, pp. 946-958, 2017.
Ann Marie Schmidt et al., "A Novel Cellular Receptor for Advanced Glycation End Products", Diabetes, vol. 45, Suppl. 3, Jul. 1996.
Junya Shimazaki et al. "Systemic Involvement Of High-Mobility Group Box 1 Protein and Therapeutic Effect Of Anti-High-Mobility Group Box 1 Protein Antibody In A Rat Model Of Crush Injury", Shock, vol. 37, No. 6, pp. 634-638, Feb. 6, 2012.
KA Shirey et al., "Novel strategies for targeting innate immune responses to influenza", Mucosa Immunology, vol. 9, No. 5, Sep. 2016.
J. Skrha Jr. et al., "Relationship of Soluble RAGE and RAGE Ligands HMGB1 and EN-RAGE to Endothelial Dysfunction in Type 1 and Type 2 Diabetes Mellitus", Exp Clin Endocrinol Diabetes, 120: 277-281, 2012.
Jennifer Simpson et al., "Respiratory Syncytial Virus Infection Promotes Necroptosis and HMGB1 Release by Airway Epithelial Cells", American Journal of Respiratory and Critical Care Medicine, vol. 201, No. 11, p. 1358-1371, Jun. 1, 2020.
Kari Ann Shirey et al., "The TLR4 Antagonist, Eritoran, Protects Mice from Lethal Influenza Infection", Nature, 497(7450): 498-502, May 23, 2013.
A Tanaka et al., "Serum high-mobility group box 1 is correlated with interferon-α and may predict disease activity in patients with systemic lupus erythematosus", Lupus, 28, p. 1120-1127, 2019.
Jonas Sundén-Cullberg et al., "Persistent elevation of high mobility group box-1 protein (HMGB1) in patients with severe sepsis and septic shock", Crit Care Med, vol. 33, No. 3, p. 564-573, 2005.
Chhinder P. Sodhi et al., "Intestinal Epithelial TLR-4 Activation Is Required for the Development of Acute Lung Injsury after Trauma/Hemorrhagic Shock via the Release of HMGB1 from the Gut", The Journal of Immunology, 194:4931-4939, Apr. 10, 2015.
Junichi Tanaka et al., "Recombinant human soluble thrombomodulin prevents peripheral HMGB1-dependent hyperalgesia in rats", British Journal of Pharmacology, 170:1233-1241, 2013.
Menno D de Jong et al., "Fatal outcome of human influenza A (H5N1) is associated with high viral load and hypercytokinemia", Nature Medicine, vol. 12, Number, p. 1203-1207, 10, Oct. 2006.
Taylor M Parker et al., "The Danger Zone: Systematic Review Of The Role Of Hmgb1 Danger Signaling In Traumatic Brain Injury", Brain Inj., 31(1): 2-8, 2017.
Jane Tian et al., "Toll-like receptor 9-dependent activation by DNA-containing immune complexes is mediated by HMGB1 and RAGE", Nature Immunology, vol. 8, No. 5, p. 487-496, May 2007.
C.F. Tsao et al., "Expression of high-mobility group box protein 1 in diabetic foot atherogenesis", Genetics and Molecular Research 14 (2): 4521-4531, 2015.
Chia-Cheng Tseng et al., "Impact of Serum Biomarkers and Clinical Factors on Intensive Care Unit Mortality and 6-Month Outcome in Relatively Healthy Patients with Severe Pneumonia and Acute Respiratory Distress Syndrome", Disease Markers, vol. 2014, Article ID 804654, p. 1-9, 2014.
Allan Tsung et al., "Increasing numbers of hepatic dendritic cells promote HMGB1-mediated ischemia-reperfusion injury", Journal of Leukocyte Biology, vol. 81, p. 119-128, Jan. 2007.
Jeffery K. Taubenberger et al., "The Pathology of Influenza Virus Infections", Annu Rev Pathol, 3: 499-522, 2008.

Ulf Andersson et al., "HMGB1 Is a Therapeutic Target for Sterile Inflammation and Infection", Annu Rev Immunol., 29: 139-162, 2011.
Sergio I. Valdés-Ferrer et al., "High-Mobility Group Box 1 Mediates Persistent Splenocyte Priming In Sepsis Survivors: Evidence From A Murine Model" Shock, 40(6): 492-495, Dec. 2013.
Sergio I Valdés-Ferrer et al., "HMGB1 Mediates Anemia of Inflammation in Murine Sepsis Survivors", MOL MED 21:951-958, 2015.
Lisa K. Vande Vusse et al., "The Epidemiology of Transfusion-related Acute Lung Injury Varies According to the Applied Definition of Lung Injury Onset Time", AnnalsATS, vol. 12, No. 9, p. 1328-1335, Sep. 2015.
Marieke A.D van Zoelen et al., "Receptor for advanced glycation end products is detrimental during influenza A virus pneumonia" Virology, 391 (2): 265-273, Sep. 1, 2009.
Sonya VanPatten et al., "High Mobility Group Box-1 (HMGb1): Current Wisdom and Advancement as a Potential Drug Target", Journal of Medicinal Chemistry, vol. 61, p. 5093-5107, 2018.
Jean Louis Vincent et al., "Anemia and Blood Transfusion in Critically ill Patients", JAMA, vol. 288, No. 12, p. 1499-1507, Sep. 25, 2002.
Jozica Vasl et al., "Novel Roles of Lysines 122, 125, and 58 in Functional Differences between Human and Murine MD-2", The Journal of Immunology, 183:5138-5145, Sep. 25, 2009.
Wenbin Wan et al. "The Emerging Role of HMGB1 in Neuropathic Pain: A Potential Therapeutic Target for Neuroinflammation" Journal of Immunology Research, vol. 2016, Article ID 6430423, p. 1-9, 2016.
Emilie Venereau et al., "Mutually exclusive redox forms of HMGB1 promote cell recruitment or proinflammatory cytokine release", J. Exp. Med., vol. 209, No. 9, p. 1519-1528, 2012.
Hsiang-Ling Wang et al., "Circulating level of high mobility group box-1 predicts the severity of community-acquired pneumonia: Regulation of inflammatory responses via the c-Jun N-terminal signaling pathway in macrophages", Molecular Medicine Reports 16: 2361-2366, 2017.
Ye-song Wang et al., "Tanshinone IIA Attenuates Chronic PancreatitisInduced Pain in Rats via Downregulation of HMGB1 and TRL4 Expression in the Spinal Cord", Pain Physician, 18:E615-E628, ISSN 2150-1149, 2015.
Bing Wu et al., "Short-time pretreatment of rosuvastatin attenuates myocardial ischemia and reperfusion injury by inhibiting high mobility group box 1 protein expression, International Journal of Cardiology", 168(5):4946-8, 2013.
Hui Xiang et al., "Dexmedetomidine Controls Systemic Cytokine Levels through the Cholinergic Anti-inflammatory Pathway", Inflammation, vol. 37, No. 5, p. 1763-1770, Oct. 2014.
Jian-e Yan et al., "Streptozotocin-induced diabetic hyperalgesia in rats is associated with upregulation of toll-like receptor 4 expression", Neuroscience Letters 526, p. 54-58, 2012.
J Xu et al., "Macrophage endocytosis of high-mobility group box 1 triggers pyroptosis", Cell Death and Differentiation, 21, p. 1229-1239, 2014.
Peng Z. Meng et al., "Protective Effect of Dexmedetomidine on Endotoxin-Induced Acute Lung Injury in Rats", Medical Science Monitor, 24: 4869-4875, 2018.
Huan Yang et al., Identification of CD163 as an antiinflammatory receptor for HMGB1-haptoglobin complexes, JCI Insight., 1 (7):e85375, 2016.
Huan Yang et al., "Targeting HMGB1 in inflammation", Biochim Biophys Acta., 1799(0): p. 149-156, 2010.
Huan Yang et al., "A critical cysteine is required for HMGB1 binding to Toll-like receptor 4 and activation of macrophage cytokine release", PNAS, vol. 107, No. 26, p. 11942-11947, Jun. 2010.
Huan Yang et al., "Inhibition of HMGB1/RAGE-mediated endocytosis by HMGB1 antagonist box A, anti-HMGB1 antibodies, and cholinergic agonists suppresses inflammation", Molecular Medicine, 25:13, 2019.
Huan Yang et al., "The haptoglobin beta subunit sequesters HMGB1 toxicity in sterile and infectious inflammation", J Intern Med., July; 282(1): 76-93, 2017.

(56) References Cited

OTHER PUBLICATIONS

Huan Yang et al., "MD-2 is required for disulfide HMGB1-dependent TLR4 signaling", J. Exp. Med., vol. 212 No. 1, p. 5-14, 2015.
Huan Yang et al., "High Mobility Group Box Protein 1 (HMGB1): The Prototypical Endogenous Danger Molecule", MOL MED 21 (Supplement 1), S6-S12, 2015.
Huan Yang et al., "Redox Modification of Cysteine Residues Regulates the Cytokine Activity of High Mobility Group Box-1 (HMGB1)", MOL MED 18:250-259, 2012. (Retracted Article).
Huan Yang et al., "Reversing established sepsis with antagonists of endogenous high-mobility group box 1", PNAS, vol. 101, No. 1, p. 296-301, Jan. 6, 2004.
Sachin Yende et al., "Long-term Outcomes from Sepsis", Current Infectious Disease Reports, 9:382-386, 2007.
Runkuan Yang et al., "Anti-HMGB1 Neutralizing Antibody Ameliorates Gut Barrier Dysfunction and Improves Survival after Hemorrhagic Shock", MOL MED 12(4-6) 105-114, Apr.-Jun. 2006.
Yao Yu et al., "The role of high mobility group box 1 (HMGB-1) in the diabetic retinopathy inflammation and apoptosis", Int J Clin Exp Pathol, 8(6):6807-6813, 2015.
Y. Zhang et al., "Ketamine alleviates LPS induced lung injury by inhibiting HMGB1-RAGE level", European Review for Medical and Pharmacological Sciences, 22: 1830-1836, 2018.
Haiyan Zhang et al., "Rosuvastatin reduces the pro-inflammatory effects of adriamycin on the expression of HMGB1 and RAGE in rats", International Journal Of Molecular Medicine 42: 3415-3423, 2018.
Tao Zhu et al., "Toll-like receptor 4 and tumor necrosis factor-alpha as diagnostic biomarkers for diabetic peripheral neuropathy", Neuroscience Letters, 585, 28-32, 2015.
Xin Zhao et al., "Inhibition of CaMKIV relieves streptozotocin-induced diabetic neuropathic pain through regulation of HMGB1", BMC Anesthesiology, 16:27, 2016.
Shuang-feng Zi et al., "Dexmedetomidine-mediated protection against septic liver injury depends on TLR4/MyD88/NF-κB signaling down regulation partly via cholinergic anti-inflammatory mechanisms", International Immunopharmacology, 76, 105898, 2019.
Mei Zong et al., "TLR4 as receptor for HMGB1 induced muscle dysfunction in myositis", Ann Rheum Dis, 72:1390-1399, 2013.
Ulf Andersson et al., "High-mobility group box 1 protein (HMGB1) operates as an alarmin outside as well as inside cells", Seminars in Immunology, 38, 40-48, 2018.
N.M. Agalave et al., "Abstracts from the Annual Scientific Meeting of the Scandinavian Association for the Study of Pain", Scandinavian Journal of Pain 8, p. 47-54, 2015. (Abstract only).
Lionel Apetoh et al., "The interaction between HMGB1 and TLR4 dictates the outcome of anticancer chemotherapy and radiotherapy", Immunological Review, vol. 220, p. 47-59, 2007.
Daniela Damjanovic et al., "Immunopathology in influenza virus infection: Uncoupling the friend from foe", Clinical Immunology, vol. 144, p. 57-69, 2012.
Vera Bril, "Treatments for diabetic neuropathy", Journal of the Peripheral Nervous System 17(Supplement), p. 22-27, 2012.
Nabanita Das et al., "HMGB1 Activates Proinflammatory Signaling via TLR5 Leading to Allodynia", Cell Reports, vol. 17, p. 1128-1140, Oct. 18, 2016.
Graham H. Goodwin et al., "A New Group of Chromatin-Associated Proteins with a High Content of Acidic and Basic Amino Acids", Eur. J. Biochem. 38, p. 14-19, 1973.
M K Eskandari et al., "Anti-tumor necrosis factor antibody therapy fails to prevent lethality after cecal ligation and puncture or endotoxemia", The Journal of Immunology, vol. 148, p. 2724-2730, 1992.
Satoshi Hagiwara et al., "Effects of hyperglycemia and insulin therapy on high mobility group box 1 in endotoxin-induced acute lung injury in a rat model", Crit Care Med, vol. 36, No. 8, p. 2407-2413, 2008.

Qian-Feng Han et al., "Simvastatin protects the heart against ischemia reperfusion injury via inhibiting HMGB1 expression through PI3K/Akt signal pathways", International Journal of Cardiology, vol. 201, p. 568-569, 2015.
Jared M. Huston et al., "Transcutaneous vagus nerve stimulation reduces serum high mobility group box 1 levels and improves survival in murine sepsis", Crit Care Med, vol. 35, No. 12, 2007.
Gun-Soo Hong et al., "Non-invasive transcutaneous auricular vagus nerve stimulation prevents postoperative ileus and endotoxemia in mice", Neurogastroenterology & Motility, 31 :e13501, 2019.
Yoshinori Ito et al., "Increased levels of cytokines and high-mobility group box 1 are associated with the development of severe pneumonia, but not acute encephalopathy, in 2009 H1N1 influenza-infected children", Cytokine, vol. 56, p. 180-87, 2011.
Rui Kang et al., "HMGB1 in health and disease", Molecular Aspects of Medicine, vol. 40, p. 1-116, 2014.
Hulya Karatas et al., "Spreading Depression Triggers Headache by Activating Neuronal Panx1 Channels", Science, vol. 339, p. 1092-1095, Mar. 1, 2013.
Xin Kuang et al., "Effects of intrathecal epigallocatechin gallate, an inhibitor of Toll-like receptor 4, on chronic neuropathic pain in rats", European Journal of Pharmacology, vol. 676, p. 51-56, 2012.
Li Li et al., "Heparin inhibits the inflammatory response induced by LPS and HMGB1 by blocking the binding of HMGB1 to the surface of macrophages", Cytokine, vol. 72, p. 36-42, 2015.
Yan Ling et al., "Heparin changes the conformation of high-mobility group protein 1 and decreases its affinity toward receptor for advanced glycation endproducts in vitro", International Immunopharmacology, vol. 11, p. 187-193, 2011.
Yong-Jie Lian et al., "Ds-HMGB1 and fr-HMGB induce depressive behavior through neuroinflammation in contrast to nonoxid-HMGB1", Brain, Behavior, and Immunity, vol. 59, p. 322-332, 2017.
Takeshi Nishida et al. "Involvement of high mobility group box 1 in the development and maintenance of chemotherapy-induced peripheral neuropathy in rats", Toxicology, vol. 365, p. 48-58, 2016.
Yuan Liu et al., "HMGB1: Roles in base excision repair and related function", Biochimica et Biophysica Acta, vol. 1799:119-130, 2010.
Nobuyuki Nosaka et al., "Anti-high mobility group box-1 monoclonal antibody treatment of brain edema induced by influenza infection and lipopolysaccharide", Journal of Medical Virology, 90:1192-1198, 2018.
Yu Okuma et al., "Anti-High Mobility Group Box-1 Antibody Therapy for Traumatic Brain Injury", Annals of Neurology, vol. 72, No. 3, p. 373-384, 2012.
Catharine Paules et al., "Influenza", Lancet, 390: p. 697-707, 2017.
Karlheinz Peter et al., "HMGB1 signals danger in acute coronary syndrome: Emergence of a new risk marker for cardiovascular death?" Atherosclerosis, 221:317-318, 2012.
Prasad Rallabhandi et al., "Respiratory Syncytial Virus Fusion Protein-Induced Toll-Like Receptor 4 (TLR4) Signaling Is Inhibited by the TLR4 Antagonists *Rhodobacter sphaeroides* Lipopolysaccharide and Eritoran (E5564) and Requires Direct Interaction with MD-2", mBio, vol. 3, Issue 4, Jul./Aug. 2012.
Joel Rasmuson et al., "Heparinoid sevuparin inhibits *Streptococcus*-induced vascular leak through neutralizing neutrophil-derived proteins", The Faseb Journal, vol. 33, e00218-12, p. 10443-10452, Sep. 2019.
Peng-Cheng Ren et al., "High-mobility group box 1 contributes to mechanical allodynia and spinal astrocytic activation in a mouse model of type 2 diabetes", Brain Research Bulletin, 88:332-337, 2012.
Madoka Shirasawa et al., "Receptor for advanced glycation endproducts is a marker of type I lung alveolar cells", Genes to Cells, vol. 9, p. 165-174, 2004.
Masayuki Shibasaki et al., "Induction of high mobility group box-1 in dorsal root ganglion contributes to pain hypersensitivity after peripheral nerve injury", Pain, 149:514-521, 2010.
Wei Tong et al., "Spinal high-mobility group box 1 contributes to mechanical allodynia in a rat model of bone cancer pain", Biochemical and Biophysical Research Communications, 395:572-576, 2010.

(56) References Cited

OTHER PUBLICATIONS

Peter C. Taylor et al., "Anti-TNF biologic agents: still the therapy of choice for rheumatoid arthritis", Nat. Rev. Rheumatol, vol. 5, p. 578-582, Oct. 2009.

Haichao Wang et al., "HMG-1 as a Late Mediator of Endotoxin Lethality in Mice", Science, vol. 285, p. 248-251, Jul. 9, 1999.

Allan Tsung et al., "HMGB1 release induced by liver ischemia involves Toll-like receptor 4—dependent reactive oxygen species production and calcium-mediated signaling", JEM, vol. 204, No. 12, p. 2913-2923, Nov. 26, 2007.

Kazuma Yamakawa et al., "Recombinant Human Soluble Thrombomodulin in Sepsis-Induced Coagulopathy: An Updated Systematic Review and Meta-Analysis", Thrombosis and Haemostasis, vol. 119, No. 1, p. 56-65, 2019.

Huan Yang et al., "The many faces of HMGB1: molecular structure-functional activity in inflammation, apoptosis, and chemotaxis", Journal of Leukocyte Biology, vol. 93, p. 865-873, Jun. 2013.

Zhaowei Zhu et al., "Statin protects endothelial cell against ischemia reperfusion injury through HMGB1/TLR4 pathway", International Journal of Cardiology, 203:74, 2016. (Abstract only).

Hailan Zhao et al., "HMGB-1 as a Potential Target for the Treatment of Diabetic Retinopathy", Medical Sci. Monit., 21 : p. 3062-3067, 2015.

L. Zhu et al., "High-Mobility Group Box 1 Induces Neuron Autophagy In A Rat Spinal Root Avulsion Model", Neuroscience, 315:286-295, 2016.

Nader E. Abo-Dya et al., "Benzotriazole-Mediated Synthesis of Aza-peptides: En Route to an Aza-Leuenkephalin Analogue", The Journal of Organic Chemistry, 78:3541-3552, 2013.

Ilker Avan et al., "Peptidomimetics via modifications of amino acids and peptide bonds", Chemical Society Reviews, 43:3575-3594, 2014.

\* cited by examiner

Fig. 1
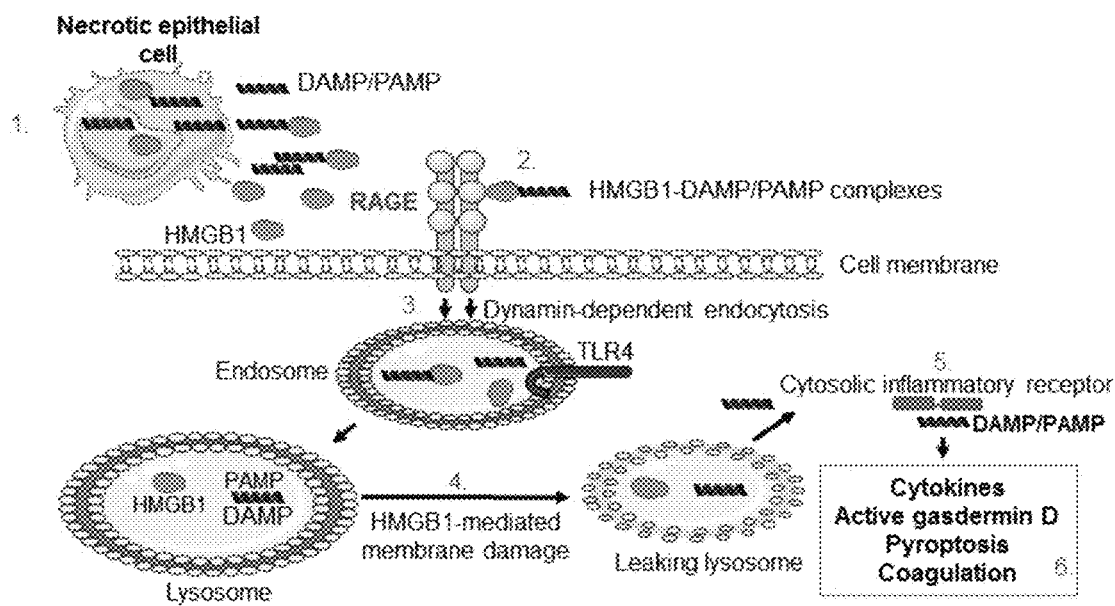
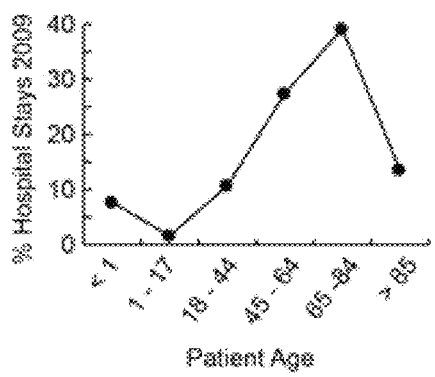
Fig 2A
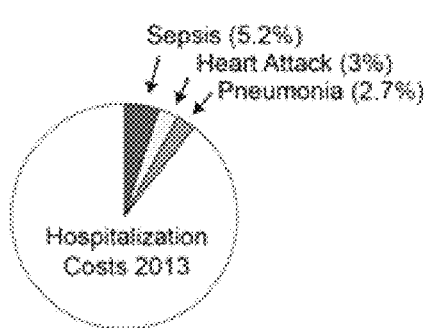
Fig 2B

Stability of P5779 (SEQ ID NO: 1) and K883 in mice serum

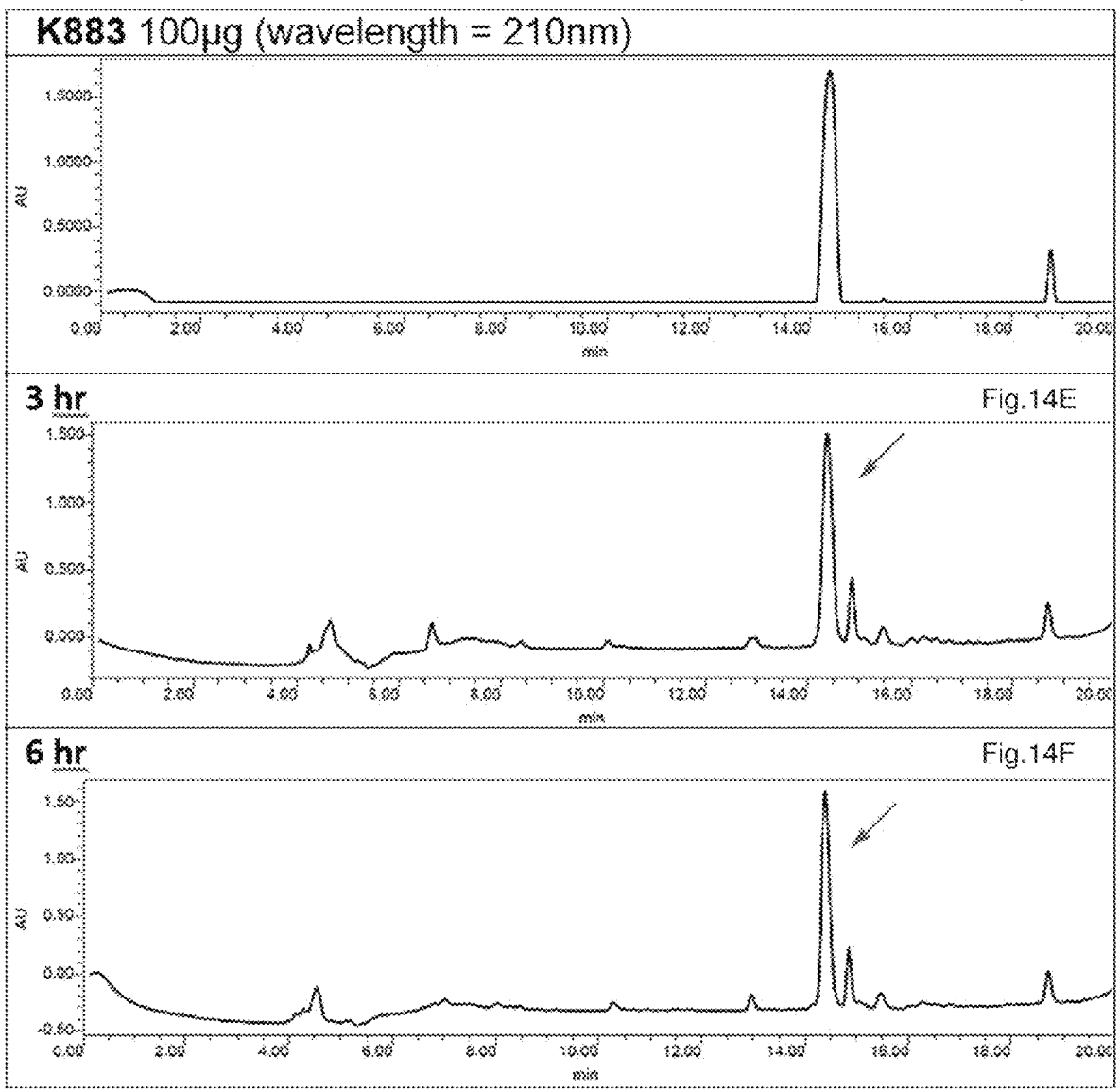
Stability of P5779 (SEQ ID NO: 1) and K883 in mice serum

*: P<0.05 vs. HMGB1 alone

*: P<0.05

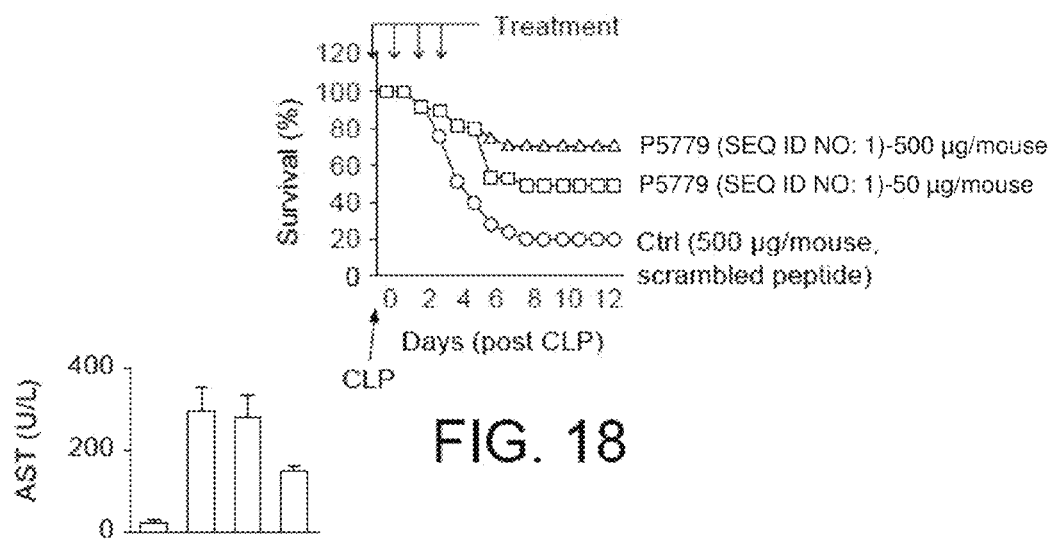
FIG. 18
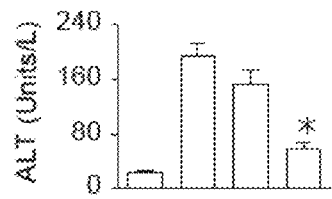
FIG. 19A
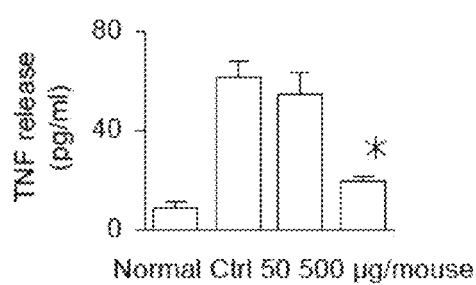
FIG. 19B
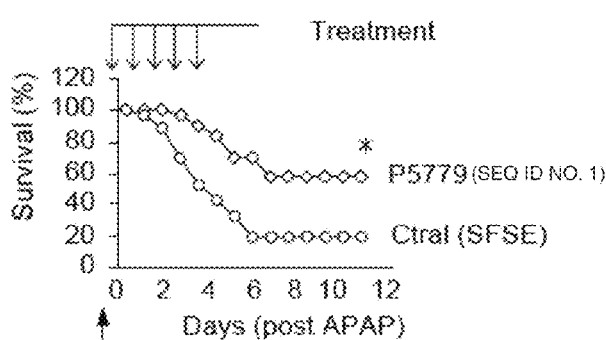
FIG. 19E
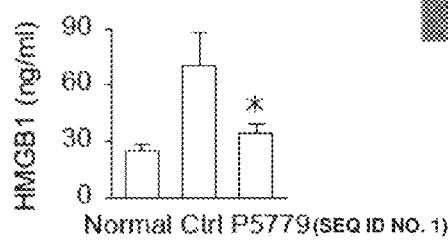
FIG. 19C
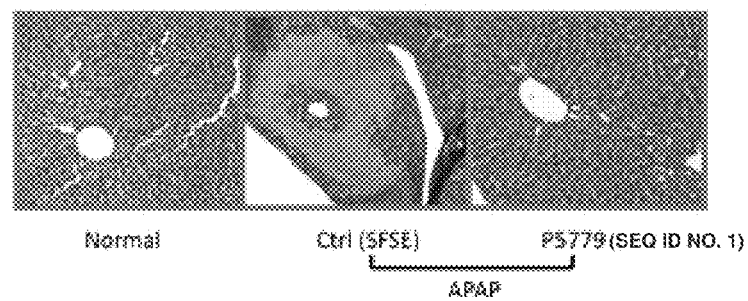
FIG. 19D
FIG. 19F

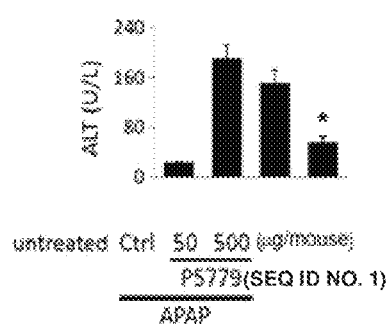
Fig 20A
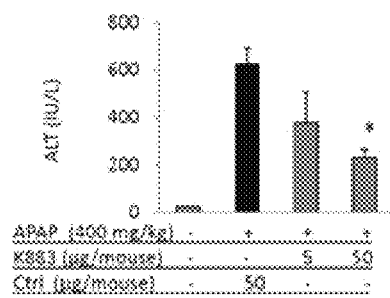
Fig 20B
*: P<0.05 vs. control group
Fig 21A
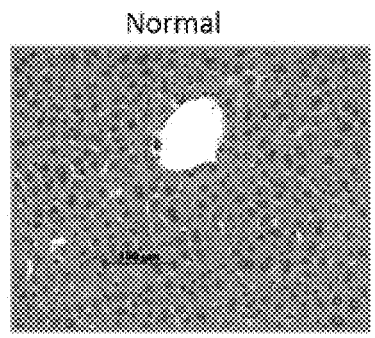
Normal
Scores: 0±0.2
Fig 21B
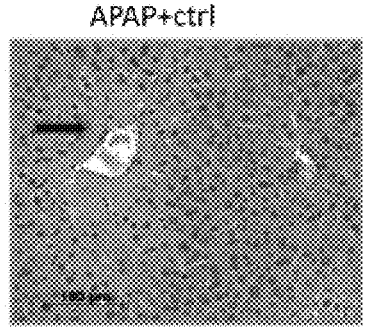
APAP+ctrl
1.9±0.3
Fig 21C
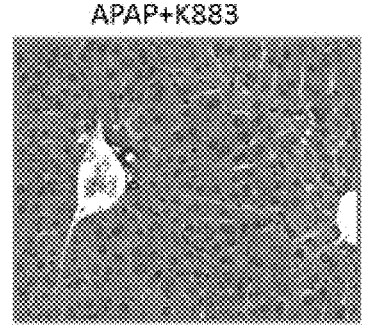
APAP+K883
0.4±0.2
Arrow: necrosis

*: $p<0.05$ vs. control group

Fig. 25
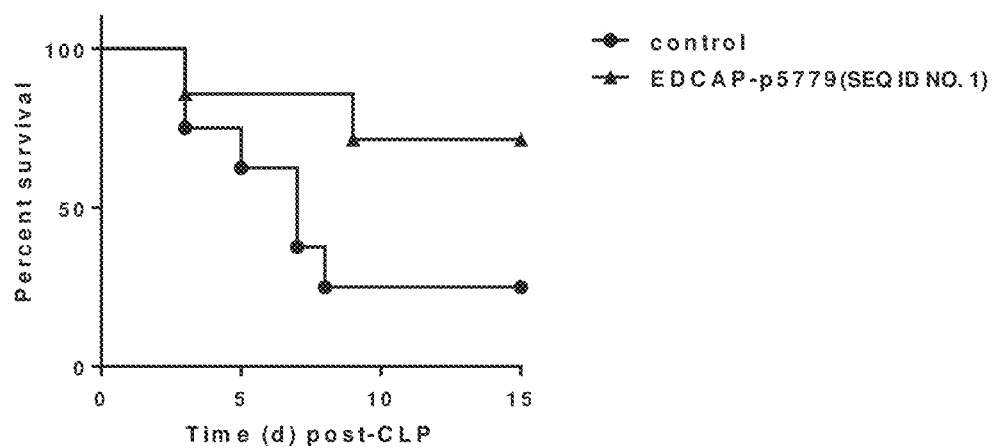
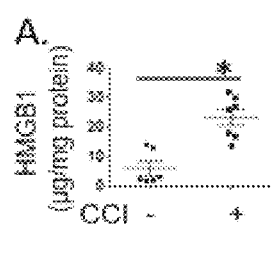
Fig 26A
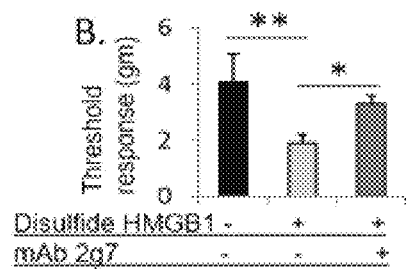
Fig 26B

Fig 31A
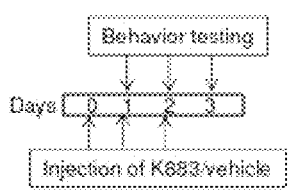
Fig. 31B
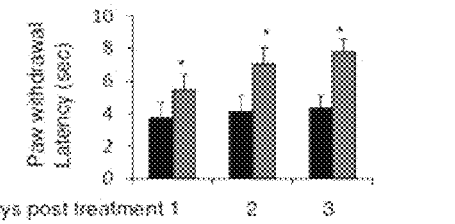
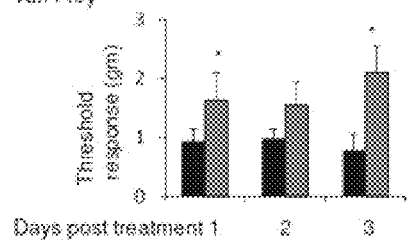
Fig. 31C
Fig 32A
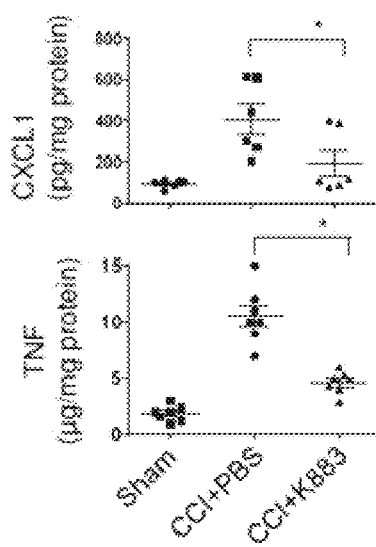
Fig 32C
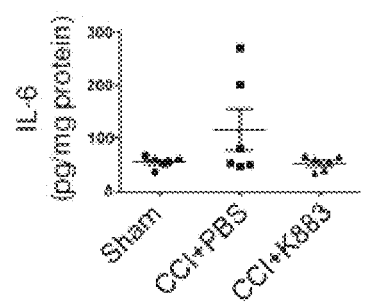
Fig 32B
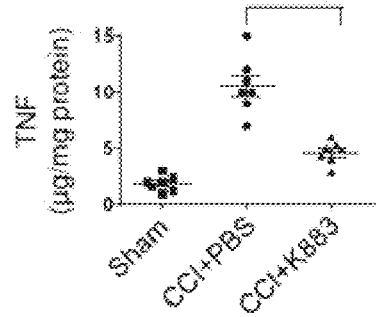

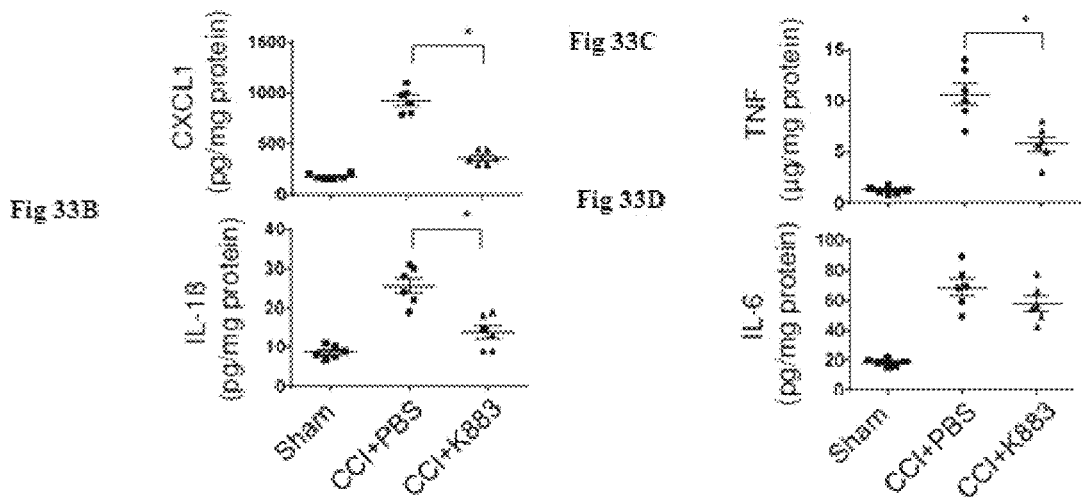
Fig 33A
Fig 33B
Fig 33C
Fig 33D
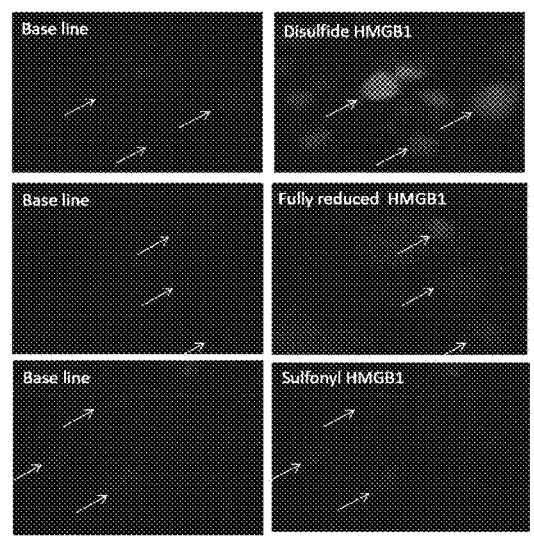
Fig. 34

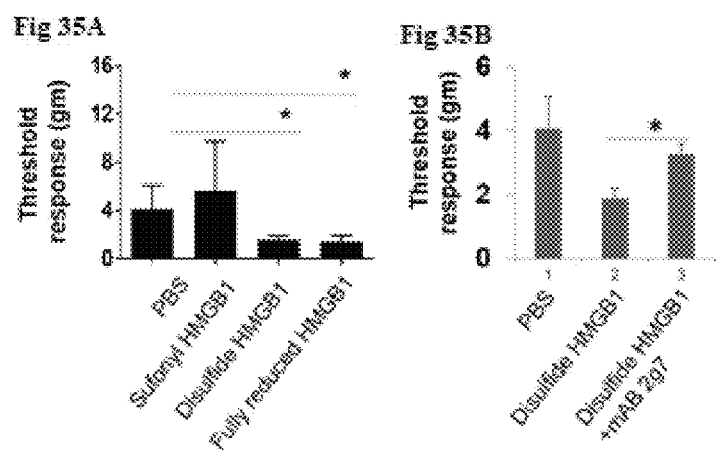

HMGB1 ANTAGONIST

This application claims the benefit of U.S. Provisional Application Nos. 62/845,568, 62/845,576 and 62/845,578, all filed on May 9, 2019, and all hereby incorporated by reference.

FIELD OF THE INVENTION

The present invention is related to the use of HMGB1 antagonists in the treatment and/or prevention and/or inhibition of severe sepsis in mammals, e.g., humans, and pharmaceutical compositions for the same comprising HMGB1 antagonists in an effective amount to treat and/or prevent and/or inhibit this condition.

BACKGROUND OF THE INVENTION

High mobility group box 1 (HMGB1) was first identified as a DNA-binding protein; it is translocated to the nucleus in healthy cells. (Baker, C., et al., *Physical studies of the nonhistone chromosomal proteins HMG-U and HMG-2*, Biochemistry, 1976, 15(8): p. 1645-9); (Bertheloot, D, *HMGB1, IL-1alpha, IL-33 and S100 proteins: dual function alarmins*, Cell Mol Immunol, 2016; Tsung, A., S. Tohme, and T. R. Billiar, *High-mobility group box-1 in sterile inflammation*, J Intern Med, 2014, 276(5): p. 425-43; Lotze, M. T. and K. J. Tracey, *High-mobility group box 1 protein (HMGB1): nuclear weapon in the immune arsenal*, Nat Rev Immunol, 2005, 5(4): p. 331-42). Cellular damage, necrosis, or apoptotic cell fragments result in the passive release of HMGB1 into the extracellular space (Scaffidi, P., T. Misteli, and M. E. Bianchi, *Release of chromatin protein HMGB1 by necrotic cells triggers inflammation*, Nature, 2002, 418 (6894): p. 191-5), which can recruit leukocytes to the site of an injury or infection. HMGB1 can also be secreted by monocytes, tissue macrophages, and other cell of the innate immune system when these cells are activated by pathogen-derived stimuli, exosomes, or pro-inflammatory cytokines (Andersson, U. and K. J. Tracey, *HMGB1 is a therapeutic target for sterile inflammation and infection*, Annu Rev Immunol, 2011, 29: p. 139-62; Bertheloot, D, *HMGB1, IL-1 alpha, IL-33 and S100 proteins: dual-function alarmins*, Cell Mol Immunol, 2016). Depending upon its oxidation state and which of the multiple distinct receptors it interacts with, extracellular HMGB1 can trigger a variety of outcomes (reviewed in Bertheloot, D, *HMGB1, IL-1alpha, IL-33 and S100 proteins: dual function alarmins*, Cell Mol Immunol, 2016 and Harris, H. E., *HMGB1: a multifunctional alarmin driving autoimmune and inflammatory disease*, Nat Rev Rheumatol, 2012, 8(4): p. 195-202), including secretion of additional HMGB1. When this feed-forward loop becomes dysregulated, as in patients with sepsis, it can create a vicious cycle that stokes systemic inflammation by activating macrophages through the TLR4 receptor (Apetoh, L., et al., *The interaction between HMGB1 and TLR4 dictates the outcome of anticancer chemotherapy and radiotherapy*, Immunol Rev, 2007, 220: p. 47-59; Apetoh, L., et al., *Toll-like receptor 4-dependent contribution of the immune system to anticancer chemotherapy and radiotherapy*, Nat Med, 2007, 13(9): p. 1050-9; Fan, J., et al., *Hemorrhagic shock induces NAD(P)H oxidase activation in neutrophils: role of HMGB1-TLR4 signaling*, J Immunol, 2007, 178(10): p. 6573-80; Tsung, A., et al., *HMGB1 release induced by liver ischemia involves Toll-like receptor 4 dependent reactive oxygen species production and calcium-mediated signaling*, J Exp Med, 2007, 204(12): p. 2913-23; Tsung, A., et al., *Increasing numbers of hepatic dendritic cells promote HMGB1-mediated ischemia-reperfusion injury*, J Leukoc Biol, 2007, 81(1): p. 119-28).

HMGB1 is a highly conserved protein that is central to the pathogenesis of sterile and pathogen-induced inflammation (Andersson, U., *HMGB1 is a therapeutic target for sterile inflammation and infection*, Annu Rev Immunol, 2011, 29: p. 139-62). Lethal organ failure and epithelial barrier failure without shock are driven by HMGB1. HMGB1 release is driven by a positive feedback loop that causes circulating HMGB1 levels generally to rise as disease progresses.

HMGB1 is a key member of the damage-associated molecule pattern molecules (DAMPs) and it therefore plays an important role in systemic inflammation and has a pathogenic role in infectious diseases like viral or bacterial infections. Virally infected or otherwise stressed cells will release endogenous DAMPs to alarm the environment about a loss of intracellular homeostatic balance. HMGB1 is one of the most extensively studied DAMPs and is involved in the pathogenesis of many inflammatory diseases of infectious or sterile origin. (Andersson U, et al., *HMGB1 is a therapeutic target for sterile inflammation and infection*, Annu Rev Immunol, 2011; 29:139-62; Kang R, et al., *HMGB1 in health and disease*). Molecular aspects of medicine, 2014; 40:1-116. HMGB1 is a ubiquitous, evolutionary extremely conserved chromatin-binding protein present in all mammalian nucleated cells plus platelets. This 25 kD protein is 99% identical in mammals. The intranuclear functions involve regulation of gene transcription, chromatin repair, and additional tasks. HMGB1 may, in addition, be passively extracellularly released as a prototypical DAMP from dying cells or actively secreted by stressed or activated cells present in any tissue. (Andersson U, et. al., *High-mobility group box 1 protein (HMGB1) operates as an alarmin outside as well as inside cells*, Semin Immunol, 2018; 38:40-8). Active HMGB1 release starts with a regulated translocation of the nuclear pool of HMGB1 to the cytosol. (Bonaldi T, et al., *Monocytic cells hyperacetylate chromatin protein HMGB1 to redirect it towards secretion*, The EMBO Journal, 2003; 22(20):5551-60). Type 1 and type 2 interferons are highly potent endogenous molecules that initiate this intracellular relocalization of HMGB1. (Lu B, et al., *JAK/STAT1 signaling promotes HMGB1 hyperacetylation and nuclear translocation*, Proceedings of the National Academy of Sciences of the United States of America, 2014; 111(8):3068-73; Tanaka A, et al, *Serum high-mobility group box 1 is correlated with interferon-alpha and may predict disease activity in patients with systemic lupus erythematosus*, Lupus, 2019; 28(9):1120-7). Consequently, administration of interferons as therapeutic antiviral compounds risks to increase extracellular HMGB1 levels, which may promote inflammation rather than mediate beneficial effects. Excessive extracellular HMGB1 quantities cause tissue damage and organ dysfunction. For example, lethality in bacterial pneumonia complicated by ARDS was strongly predicted by initial appropriate antibiotic use and day 1 and day 3 plasma HMGB1 levels. (Tseng C C, et al, *Impact of serum biomarkers and clinical factors on intensive care unit mortality and 6-month outcome in relatively healthy patients with severe pneumonia and acute respiratory distress syndrome*, Disease Markers, 2014; 2014:804654). Preclinical treatment with HMGB1-specific antagonists ameliorates inflammation and improves survival in many models of acute or chronic inflammatory diseases. (Andersson U, Tracey K J, HMGB1 is a therapeutic target for sterile inflammation and infection, Annu Rev Immunol, 2011; 29:139-62; Kang R, et al., *HMGB1 in health and* disease, Molecular Aspects of Medicine, 2014; 40:1-116; Andersson U, et al., *Extracellular HMGB1 as a therapeutic target in inflammatory diseases*, Expert Opin Ther Targets, 2018; 22(3):263-77). However, therapy with HMGB1-specific antagonists has not yet been studied in clinical trials.

HMGB1 receptor usage that generates inflammation is entirely dependent on whether HMGB1 acts on its own or in complex with partner molecules. HMGB1 has a strong bipolar charge and is prone to complex-bind other proinflammatory molecules including DNA, RNA, histones, nucleosomes, LPS, SDF-1, IL-1α, IL-1β and additional factors. (Andersson U, et al., *High-mobility group box 1 protein (HMGB1) operates as an alarmin outside as well as inside cells*, Semin Immunol, 2018; 38:40-8; Tian J, et al, *Toll-like receptor 9-dependent activation by DNA-containing immune complexes is mediated by HMGB1 and RAGE*, Nature Immunology. 2007; 8(5):487-96; Huang W, et al, *High-mobility group box 1 impairs airway epithelial barrier function through the activation of the RAGE/ERK pathway*, International Journal of Molecular Medicine. 2016; 37(5): 1189-98; Deng M, et al, *The Endotoxin Delivery Protein HMGB1 Mediates Caspase-11-Dependent Lethality in Sepsis*, Immunity, 2018; 49(4):740-53.e7; Porat A, et al., *DNA-Mediated Interferon Signature Induction by SLE Serum Occurs in Monocytes Through Two Pathways: A Mechanism to Inhibit Both Pathways*, Frontiers in Immunology, 2018; 9:2824). The original discovery of HMGB1 was based on its ability to bind nuclear DNA. (Goodwin G H, et al., *A new group of chromatin-associated proteins with a high content of acidic and basic amino acids*, European Journal of Biochemistry, 1973; 38(1):14-9). The number of suggested cognate receptors for extracellular HMGB1 reported in the literature is quite extensive. However, only two receptor systems, the receptor for advanced glycation end products (RAGE) and toll-like receptor 4 (TLR4), are fully confirmed to act as functional HMGB1 receptors. (Rauvala H, Rouhiainen A, *RAGE as a receptor of HMGB1 (Amphoterin): roles in health and disease*, Current Molecular Medicine, 2007; 7(8):725-34; Yang H, et al., *A critical cysteine is required for HMGB1 binding to Toll-like receptor 4 and activation of macrophage cytokine release*, Proceedings of the National Academy of Sciences of the United States of America, 2010; 107(26):11942-7; Yang H, et al., *MD-2 is required for disulfide HMGB1-dependent TLR4 signaling*, The J. Exp Med, 2015; 212(1):5-14 (18-20)). Many receptor systems claimed to operate as HMGB1 receptors are actually receptors for molecules complex-bound to HMGB1.

The receptor for advanced glycation end products (RAGE) was originally identified in diabetes research as a cell surface receptor generating a cascade of intracellular signaling, including nuclear NF-kB translocation and proinflammatory cytokine release. (Schmidt A M, et al., *RAGE: a novel cellular receptor for advanced glycation end products*, Diabetes, 1996; 45 Suppl 3: S77-80). It was later discovered that RAGE is a multiligand receptor and that HMGB1 is one out of many ligands. (Rauvala H, Rouhiainen A, *RAGE as a receptor of HMGB1 (Amphoterin): roles in health and disease*, Current Molecular Medicine, 2007; 7(8):725-34). The HMGB1-RAGE axis triggers neutrophil-mediated injury amplification following necrosis (Huebener P, et al., *The HMGB1/RAGE axis triggers neutrophil-mediated injury amplification following necrosis*, The Journal of Clinical Investigation. 2015; 125(2):539-50) something that is of great significance for the pathogenesis of acute lung injury. Interestingly, HMGB1-RAGE interaction does not primarily lead to proinflammatory intracellular signaling. Macrophages expressing RAGE, but engineered to lack TLR4 expression, do not produce proinflammatory cytokines in response to stimulation by HMGB1 of any redox isoform. (Yang H, et al., *A critical cysteine is required for HMGB1 binding to Toll-like receptor 4 and activation of macrophage cytokine release*, Proceedings of the National Academy of Sciences of the United States of America, 2010; 107(26):11942-7). That is not the expected result if HMGB1-RAGE interaction mediated cytokine release in a direct mode.

Recent observations demonstrate that RAGE provides a transport route for HMGB1 and HMGB1-partner molecule complexes by endocytosis to the endolysosomal compartment. (Deng M, et al., *The Endotoxin Delivery Protein HMGB1 Mediates Caspase-11-Dependent Lethality in Sepsis*, Immunity, 2018; 49(4):740-53.e7; Porat A, et al, *DNA-Mediated Interferon Signature Induction by SLE Serum Occurs in Monocytes Through Two Pathways: A Mechanism to Inhibit Both Pathways*, Frontiers in Immunology, 2018; 9:2824; Lin H J, et al., *Coalescence of RAGE in Lipid Rafts in Response to Cytolethal Distending Toxin-Induced Inflammation*, Frontiers in Immunology, 2019; 10:109; Yang H, et al., *Inhibition of HMGB1/RAGE-mediated endocytosis by HMGB1 antagonist box A, anti-HMGB1 antibodies, and cholinergic agonists suppresses inflammation*, Molecular Medicine (Cambridge, Mass.), 2019; 25(1):13; Jia C, et al., *Endothelial cell pyroptosis plays an important role in Kawasaki disease via HMGB1/RAGE/cathespin B signaling pathway and NLRP3 inflammasome activation*, Cell Death Dis, 2019; 10(10):778; Xu J, et al., *Macrophage endocytosis of high-mobility group box 1 triggers pyroptosis*, Cell Death and Differentiation, 2014; 21(8):1229-39). The HMGB1/RAGE-assisted cellular import system performs an important task by alerting cells about a dangerous environment. Most importantly, HMGB1 has a unique ability to act as a detergent in the lysosomal membrane due to the acidic conditions inside the lysosome system. (Deng M, et al., *The Endotoxin Delivery Protein HMGB1 Mediates Caspase-11-Dependent Lethality in Sepsis*, Immunity, 2018; 49(4):740-53.e7). The HMGB1-transported partner molecules will thus avoid the expected degradation in the lysosomes and instead leak out from the permeabilized lysosomes into the cytosol to reach cognate cytoplasmic receptors which will be activated to cause inflammation. This biology may have tremendously important consequences for the pathogenesis of severe pulmonary inflammation. Only two human organs, the lungs and skin (Shirasawa M, et al., *Receptor for advanced glycation end-products is a marker of type I lung alveolar cells*, Genes to Cells: Devoted to Molecular & Cellular mechanisms, 2004; 9(2):165-74; Guo W A, et al., *The receptor for advanced glycation end products and acute lung injury/acute respiratory distress syndrome*, Intensive Care Medicine. 2012; 38(10):1588-98), display a high constitutive cell surface RAGE expression and the critical cognate HMGB1 receptor RAGE is thus abundantly expressed in the lower respiratory tract. It has been demonstrated in preclinical and clinical studies that severe respiratory infections including influenza and human respiratory syncytial virus (HRSV) generate a substantial extracellular HMGB1 release in the inflamed lungs and that HMGB1-specific antagonists ameliorate these conditions. (Ito Y, et al, *Increased levels of cytokines and high-mobility group box 1 are associated with the development of severe pneumonia, but not acute encephalopathy, in 2009 H1N1 influenza-infected children.*, Cytokine, 2011; 56(2):180-7; Nosaka N, et al., *Anti-high mobility group box-1 monoclonal antibody treatment provides protection against influenza A virus (H1N1)-induced pneumonia in mice*, Critical Care (London, England) 2015; 19:249; Nosaka N, et al., *Anti-high mobility group box-1 monoclonal antibody treatment of brain edema induced by influenza infection and lipopolysaccharide*, Journal of Medical Virology. 2018; 90(7):1192-8; Hatayama K, et al., *Combined effect of anti-high-mobility group box-1 monoclonal antibody and peramivir against influenza A virus-induced pneumonia in mice*, Journal of Medical Virology, 2019; 91(3):361-9; Manti S, et al., *Induction of high-mobility group Box-1 in vitro and in vivo by respiratory syncytial virus*, Pediatr Res, 2018; 83(5):1049-56; Rayavara K, et al., *Proinflammatory Effects of Respiratory Syncytial Virus-Induced Epithelial HMGB1 on Human Innate Immune Cell Activation*, J Immunol, 2018; 201(9):2753-66; Rallabhandi P, et al., *Respiratory syncytial virus fusion protein-induced toll-like receptor 4 (TLR4) signaling is inhibited by the TLR4 antagonists Rhodobacter sphaeroides lipopolysaccharide and eritoran (E5564) and requires direct interaction with MD-2*, mBio, 2012; 3(4); Simpson J, et al., *RSV Infection Promotes Necroptosis and HMGB1 Release by Airway Epithelial Cells*, American Journal of Respiratory and Critical Care Medicine, 2020 (29-36)). HMGB1 accumulates locally due to passive release from dying cells and activate secretion from innate immunity cells and additional cell types. Furthermore, virus-induced cell death also generates huge quantities of extracellular DNA, RNA, nucleosomes and histones. These molecules are of no major concern as long as they remain extracellularly or get degraded in the lysosomes after cellular import. The potential threat is that these nuclear danger-molecules will get access to their cognate cytosolic pattern recognition receptors, which will fuel inflammation including inflammasome activation. Excessive amounts of extracellular HMGB1 and abundant cell surface RAGE expression in the tissue may enable an intracellular transport of extracellular DNA and RNA to get access to their potent cytosolic cognate receptors cGAS, AIM2, RIG-I and additional nucleic acid receptors with sometimes overwhelming inflammation as the end result. (Andersson U, et al., *High-mobility group box 1 protein (HMGB1) operates as an alarmin outside as well as inside cells*, Semin Immunol, 2018; 38:40-8). See FIG. 1

FIG. 1 shows inflammation induced by HMGB1-partner molecule complexes. As seen in FIG. 1, necrotic cells release DAMP and pathogen-associated molecular patterns (PAMP) molecules extracellularly where they form complexes with HMGB1 released from dying or activated cells (1); these complexes bind to RAGE abundantly expressed in the lungs (2); and get endocytosed to endosomes having TLR receptors including TLR4 which may be activated by HMGB1 (3); HMGB1 and partner molecules translocate to lysosomes, where HMGB1 acts like a detergent under the acidic conditions and disrupts the lysosomal membrane enabling HMGB1-partner molecules access to the cytosol (4); the translocated molecules bind and activate reciprocal cytoplasmic receptors generating inflammasome activation and additional proinflammatory events (5); the subsequent outcome production and extracellular release of cytokines via pore formation in the cell surface membrane accomplished by oligomerized gasdermin D. The final outcome is pyroptosis. Active gasdermin D also rotates and translocates phosphatidylserine molecules to the outside of the cell surface membrane and induces tissue factor on endothelial cells. This biology initiates coagulation (6).

The redox state of the three cysteines present in HMGB1 is key when HMGB1 acts on its own as a pro-inflammatory DAMP. Gentle oxidation generating a disulfide bond between Cys23 and Cys45 with Cys106 retaining its thiol group forms an HMGB1 redox isoform (disulfide HMGB1) that like lipopolysaccharide (LPS) is a potent functional TLR4 ligand. (Kang R, et al. *HMGB1 in health and disease*, Molecular aspects of medicine, 2014; 40:1-116). Disulfide HMGB1 binds at low nanomolar avidity to the TLR4 co-receptor MD-2, in an analogous way to LPS but at a different position. (Yang H, et al., *MD-2 is required for disulfide HMGB1-dependent TLR4 signaling*, The J Exp Med, 2015; 212(1):5-14). Disulfide HMGB1-TLR4 stimulation induces a substantial production of proinflammatory cytokines both in vivo and in vitro. (Yang H, et al., *A critical cysteine is required for HMGB1 binding to Toll-like receptor 4 and activation of macrophage cytokine release*, Proceedings of the National Academy of Sciences of the United States of America, 2010; 107(26):11942-7). The clinical outcome of murine influenza infection has been demonstrated to be significantly improved by TLR4-specific antagonists. A small-molecule TLR4-specific antagonist (P5779 (SEQ ID NO: 1)) that selectively prevents HMGB1-MD-2 interaction, but not LPS from binding to MD-2, protected mice from influenza virus-induced lethality and reduced proinflammatory cytokine gene expression in the lungs. (Shirey K A, et al., *The TLR4 antagonist Eritoran protects mice from lethal influenza infection.*, Nature, 2013; 497(7450):498-502).

HMGB1/RAGE/TLR4 plays a role in the pathogenesis of severe pulmonary inflammation. Influenza viruses cause 3-5 million severe cases and 250,000-500,000 deaths worldwide annually. (Paules C, et al., *Influenza*, Lancet (London, England), 2017; 390(10095):697-708). These viruses, like the SARS-CoV-2 virus, replicate in respiratory epithelial cells and cause necrotic tissue damage. Influenza-infected patients express substantially increased systemic HMGB1 levels that are associated with the development of severe pneumonia. (Ito Y, et al., *Increased levels of cytokines and high-mobility group box 1 are associated with the development of severe pneumonia, but not acute encephalopathy, in 2009 H1N1 influenza-infected children*, Cytokine, 2011; 56(2):180-7).

Gene-deficient TLR4 as well as gene-deficient RAGE mice are partially protected from influenza-induced lethality. (van Zoelen M A, et al., *Receptor for advanced glycation end products is detrimental during influenza A virus pneumonia*, Virology, 2009; 391(2):265-73; Nhu Q M, et al., *Novel signaling interactions between proteinase-activated receptor 2 and Toll-like receptors in vitro and in vivo*, Mucosal Immunology, 2010; 3(1):29-39). Successful preclinical treatment results using specific HMGB1-, TLR4- or RAGE-antagonists further support that the HMGB1/RAGE/TLR4-axis is central in the pathogenesis of influenza infections. Treatment with anti-HMGB1 mAb provided partial protection against pneumonia as well as encephalopathy in murine models of influenza infections despite that the treatments did not affect virus propagation in the lungs. (Nosaka N, et al., *Anti-high mobility group box-1 monoclonal antibody treatment provides protection against influenza A virus (H1N1)-induced pneumonia in mice*, Critical Care (London, England), 2015; 19:249; Nosaka N, et al., *Anti-high mobility group box-1 monoclonal antibody treatment of brain edema induced by influenza infection and lipopolysaccharide*, Journal of Medical Virology, 2018; 90(7):1192-8; Hatayama K, et al., *Combined effect of anti-high-mobility group box-1 monoclonal antibody and peramivir against influenza A virus-induced pneumonia in mice*, Journal of Medical Virology, 2019; 91(3):361-9). Combined anti-HMGB1 mAb and anti-viral treatment offered almost complete protection. (Hatayama K, et al., *Combined effect of anti-high-mobility group box-1 monoclonal antibody and peramivir against* influenza A virus-induced pneumonia in mice, Journal of Medical Virology, 2019; 91(3):361-9). Improved survival combined with significantly attenuated histological changes and neutrophil infiltration in the lungs of influenza-inoculated mice were recorded, despite that the treatment was based on xenogenic polyclonal antibodies against HMGB1. (Hou X Q, et al., *Potential role of high-mobility group box 1 protein in the pathogenesis of influenza H5N1 virus infection*, Acta virologica. 2014; 58(1):69-75). Therapy with eritoran, a TLR4 blocking compound ameliorated murine influenza-induced lung injury by inhibiting the cytokine storm. Eritoran has been reported to block HMGB1-mediated TLR4-dependent signaling in vitro, and to inhibit extracellular HMGB1 release in vivo by preventing necroptotic cell death in respiratory epithelial cells. (Shirey K A, et al., *The TLR4 antagonist Eritoran protects mice from lethal influenza infection*, Nature, 2013; 497(7450):498-502; Shirey K A, et al., *Novel strategies for targeting innate immune responses to influenza*, Mucosal Immunology, 2016; 9(5):1173-82).

Human respiratory syncytial virus ("HRSV") is a leading cause of serious lower respiratory tract infection (bronchiolitis and pneumonia) during infancy (Shi T, et al., *Global, regional, and national disease burden estimates of acute lower respiratory infections due to respiratory syncytial virus in young children in 2015: a systematic review and modelling study*, Lancet (London, England), 2017; 390 (10098):946-58) but can also cause severe morbidity and mortality in the elderly and in immunocompromised individuals. HRSV replicates in respiratory epithelial cells and promotes necroptosis and HMGB1 release. (Simpson J, et al., *RSV Infection Promotes Necroptosis and HMGB1 Release by Airway Epithelial Cells*, American Journal of Respiratory and Critical Care Medicine, 2020). High HMGB1 levels have been recorded in nasopharyngeal secretion from infected children. (Id.) Experimental RSV infections respond well to therapies based on the HMGB1 antagonist glycyrrhizin (Manti S, et al., *Induction of high-mobility group Box-1 in vitro and in vivo by respiratory syncytial virus*, Pediatr Res, 2018; 83(5):1049-5633) as well as to the synthetic TLR4 antagonist eritoran. (Rallabhandi P, et al., *Respiratory syncytial virus fusion protein-induced toll-like receptor 4 (TLR4) signaling is inhibited by the TLR4 antagonists Rhodobacter sphaeroides lipopolysaccharide and eritoran (E5564) and requires direct interaction with MD-2*, mBio, 2012; 3(4)).

In studies of patients with community-acquired bacterial pneumonia, HMGB1 levels were elevated in all patients and higher circulating HMGB1 was associated with disease severity and mortality. (Angus D C, et al., *Circulating high-mobility group box 1 (HMGB1) concentrations are elevated in both uncomplicated pneumonia and pneumonia with severe sepsis*, Critical Care Medicine, 2007; 35(4): 1061-7; Wang H L, et al., *Circulating level of high mobility group box1 predicts the severity of community acquired pneumonia: Regulation of inflammatory responses via the cJun Nterminal signaling pathway in macrophages*, Molecular Medicine Reports, 2017; 16(3):2361-6). Patients with severe pneumonia and ARDS requiring mechanical ventilation experience high rates of ICU mortality. *Pseudomonas aeruginosa* cause neutrophilic lung inflammation in cystic fibrosis patients, who express high HMGB1 levels in bronchoalveolar lavage fluid. Systemic treatment with anti-HMGB1 mAb in a preclinical cystic fibrosis model conferred significant protection against *P. aeruginosa*-induced neutrophil recruitment, protein leak, and lung injury. (Entezari M, et al., *Inhibition of high-mobility group box 1 protein (HMGB1) enhances bacterial clearance and protects against Pseudomonas Aeruginosa pneumonia in cystic fibrosis*, Molecular Medicine (Cambridge, Mass.), 2012; 18:477-85). Treatment with partially desulfated heparin, a derivative with anti-inflammatory properties but minimal anti-coagulatory effects in two different models of pneumonia reduced airway HMGB1 levels and neutrophilic lung injury. (Griffin K L, et al., *2-O, 3-O-desulfated heparin inhibits neutrophil elastase-induced HMGB-1 secretion and airway inflammation*, American Journal of Respiratory Cell and Molecular Biology, 2014; 50(4):684-9; Sharma L, et al., *Partially-desulfated heparin improves survival in Pseudomonas pneumonia by enhancing bacterial clearance and ameliorating lung injury*, Journal of immunotoxicology, 2014; 11(3):260-7).

Experimental work has unambiguously demonstrated a central mechanistic role for HMGB1-mediated injury amplification and pulmonary inflammation in diverse conditions including trauma, shock, and ischemia-reperfusion-injury. (Sodhi C P, et al., *Intestinal Epithelial TLR-4 Activation Is Required for the Development of Acute Lung Injury after Trauma/Hemorrhagic Shock via the Release of HMGB1 from the Gut*., J Immunol, 2015; 194(10):4931-9; Yang R, et al., *Anti-HMGB1 neutralizing antibody ameliorates gut barrier dysfunction and improves survival after hemorrhagic shock*, Molecular Medicine (Cambridge, Mass.), 2006; 12(4-6):105-14; Levy R M, et al., *Systemic inflammation and remote organ injury following trauma require HMGB1*, American Journal of Physiology Regulatory, Integrative and Comparative Physiology, 2007; 293(4):R1538-44; Shimazaki J, et al., *Systemic involvement of high-mobility group box 1 protein and therapeutic effect of anti-high-mobility group box 1 protein antibody in a rat model of crush injury*, Shock (Augusta, Ga.), 2012; 37(6):634-8; Okuma Y, et al., *Anti-high mobility group box-1 antibody therapy for traumatic brain injury*, Annals of Neurology, 2012; 72(3):373-84; Kaczorowski D J, et al., *Innate immune mechanisms in ischemia/reperfusion*, Frontiers in Bioscience (Elite edition), 2009; 1:91-8 (53-58)). A recent observational study of trauma patients reported that a biphasic release of HMGB1, 3-6 h after injury, was a powerful predictor of outcome. (Ottestad W, et al., *Biphasic Release of the Alarmin High Mobility Group Box 1 Protein Early After Trauma Predicts Poor Clinical Outcome*, Critical Care Medicine, 2019; 47(8):e614-e22). The second wave HMGB1 plasma release was a consistent and highly accurate predictor of the duration of the subsequent need for ventilator support, reflecting secondary remote lung injury. Interestingly, HMGB1 rendered robust predictors like injury severity and physiological derangement (base deficit) insignificant in multivariable models of outcome.

Sepsis

Severe sepsis ("sepsis") is characterized by uncontrolled systemic inflammation in response to an infection or injury. Sepsis results in acute organ damage and ultimately failure; the mortality rate for untreated sepsis often exceeds 60%. Although severe sepsis and the danger it poses to patients has been recognized since the founding of Western medicine, its pathogenesis has remained obscure until the last two decades, and it was only recognized by the CDC as a medical emergency in August 2016. (Colby, S. and J. Ortman, Projections of the Size and Composition of the U.S. Population: 2014 to 2060, in *Current Population Reports*, 2014, U.S. Census Bureau: Washington, D.C.) Severe sepsis ("sepsis" hereafter) is a syndrome in which an infectious agent—bacteria or sometimes fungi—triggers runaway systemic inflammation leading to acute organ damage and ultimately failure. The initiating infection may be contracted through injury, but, for a majority of cases the causative organism and the point of entry are never conclusively determined. Without treatment, sepsis is frequently fatal. Vigilance, improved antimicrobial therapies, and advances in intensive care to support organ function have dramatically improved survival. Nevertheless, a bout of sepsis can have long-lasting physical and cognitive consequences for the patient, a fact that is becoming more apparent as the number of survivors grows. (Angus, D. C., *The lingering consequences of sepsis: a hidden public health disaster?* JAMA, 2010, 304(16): p. 1833-4; Iwashyna, T. J., et al., *Long-term cognitive impairment and functional disability among survivors of sepsis*, JAMA, 2010, 304(16): p. 1787-94; Yende, S. and D. C. Angus, *Long-term outcomes from sepsis*, Curr Infect Dis Rep, 2007, 9(5): p. 382-6.)

Sepsis is the sixth-leading cause of hospitalization in the United States (C M, T. and A. R M, *National Inpatient Hospital Costs: The Most Expensive Conditions by Payer*, 2011., in HCUP Statistical Brief #160. 2013, Agency for Healthcare Research and Quality: Rockville, Md.) and is the most expensive condition treated due to the necessity of a stay in the Intensive Care Unit (ICU) to resolve most cases. Rates of sepsis are similar in other economically advantaged countries; data for sepsis incidence is lacking in poorer countries and those without access to modern medical care. It has been estimated that >19 million patients worldwide develop sepsis annually, but this number likely substantially underestimates the problem. (Adhikari, N. K., et al., *Critical care and the global burden of critical illness in adults*, Lancet, 2010, 376(9749): p. 1339-46; Fleischmann, C., et al., *Assessment of Global Incidence and Mortality of Hospital-treated Sepsis Current Estimates and Limitations*, Am J Respir Crit Care Med, 2016, 193(3): p. 259-72). In the United States, sepsis is the sixth most common reason for hospitalization and consumes 5.2% of total hospital costs, more than any other disease or disorder (C M, T. and A. R M, *National Inpatient Hospital Costs: The Most Expensive Conditions by Payer*, 2011, in HCUP Statistical Brief #160, 2013, Agency for Healthcare Research and Quality: Rockville, Md.) These considerations prompted the CDC to declare sepsis a medical emergency in 2016. (Control, C.f.D. CDC VitalSigns, 2016, cited Aug. 24, 2016). Given the lasting physical and cognitive impairments to which survivors are prone and the lack of any approved treatment, there is clearly a compelling need for a cost-effective treatment for sepsis.

There is a high social cost to sepsis which resulted in more than 1.6 million inpatient hospital stays in 2009 (Elixhauser, A., *Septicemia in U.S. Hospital,* 2009, in HCUP Statistical Brief #122. 2001, Agency for Healthcare Research and Quality: Rockville, Md.). Although mortality from sepsis has declined in recent decades, it remains above 25% and was the leading cause of hospital death in 2009. (Id.; Angus, D. C., *Sepsis and septic shock*, N Engl J Med, 2013, 369(9): p. 840-51). Patients with weakened immune systems are especially vulnerable. Indeed, more than one third of hospitalizations for patients aged 65-84 years carried a primary or secondary indication of sepsis (FIG. 2A).

The growing number of patients who survive the acute phase of sepsis have revealed that the danger associated with the disease extends long after the initial hospital discharge. The long-term mortality after sepsis is approximately 50% in the first year (Yende, S., *Long-term outcomes from sepsis*, Curr Infect Dis Rep, 2007, 9(5): p. 382-6), rising to >81% over five years (Iwashyna, T. J., et al., *Long-term cognitive impairment and functional disability among survivors of sepsis*, JAMA, 2010, 304(16): p. 1787-94). One common sequela of sepsis in survivors is persistent anemia, which occurs in up to 60% of survivors and is associated with poor outcome (Milbrandt, E. B., et al., *Predicting late anemia in critical illness*, Crit Care, 2006, 10(1): p. R39; Nemeth, E., *Anemia of inflammation*, Hematol Oncol Clin North Am, 2014, 28(4): p. 671-81, vi.; Vincent, J. L., et al., *Anemia and blood transfusion in critically ill patients*, JAMA, 2002, 288(12): p. 1499-507). Sepsis survivors are also more prone to exhibit diminished physical and/or cognitive function following their illness than age-matched controls hospitalized for non-sepsis indications (Iwashyna, T. J., et al., *Long-term cognitive impairment and functional disability among survivors of sepsis*, JAMA, 2010, 304(16): p. 1787-94). These persistent impairments can lead to mood disorders and other sequelae that erode patient quality of life and can strain caregivers (Angus, D. C., *The lingering consequences of sepsis: a hidden public health disaster?* JAMA, 2010, 304(16): p. 1833-4), causing Iwashyna and colleagues (2010) to conclude, "the burden of sepsis survivorship is a substantial, under-recognized public health problem with major implications for patients, families, and the health care system."

There is also a high economic cost associated with sepsis. In 2011, the aggregate cost for treating sepsis was $20.3 billion, consuming 5.2% of the cost for all hospitalizations and making it the most expensive condition treated (C M, T. and A. R M, *National Inpatient Hospital Costs: The Most Expensive Conditions by Payer*, 2011., in HCUP Statistical Brief #160. 2013, Agency for Healthcare Research and Quality: Rockville, Md.; Elixhauser, A., B. Friedman, and E. Stranges, *Septicemia in U.S. Hospital,* 2009, in HCUP Statistical Brief #122.2001, Agency for Healthcare Research and Quality: Rockville, Md.) (see FIG. 2B, showing the costs of treating sepsis exceeded those of all other indications, again showing the prevalence and cost of sepsis). In the decade terminating in 2008, the costs of treating sepsis ballooned at >11% annually. One driver of this growth is the increased incidence of sepsis, a trend that is unlikely to abate as the US population greys (Colby, S. and J. Ortman, *Projections of the Size and Composition of the U.S. Population: 2014 to 2060*, in Current Population Reports, 2014, U.S. Census Bureau: Washington, D.C.) At the same time, the cost per stay for treating sepsis has grown substantially (C M, T. and A. R M, *National Inpatient Hospital Costs: The Most Expensive Conditions by Payer*, 2011., in HCUP Statistical Brief #160. 2013, Agency for Healthcare Research and Quality: Rockville, Md.). With no approved therapy for sepsis and fewer than one in three patients showing signs of active infection (Angus, D. C., *Sepsis and septic shock*, N Engl J Med, 2013, 369(9): p. 840-51), treatment focuses of monitoring and supporting organ function, typically in an Intensive Care Unit (ICU) or similar context.

The early clinical manifestations of sepsis include fever, elevated heart rate, and increased respirations, which can make it difficult to distinguish from other common ailments like flu or a cold. As more organ systems become compromised, patients typically present with significantly decreased urine output (kidney dysfunction), delirium (impaired CNS function), labored breathing, and an erratic cardiac rhythm. These manifestations can vary greatly from patient to patient, depending on the site and cause of infection, the prior health of the patient, and the time elapsed between infection and treatment. (Id.) The final stage of the disease, septic shock, is marked by plummeting blood pressure that is refractory to fluid support.

Although the first description of sepsis was likely recorded by Hippocrates (Hippocrates, *Hippocratic Writings*, 1983: The Penguin Group), the etiology of sepsis remained enigmatic until the recognition that dysregulation of the patient's own innate immune response precipitates the systemic inflammation that drives sepsis (Andersson, U., *HMGB1 is a therapeutic target for sterile inflammation and infection*, Annu Rev Immunol, 2011, 29: p. 139-62; Angus, D. C., *Sepsis and septic shock*, N Engl J Med, 2013, 369(9): p. 840-51; Cerra, F. B., *The systemic septic response: multiple systems organ failure*, Crit Care Clin, 1985, 1(3): p. 591-607).

Elucidating the underlying molecular mechanisms has illuminated a related paradox: sepsis-like symptoms that emerge after sterile injury (e.g., ischemia/reperfusion injury) stem from activating many of the same pathways (Chen, G. Y., *Sterile inflammation: sensing and reacting to damage*, Nat Rev Immunol, 2010, 10(12): p. 826-37; Tsung, A., S. Tohme, *High-mobility group box-1 in sterile inflammation*, J Intern Med, 2014, 276(5): p. 425-43). This mechanistic overlap poses the tantalizing possibility that a single intervention could find clinical application in treating sepsis, autoimmune conditions, and other systemic inflammation syndromes.

Previous efforts to treat sepsis by controlling systemic inflammation have all failed, most likely due to the unfavorable kinetics of the intended targets. For example, drugs intended to antagonize early effectors of inflammation, such as TNFα (tumor necrosis factor), have such early and short therapeutic windows (within minutes to an hour of infection/injury) that they are unrealistic clinical candidates (Reinhart, K, *Anti-tumor necrosis factor therapy in sepsis: update on clinical trials and lessons learned*, Crit Care Med, 2001, 29(7 Suppl): p. S121-5). Indeed, targeting the early effectors of inflammation can be harmful; administering anti-TNFα actually worsens survival in a mouse model of sepsis (Evans, G. F., et al., *Differential expression of interleukin-1 and tumor necrosis factor in murine septic shock models*, Circ Shock, 1989, 29(4): p. 279-90; Eskandari, M. K., et al., *Anti-tumor necrosis factor antibody therapy fails to prevent lethality after cecal ligation and puncture or endotoxemia*, J Immunol, 1992, 148(9): p. 2724-30; Remick, D., et al., *Blockade of tumor necrosis factor reduces lipopolysaccharide lethality, but not the lethality of cecal ligation and puncture*, Shock, 1995, 4(2): p. 89-95). Acute shock and tissue injury are mediated by TNF and other early effectors of inflammation. This result illustrates an important distinction between early pro-inflammatory effectors, like TNFα, and HMGB1, a late mediator of inflammation.

The dramatically slower kinetics of HMGB1 release enable HMGB1 to be targeted at clinically realistic time points in experimental models of sepsis: administering HMGB1 antagonists up to 24 hours after onset still provides significant therapeutic benefits. This is a unique result compared to all other interventions directed against the range of pro-inflammatory molecules implicated in sepsis.

Wang, H., et al. were the first to identify the pro-inflammatory activity of HMGB1 (Wang, H., et al., *HMG-1 as a late mediator of endotoxin lethality in mice*, Science, 1999, 285(5425): p. 248-51) and to demonstrate the beneficial effects of inhibiting HMGB1 signaling in animal models of sepsis (Yang, H., et al., *Reversing established sepsis with antagonists of endogenous high-mobility group box 1*, Proc Natl Acad Sci USA, 2004, 101(1): p. 296-301). Targeting HMGB1 offers the opportunity to develop agents that can be given to patients during crisis to reduce mortality and during recovery to mitigate lingering sequelae. Further, developing HMGB1 therapeutics has the potential to be ground-breaking for myriad other diseases, in contexts as diverse as treating rheumatoid arthritis (Schierbeck, H., et al., *Monoclonal anti-HMGB1 (high mobility group box chromosomal protein 1) antibody protection in two experimental arthritis models*, Mol Med, 2011, 17(9-10): p. 1039-44), suppressing inflammation following organ transplantation[31], or mitigating lung pathologies associated with viral and/or bacterial infection (Entezari, M., et al., *Inhibition of high-mobility group box 1 protein (HMGB1) enhances bacterial clearance and protects against Pseudomonas Aeruginosa pneumonia in cystic fibrosis*, Mol Med, 2012, 18: p. 477-85; Nosaka, N., et al., *Anti-high mobility group box-1 monoclonal antibody treatment provides protection against influenza A virus (H1N1)-induced pneumonia in mice*, Crit Care, 2015, 19: p. 249).

Despite its long clinical history, the pathogenesis of sepsis had been poorly understood until the last two decades, when the molecular identity of the primary late mediator of inflammation, HMGB1, was discovered. (Wang, H., et al., *HMG-1 as a late mediator of endotoxin lethality in mice*, Science, 1999, 285(5425): p. 248-51). HMGB1 is released passively by damaged and necrotic cells to recruit leukocytes to the site of infection or injury; in turn, these innate immune cells actively release HMGB1 to amplify the inflammatory response to fight active infection or promote wound healing. (Andersson, U. and K. J. Tracey, *HMGB1 is a therapeutic target for sterile inflammation and infection*, Annu Rev Immunol, 2011, 29: p. 139-62; Bertheloot, D. and E. Latz, *HMGB1, IL-1 alpha, IL-33 and S100 proteins: dual function alarmins*, Cell Mol Immunol, 2016). It is the dysregulation of HMGB1 signaling that leads to sepsis.

HMGB1 antagonists have shown considerable promise in rodent models of sepsis for promoting survival and mitigating long-term sequelae, even when provided days after the onset of sepsis. Mice injected with a monoclonal antibody (mAb), 2G7 that binds and neutralizes HMGB1 had significantly lower mortality than untreated mice or those injected with control IgG that does not recognize HMGB1. (Qin, S., et al., *Role of HMGB1 in apoptosis-mediated sepsis lethality*, J Exp Med, 2006, 203(7): p. 1637-42); See also, U.S. Pat. No. 8,138,141, incorporated herein by reference). In addition, mice who received mAb 2G7 treatment starting more than a week after the onset of sepsis showed marked improvement of sepsis-associated persistent anemia. (Valdes-Ferrer, S. I., et al., *HMGB1 mediates anemia of inflammation in murine sepsis survivors*, Mol Med, 2015). Hence, the therapeutic window for mAb 2G7 is unique and conveniently wide compared to other interventions that selectively target pro-inflammatory cytokines. Another strategy to interrupt HMGB1 signaling is to interfere with HMGB1 binding to its receptors. HMGB1 can trigger the release of pro-inflammatory cytokines through the TLR4 receptor.

Despite its prevalence, there is no approved treatment for sepsis. The sole pharmacological intervention to receive FDA approval, activated protein C, was pulled from the market following concerns over safety and lack of efficacy (Bernard, G. R., et al., *Efficacy and safety of recombinant human activated protein C for sepsis*, N Engl J Med, 2001, 344(10): p. 699-709). Systemic inflammation in sepsis likely is driven by the alarmin protein High Mobility Group Box-1 protein (HMGB1). Levels of circulating HMGB1 increase with sepsis severity (Wang, H., et al., *HMG-1 as a late mediator of endotoxin lethality in mice*, Science, 1999, 285(5425): p. 248-51; Gibot, S., et al., *High-mobility group box 1 protein plasma concentrations during septic shock*, Intensive Care Med, 2007, 33(8): p. 1347-53; Sunden-Cullberg, J., et al., *Persistent elevation of high mobility group box-1 protein (HMGB1) in patients with sepsis and septic shock*, Crit Care Med, 2005, 33(3): p. 564-73), while the appearance of anti-HMGB1 autoantibodies correlates with improved outcomes (Barnay-Verdier, S., et al., *Emergence of autoantibodies to HMGB1 is associated with survival in patients with septic shock*, Intensive Care Med, 2011, 37(6): p. 957-62) Likewise, injecting HMGB1 antagonists rescues survival and other symptoms in a dose-dependent manner (Qin, S., et al., *Role of HMGB1 in apoptosis-mediated sepsis lethality*, J Exp Med, 2006, 203(7): p. 1637-42; Valdes-Ferrer, S. I., et al., *HMGB1 mediates anemia of inflammation in murine sepsis survivors*, Mol Med, 2015; Yang, H., et al., *MD-2 is required for disulfide HMGB1-dependent TLR4 signaling*, J Exp Med, 2015, 212 (1): p. 5-14; Yang, H., et al., *Reversing established sepsis with antagonists of endogenous high-mobility group box 1*, Proc Natl Acad Sci USA, 2004, 101(1): p. 296-301).

Severe Acute Respiratory Syndrome (SARS)

Coronaviruses (Order Nidovirales, family Coronaviridae, Genus Coronavirus) are enveloped positive-stranded RNA viruses that bud from the endoplasmic reticulum-Golgi intermediate compartment or the cis-Golgi network. Coronaviruses infect humans and animals and it is thought that there could be a coronavirus that infects every animal. Two human coronaviruses, 229E and OC43, are known to be the major causes of the common cold and can occasionally cause pneumonia in older adults, neonates, or immunocompromised patients. Human coronaviruses belonging to the Order Nidovirales specifically to the family Coronaviridae, were first identified in the mid-1960s. Six coronaviruses that have been previously known to infect humans are: alpha coronaviruses 229E and NL63, and beta coronaviruses OC43, HKU1, SARS-CoV (the coronavirus that causes severe acute respiratory syndrome, or SARS), and MERS-CoV (the coronavirus that causes Middle East Respiratory Syndrome, or MERS).

Severe acute respiratory syndrome (SARS) is caused by a newly identified virus. SARS is a respiratory illness that has recently been reported in Asia, North America, and Europe. The causative agent of SARS was identified as a coronavirus. The World Health Organization reports that the cumulative number of reported probable cases of SARS from Nov. 1, 2002 to Jul. 11, 2003 is 8,437 with 813 deaths, nearly a 10% death rate. Scientists currently believe that SARS will not be eradicated but will cause seasonal epidemics like the cold or influenza viruses.

A highly pathogenic coronavirus named SARS-CoV-2 (previously known as 2019-nCoV) emerged in December 2019 in Wuhan, China, and is rapidly spreading around the world. The virus has high sequence homology with SARS-CoV, with clinical symptoms similar to those reported for SARS-CoV and MERS-CoV. The most characteristic symptom of patients with SARS-CoV is respiratory distress which is often acute and the primary cause of death. SARS-CoV was first identified in the Hubei province of China in December 2019. As of Mar. 11, 2020, it was declared a pandemic by the World Health Organization (WHO), acknowledging that the virus will likely spread to all countries on the globe. As of Mar. 19, 2020, the virus had infected more than 218,800 people worldwide, according to Johns Hopkins University, which is tracking cases reported by the World Health Organization and additional sources. This virus is spreading rapidly across the globe, having more than doubled the number of infected humans in a two-week period prior to Mar. 19, 2020. In response to the outbreak, countries such as Italy, France and the Philippines have enacted policies similar to those seen in China, placing millions under full or partial lockdowns. World-wide, there are currently strict travel restrictions affecting hundreds of millions of citizens. In some hard-hit cities, residents have been unable to leave their apartments for more than a month, while transport between major population hubs has been limited or halted altogether.

SARS-CoV-2 causes mild symptoms in most patients but may, for unresolved reasons, generate acute respiratory distress syndrome in vulnerable individuals and may cause pneumonia. SARS-CoV-2 primarily infects respiratory epithelial cells utilizing angiotensin-converting enzyme 2 receptors to enter the cells. Certain patients will go on to develop acute lung injury progressing to severe acute respiratory distress syndrome (ARDS) with sometimes lethal outcome. (Rothan H A, Byrareddy S N, *The epidemiology and pathogenesis of coronavirus disease (COVID-19) outbreak*, Journal of autoimmunity, 2020:102433; Lake M A, *What we know so far: COVID-19 current clinical knowledge and research*, Clinical medicine (London, England), 2020; Huang C, et al., *Clinical features of patients infected with 2019 novel coronavirus in Wuhan, China*, Lancet (London, England), 2020; 395(10223):497-506; Guan W J, et al., *Clinical Characteristics of Coronavirus Disease 2019 in China*, The New England Journal of Medicine, 2020). There is presently no approved treatment targeting molecules driving the inflammatory process. In the absence of an approved anti-viral treatment or vaccination, there is an urgent need to identify key pathogenic molecules in bacterial and viral respiratory infections such as influenza, and in particular SARS-CoV-2, attainable to target with existing therapeutic compounds.

Acute Lung Injury

Acute lung injury (ALI) is a syndrome in which dysregulated immune signaling causes pathologic inflammation of the lungs that damages the pulmonary epithelium and vasculature, leading to acute respiratory insufficiency and, frequently, death, with this syndrome being marked by respiratory insufficiency, bilateral immune cell infiltrates and edema, and acute hypoxemia. (Rubenfeld G D, *Incidence and outcomes of acute lung injury*, N Engl J Med. 2005; 353(16):1685-93). ALI can be triggered by insults ranging from infection, gastric acid aspiration, smoke inhalation, or sepsis. (Imai Y, *Identification of oxidative stress and Toll-like receptor 4 signaling as a key pathway of acute lung injury*, Cell. 2008; 133(2):235-49; Johnson E R, *Acute lung injury: epidemiology, pathogenesis, and treatment*, J Aerosol Med Pulm Drug Deliv. 2010; 23(4):243-52; Vande Vusse L K, *The Epidemiology of Transfusion-related Acute Lung Injury Varies According to the Applied Definition of Lung Injury Onset Time*, Ann Am Thorac Soc. 2015; 12(9): 1328-35). ALI results from runaway immune signaling: infected/injured epithelial cells release pro-inflammatory signals that attract innate immune cells to the lungs, and these infiltrating macrophages and neutrophils compound epithelial damage while releasing additional pro-inflammatory and/or cytotoxic signals. Unchecked, this feedback loop establishes and reinforces a damaging cycle that compromises the junction between the lung epithelium and alveolar-capillary membrane, leading to impaired gas exchange and edema. (Johnson E R, *Acute lung injury: epidemiology, pathogenesis, and treatment*, J Aerosol Med Pulm Drug Deliv. 2010; 23(4):243-52). If the pathology progresses sufficiently, it can culminate in respiratory failure and death. (Imai Y, *Identification of oxidative stress and Toll-like receptor 4 signaling as a key pathway of acute lung injury*, Cell, 2008; 133(2):235-49; Johnson E R, Matthay M A, *Acute lung injury: epidemiology, pathogenesis, and treatment*, Johnson E R, *Acute lung injury: epidemiology, pathogenesis, and treatment*, J Aerosol Med Pulm Drug Deliv., 2010; 23(4):243-52; Rubenfeld G D, *Incidence and outcomes of acute lung injury*, N Engl J Med. 2005; 353(16):1685-93). FIG. 3 is a graphical representation of ALI incidence and mortality across age cohorts, subdivided by predisposing factors.

ALI has been described in the medical literature since 1967 (Ashbaugh D G, *Acute respiratory distress in adults*, Lancet, 1967; 2(7511):319-23), yet there remains no effective pharmacotherapy. (Cepkova M, *Pharmacotherapy of acute lung injury and the acute respiratory distress syndrome*, J Intensive Care Med, 2006; 21(3):119-43; Raghavendran K, *Pharmacotherapy of acute lung injury and acute respiratory distress syndrome*, Curr Med Chem., 2008; 15(19):1911-24).

Acute Lung Injury is an inflammatory disorder. When cells of the alveolar epithelium become damaged through injury or infection, they release pro-inflammatory signals to recruit macrophages and neutrophils into the alveolar space. These innate immune cells phagocytose necrotic and apoptotic cells and assist with controlling the pathogen load, along with releasing cytotoxic and pro-inflammatory cytokines and HMGB1. (Johnson E R, *Acute lung injury: epidemiology, pathogenesis, and treatment*, J Aerosol Med Pulm Drug Deliv., 2010; 23(4):243-52; Damjanovic D, *Immunopathology in influenza virus infection: uncoupling the friend from foe*, Clin Immunol., 2012; 144(1):57-69; Lin K L, *CCR2+ monocyte-derived dendritic cells and exudate macrophages produce influenza-induced pulmonary immune pathology and mortality*, J Immunol., 2008; 180(4):2562-72). This positive feedback loop becomes dysregulated during ALI, with pathological and often fatal results. FIGS. 4A and 4B show how dysregulated inflammation causes ALI with FIG. 4A showing the feedback loop that drives immunopathology in ALI and FIG. 4B showing how HMGB1 levels roughly correlate with tissue damage and negative outcomes. FIG. 4 B is adapted from Andersson U, *HMGB1 is a therapeutic target for sterile inflammation and infection*, Annu Rev Immunol., 2011; 29:139-62.

Hallmarks of ALI include excessive neutrophil infiltration leading to damage to healthy epithelium adjacent to the original injury site (Johnson E R, *Acute lung injury: epidemiology, pathogenesis, and treatment*, J Aerosol Med Pulm Drug Deliv., 2010; 23(4):243-52; Taubenberger J K, Morens D M, *The pathology of influenza virus infections*, Annu Rev Pathol., 2008; 3:499-522.27), loss of epithelial membrane integrity and accumulation of proteinaceous fluid in the lungs (Johnson E R, *Acute lung injury: epidemiology, pathogenesis, and treatment*, J Aerosol Med Pulm Drug Deliv., 2010; 23(4):243-52), and abnormally high levels of cytokines and chemokines in the serum and lungs. The severity of this cytokine storm often correlates with fatal outcomes. (Johnson E R, J Aerosol Med Pulm Drug Deliv., 2010; 23(4):243-52; Damjanovic D, *Immunopathology in influenza virus infection: uncoupling the friend from foe*, Clin Immunol. 2012; 144(1):57-69; Lin K L, *CCR2+ monocyte-derived dendritic cells and exudate macrophages produce influenza-induced pulmonary immune pathology and mortality*, J Immunol., 2008; 180(4):2562-72. PubMed PMID: 18250467; Taubenberger J K, *Fatal outcome of human influenza A (H5N1) is associated with high viral load and hypercytokinemia*, Nat Med., 2006; 12(10):1203-7; The pathology of influenza virus infections, Annu Rev Pathol., 2008; 3:499-522; de Jong M D, *Fatal outcome of human influenza A (H5N1) is associated with high viral load and hypercytokinemia*, Nat Med., 2006; 12(10):1203-7).

Acute respiratory infection caused by influenza is one of the most common causes of ALI. Although seasonal and pandemic flu strains differ in virulence, they share a common pathology in that ALI is a hallmark of cases of severe illness. Other risk factors that lead to dysregulated inflammatory signaling in the lung can trigger ALI. These include sepsis, non-influenza pulmonary infections, smoke or toxic gas inhalation, gastric acid aspiration, and transfusion reactions, among others. (Imai Y, *Identification of oxidative stress and Toll-like receptor 4 signaling as a key pathway of acute lung injury*, Cell, 2008; 133(2):235-49; Johnson E R, *Acute lung injury: epidemiology, pathogenesis, and treatment*, J Aerosol Med Pulm Drug Deliv., 2010; 23(4):243-52; Vande Vusse L K, *The Epidemiology of Transfusion-related Acute Lung Injury Varies According to the Applied Definition of Lung Injury Onset Time*, Ann Am Thorac Soc., 2015; 12(9):1328-35). Mechanical ventilation and other treatments for ALI also can cause additional airway injury that exacerbates the condition. (Parsons P E, *Network NARDSCT. Lower tidal volume ventilation and plasma cytokine markers of inflammation in patients with acute lung injury*, Crit Care Med. 2005; 33(1):1-6; discussion 230-2; Ranieri V M, *Effect of mechanical ventilation on inflammatory mediators in patients with acute respiratory distress syndrome: a randomized controlled trial*, JAMA, 1999; 282(1):54-61).

The incidence of ALI in the United States has been estimated at approximately 200,000 cases annually. (Martin T R, *A TRIFfic perspective on acute lung injury*, Cell, 2008; 133(2):208-10; Rubenfeld G D, *Incidence and outcomes of acute lung injury*, N Engl J Med. 2005; 353(16):1685-93) Extrapolating this rate to the world population (likely an underestimation) suggests that there are more than 4.5 million ALI cases globally each year. The prevalence and severity of ALI increases with age and the presence of predisposing clinical factors (see FIGS. 4A and 4B adapted from Rubenfeld G D, *Incidence and outcomes of acute lung injury*, N Engl J Med., 2005; 353(16):1685-93), with the mortality risk varying from 29% to over 40% for the elderly. (Johnson E R, *Acute lung injury: epidemiology, pathogenesis, and treatment*, J Aerosol Med Pulm Drug Deliv., 2010; 23(4):243-52). Patients who survive ALI face diverse and lasting challenges from cognitive and motor deficits to psychiatric and mood disorders. (Rubenfeld G D, *Incidence and outcomes of acute lung injury*, N Engl J Med. 2005; 353(16):1685-93); Herridge M S, *Canadian Critical Care Trials G. One-year outcomes in survivors of the acute respiratory distress syndrome*, N Engl J Med, 2003; 348(8): 683-93; Ruhl A P, *Health care resource use and costs of two-year survivors of acute lung injury. An observational cohort study*, Ann Am Thorac Soc., 2015; 12(3):392-401; Schelling G, *Health-related quality of life and posttraumatic stress disorder in survivors of the acute respiratory distress syndrome*, Crit Care Med., 1998; 26(4):651-9). Indeed, it has been estimated that ALI survivors consume more than $2 billion in healthcare in the U.S. annually. (Ruhl A P, *Health care resource use and costs of two-year survivors of acute lung injury. An observational cohort study*, Ann Am Thorac Soc., 2015; 12(3):392-401), and these numbers likely will double as the graying U.S. population swells the number of people at high risk due to age. (Rubenfeld G D, *Incidence and outcomes of acute lung injury*, N Engl J Med, 2005; 353(16):1685-93). Thus, there is a compelling need for a cost-effective treatment for ALI.

The social and economic costs of ALI are high, with approximately 75,000 people succumbing to ALI in the U.S.

each year (Rubenfeld G D, *Incidence and outcomes of acute lung injury*, N Engl J Med., 2005; 353(16):1685-93). The intensive support that ALI patients require to survive the acute phase consumes a staggering level of medical resources. For example, it has been estimated that ALI is responsible for a combined 2.2 million ICU days for patients annually. Moreover, the costs of ALI extend far beyond the initial ICU stay: approximately two-thirds of survivors require extended rehabilitative care before they can be discharged to home. Without a breakthrough treatment, these numbers could double in the next 25 years due to the explosion in the proportion of the US population who are at high-risk due to age.

Cognitive abnormalities, weakness, depression, and even post-traumatic stress disorder are common and lingering sequelae for which ALI survivors are treated that frequently require inpatient admission to hospitals of skilled nursing/rehabilitation facilities. (Rubenfeld G D *Incidence and outcomes of acute lung injury*, N Engl J Med., 2005; m353 (16):1685-93; Herridge M S, *Canadian Critical Care Trials G. One-year outcomes in survivors of the acute respiratory distress syndrome*, N Engl J Med., 2003; 348(8):683-93; Ruhl A P *Health care resource use and costs of two-year survivors of acute lung injury*. An observational cohort study, Ann Am Thorac Soc., 2015; 12(3):392-401; Schelling G, *Health-related quality of life and posttraumatic stress disorder in survivors of the acute respiratory distress syndrome*, Crit Care Med., 1998; 26(4):651-9). Indeed, one study that followed ALI survivors for two years after their initial discharge observed that 80% were readmitted at a median cost of $35,529 during the study period, primarily in the first year. (Ruhl A P, *Health care resource use and costs of two-year survivors of acute lung injury, An observational cohort study*, Ann Am Thorac Soc. 2015; 12 (3):392-401). Thus, a conservative estimate of the ongoing costs incurred to treat ALI survivors in the U.S. exceeds $2 billion annually.

Although ALI may be precipitated by diverse insults, recent evidence suggests that the over-production of pro-inflammatory molecules that ultimately leads to pathology is mediated by the Toll-like Receptor TLR4 and HMGB1, the primary late mediator of inflammation. (Imai Y, *Identification of oxidative stress and Toll-like receptor 4 signaling as a key pathway of acute lung injury*, Cell, 2008; 133(2):235-49; Nosaka N, *Anti-high mobility group box-1 monoclonal antibody treatment provides protection against influenza A virus (H1N1)-induced pneumonia in mice*, Crit Care, 2015; 19:249; Shirey K A, Lai W, *Novel strategies for targeting innate immune responses to influenza*, Mucosal Immunol., 2016; 9(5):1173-82; Shirey K A, *The TLR4 antagonist Eritoran protects mice from lethal influenza infection*, Nature, 2013; 497(7450):498-502). HMGB1, whose major signaling receptor is TLR4, is released passively by apoptotic and necrotic cells to recruit leukocytes to the site of infection or injury; in turn, these innate immune cells actively release HMGB1 to amplify the inflammatory response to fight active infection or promote wound healing. A breakdown in the regulation of this feedback loop can lead to uncontrolled inflammation. Mice deficient for TLR4 are less susceptible to ALI (Imai Y, *Identification of oxidative stress and Toll-like receptor 4 signaling as a key pathway of acute lung injury*, Cell. 2008; 133(2):235-49; Martin T R, *A TRIFfic perspective on acute lung injury*, Cell, 2008; 133 (2):208-10) and a TLR4 antagonist protects against lethality in influenza-induced ALI. (Shirey K A, *Novel strategies for targeting innate immune responses to influenza. Mucosal Immunol,* 2016; 9(5):1173-82; Shirey K A, *The TLR4 antagonist Eritoran protects mice from lethal influenza infection*, Nature, 2013; 497(7450):498-502). Likewise, HMGB1 antagonists promote survival when administered following lethal influenza infection. Mice injected with a monoclonal antibody (mAb) that binds and neutralizes HMGB1 had significantly lower mortality than those injected with control IgG that does not recognize HMGB1. (Nosaka N, *Anti-high mobility group box-1 monoclonal antibody treatment provides protection against influenza A virus (H1N1)-induced pneumonia in mice*, Crit Care, 2015; 19:249: See also, U.S. Pat. No. 8,138,141, incorporated herein by reference). Another strategy to interrupt HMGB1 signaling is to interfere with HMGB1 binding to the TLR4/MD-2 receptor complex.

Peripheral Neuropathy

Over 29 million people are diagnosed with diabetes in the U.S., and another 86 million adults have prediabetes, with an estimated 15 to 30 percent of people with prediabetes developing type 2 diabetes within five years. (Control CfD, Prevention, *National diabetes statistics report: estimates of diabetes and its burden in the United States*, Atlanta, Ga.: US Department of Health and Human Services, (2014)). The most common complication of diabetes is diabetic peripheral neuropathy (DPN), a painful condition with a lifetime prevalence of 66%. (Charnogursky, G., *Diabetic neuropathy*, Handbook of clinical neurology, 2014; 120: 773-785); Dyck P. J., *The prevalence by staged severity of various types of diabetic neuropathy, retinopathy, and nephropathy in a population-based cohort: the Rochester Diabetic Neuropathy Study*, Neurology, 1993; 43(4): 817-824). The total annual cost of DPN and its complications in the U.S. was estimated to be between $4.6 and $13.7 billion in 2001, and DPN accounts for up to 27% of direct medical costs of diabetes. (Gordois A, *The health care costs of diabetic peripheral neuropathy in the US*, Diabetes Care, June 2003; 26(6):1790-1795). The only treatments currently available for DPN are disease state modifiers such as tight blood glucose control, and chronic pain medication. (Bril V., *Treatments for diabetic neuropathy*, Journal of the Peripheral Nervous System, 2012; 17(s2):22-27; Javed S., *Treatment of painful diabetic neuropathy*, Therapeutic advances in chronic disease, 2015; 6(1):15-28). However, even with intensive insulin therapy, approximately 25% of patients still developed DPN (Control D, Group CTR, *The effect of intensive treatment of diabetes on the development and progression of long-term complications in insulin-dependent diabetes mellitus*, N. Engl. J. Med., 1993; (329): 977-986). As diabetic neuropathic pain responds poorly to current standard pain treatments (Baron R., *Neuropathic pain: diagnosis, pathophysiological mechanisms, and treatment*, The Lancet Neurology, 2010; 9(8): 807-819), novel mechanisms mediating the development of neuropathic pain have been proposed. (Dworkin R. H., *Advances in neuropathic pain: diagnosis, mechanisms, and treatment recommendations*, Archives of neurology, 2003; 60(11): 1524-1534; Dray A., *Neuropathic pain: emerging treatments*, British Journal of Anaesthesia. 2008; 101(1): 48-58); Ossipov M. H., *Challenges in the development of novel treatment strategies for neuropathic pain*, NeuroRx, 2005; 2(4): 650-661; Costigan M., *Neuropathic pain: a maladaptive response of the nervous system to damage*, Annual review of neuroscience, 2009; 32: 1-32). Few of these mechanisms have been translated into an effective mechanism-based therapy. (Dworkin R. H., *Advances in neuropathic pain: diagnosis, mechanisms, and treatment recommendations*, Archives of neurology, 2003; 60(11): 1524-1534; Ossipov M. H., *Chal-* lenges in the development of novel treatment strategies for neuropathic pain, NeuroRx, 2005; 2(4): 650-661).

As discussed above, HMGB1 is a late mediator of inflammation. In animals, all cells synthesize HMGB1; healthy cells sequester it in the nucleus, where it serves as a transcription factor. (Andersson U, *HMGB1 is a therapeutic target for sterile inflammation and infection*, Annu Rev Immunol., 2011; 29:139-62; Wang H, *HMG-1 as a late mediator of endotoxin lethality in mice*, Science, 1999; 285(5425):248-51). Cellular damage, necrosis, and apoptosis result in the passive release of HMGB1 into the extracellular space, which can recruit leukocytes to the site of an injury or infection. In turn, these monocytes, tissue macrophages, and other cells of the innate immune system actively secrete HMGB1 when activated by pathogen-derived stimuli, exosomes, or pro-inflammatory cytokines. Depending upon its oxidation state and which of its receptors are engaged, extracellular HMGB1 can trigger a variety of outcomes (reviewed in Lotze M T, *High-mobility group box 1 protein (HMGB1): nuclear weapon in the immune arsenal* Nat Rev Immunol., 2005; 5(4):331-42; Yang H, *Targeting HMGB1 in inflammation*, Biochim Biophys Acta., 2010; 1799(1-2):149-56 and Harris H E, *HMGB1: a multifunctional alarmin driving autoimmune and inflammatory disease*, Nat Rev Rheumatol., 2012; 8(4):195-202), including secretion of additional HMGB1 to sustain the immune response until the insult is resolved. These characteristics, pro-inflammatory cytokine activity and prolonged release, recommend HMGB1 as an attractive therapeutic target in inflammatory diseases. (Andersson U, *HMGB1 is a therapeutic target for sterile inflammation and infection*, Annu Rev Immunol, 2011; 29:139-62).

HMGB1 is now well known as a critical mediator in inflammation, with animal studies demonstrating that HMGB1 is a key mediator of inflammation, interacting with as many as 15 distinct receptor systems (Maeda T., *HMGB1 as a potential therapeutic target for neuropathic pain*, Journal of Pharmacological Sciences., 2013; 123(4): 301-305; Wan W., *The emerging role of HMGB1 in neuropathic pain: a potential therapeutic target for neuroinflammation*, Journal of Immunology Research, (2016); Andersson U., *HMGB1 is a therapeutic target for sterile inflammation and infection*, Annual Review of Immunology, 2011; 29:139-162; Yang H., *The many faces of HMGB1: molecular structure functional activity in inflammation, apoptosis, and chemotaxis*, Journal of Leukocyte Biology, 2013; 93(6): 865-873); and causing organ damage and epithelial barrier failure in trauma, sepsis, shock and ischemia/reperfusion injury. (Wan W., *The emerging role of HMGB1 in neuropathic pain: a potential therapeutic target for neuroinflammation*, Journal of Immunology Research, (2016); Andersson U., *HMGB1 is a therapeutic target for sterile inflammation and infection*, Annual Review of Immunology, 2011; 29: 139-162; Magna M, *The role of HMGB1 in the pathogenesis of inflammatory and autoimmune diseases*, Molecular Medicine, 2014; 20(1):138; Peter K., *HMGB1 signals danger in acute coronary syndrome: emergence of a new risk marker for cardiovascular death?* Atherosclerosis, 2012; 221(2): 317-318; Liu Y., *HMGB1: roles in base excision repair and related function*, Biochimica et Biophysica Acta (BBA)-Gene Regulatory Mechanisms, 2010; 1799(1): 119-130). While HMGB1 is a well-established mediator in inflammatory diseases, only recently have investigators begun to address the role of HMGB1 in pain. Recent work has shown that HMGB1 plays a vital role in the pathophysiological mechanisms of pain, including cancer, arthritis, pancreatitis-induced pain, headache, and peripheral nerve injury induced neuropathic pain. (Nishida T., *Involvement of high mobility group box 1 in the development and maintenance of chemotherapy-induced peripheral neuropathy in rats*, Toxicology, 2016; 365: 48-58; Feldman P., *The persistent release of HMGB1 contributes to tactile hyperalgesia in a rodent model of neuropathic pain*, Journal of Neuroinflammation, 2012; 9(1): 180; Allette Y. M., *Identification of a functional interaction of HMGB1 with Receptor for Advanced Glycation End products in a model of neuropathic pain*, Brain, Behavior, and Immunity. 2014; 42:169-177; Kuang X., *Effects of intrathecal epigallocatechin gallate, an inhibitor of Toll-like receptor 4, on chronic neuropathic pain in rats*, European Journal of Pharmacology, 2012; 676(1): 51-56; Nakamura Y., *Neuropathic pain in rats with a partial sciatic nerve ligation is alleviated by intravenous injection of monoclonal antibody to high mobility group box-1*, PloS One, 2013; 8(8): e73640; Shibasaki M., *Induction of high mobility group box-1 in dorsal root ganglion contributes to pain hypersensitivity after peripheral nerve injury*, Pain, 2010; 149(3): 514-521; Grace P. M., *Pathological pain and the neuroimmune interface*, Nature Reviews Immunology, 2014; 14(4): 217-231; Tong W., *Spinal high-mobility group box 1 contributes to mechanical allodynia in a rat model of bone cancer pain*, Biochemical and Biophysical Research Communications, 2010; 395(4): 572-576; Agalave N. M., *Spinal HMGB1 induces TLR4-mediated long-lasting hypersensitivity and glial activation and regulates pain-like behavior in experimental arthritis*, PAIN®, 2014; 155(9): 1802-1813; Ma Y-Q, *Tanshinone IIA downregulates HMGB1 and TLR4 expression in a spinal nerve ligation model of neuropathic pain*, Evidence-Based Complementary and Alternative Medicine, (2014); Maeda T., *HMGB1 as a potential therapeutic target for neuropathic pain*, Journal of pharmacological sciences., 2013; 123(4): 301-305; Chacur M., *A new model of sciatic inflammatory neuritis (SIN): induction of unilateral and bilateral mechanical allodynia following acute unilateral peri-sciatic immune activation in rats*, Pain, 2001; 94(3): 231-244; Tanaka J., *Recombinant human soluble thrombomodulin prevents peripheral HMGB1-dependent hyperalgesia in rats*, British Journal of Pharmacology, 2013; 170(6): 1233-1241; Karatas H., *Spreading depression triggers headache by activating neuronal Panx1 channels*, Science, 2013; 339(6123): 1092-1095; Das N., *HMGB1 activates proinflammatory signaling via TLR5 leading to allodynia*, Cell Reports, 2016; 17(4): 1128-1140). Persistent inflammation in response to excessively released HMGB1 contributes to the sequelae of inflammatory pain. Because of the similarities of inflammatory response in the development of diabetes, the role of HMGB1 and HMGB1-mediated inflammatory pathways in adipose tissue inflammation, insulin resistance, and islet dysfunction in diabetes, as well as painful DPN, have also been reported. (Zhao X., *Inhibition of CaMKIV relieves streptozotocin-induced diabetic neuropathic pain through regulation of HMGB1*, BMC Anesthesiology, 2016; 16(1): 27; Ren P-C, *High-mobility group box 1 contributes to mechanical allodynia and spinal astrocytic activation in a mouse model of type 2 diabetes*, Brain Research Bulletin, 2012; 88(4): 332-337; Abu El-Asrar AM, *The proinflammatory cytokine high-mobility group box-1 mediates retinal neuropathy induced by diabetes*, Mediators of Inflammation, (2014); Tsao C., *Expression of high-mobility group box protein 1 in diabetic foot atherogenesis*, Genetics and Molecular Research, 2015; 14(2): 4521-4531; Zhao H., *HMGB-1 as a potential target for the treatment of diabetic retinopathy*, Medical Science Monitor: International Medical Journal Of Experimental And Clinical Research, 2015; 21: 3062). Given that HMGB1-TLR4/MD-2 signaling pathway plays a pivotal role in inflammation, HMGB1 and its downstream receptor TLR4 may serve as potential antidiabetic targets.

Growing evidence supports that high-mobility group box 1 protein (HMGB1) plays a vital role in the pathophysiological mechanisms of neuropathic pain (NP). (Nishida T., *Involvement of high mobility group box 1 in the development and maintenance of chemotherapy-induced peripheral neuropathy in rats*, Toxicology, 2016; 365: 48-58; Feldman P., *The persistent release of HMGB1 contributes to tactile hyperalgesia in a rodent model of neuropathic pain*, Journal of neuroinflammation, 2012; 9(1): 180; Allette Y. M., *Identification of a functional interaction of HMGB1 with Receptor for Advanced Glycation End products in a model of neuropathic pain*, Brain, Behavior, And Immunity, 2014; 42:169-177; Kuang X., *Effects of intrathecal epigallocatechin gallate, an inhibitor of Toll-like receptor 4, on chronic neuropathic pain in rats*, European Journal Of Pharmacology, 2012; 676(1): 51-56; Nakamura Y., *Neuropathic pain in rats with a partial sciatic nerve ligation is alleviated by intravenous injection of monoclonal antibody to high mobility group box-1*, Plos One, 2013; 8(8): e73640; Shibasaki M., *Induction of high mobility group box-1 in dorsal root ganglion contributes to pain hypersensitivity after peripheral nerve injury*, Pain, 2010; 149(3): 514-521; Grace P. M., *Pathological pain and the neuroimmune interface*, Nature Reviews Immunology, 2014; 14(4): 217-231; Tong W., *Spinal high-mobility group box 1 contributes to mechanical allodynia in a rat model of bone cancer pain*, Biochemical And Biophysical Research Communications, 2010; 395(4): 572-576; Agalave N. M., *Spinal HMGB1 induces TLR4-mediated long-lasting hypersensitivity and glial activation and regulates pain-like behavior in experimental arthritis*, PAIN®, 2014; 155(9): 1802-1813; Ma Y-Q, *Tanshinone IIA downregulates HMGB1 and TLR4 expression in a spinal nerve ligation model of neuropathic pain*, Evidence-Based Complementary and Alternative Medicine, (2014); Maeda T., *HMGB1 as a potential therapeutic target for neuropathic pain*, Journal Of Pharmacological Sciences, 2013; 123(4): 301-305; Chacur M., *A new model of sciatic inflammatory neuritis (SIN): induction of unilateral and bilateral mechanical allodynia following acute unilateral peri-sciatic immune activation in rats*, Pain, 2001; 94(3): 231-244; Tanaka J., *Recombinant human soluble thrombomodulin prevents peripheral HMGB1-dependent hyperalgesia in rats*, British Journal Of Pharmacology, 2013; 170(6): 1233-1241; Karatas H., *Spreading depression triggers headache by activating neuronal Panx1 channels*, Science, 2013; 339(6123): 1092-1095) (Das N., *HMGB1 activates proinflammatory signaling via TLR5 leading to allodynia*, Cell Reports, 2016; 17(4): 1128-1140). This includes evidence that HMGB1 plays a vital role in the pathophysiological mechanisms for diabetic neuropathic pain. (Zhao X., *Inhibition of CaMKIV relieves streptozotocin-induced diabetic neuropathic pain through regulation of HMGB1*, BMC Anesthesiology, 2016; 16(1): 27; Ren P-C, *High-mobility group box 1 contributes to mechanical allodynia and spinal astrocytic activation in a mouse model of type 2 diabetes*, Brain Research Bulletin, 2012; 88(4): 332-337). Numerous reports and studies have shown that HMGB1 is an essential inflammatory pronociceptive factor that interacts with many other mediators. (Agalave N. M., *Spinal HMGB1 induces TLR4-mediated long-lasting hypersensitivity and glial activation and regulates pain-like behavior in experimental arthritis*, PAIN®, 2014; 155(9): 1802-1813; Maeda T., *HMGB1 as a potential therapeutic target for neuropathic pain*, Journal of Pharmacological Sciences, 2013; 123(4): 301-305) (Wan W., *The emerging role of HMGB1 in neuropathic pain: a potential therapeutic target for neuroinflammation*, Journal of Immunology Research, (2016); Yang H., *High Mobility Group Box Protein 1 (HMGB1): The Prototypical Endogenous Danger Molecule*, Molecular Medicine (Cambridge, Mass.), 2015; 21 Suppl 1: S6-S12). Lower levels of HMGB1 are bactericidal, stimulate neurite growth and enhance motility of smooth muscle cells and fibroblasts. Higher levels of HMGB1 are pathological; activate macrophages to release cytokines including TNF, IL-1α, IL-1β, IL-6, MIP1α, and IL-8 (see FIG. 5 which shows the biological effects of HMGB1). (Andersson U, Tracey K J, *HMGB1 is a therapeutic target for sterile inflammation and infection*, Annual Review of Immunology, 2011; 29: 139-162). These HMGB1-mediated inflammatory pathways underlie adipose tissue inflammation, insulin resistance, and islet dysfunction in diabetes, as well as development of painful DPN. (Zhao X., *Inhibition of CaMKIV relieves streptozotocin-induced diabetic neuropathic pain through regulation of HMGB1*, BMC Anesthesiology, 2016; 16(1): 27; Abu El-Asrar A M, *The proinflammatory cytokine high-mobility group box-1 mediates retinal neuropathy induced by diabetes*, Mediators of Inflammation, (2014); Tsao C., *Expression of high-mobility group box protein 1 in diabetic foot atherogenesis*, Genetics and Molecular Research, 2015; 14(2): 4521-4531; Zhao H., *HMGB-1 as a potential target for the treatment of diabetic retinopathy*, Medical Science Monitor: International Medical Journal of Experimental and Clinical Research, 2015; 21: 3062). Thus, HMGB1-blocking approach is beneficial to diabetic patients in general.

While inhibition of HMGB1 using neutralizing monoclonal antibody reduces neuropathic pain in multiple animal models, the challenge to the development of a safe and effective HMGB1-based treatment for painful DPN is the diverse molecular localizations and functions of HMGB1 isoforms. (Yang H., *Redox modification of cysteine residues regulates the cytokine activity of high mobility group box-1 (HMGB1)*, Molecular Medicine, 2012; 18(1): 250; Magna M, Pisetsky D S., *The role of HMGB1 in the pathogenesis of inflammatory and autoimmune diseases*, Molecular Medicine. 2014; 20(1):138; Peter K., *HMGB1 signals danger in acute coronary syndrome: emergence of a new risk marker for cardiovascular death?*, Atherosclerosis, 2012; 221(2): 317-318; Zhu L., *High-mobility group box 1 induces neuron autophagy in a rat spinal root avulsion model*, Neuroscience, 2016; 315: 286-295; Liu Y., *HMGB1: roles in base excision repair and related function*, Biochimica et Biophysica Acta (BBA)-Gene Regulatory Mechanisms, 2010; 1799(1): 119-130; Lian Y-J, *Ds-HMGB1 and fr-HMGB induce depressive behavior through neuroinflammation in contrast to nonoxid-HMGB1*, Brain, Behavior, and Immunity, 2017; 59: 322-332). It is known that there are three isoforms of HMGB1, and distinct immune functions via separate receptor systems have been attributed to each (See FIGS. 6A-6C which show the three known isoforms of HMGB1). HMGB1 contains 3 cysteines (Cys) at positions 23, 45 and 106. Evidence has accumulated that the redox status of these cysteines influences the corresponding extracellular chemokine or cytokine-inducing properties. Specifically, evidence suggests that HMGB1 with all cysteine residues reduced (fully reduced HMGB1) binds to CXCL12 and stimulates immune cell infiltration via the CXCR4 receptor. Similarly, partially oxidized HMGB1, with a Cys23-Cys45 disulfide bond and a reduced Cys106 (disulfide HMGB1), has been shown to activate immune cells via the TLR4/MD-2 receptor. Evidence suggests that all cysteines oxidized (sulfonyl HMGB1) is devoid of immune activity. (Yang H., *Redox modification of cysteine residues regulates the cytokine activity of high mobility group box-1 (HMGB1)*, Molecular Medicine, 2012; 18(1): 250) (Yang H., *MD-2 is required for disulfide HMGB1—dependent TLR4 signaling*, Journal of Experimental Medicine, 2015: jem. 20141318; Antoine D. J., *A systematic nomenclature for the redox states of high mobility group box (HMGB) proteins*, Molecular medicine, 2014; 20(1): 135; Venereau E., *Mutually exclusive redox forms of HMGB1 promote cell recruitment or proinflammatory cytokine release*, Journal of Experimental Medicine, 2012; 209(9): 1519-1528; Kim S., *Signaling of high mobility group box 1 (HMGB1) through toll-like receptor 4 in macrophages requires CD14*, Molecular Medicine, 2013; 19(1): 88).

While there is an array of established HMGB1 inhibitors, many of them lack specificity which may dampen their significance for further development. (Andersson U., *HMGB1 is a therapeutic target for sterile inflammation and infection*, Annual Review of Immunology, 2011; 29: 139-162).

Pharmacological Compounds that Inhibit HMGB1

FIG. 7 shows the inhibition of HMGB1-RAGE-TLR4-mediated inflammation by approved pharmacological compounds. The formation of proinflammatory HMGB1-partner molecule complexes is counteracted by thrombomodulin, heparin, haptoglobin, and glycyrrhizin. RAGE-HMGB1-mediated activities are inhibited by acetylcholine, heparin, statins, dexmedetomidine, and ketamine. TLR4-HMGB1 mediated activation is downregulated by acetylcholine, heparin, statins, resveratrol, dexmedetomidine, and ketamine. HMGB1-mediated disruption of lysosomal membrane is constrained by chloroquine phosphate and hydroxychloroquine.

Chloroquine

Chloroquine phosphate-based therapy in China and hydroxychloroquine treatment in South Korea have been reported to improve outcome in SARS-CoV-2 infections. Gao J, et al., *Breakthrough: Chloroquine phosphate has shown apparent efficacy in treatment of COVID-19 associated pneumonia in clinical studies*, Bioscience trends. 2020. Chloroquine-mediated alkalinization of lysosomes inhibiting HMGB1-caused lysosomal leakage is one plausible mechanism. Intact lysosome function prevents the activation of multiple proinflammatory cytosolic receptors. Furthermore, chloroquine has been demonstrated to decrease HMGB1 secretion from activated innate immunity cells. (Schierbeck H, et al., *Immunomodulatory drugs regulate HMGB1 release from activated human monocytes*, Molecular Medicine (Cambridge, Mass.). 2010; 16(9-10):343-51 (61)).

Based on the fact that HMGB1 operates as a detergent in the acidic conditions in lysosomes (Deng M, et al., *The Endotoxin Delivery Protein HMGB1 Mediates Caspase-11-Dependent Lethality in Sepsis*, Immunity, 2018; 49(4):740-53.e7 15), it is of distinct clinical interest that recent Chinese clinical studies report that chloroquine phosphate therapy exerts beneficial therapeutic effects in SARS-CoV-2 infection (Gao J, et al., *Breakthrough: Chloroquine phosphate has shown apparent efficacy in treatment of COVID-19 associated pneumonia in clinical studies*, Bioscience Trends, 2020). The drug will be included in official guidelines for therapy of SARS-CoV-2 in China (Zhonghua jie, *Expert consensus on chloroquine phosphate for the treatment of novel coronavirus pneumonia*, Chinese Journal of Tuberculosis and Respiratory Diseases, 2020; 43(3):185-8.38). Chloroquine accumulates in lysosomes and raises the pH, something that counteracts HMGB1 from operating like a detergent in the lysosomes and thus precludes lysosomal leakage of DAMP molecules to the cytosol.

Heparin

Heparin is a high affinity HMGB1 binding molecule. (Ling Y, et al., *Heparin changes the conformation of high-mobility group protein 1 and decreases its affinity toward receptor for advanced glycation endproducts in vitro*, International Immunopharmacology, 2011; 11(2):187-93: Li L, et al., *Heparin inhibits the inflammatory response induced by LPS and HMGB1 by blocking the binding of HMGB1 to the surface of macrophages*, Cytokine, 2015; 72(1):36-42; Rouhiainen A, et al, *Inhibition of Homophilic Interactions and Ligand Binding of the Receptor for Advanced Glycation End Products by Heparin and Heparin-Related Carbohydrate Structures*, Medicines (Basel, Switzerland). 2018; 5(3)). The conformation of HMGB1 changes when heparin combines with HMGB1 and this change inhibits the binding of HMGB1 to the surface of activated macrophages. (Ling Y, et al., *Heparin changes the conformation of high-mobility group protein 1 and decreases its affinity toward receptor for advanced glycation endproducts in vitro*, International Immunopharmacology, 2011; 11(2):187-93). Heparin-HMGB1 complexes are unable to induce RAGE dimerization that is required for the function of RAGE. (Rouhiainen A, et al, *Inhibition of Homophilic Interactions and Ligand Binding of the Receptor for Advanced Glycation End Products by Heparin and Heparin-Related Carbohydrate Structures*, Medicines (Basel, Switzerland). 2018; 5(3)). Heparin treatment reduced the lethality in mice exposed to LPS-HMGB1 complexes. (Li L, et al., *Heparin inhibits the inflammatory response induced by LPS and HMGB1 by blocking the binding of HMGB1 to the surface of macrophages*, Cytokine, 2015; 72(1):36-42). However, a clinical utilization of heparin as an anti-inflammatory agent carries a risk of causing life-threatening bleeding. There are modified heparin preparations with very low anticoagulant activity that could be considered for this purpose, and one such heparinoid compound has been successfully tested in phase I/II studies of *Plasmodium falciparum* malaria disease in patients. (Leitgeb A M, et al., *Inhibition of merozoite invasion and transient de-sequestration by sevuparin in humans with Plasmodium falciparum malaria*, PLoS One, 2017; 12(12):e0188754). This molecule also prevented neutrophil-induced lung plasma leakage in a murine sepsis model. (Rasmuson J, et al., *Heparinoid sevuparin inhibits Streptococcus-induced vascular leak through neutralizing neutrophil-derived proteins*, Faseb J. 2019; 33(9):10443-52. Neutrophil-mediated pathology is of central importance in acute lung injury.

Thrombomodulin

Thrombomodulin is an endothelial cell thrombin receptor known to convert thrombin into an anticoagulant. Soluble thrombomodulin also binds to HMGB1 and aids the proteolytic cleavage of HMGB1 by thrombin. (Abeyama K, et al., *The N-terminal domain of thrombomodulin sequesters high-mobility group-B1 protein, a novel antiinflammatory mechanism*, The Journal of Clinical Investigation. 2005; 115(5): 1267-74). There is a great number of clinical and preclinical reports of successful thrombomodulin treatment in inflammatory conditions. (Ito T, et al., *Thrombomodulin as an intravascular safeguard against inflammatory and thrombotic diseases*, Expert Opin Ther Targets, 2016; 20(2):151-8). Recombinant thrombomodulin is efficaciously used in Japan to treat patients with disseminated intravascular coagulation in sepsis. (Yamakawa K, et al., *Recombinant*

*Human Soluble Thrombomodulin in Sepsis-Induced Coagulopathy: An Updated Systematic Review and Meta-Analysis*, Thrombosis and Haemostasis, 2019; 119(1):56-65).

Haptoglobin

The major mission of the acute phase protein haptoglobin is to bind and eliminate extracellular hemoglobin, but haptoglobin also captures extracellular HMGB1. (Yang H, et al., *Identification of CD163 as an antiinflammatory receptor for HMGB1-haptoglobin complexes*, JCI Insight, 2016; 1(7)). Hemorrhage in an inflammatory process will dislocate HMGB1 from haptoglobin and fuel inflammation, since haptoglobin has an exceptionally strong affinity for hemoglobin. Haptoglobin-HMGB1 complexes bind to CD163 on macrophages activating an anti-inflammatory response mediated via production of IL-10 and heme-oxygenase 1. (Id.) Therapeutic administration of haptoglobin improved septic shock, lung injury, and survival in an experimental pneumonia model. (Remy K E, et al., *Haptoglobin improves shock, lung injury, and survival in canine pneumonia*. JCI Insight. 2018; 3(18)). Haptoglobin is approved in Japan to treat patients with trauma, burns, and transfusion-related hemolysis.

Resveratrol

Resveratrol is a phytoalexin phenol molecule acting as a protective endogenous antibiotic when produced in plants under stress. Resveratrol suppresses TLR4 expression (Yang Y, et al., *Resveratrol reduces the proinflammatory effects and lipopolysaccharide-induced expression of HMGB1 and TLR4 in RAW264.7 cells*, Cellular Physiology and Biochemistry: International Journal of Experimental Cellular Physiology, Biochemistry, and Pharmacology. 2014; 33(5):1283-92) and both in vitro and in vivo studies demonstrate that resveratrol activates SIRT1 to reduce HMGB1/TLR4/MyD88/NF-κB signaling. (Le K, et al., *SIRT1-regulated HMGB1 release is partially involved in TLR4 signal transduction: A possible anti-neuroinflammatory mechanism of resveratrol in neonatal hypoxic-ischemic brain injury*, International Immunopharmacology, 2019; 75:105779 (73)). These results indicate that resveratrol ameliorates inflammation in part via inhibited HMGB1/TLR4-mediated signaling.

Statins

Statins are used extensively for treatment of cardiovascular diseases due to their cholesterol-lowering effects, but they also exert beneficial anti-inflammatory effects. These effects are partly brought about by inhibition of both the HMGB1/TLR4- and HMGB1/RAGE-mediated pathways. (Liu M, et al., Simvastatin suppresses vascular inflammation and atherosclerosis in ApoE(-/-) mice by downregulating the HMGB1-RAGE axis, Acta Pharmacologica Sinica, 2013; 34(6):830-6; Wu B, et al., *Short-time pretreatment of rosuvastatin attenuates myocardial ischemia and reperfusion injury by inhibiting high mobility group box 1 protein expression*, International Journal of Cardiology, 2013; 168 (5):4946-8; Han Q F, et al., *Simvastatin protects the heart against ischemia reperfusion injury via inhibiting HMGB1 expression through PI3K/Akt signal pathways*, International Journal of Cardiology, 2015; 201:568-9; Zhu Z, Fang Z, *Statin protects endothelial cell against ischemia reperfusion injury through HMGB1/TLR4 pathway*, International Journal of Cardiology, 2016; 203:74; Zhang H, et al., *Rosuvastatin reduces the pro-inflammatory effects of adriamycin on the expression of HMGB1 and RAGE in rats*, International Journal of Molecular Medicine, 2018; 42(6):3415-23). The expression of HMGB1, RAGE, and TLR4 were all reduced by statin treatment in different vascular inflammatory diseases.

Glycyrrhizin

Glycyrrhizin is an active component extracted from licorice plant roots and acts as an HMGB1 antagonist. It is widely utilized in traditional Chinese medicine to treat inflammatory conditions. Glycyrrhizin attenuated pulmonary inflammation, decreased microvascular permeability and HMGB1 release in an experimental model of LPS-induced acute lung injury. (Qu L, et al., *Glycyrrhizic acid ameliorates LPS-induced acute lung injury by regulating autophagy through the PI3K/AKT/mTOR pathway*, American Journal of Translational Research, 2019; 11(4):2042-55).

Acetylcholine

RAGE-mediated endocytosis of HMGB1 complexes with other proinflammatory molecules is restrained by acetylcholine, α7 nicotinic acetylcholine receptor (α7nAChR) agonists, recombinant HMGB1 box A protein, one anti-HMGB1 mAb (2G7), and dynamin inhibitors as revealed by in vitro experiments. (Yang H, et al., *Inhibition of HMGB1/RAGE-mediated endocytosis by HMGB1 antagonist box A, anti-HMGB1 antibodies, and cholinergic agonists suppresses inflammation*. Molecular Medicine (Cambridge, Mass.). 2019; 25(1):13). Acetylcholine signaling via α7nAChR has also been reported to protect against LPS-induced acute lung injury by inhibiting the TLR4/MyD88/NF-κB signaling pathway. (Zi S F, et al., *Dexmedetomidine-mediated protection against septic liver injury depends on TLR4/MyD88/NF-kappaB signaling downregulation partly via cholinergic anti-inflammatory mechanisms*, International Immunopharmacology, 2019; 76:105898).

Acetylcholine-mediated amelioration of inflammation can be accomplished by electrical stimulation of the vagus nerve. (Pavlov V A, et al., *Molecular and Functional Neuroscience in Immunity*, Annu Rev Immunol, 2018; 36:783-812). Surgical implantation of vagus nerve pacemakers has demonstrated highly beneficial therapeutical results in rheumatoid arthritis and Crohn's disease. (Koopman F A, et al., *Vagus nerve stimulation inhibits cytokine production and attenuates disease severity in rheumatoid arthritis*, Proceedings of the National Academy of Sciences of the United States of America, 2016; 113(29):8284-9. (82)). A need for surgery can be circumvented by transauricular vagus nerve stimulation using an external pulse generator, which is an inexpensive device meant for personal use. (Hong G S, et al., *Non-invasive transcutaneous auricular vagus nerve stimulation prevents postoperative ileus and endotoxemia in mice*, Neurogastroenterology and Motility: the Official Journal of the European Gastrointestinal Motility Society, 2019; 31(3): e13501). Furthermore, transcutaneous vagus nerve stimulation reduced systemic HMGB1 levels and improved survival in an experimental sepsis model. (Huston J M, et al., *Transcutaneous vagus nerve stimulation reduces serum high mobility group box 1 levels and improves survival in murine sepsis*, Critical Care Medicine, 2007; 35(12):2762-8).

Galantamine

Another approach to confer cholinergic control over inflammation might be to use the centrally acting acetylcholinesterase inhibitor galantamine. (Pavlov V A, et al., *Molecular and Functional Neuroscience in Immunity*, Annu Rev Immunol, 2018; 36:783-812). Galantamine is in clinical use for counteracting cognitive impairment in Alzheimer's disease, but has also been demonstrated to ameliorate inflammation in the metabolic syndrome. (Consolim-Colombo F M, et al., *Galantamine alleviates inflammation and insulin resistance in patients with metabolic syndrome in a randomized trial*, JCI Insight, 2017; 2(14)).

Dexmedetomidine

Dexmedetomidine is a potent α2-adrenergic receptor agonist widely used for sedation in intensive care medicine. The compound also reduces systemic proinflammatory cytokine release through the cholinergic anti-inflammatory pathway via α7nAChR-dependent signaling. (Xiang H, et al., *Dexmedetomidine controls systemic cytokine levels through the cholinergic anti-inflammatory pathway*, Inflammation, 2014; 37(5):1763-70). Administration of dexmedetomidine has been demonstrated to increase the discharge frequency of cervical vagus nerves resulting in reduced release of proinflammatory mediators and improved survival in experimental endotoxemia. (Id.) Histological studies of lung sections from LPS-induced lung injury revealed reduced expression of TLR4 and HMGB1. (Meng L, et al., *The protective effect of dexmedetomidine on LPS-induced acute lung injury through the HMGB1-mediated TLR4/NF-kappaB and PI3K/Akt/mTOR pathways*, Mol Immunol, 2018; 94:7-17). Furthermore, combined dexmedetomidine-ketamine treatment mitigated pulmonary inflammatory response induced by ventilator-induced lung injury in endotoxemic rats. (Yang C L, et al., *Protective effects of dexmedetomidine-ketamine combination against ventilator-induced lung injury in endotoxemia rats*, The Journal of Surgical Research. 2011; 167(2):e273-81).

Ketamine

Ketamine is another extensively used pharmacological substance in anesthesia and is judged as safe and to facilitate hemodynamically stable anesthesia or sedation. It also mediates anti-inflammatory functions including inhibition of HMGB1 secretion from activated macrophages (89). Furthermore, ketamine has been shown to attenuate sepsis-induced acute lung injury via a functional down-regulation of the HMGB1-RAGE pathway in preclinical studies. (Zhang Y, et al., *Ketamine alleviates LPS induced lung injury by inhibiting HMGB1-RAGE level*, European Review for Medical and Pharmacological Sciences, 2018; 22(6): 1830-6). Ketamine reduced the recruitment of neutrophils and monocytes into the inflamed lungs, diminished myeloperoxidase activity and the expression of HMGB1 and TLR4. (Li K, et al., *Ketamine attenuates sepsis-induced acute lung injury via regulation of HMGB1-RAGE pathways*, International Immunopharmacology, 2016; 34:114-28; Qin M Z, et al., *Ketamine effect on HMGB1 and TLR4 expression in rats with acute lung injury*, International Journal of Clinical and Experimental Pathology, 2015; 8(10):12943-8). Since SARS-CoV-2 patients with severe ARDS may need a long period with ventilator support, ketamine could be considered to be incorporated into the sedation protocol for these patients.

P5779 (SEQ ID NO: 1)

A small peptide antagonist, P5779 (SEQ ID NO: 1), that inhibits HMGB1 from binding to the TLR4/MD-2 receptor complex, blocks this signaling and significantly improves survival in mice when administered after a lethal dose of influenza (Shirey K A, *Novel strategies for targeting innate immune responses to influenza*, Mucosal Immunol., 2016; 9(5):1173-82). This peptide also has therapeutic benefit in mouse models of sepsis and acute liver toxicity. (Yang H, *MD-2 is required for disulfide HMGB1-dependent TLR4 signaling*, J Exp Med., 2015; 212(1):5-14).

OBJECTS AND SUMMARY OF THE INVENTION

It is an object of the invention to treat sepsis by targeting HMGB1.

It is an object of the invention to treat sepsis by targeting HMGB1 using an HMGB1 antagonist(s) as a therapeutic agent(s) for reducing mortality and rescuing long-lasting sequelae of sepsis.

It is a further object of the invention to treat sepsis by targeting HMGB1 using an HMGB1 antagonist that has a significantly greater in vitro and in vivo stability than previously known small molecules or non-antibody HMGB1 antagonists.

It is a further object of the invention to treat sepsis by targeting HMGB1 using an HMGB1 antagonist that is a peptidomimetic small molecule modeled after an HMGB1 antagonist tetramer peptide.

It is a further object of the invention to treat sepsis by targeting HMGB1 using an HMGB1 antagonist tetramer peptide which has been stabilized by azatide linkages.

It is a further object of the invention for the HMGB1 antagonist K883 to be used in the treatment and/or prevention and/or inhibition of severe sepsis in mammals.

It is an object of this invention to develop novel therapeutic approaches to treat ALI, including influenza-induced ALI, and other forms of inflammatory disease to reduce morbidity and mortality.

It is an object of the invention to treat ALI by targeting HMGB1.

It is a further objection of the invention is to advance a small molecule for reducing mortality and pathology associated with ALI.

It is a further object of the invention to develop a novel therapeutic to restrain the unchecked inflammation that precipitates ALI.

It is a further object of the invention to treat ALI by targeting HMGB1 using an HMGB1 antagonist that has a significantly greater in vitro and in vivo stability than previously known small molecules or non-antibody HMGB1 antagonists.

It is a further object of the present application to evaluate therapeutic potential of certain HMGB1 antagonists for reducing influenza-induced ALI in mice.

It is a further object of the invention to provide treat ALI by targeting HMGB1 using an HMGB1 antagonist that is a peptidomimetic small molecule modeled after an HMGB1 antagonist tetramer peptide.

It is a further object of the invention to treat ALI by targeting HMGB1 using an HMGB1 antagonist tetramer peptide which has been stabilized by azatide linkages.

It is a further object of the invention for the HMGB1 antagonist K883 to be used in the treatment and/or prevention and/or inhibition of ALI in mammals.

It is a further object of the invention to attenuate HMGB1-driven inflammation (e.g., caused by ALI) without impairing the immune response to microbes.

It is a further object of the invention to provide a novel therapeutic target, HMGB1/TLR4/MD-2 signaling, for treating acute lung injury, a condition that kills one in three afflicted patients.

It is a further goal to develop a novel therapeutic to restrain the unchecked inflammation that precipitates ALI.

It is an object of this invention to develop novel therapeutic approaches to treat bacterial and viral respiratory infections such as influenza and SARS-CoV-2, to reduce morbidity and mortality.

It is an object of the invention to treat bacterial and viral respiratory infections such as influenza and SARS-CoV-2 by targeting HMGB1.

It is a further objection of the invention is to advance a small molecule for reducing mortality and pathology associated with bacterial and viral respiratory infections such as influenza and SARS-CoV-2.

It is a further object of the invention to develop a novel therapeutic to restrain the unchecked inflammation that precipitates bacterial and viral respiratory infections such as influenza and SARS-CoV-2.

It is a further object of the invention to treat bacterial and viral respiratory infections such as influenza and SARS-CoV-2 by targeting HMGB1 using an HMGB1 antagonist that has a significantly greater in vitro and in vivo stability than previously known small molecules or non-antibody HMGB1 antagonists.

It is a further object of the present application to evaluate therapeutic potential of certain HMGB1 antagonists for reducing ALI induced by bacterial and viral respiratory infections such as influenza and SARS-CoV-2.

It is a further object of the invention to provide treat bacterial and viral respiratory infections such as influenza and SARS-CoV-2 by targeting HMGB1 using an HMGB1 antagonist that is a peptidomimetic small molecule modeled after an HMGB1 antagonist tetramer peptide.

It is a further object of the invention to treat bacterial and viral respiratory infections such as influenza and SARS-CoV-2 by targeting HMGB1 using an HMGB1 antagonist tetramer peptide which has been stabilized by azatide linkages.

It is a further object of the invention for the HMGB1 antagonist K883 to be used in the treatment and/or prevention and/or inhibition of bacterial and viral respiratory infections such as influenza and SARS-CoV-2 in mammals.

It is a further object of the invention to attenuate HMGB1-driven inflammation (e.g., caused by bacterial and viral respiratory infections such as influenza and SARS-CoV-2 without impairing the immune response to microbes.

It is a further object of the invention to provide a novel therapeutic target, HMGB1/TLR4/MD-2 signaling, for treating bacterial and viral respiratory infections such as influenza and SARS-CoV-2.

It is a further goal to develop a novel therapeutic to restrain the unchecked inflammation caused by bacterial and viral respiratory infections such as influenza and SARS-CoV-2 that precipitates ALI.

It is also an object of the present invention to selectively target a HMGB1 isoform-specific signaling pathway that plays a critical role in the occurrence and development of Neuropathic Pain for the treatment of painful Diabetic Peripheral Neuropathy (DPN). (Agalave N., *Spinal disulfide HMGB1, but not all-thiol HMGB1, induces mechanical hypersensitivity in a TLR4-dependent manner*, Scandinavian Journal of Pain, 2015; 8: 47; Wang Y., *Tanshinone IIA Attenuates Chronic Pancreatitis-Induced Pain in Rats via Downregulation of HMGB1 and TRL4 Expression in the Spinal Cord*, Pain Physician, 2014; 18(4): E615-628).

It is a further object of the invention to treat neuropathic pain, and in particular DPN, by targeting HMGB1 and the HMGB1 isoform specific signaling pathway.

It is a further object of the invention to treat neuropathic pain, and in particular DPN, by targeting HMGB1 using an HMGB1 antagonist(s) as a therapeutic agent(s) for reducing painful DPN.

It is also an object of the present invention to treat diabetic patients in general by targeting HMGB1-mediated inflammatory pathways which underlie adipose tissue inflammation, insulin resistance and islet dysfunction in diabetes.

It is a further object of the invention to treat neuropathic pain, and in particular DPN by targeting HMGB1 using an HMGB1 antagonist that has a significantly greater in vitro and in vivo stability than previously known small molecules or non-antibody HMGB1 antagonists.

It is a further object of the invention to treat neuropathic pain, and in particular DPN by targeting HMGB1 using an HMGB1 antagonist that has improved oral bioavailability than previously known HMGB1 antagonists.

It is a further object of the invention to treat neuropathic pain, and in particular DPN by targeting HMGB1 using an HMGB1 antagonist that is suitable for subcutaneous administration.

It is a further object of the invention to treat neuropathy pain, and in particular DPN, by targeting HMGB1 using an HMGB1 antagonist that is a peptidomimetic small molecule modeled after an HMGB1 antagonist tetramer peptide.

It is a further object of the invention to treat neuropathic pain, and in particular DPN by targeting HMGB1 using an HMGB1 antagonist tetramer peptide which has been stabilized by azatide linkages.

It is further object of the invention to develop a K883 derivative with improved oral bioavailability when compared to K883 (>20%).

It is further object of the invention to develop a K883 derivative with improved subcutaneous bioavailability when compared to K883.

It is a further object of the invention to define PK parameters of subcutaneous K883.

It is a further object of the invention to confirm the mechanism and in vivo efficacy of selective HMGB1-TLR4/MD-2 inhibition in diabetic neuropathic pain.

It is a further object of the invention for the HMGB1 antagonist K883 to be used in the treatment and/or prevention and/or inhibition of painful diabetic peripheral neuropathy in mammals.

It is an object of the invention to develop a pharmaceutical composition comprising a therapeutically effective amount of a peptidomimetic molecule.

It is a further object to develop the above pharmaceutical compositions in an oral dosage form and in a parental dosage form.

It is a further object of the invention for the pharmaceutical composition to be a dosage form selected from the group consisting of an oral dosage form, a parenteral dosage form, a buccal dosage form, a sublingual dosage form, a nasal dosage form, an inhaler, a nebulizer, a topical dosage form, a transdermal dosage form and a suppository.

In connection with the above objects and others, the invention is directed in part to a method of treating and/or preventing and/or inhibition of severe sepsis in a mammal comprising administering to a mammal a therapeutically effective amount of a peptidomimetic small molecule modeled after an HMGB1 antagonist tetramer peptide. In certain preferred embodiments, the peptidomimetic small molecule is an HMGB1 antagonist tetramer peptide which has been stabilized with at least one azatide linkage. In further preferred embodiments, the peptidomimetic small molecule peptidomimetic small molecule is a modified P5779 (SEQ ID NO" 1) wherein the terminal peptide bonds have been replaced with azatide linkages. Most preferably, the peptidomimetic small molecule is K883.

The invention is also directed, in part, to a method of treating and/or preventing and/or inhibiting ALI in a mammal comprising administering to a mammal a therapeutically effective amount of a peptidomimetic small molecule modeled after an HMGB1 antagonist tetramer peptide. In certain preferred embodiments, the peptidomimetic small molecule is an HMGB1 antagonist tetramer peptide which has been stabilized with at least one azatide linkage. In further preferred embodiments, the peptidomimetic small molecule is a modified P5779 (SEQ ID NO: 1) wherein the terminal peptide bonds have been replaced with azatide linkages. Most preferably, the peptidomimetic small molecule is K883.

The invention is also directed, in part, to a method of treating and/or preventing and/or inhibiting the adverse consequences of bacterial and viral respiratory infections where increased HMGB1 is implicated, such as in infections by influenza and/or corona viruses such as SARS-CoV-2, in a mammal comprising administering to a mammal a therapeutically effective amount of a peptidomimetic small molecule modeled after an HMGB1 antagonist tetramer peptide. In certain preferred embodiments, the peptidomimetic small molecule is an HMGB1 antagonist tetramer peptide which has been stabilized with at least one azatide linkage. In further preferred embodiments, the peptidomimetic small molecule is a modified P5779 (SEQ ID NO: 1) wherein the terminal peptide bonds have been replaced with azatide linkages. Most preferably, the peptidomimetic small molecule is K883.

The invention is additionally directed, in part, to a method of treating and/or preventing and/or inhibiting neuropathic pain, and in particular, diabetic peripheral neuropathy (DPN) in a mammal comprising administering to a mammal a therapeutically effective amount of a peptidomimetic small molecule modeled after an HMGB1 antagonist tetramer peptide. In certain preferred embodiments, the peptidomimetic small molecule is an HMGB1 antagonist tetramer peptide which has been stabilized with at least one azatide linkage. In certain preferred embodiments of the invention, the peptidomimetic small molecule is a modified P5779 (SEQ ID NO: 1) wherein at least one terminal peptide bond has been replaced with an azatide linkage. Most preferably, the peptidomimetic small molecule is K883.

The invention is further directed in part to a method of treating and/or preventing and/or inhibiting neuropathic pain and/or inhibiting, and in particular, DPN in a mammal comprising administering to a mammal a therapeutically effective amount of a peptidomimetic small molecule modeled after an HMGB1 antagonist tetramer peptide, wherein the peptidomimetic small molecule is K883, a derivative of K883 or a derivative of P5779 (SEQ ID NO: 1).

The invention is further directed to pharmaceutical compositions containing K883. The pharmaceutical compositions may be formulated for oral delivery, parenteral (e.g., intravenous) delivery. In further embodiments, the pharmaceutical composition containing K883 may be designed for buccal or sublingual delivery, nasal delivery, inhalation or nebulization delivery, topical or transdermal delivery, or as a suppository.

In certain preferred embodiments, a pharmaceutical composition containing a therapeutically effective amount of K883 is administered to a mammal (e.g., human) suffering from severe sepsis. In certain other preferred embodiments, a pharmaceutical composition containing a therapeutically effective amount of K883 is administered to a mammal (e.g., human) suffering from ALI. In certain other preferred embodiments, a pharmaceutical composition containing a therapeutically effective amount of K883 is administered to a mammal (e.g., human) suffering from bacterial and/or viral respiratory infections such as influenza and SARS-CoV-2. In certain other preferred embodiments, a pharmaceutical composition containing a therapeutically effective amount of K883 is administered to a mammal (e.g., human) suffering from neuropathic pain and in particular diabetic peripheral neuropathy (DPN). The pharmaceutical composition may be administered orally, parenterally (e.g., intravenously, subcutaneously, intramuscularly), or via buccal, intranasal, inhalation or nebulization delivery, transdermal, topical, or sublingual routes, or via suppository.

Certain preferred embodiments of the invention are directed to pharmaceutical compositions, the aqueous (water) solubility of the HMGB1 antagonist tetramer peptide which has been stabilized with at least one azatide linkage is greater than about 1 mg/ml. In other preferred embodiments, the aqueous (water) solubility of the HMGB1 antagonist tetramer peptide which has been stabilized with at least one azatide linkage is greater than about 5 mg/ml.

In certain preferred embodiments of the invention, the HMGB1 antagonist tetramer peptide which has been stabilized with at least one azatide linkage is stable for greater than 30 minutes, greater than 45 minutes or most preferably greater than 60 minutes in plasma or simulated stomach acid.

In certain preferred embodiments of the invention, HMGB1 antagonist tetramer peptide is stabilized with at least one azatide linkage and then is incorporated into an oral pharmaceutical composition.

Certain embodiments of the invention are directed to a method of treating and/or preventing and/or inhibiting severe sepsis. Certain preferred embodiments of the invention are directed to a method of treating and/or preventing and/or inhibiting severe sepsis, in a mammal comprising administering to a mammal a therapeutically effective amount of a peptidomimetic small molecule modeled after an HMGB1 antagonist tetramer peptide. In preferred embodiments, the peptidomimetic small molecule is an HMGB1 antagonist tetramer peptide which has been stabilized with at least one azatide linkage and in certain preferred embodiments, the peptidomimetic small molecule is a modified P5779 (SEQ ID NO: 1). In certain preferred embodiments, the modified P5779 (SEQ ID NO: 1) has at least one azatide linkage located at a terminal peptide bond. In certain preferred embodiments, the modified P5779 (SEQ ID NO: 1) has terminal peptide bonds which have been replaced with azatide linkages. In preferred embodiments, the peptidomimetic small molecule is K883. In certain embodiments, the peptidomimetic small molecule is a derivative of K883 or P5779 (SEQ ID NO: 1). In certain embodiments of the K883 is combined with an excipient comprising PBS:PEG 300:propylene glycol:polysorbate 80 at 50:40:5:5. In preferred embodiments, the mammal is a human. In preferred embodiments, the method of administration is selected from oral delivery, parenteral delivery, buccal delivery, sublingual delivery, nasal delivery, inhalation delivery, nebulization delivery, topical delivery, transdermal delivery and suppository delivery. In certain embodiments, the modified P5779 (SEQ ID NO: 1) is stable for greater than 60 minutes in plasma or simulated stomach acid. In certain embodiments, the aqueous solubility of the modified P5779 (SEQ ID NO: 1) is greater than about 1 mg/ml and in other embodiments, the aqueous solubility of the modified P5779 (SEQ ID NO: 1) is greater than about 5 mg/ml In certain preferred embodiments of the invention, the method is a treatment of sepsis, comprising identifying a human patient exhibiting symptoms of sepsis, and administering K883.

Certain embodiments of the invention are directed to a method of treatment and/or prevention and/or inhibition comprising treating a mammal for a disease or condition selected from the group consisting of non-influenza pulmonary infections, smoke or toxic gas inhalation, gastric acid aspiration, transfusion reactions, reactions and injuries caused by mechanical ventilation arthritis, colitis, sterile ischemia, traumatic injury, cancer and infection, hemorrhagic shock, endotoxemia, gastrointestinal disorders including gastrointestinal inflammation, inflammatory bowel disease such as cecal perforation, intraperitoneal LPS injection, and IBD based on chemically induced colitis, respiratory disorders including sepsis, inflammatory lung injury, acute lung injury, patients subjected to long-term ventilator therapy and cystic fibrosis, autoimmune diseases such as arthritis, dermatomyositis, multiple sclerosis, systemic lupus erythematosus (SLE), celiac disease, chronic fatigue syndrome, Crohn's disease, type 1 diabetes, Graves disease, juvenile arthritis, chronic Lyme disease, myocarditis, myositis, polymyositis, post-myocardial infarction syndrome, psoriasis, psoriatic arthritis, reactive arthritis, rheumatic fever, scleroderma, Sjogren's syndrome, thrombocytopenia, ulcerative colitis; neurodegenerative diseases including Alzheimer's, mild cognitive impairment (pre-Alzheimer's), Parkinson's disease, amyotrophic lateral sclerosis (ALS); arthritis including osteoarthritis (OA), arthritic joint inflammation, juvenile idiopathic arthritis (JIA) and serum rheumatoid arthritis (RA); asthma; cancer, including pancreatic cancer, colorectal cancer, skin cancers including melanoma; cardiac and vessel disease including coronary artery disease (CAD), coronary heart disease, acute coronary, and atherosclerosis, heart failure; metabolic disorders including type 2 diabetes; β-cell transplantation in diabetes; lung injury and lung related diseases including COPD, pulmonary hypertension, pulmonary fibrosis and pneumonia; Intensive care unit patients being treated for various conditions including sepsis, systemic inflammatory response syndrome, severe trauma, blunt chest trauma, hemorrhagic shock/trauma, traumatic brain injury, stroke, spinal cord injury, influenza, chemical toxicity, severe viral or bacterial infections; post-sepsis impairments including cognitive impairments, persistent splenomegaly, post sepsis anemia; post-surgery neurocognitive disorders; drug induced liver injury including acetaminophen-induced liver injury, ethanol-induced liver diseases, cryopyrin-associated autoinflammatory syndrome, bleomycin induced lung fibrosis and paracetamol intoxication; nociceptive pain; ischemia (with or without reperfusion), including cardiac ischemia, cerebral ischemia and skeletal muscle ischemia; inflammatory bowel disease; kidney and liver related disease including kidney failure and liver failure, hepatic ischemia/reperfusion injury, acute kidney injury (CHD), chronic kidney disease (CKD), acute liver failure (ALF) including ALF-SIRS and ALF-systemic, liver fibrosis and alcoholic liver disease; trauma/ischemia caused by transplant and graft-versus-host disease; obesity/metabolic syndrome; pancreatitis; pregnancy complication such as preeclampsia; epilepsy; pulmonary arterial hypertension (PAH); chronic pain; chronic inflammation; chronic inflammatory diseases including chronic obstructive pulmonary disease (COPD), atherosclerosis and arthritic joint inflammation; and other diseases causing moderate to severe pain but not limited to post-surgical pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, and injuries, peptic ulcers, gastritis, regional enteritis, ulcerative colitis, diverticulitis or with a recurrent history of gastrointestinal lesions; GI bleeding, coagulation disorders including anemia such as hypoprothrombinemia, hemophilia or other bleeding problems; kidney disease, chronic fatigue syndrome, traumatic brain injury, concussion and migraines wherein the treatment/prevention/inhibition comprises administering to the mammal a therapeutically effective amount of a peptidomimetic small molecule modeled after an HMGB1 antagonist tetramer peptide. Certain preferred embodiments of the invention are directed to a method of treating and/or preventing and/or inhibiting one of the afore-mentioned diseases, in a mammal comprising administering to a mammal a therapeutically effective amount of a peptidomimetic small molecule modeled after an HMGB1 antagonist tetramer peptide. In preferred embodiments, the peptidomimetic small molecule is an HMGB1 antagonist tetramer peptide which has been stabilized with at least one azatide linkage and in certain preferred embodiments, the peptidomimetic small molecule is a modified P5779 (SEQ ID NO: 1). In certain preferred embodiments, the modified P5779 (SEQ ID NO: 1) has at least one azatide linkage located at a terminal peptide bond. In certain preferred embodiments, the modified P5779 (SEQ ID NO: 1) has terminal peptide bonds which have been replaced with azatide linkages. In preferred embodiments, the peptidomimetic small molecule is K883. In certain embodiments, the peptidomimetic small molecule is a derivative of K883 or P5779 (SEQ ID NO: 1). In certain embodiments of the K883 is combined with an excipient comprising PBS:PEG 300:propylene glycol:polysorbate 80 at 50:40:5:5. In preferred embodiments, the mammal is a human. In preferred embodiments, the method of administration is selected from oral delivery, parenteral delivery, buccal delivery, sublingual delivery, nasal delivery, inhalation delivery, nebulization delivery, topical delivery, transdermal delivery and suppository delivery. In certain embodiments, the modified P5779 (SEQ ID NO: 1) is stable for greater than 60 minutes in plasma or simulated stomach acid. In certain embodiments, the aqueous solubility of the modified P5779 (SEQ ID NO: 1) is greater than about 1 mg/ml and in other embodiments, the aqueous solubility of the modified P5779 (SEQ ID NO: 1) is greater than about 5 mg/ml In certain preferred embodiments of the invention, the method is a treatment for one of the diseases or conditions above, comprising identifying a human patient exhibiting symptoms of the disease or condition, and administering K883.

Certain embodiments of the invention are directed to a method of treating, preventing or inhibiting adverse conditions relating to surgery or the administration of anticoagulants, comprising administering to the mammal a therapeutically effective amount of a peptidomimetic small molecule modeled after an HMGB1 antagonist tetramer peptide prior to the surgery or the administration of the anticoagulants. Certain preferred embodiments of the invention are directed treating or inhibiting adverse conditions relating to surgery or the administration of anticoagulants in a mammal comprising administering to a mammal a therapeutically effective amount of a peptidomimetic small molecule modeled after an HMGB1 antagonist tetramer peptide. In preferred embodiments, the peptidomimetic small molecule is an HMGB1 antagonist tetramer peptide which has been stabilized with at least one azatide linkage and in certain preferred embodiments, the peptidomimetic small molecule is a modified P5779 (SEQ ID NO: 1). In certain preferred embodiments, the modified P5779 (SEQ ID NO: 1) has at least one azatide linkage located at a terminal peptide bond.

In certain preferred embodiments, the modified P5779 (SEQ ID NO: 1) has terminal peptide bonds which have been replaced with azatide linkages. In preferred embodiments, the peptidomimetic small molecule is K883. In certain embodiments, the peptidomimetic small molecule is a derivative of K883 or P5779 (SEQ ID NO: 1). In certain embodiments of the K883 is combined with an excipient comprising PBS:PEG 300:propylene glycol:polysorbate 80 at 50:40:5:5. In preferred embodiments, the mammal is a human. In preferred embodiments, the method of administration is selected from the group consisting of oral delivery, parenteral delivery, buccal delivery, sublingual delivery, nasal delivery, inhalation delivery, nebulization delivery, topical delivery, transdermal delivery and suppository delivery. In certain embodiments, the modified P5779 (SEQ ID NO: 1) is stable for greater than 60 minutes in plasma or simulated stomach acid. In certain embodiments, the aqueous solubility of the modified P5779 (SEQ ID NO: 1) is greater than about 1 mg/ml and in other embodiments, the aqueous solubility of the modified P5779 (SEQ ID NO: 1) is greater than about 5 mg/ml In certain preferred embodiments of the invention, the method is a treatment of adverse conditions relating to surgery or the administration of anticoagulants, comprising identifying a human patient exhibiting symptoms of adverse conditions relating to surgery or the administration of anticoagulants, and administering K883.

Certain embodiments of the invention are directed to a method of treating and/or preventing and/or inhibiting ALI. Certain embodiments of the invention are directed to a method of treating and/or preventing and/or inhibiting ALI, and in particular reducing influenza-induced ALI in a mammal comprising administering to a mammal a therapeutically effective amount of a peptidomimetic small molecule modeled after an HMGB1 antagonist tetramer peptide. In certain embodiments, the peptidomimetic small molecule is an HMGB1 antagonist tetramer peptide which has been stabilized with at least one azatide linkage. In certain embodiments, the invention is directed to a method for preparing a treatment for acute lung injury, comprising modifying P5779 (SEQ ID NO: 1) with at least one azatide linkage and in certain further embodiments, the modified P5779 (SEQ ID NO: 1) has at least one azatide linkage located at a terminal peptide bond. In certain further embodiments, the modified P5779 (SEQ ID NO: 1) is K883. In certain embodiments, the peptidomimetic small molecule is a derivative of K883 or P5779 (SEQ ID NO: 1). In certain embodiments, the peptidomimetic small molecule is a modified P5779 (SEQ ID NO: 1) wherein at least one terminal peptide bond has been replaced with an azatide linkage and in certain embodiments, the peptidomimetic small molecule is a modified P5779 (SEQ ID NO: 1) wherein the terminal peptide bonds have been replaced with azatide linkages. In certain embodiments, the mammal is a human. In certain embodiments, the method of administration is selected from the group consisting of oral delivery, parenteral delivery, buccal delivery, sublingual delivery, nasal delivery, inhalation delivery, nebulization delivery, topical delivery, transdermal delivery and suppository delivery. In certain embodiments, the aqueous solubility of the modified P5779 (SEQ ID NO: 1) is greater than about 1 mg/ml and in other embodiments, the aqueous solubility of the modified P5779 (SEQ ID N: 1) is greater than about 5 mg/ml. In certain embodiments, the modified P5779 (SEQ ID NO: 1) is stable for greater than 60 minutes in plasma or simulated stomach acid. In certain preferred embodiments, the therapeutically effective amount is orally administered to the mammal and in other preferred embodiments, the therapeutically effective amount is intravenously administered to the mammal. In certain preferred embodiments, the peptidomimetic small molecule is K883. In certain preferred embodiments, the K883 is combined with an excipient comprising PBS:PEG 300:propylene glycol:polysorbate 80 at 50:40:5:5. In certain preferred embodiments, the method of treatment of acute lung injury, comprises identifying a human patient exhibiting symptoms of acute lung injury, and administering K883.

Certain embodiments of the invention are directed to a method of treating and/or preventing and/or inhibiting bacterial and viral respiratory infections such as influenza and SARS-CoV-2 severe sepsis. Certain embodiments of the invention are directed to a method of treating and/or preventing and/or inhibiting the effects of COVID-19 or other SARS viruses in a mammal comprising administering to a mammal a therapeutically effective amount of a peptidomimetic small molecule modeled after an HMGB1 antagonist tetramer peptide. In certain embodiments, the peptidomimetic small molecule is an HMGB1 antagonist tetramer peptide which has been stabilized with at least one azatide linkage. In certain embodiments, the invention is directed to a method for preparing a treatment of the effects of COVID-19 or other SARS viruses, comprising modifying P5779 (SEQ ID NO: 1) with at least one azatide linkage and in certain further embodiments, the modified P5779 (SEQ ID NO: 1) has at least one azatide linkage located at a terminal peptide bond. In certain further embodiments, the modified P5779 (SEQ ID NO: 1) is K883. In certain embodiments, the peptidomimetic small molecule is a derivative of K883 or P5779 (SEQ ID NO: 1). In certain embodiments, the peptidomimetic small molecule is a modified P5779 (SEQ ID NO: 1) wherein at least one terminal peptide bond has been replaced with an azatide linkage and in certain embodiments, the peptidomimetic small molecule is a modified P5779 (SEQ ID NO: 1) wherein the terminal peptide bonds have been replaced with azatide linkages. In certain embodiments, the mammal is a human. In certain embodiments, the method of administration is selected from the group consisting of oral delivery, parenteral delivery, buccal delivery, sublingual delivery, nasal delivery, inhalation delivery, nebulization delivery, topical delivery, transdermal delivery and suppository delivery. In certain preferred embodiments, the therapeutically effective amount is orally administered to the mammal and in other preferred embodiments, the therapeutically effective amount is intravenously administered to the mammal. In certain preferred embodiments, the peptidomimetic small molecule is K883. In certain preferred embodiments, the K883 is combined with an excipient comprising PBS:PEG 300:propylene glycol:polysorbate 80 at 50:40:5:5. In certain preferred embodiments, the method of treatment of the effects of COVID-19 or other SARS viruses, comprises identifying a human patient exhibiting symptoms of COVID-19 or other SARS viruses, and administering K883. In certain preferred embodiments, the invention is directed to a method of treating and/or preventing and/or inhibiting bacterial and viral respiratory infections such as influenza and SARS-CoV-2 in a mammal comprising administering to a mammal a therapeutically effective amount of a peptidomimetic small molecule modeled after an HMGB1 antagonist tetramer peptide.

Certain embodiments of the invention are directed to a method of treating and/or preventing and/or inhibiting of peripheral neuropathy. Certain further embodiments of the invention are directed to the neuropathic pain being diabetic neuropathic pain. In other preferred embodiments, the invention is directed to a method of treating and/or preventing and/or inhibiting peripheral neuropathy, and in particular DPN in a mammal comprising administering to a mammal a therapeutically effective amount of a peptidomimetic small molecule modeled after an HMGB1 antagonist tetramer peptide. In certain embodiments, the peptidomimetic small molecule is an HMGB1 antagonist tetramer peptide which has been stabilized with at least one azatide linkage. In certain preferred embodiments the peptidomimetic small molecule is a modified P5779 (SEQ ID NO: 1) wherein at least one terminal peptide bond has been replaced with an azatide linkage and in certain preferred embodiments, the peptidomimetic small molecule peptidomimetic small molecule is a modified P5779 (SEQ ID NO: 1) wherein the terminal peptide bonds have been replaced with azatide linkages. In certain preferred embodiments, the invention is directed to a method of preparing a treatment for neuropathic pain, comprising modifying P5779 (SEQ ID NO: 1) with at least one azatide linkage and in other preferred embodiments comprises modifying P5779 (SEQ ID NO: 1) with at least one azatide linkage located at a terminal peptide bond. In certain preferred embodiments, the peptidomimetic small molecule is K883. In certain embodiments, the peptidomimetic small molecule is a derivative of K883 or P5779 (SEQ ID NO: 1). In certain further embodiments, the K883 is combined with an excipient comprising PBS:PEG 300:propylene glycol:polysorbate 80 at 50:40:5:5. In certain preferred embodiments, the mammal is a human. In embodiments, the method of administration is selected from the group consisting of oral delivery, parenteral delivery, buccal delivery, sublingual delivery, nasal delivery, inhalation delivery, nebulization delivery, topical delivery, transdermal delivery and suppository delivery. In certain preferred embodiments, the therapeutically effective amount is orally administered to the mammal and in other preferred embodiments, the therapeutically effective amount is intravenously administered to the mammal. In certain embodiments, the aqueous solubility of the modified P5779 (SEQ ID NO: 1) is greater than about 1 mg/ml and in other embodiments, the aqueous solubility of the modified P5779 (SEQ ID NO: 1) is greater than about 5 mg/ml. In certain embodiments, the modified P5779 (SEQ ID NO: 1) is stable for greater than 60 minutes in plasma or simulated stomach acid. In certain preferred embodiments, the invention is directed to a method of treatment of neuropathic pain, comprising identifying a human patient exhibiting symptoms of DPN, and administering K883.

Certain embodiments of the invention are directed to a pharmaceutical composition comprising a therapeutically effective amount of a peptidomimetic molecule having the chemical structure:

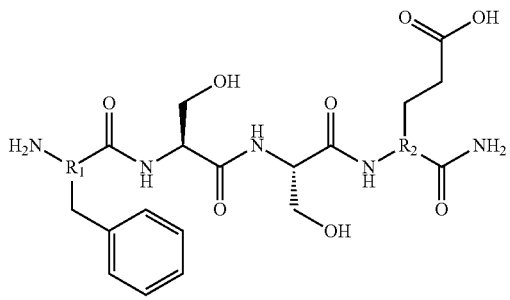

wherein R is C or N; and at least one of $R_1$ and $R_2$ is N to provide an azatide linkage, such that the peptidomimetic molecule is stabilized relative to a peptidomimetic molecule wherein both $R_1$ and $R_2$=C, and at least one pharmaceutically acceptable excipient. Certain embodiments of the present invention are directed to a pharmaceutical composition of claim 1, wherein both terminal peptide bonds have been replaced with azatide linkages such that both $R_1$ and $R_2$=N and the peptidomimetic molecule has the structure:

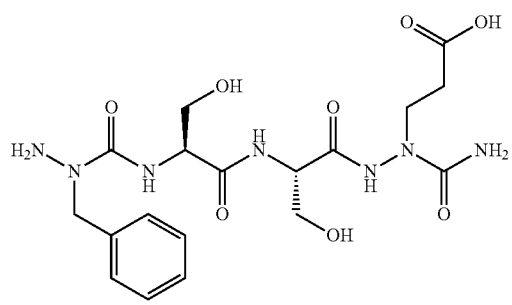

In certain embodiments, the dosage form is selected from the group consisting of an oral dosage form, a parenteral dosage form, a buccal dosage form, a sublingual dosage form, a nasal dosage form, an inhaler, a nebulizer, a topical dosage form, a transdermal dosage form and a suppository. In certain preferred embodiments, the pharmaceutical composition is an oral dosage form, an oral liquid dosage form, or a parenteral dosage form. In certain embodiments, the aqueous solubility of the peptidomimetic molecule is greater than 1 mg/ml and in other embodiments, the aqueous solubility of the peptidomimetic molecule is greater than 5 mg/ml. In certain preferred embodiments, the peptidomimetic molecule is stable for greater than 60 minutes in plasma or simulated stomach acid. In certain embodiments, the peptidomimetic molecule is combined with a pharmaceutical excipient selected from the group consisting of 1) phosphate buffered saline, 2) PEG, 3) propylene glycol and 4) polysorbate 80 and 5) combinations thereof. In certain preferred embodiments, the PEG is PEG 300. In certain embodiments, the peptidomimetic molecule is combined with a pharmaceutical excipient comprising PBS:PEG 300:propylene glycol:polysorbate 80 such that the aqueous solubility of peptidomimetic molecule is greater than 1 mg/ml and in other embodiments so that the aqueous solubility of peptidomimetic molecule is greater than 5 mg/ml. In certain embodiments, the peptidomimetic molecule is combined with a pharmaceutical excipient comprising PBS:PEG 300:propylene glycol:polysorbate 80 in a ratio of about 50:40:5:5.

Certain embodiments of the invention are directed to a pharmaceutical composition comprising a pharmaceutical composition comprising a therapeutically effective amount of a HMGB1 antagonist tetramer peptidomimetic which has been stabilized with at least one azatide linkage, and at least one pharmaceutical excipient. In certain embodiments, the HMGB1 antagonist tetramer peptidomimetic has the chemical structure:

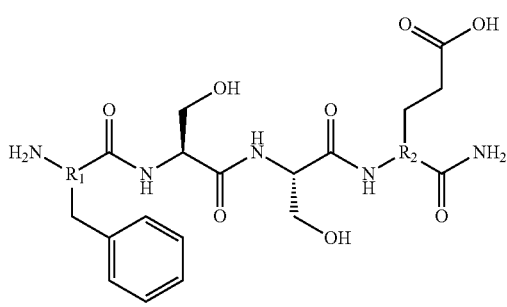

wherein R is C or N; and at least one of $R_1$ and $R_2$ is N to provide an azatide linkage, such that the HMGB1 antagonist tetramer peptidomimetic is stabilized relative to a HMGB1 antagonist tetramer peptide, P5779 (SEQ ID NO: 1), in which both $R_1$ and $R_2$=C. In other embodiments, the terminal peptide bonds have been replaced with azatide linkages such that both $R_1$ and $R_2$=N and the stabilized HMGB1 antagonist tetramer has the structure:

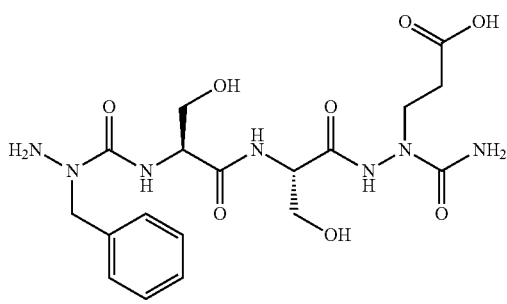 [SMILES: NC(=O)N(CCC(=O)O)NC(=O)[C@H](CO)NC(=O)[C@H](CO)NC(=O)N(N)Cc1ccccc1]

In certain embodiments, the dosage form is selected from the group consisting of an oral dosage form, a parenteral dosage form, a buccal dosage form, a sublingual dosage form, a nasal dosage form, an inhaler, a nebulizer, a topical dosage form, a transdermal dosage form and a suppository. In certain preferred embodiments, the pharmaceutical composition is an oral dosage form, an oral liquid dosage form, or a parenteral dosage form. In certain embodiments, the aqueous solubility of the peptidomimetic molecule is greater than 1 mg/ml and in other embodiments, the aqueous solubility of the peptidomimetic molecule is greater than 5 mg/ml. In certain preferred embodiments, the peptidomimetic molecule is stable for greater than 60 minutes in plasma or simulated stomach acid. In certain embodiments, the peptidomimetic molecule is combined with a pharmaceutical excipient selected from the group consisting of 1) phosphate buffered saline, 2) PEG, 3) propylene glycol and 4) polysorbate 80 and 5) combinations thereof. In certain preferred embodiments, the PEG is PEG 300. In certain embodiments, the peptidomimetic molecule is combined with a pharmaceutical excipient comprising PBS:PEG 300:propylene glycol:polysorbate 80 such that the aqueous solubility of peptidomimetic molecule is greater than 1 mg/ml and in other embodiments so that the aqueous solubility of peptidomimetic molecule is greater than 5 mg/ml. In certain embodiments, the peptidomimetic molecule is combined with a pharmaceutical excipient comprising PBS:PEG 300:propylene glycol:polysorbate 80 in a ratio of about 50:40:5:5.

In certain preferred embodiments of the invention, the peptidomimetic small molecule is an HMGB1 antagonist tetramer peptide which has been stabilized with at least one azatide linkage. In certain preferred embodiments of the invention, the peptidomimetic small molecule is a modified P5779 (SEQ ID NO: 1) wherein at least one terminal peptide bond has been replaced with an azatide linkage. In certain preferred embodiments of the invention, the peptidomimetic small molecule is a modified P5779 (SEQ ID NO: 1) wherein the terminal peptide bonds have been replaced with azatide. In certain preferred embodiments of the invention, the peptidomimetic small molecule is K883.

Certain preferred embodiments of the invention are directed to a method of treatment of severe sepsis, comprising identifying a human patient exhibiting symptoms of severe sepsis, and administering K883. Certain preferred embodiments of the invention are directed to a method of treatment of ALI, comprising identifying a human patient exhibiting symptoms of ALI and administering K883. Certain preferred embodiments of the invention are directed to a method of treatment of bacterial and viral respiratory infections such as influenza and SARS-CoV-2, comprising identifying a human patient exhibiting symptoms of a bacterial or viral respiratory infection such as influenza and SARS-CoV-2 and administering K883. Certain preferred embodiments of the invention are directed to a method of treatment of neuropathic pain, and in particular, DPN, comprising identifying a human patient exhibiting symptoms of peripheral neuropathy, and in particular DPN and administering K883.

Certain preferred embodiments of the invention are directed to a method of preparing a treatment for severe sepsis, ALI, bacterial and viral respiratory infections such as influenza and SARS-CoV-2 or peripheral neuropathy, and in particular DPN, comprising modifying P5779 (SEQ ID NO: 1) with at least one azatide linkage.

Certain preferred embodiments of the invention are directed to a method of preparing a treatment for severe sepsis, ALI, bacterial and viral respiratory infections such as influenza and SARS-CoV-2 or peripheral neuropathy, and in particular DPN, comprising modifying P5779 (SEQ ID NO: 1) with at least one azatide linkage wherein the modified P5779 (SEQ ID NO: 1) has at least one azatide linkage located at a terminal peptide bond.

Certain preferred embodiments of the invention are directed to a method of preparing a treatment for severe sepsis, ALI, bacterial and viral respiratory infections such as influenza and SARS-CoV-2 or peripheral neuropathy, and in particular DPN, comprising modifying P5779 (SEQ ID NO: 1) with at least one azatide linkage wherein the modified P5779 (SEQ ID NO: 1) is K883. In certain embodiments of the invention, the method of administration is selected from the group consisting of oral delivery, parenteral delivery, buccal delivery, sublingual delivery, nasal delivery, inhalation delivery, nebulization delivery, topical delivery, transdermal delivery and suppository delivery. In certain preferred embodiments of the invention, the therapeutically effective amount is orally administered to the mammal. In certain preferred embodiments of the invention, the therapeutically effective amount is intravenously administered to the mammal. In certain preferred embodiments of the invention, the mammal is human. In certain preferred embodiments of the invention, the K883 is combined with a mixture containing PBS:PEG 300:propylene glycol:polysorbate 80 at 50:40:5:5.

Certain preferred embodiments of the invention are directed to a pharmaceutical composition, comprising a modified P5779 (SEQ ID NO: 1) wherein at least one terminal peptide bond has been replaced with an azatide linkage. Certain preferred embodiments of the invention are directed to a pharmaceutical composition, comprising a modified P5779 (SEQ ID NO: 1) wherein the terminal peptide bonds have been replaced with azatide linkages. In certain preferred embodiments of the invention, pharmaceutical composition is a dosage form selected from the group consisting of an oral dosage form, an oral liquid dosage form, a parenteral dosage form, a buccal dosage form, a sublingual dosage form, a nasal dosage form, an inhalation dosage form, a nebulization dosage form, a topical dosage form, a transdermal dosage form and a suppository dosage form. In certain preferred embodiments of the invention, the pharmaceutical composition is K883 combined with a mixture containing PBS:PEG 300:propylene glycol:polysorbate 80 at 50:40:5:5.

In certain embodiments, the HMGB1 antagonist tetramer peptide which has been stabilized with at least one azapeptide linkage is capable of reducing influenza-induced ALI in mice such that mice treated with a pharmaceutical composition containing the HMGB1 antagonist tetramer peptide which has been stabilized with at least one azapeptide linkage have a survival greater than 50%, greater than 60% or preferably greater than 70%, a reduced lung pathology compared to untreated mice; and/or a significantly longer time to treatment onset and still achieve rescue survival when compared to P5779 (SEQ ID NO: 1). In certain embodiments the time to treatment onset with K883 is about 30% longer than the onset time required for treatment with P5779 (SEQ ID NO: 1) to achieve rescue survival. In certain embodiments the time to treatment onset with K883 is about 35% longer than the onset time required for treatment with P5779 (SEQ ID NO: 1) to achieve rescue survival. In certain other embodiments, the time to treatment onset with K883 is more than 40% longer than the onset time required for treatment with P5779 (SEQ ID NO: 1) to achieve rescue survival.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a graphical depiction of inflammation induced by HMGB1-partner molecule complexes.

FIG. 2A is a graphical representation of the proportion of hospital stays in the United States that carried sepsis as a primary or secondary indication in 2009.

FIG. 2B is a graphical representation of the percentage costs of treating sepsis in the United States.

FIG. 9A is a graphical representation showing HMGB1 levels following infection with Influenza A/PR/8/34 (H1N1) and FIG. 9B is a graphical representation showing monoclonal anti-HMGB1 rescuing lethality following H1N1 infection.

FIG. 12A demonstrates dose-responsive inhibition achieved with increasing concentrations of P5779 (SEQ ID NO: 1) (0-2000 nM) and the dose-responsive inhibition achieved with increasing concentrations of K883 (0-2000 nM) is shown in FIG. 12B.

FIGS. 14D-14F depict azapeptide K883 stability measured by HPLC from time 0 (FIG. 14D), at 3 hours (FIG. 14E), and up to 6 hours (FIG. 14F) after in vitro incubation with mouse serum. Relative absorbance is indicated on Y axes while retention times are indicated on x axes. Azapeptide K883 retains structural stability for a longer period of time than the peptide P5779 (SEQ ID NO: 1).

FIG. 15A shows the inhibition achieved with increasing concentrations of K883 (0-10 μM) in human primary macrophages and 15B shows the inhibition achieved with P5779 (SEQ ID NO: 1) (0-10 μM) in human primary macrophages. FIG. 15C shows the inhibition achieved with increasing concentrations of K883 (0-50 μM) of HMGB1-induced TNF secretion from mouse macrophages.

17A) but TNF secretion induced by other DAMPs (FIG. 17B-17G) is not inhibited by various concentrations of K883 in human macrophages.

FIG. 18 is a graphical depiction showing P5779 (SEQ ID NO: 1) peptide enhanced percentage survival in cecal ligation and puncture-sepsis.

FIGS. 19A-F are graphical depictions of effects of P5779 (SEQ ID NO: 1) on ameliorating inflammation, lethality, and tissue damage in a mouse model of APAP-induced liver injury. FIGS. 19A-D depict the serum inflammatory markers, AST (FIG. 19A), ALT (FIG. 19B), TNF (FIG. 19C), and HMGB1 (FIG. 19D) after P5779 (SEQ ID NO: 1) treatment. FIG. 19E shows increased survival after treatment with P5779 (SEQ ID NO: 1) but not control scramble peptide, while FIG. 19F depicts histology images showing treatment with HMGB1 inhibitor P5779 (SEQ ID NO: 1) reduced APAP-mediated liver injury.

FIG. 20A shows serum inflammatory markers after P5779 (SEQ ID NO: 1) treatment in the APAP-liver toxicity model, 500 ugs/mouse led to significant reductions in ALT and FIG. 20B is a graphical depiction showing that treatment with 50 ug/mouse of K883 reduced serum ALT in the liver APAP-toxicity model.

FIGS. 21A to 21C are histology images demonstrating that K883 reduces APAP-induced liver injury in the mouse model. Arrow indicates area of necrosis.

Figure 22:
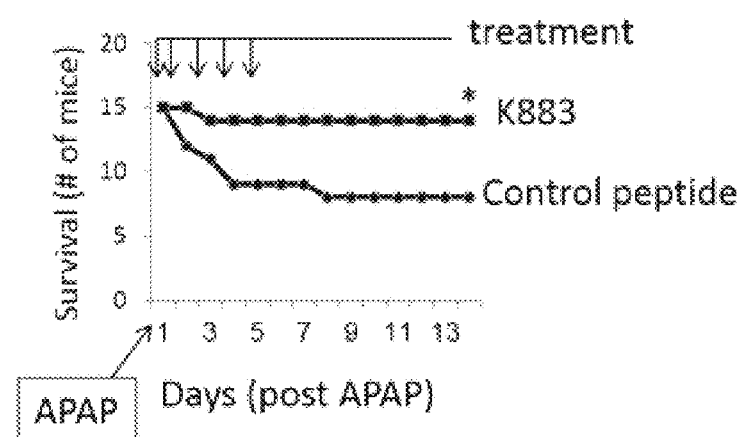

FIG. 22 shows improved survival outcome in mice that have been administered K883 in the APAP-induced liver injury model.

Figure 23:
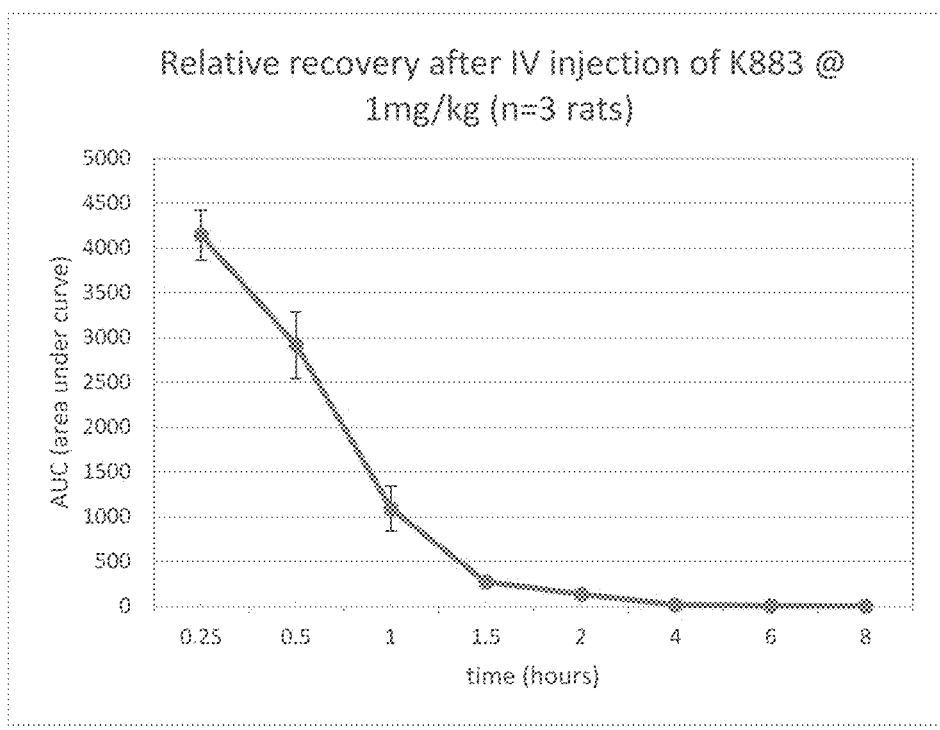

FIG. 23 is a graphical depiction showing K883 has a longer half-life in serum than P5779 (SEQ ID NO: 1) peptide (undetectable).

Figure 24:
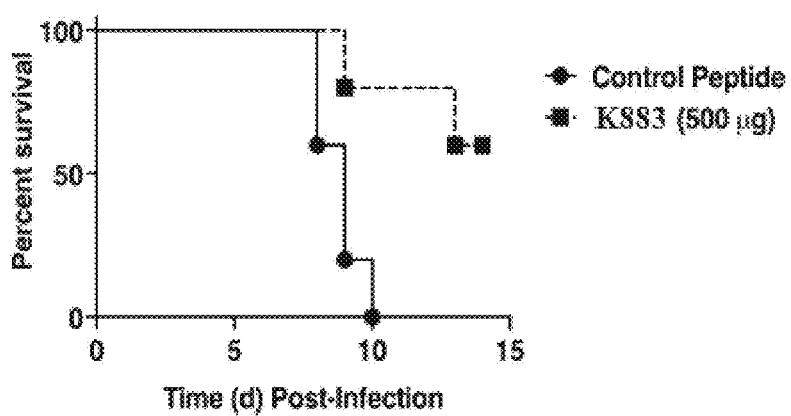

FIG. 24 is a graphical depiction showing K883 increases the survival of flu virus infected mice compared with P5779 (SEQ ID NO: 1) peptide.

FIG. 25 shows that K883 enhanced percentage survival in cecal ligation and puncture-sepsis.

FIG. 26A shows disulfide HMGB1 levels in spinal cord in chronic constriction injury (CCI) model in rats and FIG. 26B shows neutralizing effect of anti-HMGB1 antibody (mAb) 2g7.

Figure 27A:
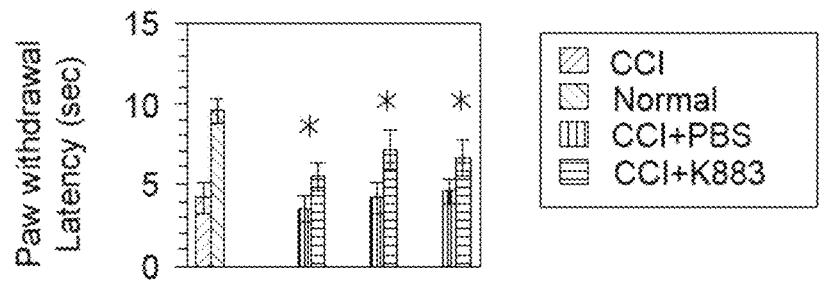
Figure 27B:
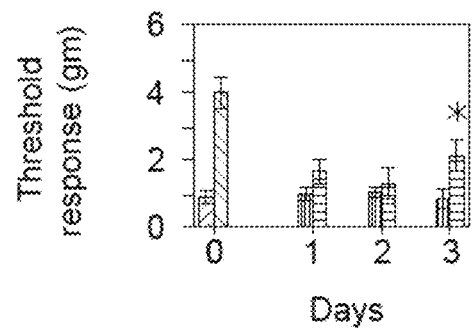

FIG. 27A and FIG. 27B are graphical depictions showing the effects of repeated K883 administration on CCI-induced neuropathic pain. (*: P<0.05 vs. CCI phosphate buffered saline group (PBS). N=6 rats/group).

Figure 28A:
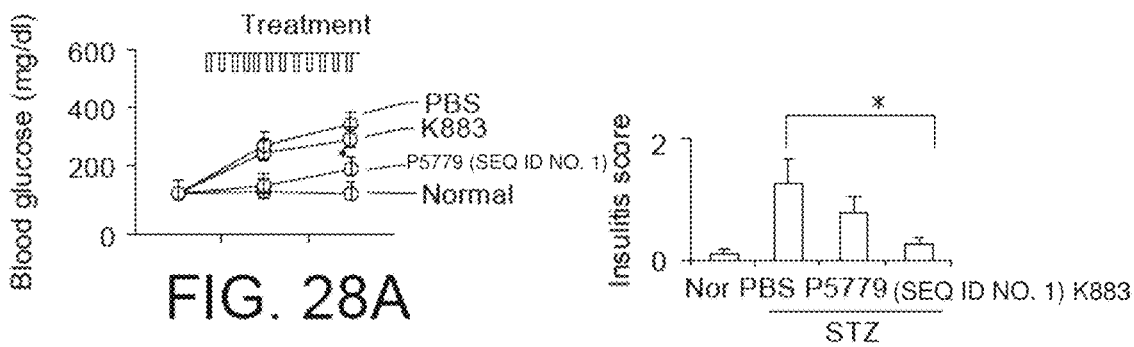
Figure 28C:
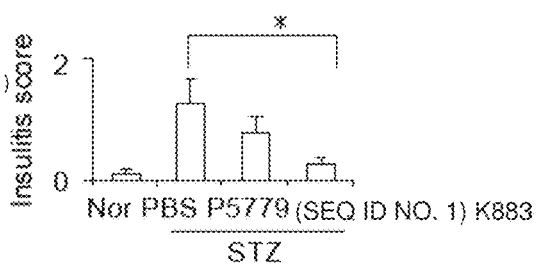
Figure 28B:
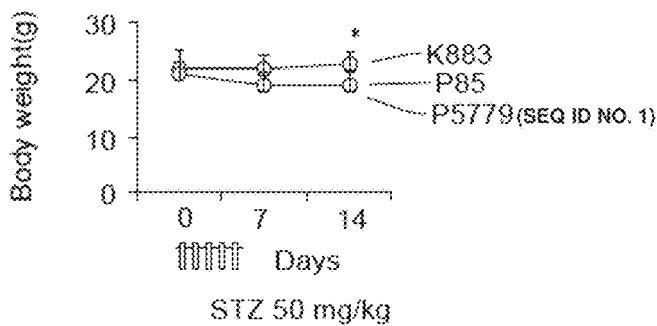

FIGS. 28A-C are graphical depictions showing the effects of P5779 (SEQ ID NO: 1) and K883 on streptozotocin (STZ) induced diabetes in mice.

Figure 29:
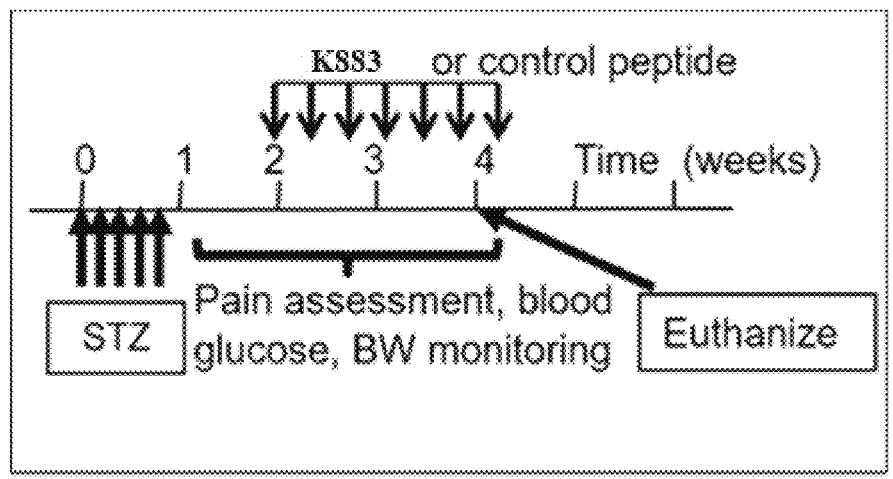
Figure 30A:
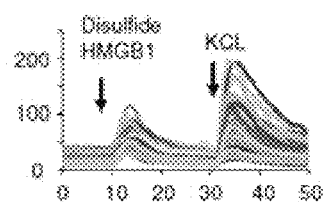
Figure 30B:
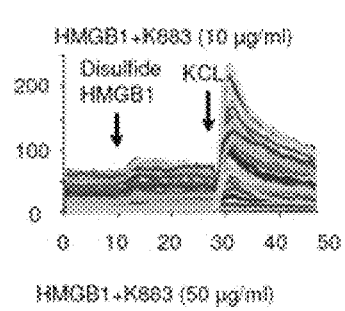
Figure 30C:
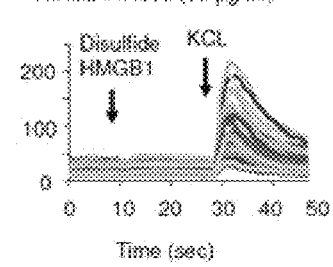
Figure 30D:
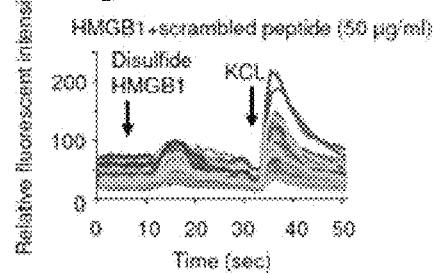
Figure 30E:
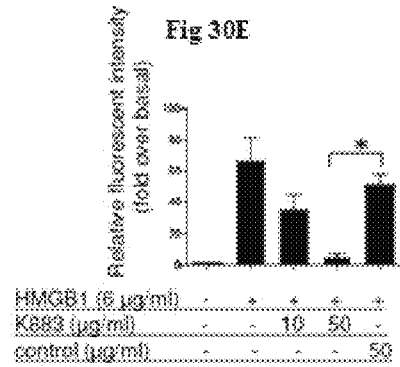

FIG. 29 shows an outline for how to determine the effects of selective HMGB1-TLR4/MD-2 inhibition on painful DPN.

FIGS. 30A-30E are graphical depictions showing inhibition by K883 of disulfide HMGB1-induced calcium influx in F11 cells.

FIGS. 31A-31C are graphical depictions showing K883 improved CCI-induced thermal and mechanical hypersensitivity over time in rats.

FIGS. 31A-31B are graphical depictions showing K883 reduces CCI-induced CXCL1 and TNF expression (DRGs).

FIG. 33A-33D are graphical depictions showing K883 reduces CCI-induced CXCL1, TNF and IL-1β expression (spine).

FIG. 34 shows the selective activation of Dorsal root ganglia (DRG) sensory neurons by disulfide HMGB1-induced Ca2+ influx.

FIG. 35A is a graphical depiction showing that HMGB1 induces neuropathic pain (mechanical allodynia) in rat paws and FIG. 35B is a graphical depiction showing mAb 2g7 ameliorates HMGB1-induced mechanical allodynia in rat paws.

DETAILED DESCRIPTION OF THE INVENTION

In accordance with the above stated objects, it is shown that administration of a peptidomimetic small molecule that replaces terminal peptide bonds with azatide linkages (e.g., K883) to a subject(s) or patient(s) in need thereof, can prevent and/or inhibit and/or treat sepsis, ALI, bacterial and viral respiratory infections such as influenza and SARS-CoV-2 and/peripheral neuropathy, in particular DPN.

The embodiments of the present invention, i.e. a rationally designed peptidomimetic small molecule, represent a huge advance in targeting HMGB1. Existing HMGB1 "inhibitors" either have numerous additional targets (e.g., glycyrrhizin) or only impinge on HMGB1 signaling indirectly (e.g., gabexate mesilate, a serine protease inhibitor). In contrast, the specificity of targeting distinct aspects of HMGB1 signaling allows the possibility of reducing systemic inflammation while preserving the immune system's response to pathogens. This selective approach represents a critical feature for treating patients who often have active systemic infections, one that currently available global immunosuppressive therapies lack. The specificity of targeting distinct aspects of HMGB1 signaling allows the possibility of ameliorating ALI through targeted immunosuppression, as well as the possibility of ameliorating bacterial and viral respiratory infections such as influenza and SARS-CoV-2. The specificity of targeting distinct aspects of HMGB1 signaling also allows the possibility of ameliorating neuropathic pain, and in particular DPN through targeted immunosuppression.

HMGB1 has been implicated in driving the progression of sepsis by the twin observations that sepsis severity roughly tracks with levels of circulating HMGB1 (Wang, H., et al., *HMG-1 as a late mediator of endotoxin lethality in mice*, Science, 1999, 285(5425): p. 248-51; Gibot, S., et al., *High-mobility group box 1 protein plasma concentrations during septic shock*, Intensive Care Med, 2007, 33(8): p. 1347-53; Sunden-Cullberg, J., et al., *Persistent elevation of high mobility group box-1 protein (HMGB1) in patients with sepsis and septic shock*, Crit Care Med, 2005, 33(3): p. 564-73) and that the presence of anti-HMGB1 autoantibodies correlates with improved outcomes (Barnay-Verdier, S., et al., *Emergence of autoantibodies to HMGB1 is associated with survival in patients with septic shock*, Intensive Care Med, 2011, 37(6): p. 957-62). Experiments in rodents have confirmed that HMGB1-mediated signaling is central for precipitating the pathogenic inflammation that leads to mortality or other sequelae in sepsis survivors. Sepsis can be induced in rodents via the cecal ligation and puncture method; it is the preferred experimental model for sepsis because it recapitulates the progression of sepsis in humans (Dejager, L., et al., *Cecal ligation and puncture: the gold standard model for polymicrobial sepsis?*, Trends Microbiol, 2011, 19(4): p. 198-208). Briefly, cecal ligation and puncture surgery involves ligating the cecum to cause necrosis of the bowel and breaching the intestine and extruding a small amount of stool to establish an active, polymicrobial intra-abdominal infection. Similar to sepsis in humans, the survival rate is between 20% to 40% when untreated (Qin, S., et al., *Role of HMGB1 in apoptosis-mediated sepsis lethality*, J Exp Med, 2006, 203(7): p. 1637-42; Yang, H., et al., *Reversing established sepsis with antagonists of endogenous* high-mobility group box 1, Proc Natl Acad Sci USA, 2004, 101(1): p. 296-301) and survivors develop a persistent microcytic, hypochromic anemia (Valdes-Ferrer, S. I., et al., *HMGB1 mediates anemia of inflammation in murine sepsis survivors*, Mol Med, 2015). Remarkably, administering HMGB1-neutralizing antibodies, even as late as 24 hours post-injury, can counteract these symptoms attributed to blocking HMGB1-mediated release of pro-inflammatory cytokines.

Figure 8A:
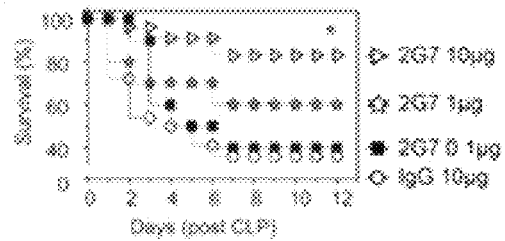
FIG. 8A is a graphical depiction of the therapeutic properties on percentage survival of different doses of murine anti-HMGB1 monoclonal antibody, mu-2G7, realized through administration twenty-four hours after cecal ligation and puncture sepsis model.
Figure 8B:
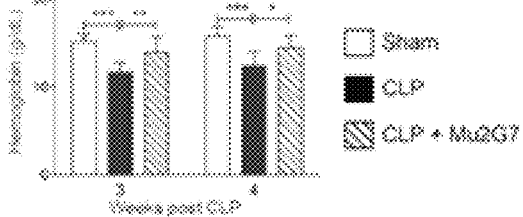
FIG. 8B is a graphical depiction showing rescue of persistent anemia measured by hemoglobin levels in murine sepsis survivors after injections of mu-2G7 on days 9-11 following cecal ligation and puncture.

As seen from FIG. 8A mice injected with polyclonal anti-HMGB1 sera for three days following cecal ligation and puncture (Yang, H., et al., *Reversing established sepsis with antagonists of endogenous high-mobility group box* 1, Proc Natl Acad Sci USA, 2004, 101(1): p. 296-301) or with a single dose of purified monoclonal Ab (mu-2G7) at 24 hours post-cecal ligation and puncture. (Qin, S., et al., *Role of HMGB1 in apoptosis-mediated sepsis lethality*, J Exp Med, 2006, 203(7): p. 1637-42) had significantly lower mortality than mice injected with a control IgG that did not react with HMGB1. This is a wide therapeutic window relative to other agents that selectively target cytokine mediators of sepsis. Importantly, anti-TNF antibodies worsen survival from sepsis in this model, highlighting the important differences between TNF and HMGB1 and their respective antagonism. In addition, FIG. 8B shows that injecting mu-2G7 on days 9-11 post-cecal ligation and puncture can substantially rescue anemia, measured by hemoglobin levels in murine sepsis survivors (Valdes-Ferrer, S. I., et al., *HMGB1 mediates anemia of inflammation in murine sepsis survivors*, Mol Med, 2015). Thus, HMGB1 antagonists may be efficacious in two distinct therapeutic windows: at diagnosis to rescue mortality and as a continuous treatment to alleviate lingering sequelae of sepsis such as anemia and cognitive decline (Chavan, S. S., et al., *HMGB1 mediates cognitive impairment in sepsis survivors*, Mol Med, 2012, 18: p. 930-7).

HMGB1 is a late mediator of inflammation. In animals, all cells synthesize HMGB1; healthy cells sequester it in the nucleus, where it serves as a transcription factor. (Andersson U, *HMGB1 is a therapeutic target for sterile inflammation and infection*, Annu Rev Immunol., 2011; 29:139-62; Wang H, *HMG-1 as a late mediator of endotoxin lethality in mice*, Science, 1999; 285(5425):248-51) Cellular damage, necrosis, and apoptosis result in the passive release of HMGB1 into the extracellular space, which can recruit leukocytes to the site of an injury or infection. In turn, these monocytes, tissue macrophages, and other cells of the innate immune system actively secrete HMGB1 when activated by pathogen-derived stimuli, exosomes, or pro-inflammatory cytokines. Depending upon its oxidation state and which of its receptors are engaged, extracellular HMGB1 can trigger a variety of outcomes (reviewed in Lotze M T, *High-mobility group box* 1 *protein (HMGB*1): *nuclear weapon in the immune arsenal* Nat Rev Immunol., 2005; 5(4):331-42; Yang H, *Targeting HMGB1 in inflammation*, Biochim Biophys Acta., 2010; 1799(1-2):149-56 and Harris H E, *HMGB1: a multifunctional alarmin driving autoimmune and inflammatory disease*, Nat Rev Rheumatol., 2012; 8(4): 195-202), including secretion of additional HMGB1 to sustain the immune response until the insult is resolved. These characteristics, pro-inflammatory cytokine activity and prolonged release, recommend HMGB1 as an attractive therapeutic target in inflammatory diseases. (Andersson U, *HMGB1 is a therapeutic target for sterile inflammation and infection*, Annu Rev Immunol, 2011; 29:139-62).

Figure 9A:
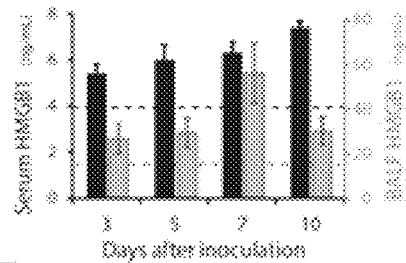
FIGS. 9A and 9B show HMGB1 in an influenza-induced model of ALI.
Figure 9B:
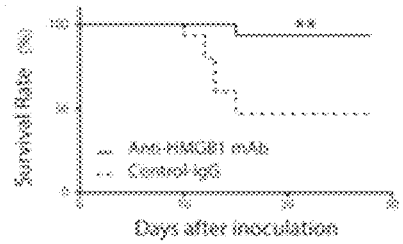

HMGB1 mediates inflammation during acute lung injury. Intra-tracheal injection of purified HMGB1 causes pulmonary edema, invasion of the alveolar space by macrophages and neutrophils, and a sharp increase in concentrations of pro-inflammatory cytokines (e.g. TNFα and IL-1β) in lung fluids. (Abraham E, *HMG-*1 *as a mediator of acute lung inflammation*, J Immunol., 2000; 165(6):2950-4). In a mouse model of influenza-induced pneumonia, Nosaka and colleagues observed elevated HMGB1 levels in serum and bronchoalveolar lavage fluid (BALF) (Nosaka N, *Anti-high mobility group box-*1 *monoclonal antibody treatment provides protection against influenza A virus (H*1*N*1*)-induced pneumonia in mice*, Crit Care, 2015; 19:249) Treating influenza-inoculated mice with a neutralizing monoclonal antibody against HMGB1 reduces inflammation (and innate immune cell infiltration) and protects against lethality (see FIG. 9). FIGS. 9A and 9B shows HMGB1 in an influenza-induced model of ALI. As seen in FIG. 9A, HMGB1 levels rise following infection with Influenza A/PR/8/34 (H1N1). Serum levels of HMGB1 (black bars) rise throughout the experiment, while HMGB1 levels in bronchoaleveolar lavage fluid (BALF; orange bars) peak one week after infection. Dotted lines=HMGB1 baseline. As seen in FIG. 9B, monoclonal anti-HMGB1 rescues lethality following H1N1 infection. FIG. 9B is adapted from Nosaka N, *Anti-high mobility group box-*1 *monoclonal antibody treatment provides protection against influenza A virus (H*1*N*1*)-induced pneumonia in mice*, Crit Care, 2015; 19:249, which shows that remarkably, this therapy does not affect viral clearance.

HMGB1 and its bound molecules have been implicated as mediators in the pathogenesis of influenza and human respiratory syncytial virus infections, viral conditions sharing distinct clinical features with SARS-CoV-2. Exaggerated host inflammatory response is a major cause of lung damage and subsequent mortality in many severe pulmonary inflammatory conditions including SARS-CoV-2. An overexcited HMGB1-RAGE-TLR4 axis can be expected in e.g. SARS-CoV-2 since the necrotic respiratory epithelial cells will contribute great quantities of extracellular HMGB1 and the cognate HMGB1-receptor RAGE is constitutively abundantly expressed specifically in the lungs. Once the pulmonary inflammation is initiated, a further pulmonary upregulation of RAGE and TLR4 will be engendered combined with an increased active HMGB1 release from innate immunity cells and from the peripheral nervous system. A substantial number of preclinical studies demonstrates that HMGB1 antagonists may ameliorate severe pulmonary inflammation regardless if it is of infectious or sterile origin. In preferred embodiments of the invention, an improved outcome in severe SARS-CoV-2 and other severe respiratory virus infections and influenza is achieved by targeting the HMGB1-RAGE-TLR4 route.

Figure 3:
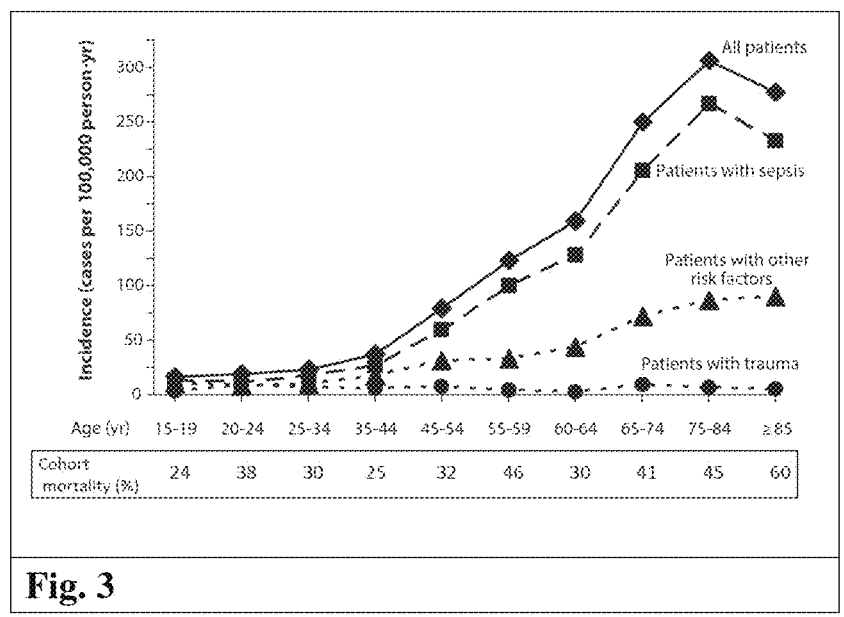
FIG. 3 is a graphical representation of ALI incidence and mortality across age cohorts, subdivided by predisposing factors.
Figure 4A:
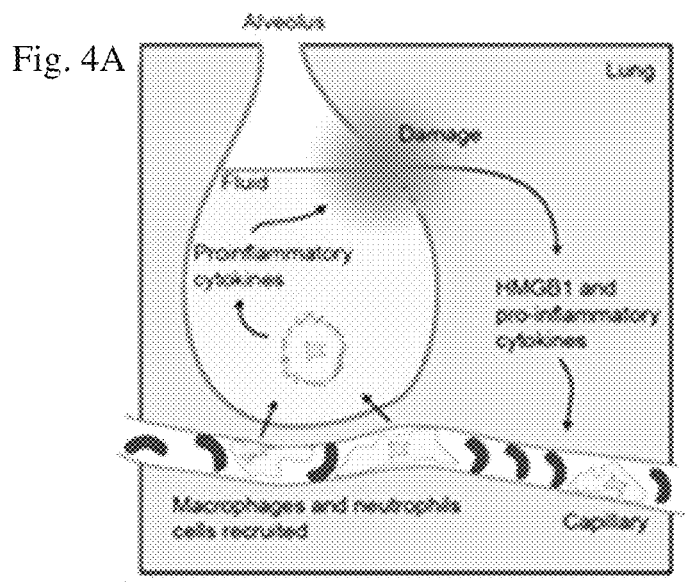
FIGS. 4A and 4B are representations of how dysregulated inflammation causes ALI with FIG. 4A depicting the feedback loop that drives immunopathology in ALI and FIG. 4B showing how HMGB1 levels roughly correlate with tissue damage and negative outcomes.
Figure 4B:
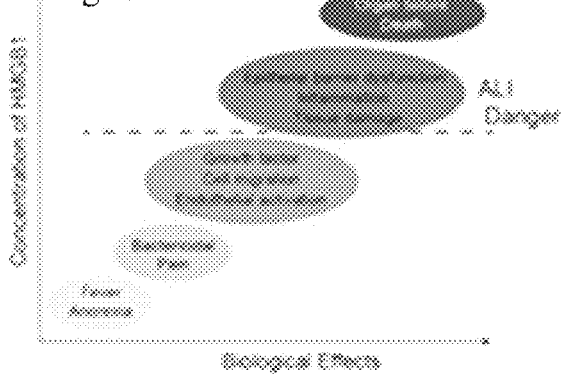
Figure 5:
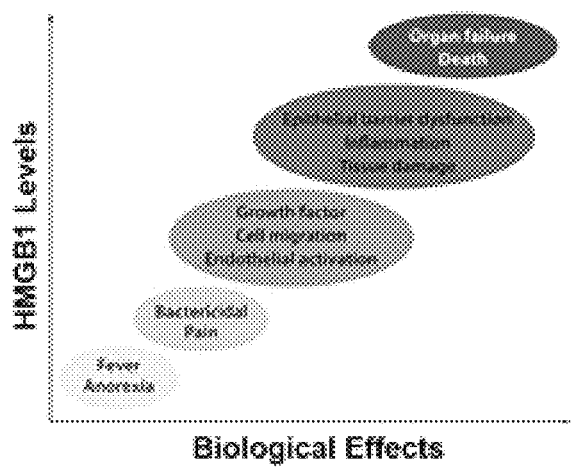
FIG. 5 is a graphical representation of the biological effects of HMGB1.
Figures 6A, 6B, 6C:
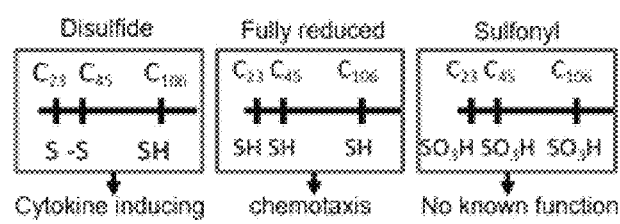
FIGS. 6A-6C shows the three known isoforms of HMGB1.
Figure 7:
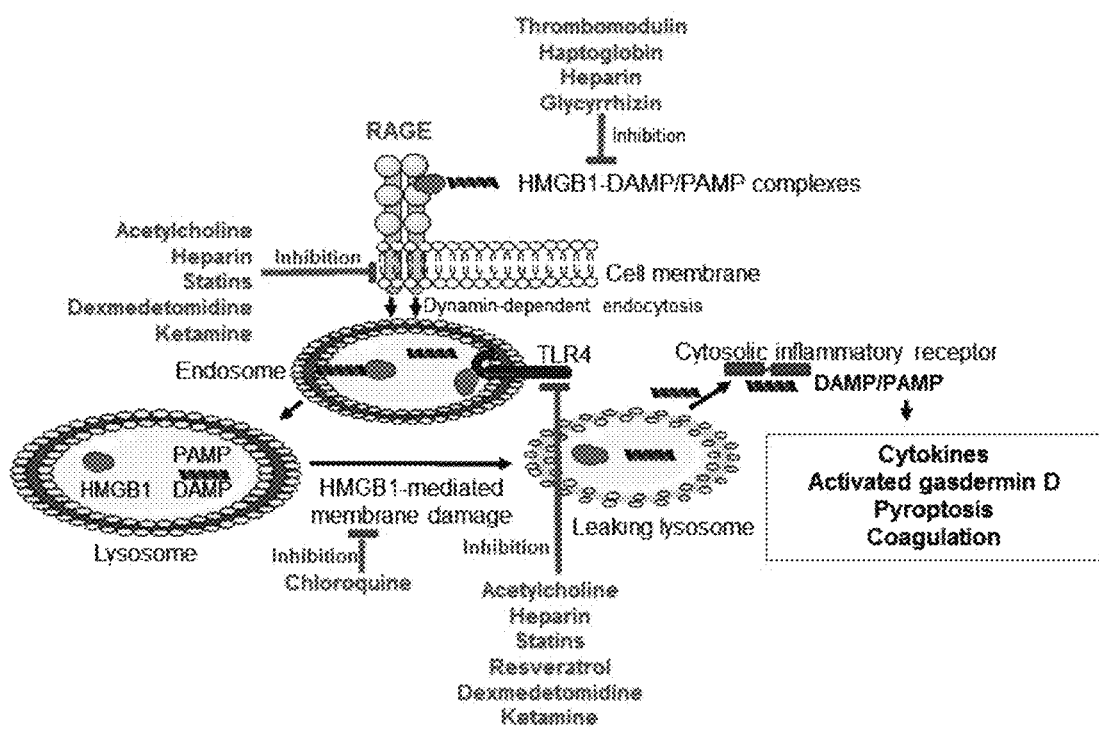
FIG. 7 is a graphical depiction of approved pharmacological compounds inhibiting HMGB1-RAGE-TLR4-mediated inflammation.

No HMGB1-specific mAbs have yet undergone clinical studies, although there are two humanized anti-HMGB1 mAbs successfully studied in preclinical inflammatory disease models. (Lundback P, et al., *A novel high mobility group box* 1 *neutralizing chimeric antibody attenuates drug-induced liver injury and postinjury inflammation in mice*, Hepatology (Baltimore, Md.), 2016; 64(5):1699-710). However, there are already approved defined molecules that could be considered to use clinically to inhibit excessive HMGB1 proinflammatory activities in exaggerated pulmonary inflammation (see FIG. 7).

Exaggerated host inflammatory response is a major cause of lung damage and subsequent mortality in many severe pulmonary inflammatory conditions including SARS-CoV-2. An overexcited HMGB1-RAGE-TLR4 axis can be expected in SARS-CoV-2 since the necrotic respiratory epithelial cells will contribute great quantities of extracellular HMGB1 and the cognate HMGB1-receptor RAGE is constitutively abundantly expressed specifically in the lungs. Once the pulmonary inflammation is initiated, a further pulmonary upregulation of RAGE and TLR4 will be engendered combined with an increased active HMGB1 release from innate immunity cells and from the peripheral nervous system. A substantial number of preclinical studies demonstrates that HMGB1 antagonists may ameliorate severe pulmonary inflammation regardless if it is of infectious or sterile origin.

The mAb mu-2G7 was evaluated as a basis of interest for developing a biologic intervention to neutralize HMGB1. The mu-2G7 antibody recognizes an epitope in the A-box DNA-binding domain of HMGB1 that allows it to differentiate between HMGB1 and the closely related protein HMGB2; it binds to HMGB1 irrespective of the protein's oxidation state and blocks all known biological activity for each isoform (Lundback, P., et al., *A novel high mobility group box* 1 *neutralizing chimeric antibody attenuates drug-induced liver injury and postinjury inflammation in mice*, Hepatology, 2016, 64(5): p. 1699-1710; Yang, H., et al., *A critical cysteine is required for HMGB1 binding to Toll-like receptor 4 and activation of macrophage cytokine release*, Proc Natl Acad Sci USA, 2010, 107(26): p. 11942-7; Venereau, E., et al., *Mutually exclusive redox forms of HMGB1 promote cell recruitment or proinflammatory cytokine release*, J Exp Med, 2012, 209(9): p. 1519-28); and it antagonizes HMGB1 independent of complement activation or any Fc interactions (Knezevic, I., H. N. Kang, and R. Thorpe, *Immunogenicity assessment of monoclonal antibody products: A simulated case study correlating antibody induction with clinical outcomes*, Biologicals, 2015, 43(5): p. 307-17). However, murine antibodies are not suitable for clinical use because their immunogenicity in humans can blunt their therapeutic efficacy and even create safety problems (Id.). To circumvent these limitations, Lundback and colleagues constructed a chimeric antibody by fusing the variable domains of 2G7 with human constant (Fc) domains of the IgG1 isotype (Lundback, P., et al., *A novel high mobility group box* 1 *neutralizing chimeric antibody attenuates drug-induced liver injury and postinjury inflammation in mice*, Hepatology, 2016, 64(5): p. 1699-1710). This architecture is analogous to that used to create infliximab (Remicade), an analogous chimeric mouse-human monoclonal antibody (Elliott, M. J., et al., *Randomised double-blind comparison of chimeric monoclonal antibody to tumour necrosis factor alpha (cA2) versus placebo in rheumatoid arthritis*, Lancet, 1994, 344(8930): p. 1105-10; Taylor, P. C. and M. Feldmann, *Anti-TNF biologic agents: still the therapy of choice for rheumatoid arthritis*, Nat Rev Rheumatol, 2009, 5(10): p. 578-82). The first anti-TNF mAb launched for clinical use, Infliximab has during the latest two decades been a tremendous clinical success to alleviate rheumatoid arthritis and inflammatory bowel diseases (IBD) administered to more than 2 million patients. Hence, humanized anti-HMGB1 based on mu-2G7 is indicated to work very well over long periods of time (Monaco, C., et al., *Anti-TNF therapy: past, present and future*, Int Immunol, 2015, 27(1): p. 55-62).

Figure 10A:
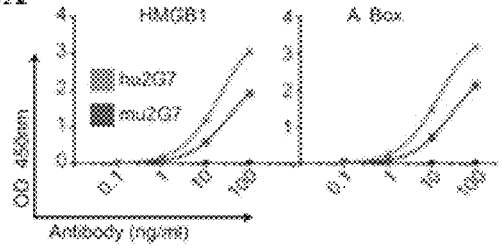
FIG. 10A is a graphical depiction showing humanized anti-HMGB1 antibody, hu-2G7 has comparable specificity to mu-2G7.
Figure 10B:
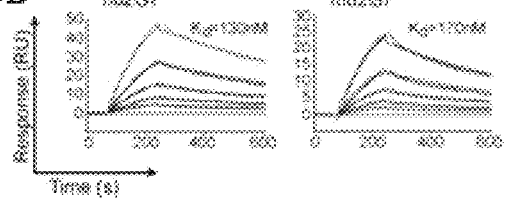
FIG. 10B is a graphical depiction showing humanized anti-HMGB1 monoclonal antibody, hu-2G7 has a higher affinity for HMGB1 than mu-2G7 with affinities analyzed by Surface Plasmon Resonance (SPR) binding studies, with Langmuir-binding used to determine dissociation constants.

FIG. 10A is a graphical depiction that shows that the humanized anti-HMGB1 antibody, called hu-2G7, retains the same specificity as mu-2G7 while displaying a slightly higher affinity than the murine antibody. FIG. 10B is a graphical depiction showing humanized anti-HMGB1 monoclonal antibody hu-2G7 has a higher affinity for HMGB1 than mu-2G7 with affinities analyzed by Surface Plasmon Resonance (SPR) binding studies, with Langmuir-binding used to determine dissociation constants. Functionally, hu-2G7 has been tested in a mouse model of acetaminophen-induced (APAP) acute liver injury, a highly HMGB1-dependent inflammatory condition, where it provided an equivalent therapeutic benefit to mu-2G7 (Lundback, P., et al., *A novel high mobility group box* 1 *neutralizing chimeric antibody attenuates drug-induced liver injury and postinjury inflammation in mice*, Hepatology, 2016, 64(5): p. 1699-1710).

A large body of in vivo and in vitro data attests to the effectiveness of HMGB1 neutralizing antibodies to reduce inflammation, yet the wholesale inactivation of HMGB1 signaling may be suboptimal in some contexts. HMGB1 facilitates inflammation in response to lipopolysaccharide (LPS) and other PAMPs. (Tsung, A., S. Tohme, and T. R. Billiar, *High-mobility group box-1 in sterile inflammation*, J Intern Med, 2014, 276(5): p. 425-43); for patients with active infections, it may be desirable to conserve HMGB1-mediated responses to PAMPs. Furthermore, in some contexts HMGB1 signaling has an anti-inflammatory effect. For example, HMGB1 complexed with haptoglobin binds CD163 to stimulate the release of anti-inflammatory cytokines, and the severity of cecal ligation and puncture sepsis is exacerbated in CD163 or haptoglobin mutants (Yang, H., et al., *Identification of CD163 as an antiinflammatory receptor for HMGB1-haptoglobin complexes*, JCI Insight, 2016, 1(7). Hence, the present invention is directed to a refined strategy for limiting HMGB1-driven inflammation by interfering with binding between HMGB1 and its receptors. The first indication of the feasibility of this approach came with the observation that injecting mice with a purified fragment of HMGB1, the A-box domain, protected against lethality after cecal ligation and puncture (Yang, H., et al., *Reversing established sepsis with antagonists of endogenous high-mobility group box* 1, Proc Natl Acad Sci USA, 2004, 101(1): p. 296-301).

Although HMGB1 is purported to interact with as many as 15 distinct receptor systems, several considerations strongly suggest that the toll-like receptor TLR4 is one of the main functional receptor systems (Yang, H., et al., *A critical cysteine is required for HMGB1 binding to Toll-like receptor 4 and activation of macrophage cytokine release*, Proc Natl Acad Sci USA, 2010, 107(26): p. 11942-7). Thus, Toll-like Receptor TLR4 has emerged as the primary pro-inflammatory signaling receptor for HMGB1 in numerous disorders in which HMGB1 has been implicated, including hemorrhagic shock, ischemia/reperfusion injury, sepsis, and others. (Apetoh L, *The interaction between HMGB1 and TLR4 dictates the outcome of anticancer chemotherapy and radiotherapy*, Immunol Rev. 2007; 220:47-59; Apetoh L, *Toll-like receptor 4-dependent contribution of the immune system to anticancer chemotherapy and radiotherapy*, Nat Med., 2007; 13(9):1050-9; Fan J, Li Y, *Hemorrhagic shock induces NAD(P)H oxidase activation in neutrophils: role of HMGB1-TLR4 signaling*, J Immunol., 2007; 178(10):6573-80. Tsung A, *HMGB1 release induced by liver ischemia involves Toll-like receptor 4 dependent reactive oxygen species production and calcium-mediated signaling*, J Exp Med., 2007; 204(12):2913-23; Zong M, *TLR4 as receptor for HMGB1 induced muscle dysfunction in myositis*, Ann Rheum Dis., 2013; 72(8):1390-9).

Extracellular HMGB1 is incapable of activating NF-κB, a hallmark of HMGB1 signaling, when TLR4 is absent or functionally blocked (Yang, H., et al., *MD-2 is required for disulfide HMGB1-dependent TLR4 signaling*, J Exp Med, 2015, 212(1): p. 5-14; Yang, H., et al., *A critical cysteine is required for HMGB1 binding to Toll-like receptor 4 and*

*activation of macrophage cytokine release*, Proc Natl Acad Sci USA, 2010, 107(26): p. 11942-7). HMGB1 also has a striking capacity to complex with a great many other inflammatory molecules, including LPS and other PAMPs, inflammatory cytokines, and danger-associated molecular patterns (DAMPs) that signify injury and cellular damage. A majority of the reported receptors likely recognize these partner molecules rather than HMGB1 per se (Hreggvidsdottir, H. S., et al., *High mobility group box protein 1 (HMGB1)-partner molecule complexes enhance cytokine production by signaling through the partner molecule receptor*, Mol Med, 2012, 18: p. 224-30). In contrast, the complex of TLR4 and the adaptor protein MD-2 specifically bind "free" (i.e., uncomplexed) HMGB1 and signal through MYD88- or TRIF-dependent pathways, ultimately leading to NF-κB activation. Therefore, the focus of the present invention is the disruption of the signaling through the TLR4/MD-2/HMGB1 axis.

Yang and colleagues identified a tetrameric peptide (P5779 (SEQ ID NO: 1)) that antagonizes the interaction between HMGB1 and MD-2, blocking activation of the toll-like receptor TLR4 and the release of pro-inflammatory cytokines. (Yang, H., et al., *MD-2 is required for disulfide HMGB1-dependent TLR4 signaling*, J Exp Med, 2015, 212 (1): p. 5-14). P5779 (SEQ ID NO: 1) seems to isolate and attenuate HMGB1-driven inflammation without impairing the immune response to pathogens. It does not inhibit pathogen-stimulated cytokine release in vitro or in vivo. (Yang H, *MD-2 is required for disulfide HMGB1-dependent TLR4 signaling*, J Exp Med., 2015; 212(1):5-14). It is protective in a diverse array of in vivo models, reducing mortality in models of ischemia/reperfusion injury, acetaminophen toxicity, and sepsis, underscoring the importance of HMGB1/MD-2/TLR4 as the major pro-inflammatory signaling axis in these models. Id. Significantly, in a mouse model of influenza-induced ALI and lethality, P5779 (SEQ ID NO: 1) reduces mortality approximately 9-fold in mice when given daily for five days beginning two days after influenza infection (see FIG. 11 which shows P5779 (SEQ ID NO: 1) rescues survival after lethal influenza infection with strain PR8), and it lowers clinical scores in survivors. (Shirey K A, *Novel strategies for targeting innate immune responses to influenza*, Mucosal Immunol., 2016; 9(5):1173-82).

Figure 11:
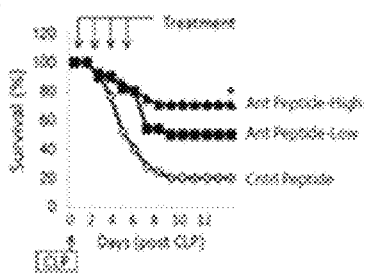
FIG. 11 is a graphical depiction of percentage survival in mice after treatment with the peptide P5779 (SEQ ID NO: 1) following cecal ligation and puncture as compared to a scrambled control peptide (SFES).

In FIG. 11, the survival advantage of injecting the peptide following cecal ligation and puncture is shown to confer a survival advantage when compared to a scrambled control peptide (SFES) which does not confer a survival advantage. Although P5779 (SEQ ID NO: 1) diminished cytokine release from macrophages exposed to recombinant HMGB1, it did not inhibit LPS-stimulated cytokine release in vitro or in vivo. This is not attributable to low in vivo activity, however, since repeat doses of the peptide reduced mortality in models of ischemia/reperfusion injury, acetaminophen toxicity, cecal ligation and puncture-induced sepsis (Id.) and acute lung injury (Shirey, K. A., et al., *Novel strategies for targeting innate immune responses to influenza*, Mucosal Immunol, 2016, 9(5): p. 1173-82). Thus, P5779 (SEQ ID NO: 1) allows TLR4/MD-2/HMGB1-driven inflammation to be attenuated without impairing the immune response to microbes. And thus, in one instance P5779 (SEQ ID NO: 1) administration blunts HMGB1-mediated activation of the TLR4/MD-2 signaling pathway and diminishes HMGB1-induced release of pro-inflammatory cytokines from macrophages.

Many studies have also demonstrated that disulfide isoform of HMGB1 can selectively interact with Toll-like receptor 4 (TLR4) to induce cytokine production. (Yang H., *Redox modification of cysteine residues regulates the cytokine activity of high mobility group box-1 (HMGB1)*, Molecular Medicine, 2012; 18(1): 250; Yang H., *MD-2 is required for disulfide HMGB1—dependent TLR4 signaling*, J Exp Med, 2015:jem. 20141318; Yang H., *The many faces of HMGB1: molecular structure functional activity in inflammation, apoptosis, and chemotaxis*, Journal of Leukocyte Biology, 2013; 93(6): 865-873; Ma F., *Disulfide high mobility group box-1 causes bladder pain through bladder Toll-like receptor* 4, BMC physiology, 2017; 17(1): 6). Given the vital role of TLR4 in neuropathic pain, (Agalave N. M., *Spinal HMGB1 induces TLR4-mediated long-lasting hypersensitivity and glial activation and regulates pain-like behavior in experimental arthritis*, PAIN®, 2014; 155(9): 1802-1813; Liu T., *Emerging role of Toll-like receptors in the control of pain and itch*, Neuroscience bulletin, 2012; 28(2): 131-144; Li Y., *Toll-like receptor 4 signaling contributes to Paclitaxel-induced peripheral neuropathy*, The Journal of Pain, 2014; 15(7): 712-725; Kim D., *Toll-like receptors in peripheral nerve injury and neuropathic pain*, Toll-like Receptors: Roles in Infection and Neuropathology: Springer, 2009: 169-186; Guo L-H, *The innate immunity of the central nervous system in chronic pain: the role of Toll-like receptors*, Cellular and Molecular Life Sciences, 2007; 64(9): 1128), the evidence that TLR4 is elevated in diabetic rodents, (Yan J-e, *Streptozotocin-induced diabetic hyperalgesia in rats is associated with upregulation of toll-like receptor 4 expression*, Neuroscience letters, 2012; 526(1): 54-58; Zhu T., *Toll-like receptor 4 and tumor necrosis factor-alpha as diagnostic biomarkers for diabetic peripheral neuropathy*, Neuroscience Letters, 2015; 585: 28-32) and patients, (Zhu T., *TLR4 and Caveolin-1 in Monocytes Are Associated With Inflammatory Conditions in Diabetic Neuropathy*, Clinical and Translational Science, 2017; 10(3): 178-184) and certain TLR4 gene polymorphism is associated with reduced risk of diabetic neuropathy in humans (Rudofsky G., *Asp299Gly and Thr399Ile genotypes of the TLR4 gene are associated with a reduced prevalence of diabetic neuropathy in patients with type 2 diabetes*, Diabetes Care, 2004; 27(1): 179-183), it is a goal of this invention to develop a therapy targeting disulfide HMGB1/TLR-4 signaling pathway to result in a novel, safe, and effective strategy for the treatment of NP and particularly of painful DPN. (Agalave N., *Spinal disulfide HMGB1, but not all-thiol HMGB1, induces mechanical hypersensitivity in a TLR4-dependent manner*, Scandinavian Journal of Pain, 2015; 8: 47; Wang Y, *Tanshinone IIA Attenuates Chronic Pancreatitis-Induced Pain in Rats via Downregulation of HMGB1 and TRL4 Expression in the Spinal Cord*, Pain Physician, 2014; 18(4): E615-628).

It is also a goal of this invention to develop a peptidomimetic small molecule for selectively targeting an HMGB1 isoform-specific signaling pathway that plays a critical role in the occurrence and development of neuropathic pain. It is a further goal of this invention to advance an HMGB1 inhibitor that can selectively bind to TLR4 adaptor molecule, myeloid differentiation factor 2 (MD-2), which is required for disulfide HMGB1-dependent TLR4 signaling. (Yang H., *MD-2 is required for disulfide HMGB1—dependent TLR4 signaling*, J Exp Med, 2015: jem. 20141318). There are no other drugs in development or clinical use that exhibit this novel mechanism of action.

The most studied HMGB1 inhibitor is the neutralizing monoclonal anti-HMGB1 mAb 2g7, which does not discriminate isoforms of HMGB1 (see Table 1). It is known that haptoglobin (a serum hemoglobin binding protein) β subunit binds HMGB1 (disulfide and fully reduced). (Yang H., *Haptoglobin (Beta) Subunit Binds and Sequesters Hmgb1 Toxicity*, Paper presented at: SHOCK2016; Yang H., *The haptoglobin beta subunit sequesters HMGB1 toxicity in sterile and infectious inflammation*, Journal of Internal Medicine, (2017)).

TABLE 1 mAb 2g7 binds to all isoforms of HMGB1

| HMGB1 isoform | Kd (M) to mAb 2g7 |
| --- | --- |
| Disulfide | $1.0 \times 10^{-8}$ |
| Fully reduced | $4.6 \times 10^{-8}$ |
| Sulfonyl | $1.2 \times 10^{-8}$ |

Although it was known that TLR4 signaling depends on the co-receptor MD-2, (Vašl J., *Novel roles of lysines 122, 125, and 58 in functional differences between human and murine MD-2*, The Journal of Immunology, 2009; 183(8): 5138-5145; Visintin A., MD-2, Immunobiology, 2006; 211 (6): 437-447), it was not known how the TLR4 receptor distinguished between HMGB1 isoforms. It is now understood that MD-2 is required for HMGB1-TLR4 signaling and that MD-2 binds specifically to the cytokine-inducing disulfide HMGB1, to the exclusion of other isoforms. (Yang H., MD-2 is required for disulfide HMGB1-dependent TLR4 signaling, J Exp Med., 2015; 212(1): 5-14).

Based on the critical role of Cys106 in dictating HMGB1/ MD-2 interaction and TLR4 signaling, and the understanding that disulfide HMGB1-dependent TLR4 signaling is the key and dominant mechanism underlying the generation of cytokines, (Yang H., Redox modification of cysteine residues regulates the cytokine activity of high mobility group box-1 (HMGB1), Molecular Medicine, 2012; 18(1): 250; Yang H., The many faces of HMGB1: molecular structure-functional activity in inflammation, apoptosis, and chemotaxis, Journal of Leukocyte Biology, 2013; 93(6): 865-873), Yang and colleagues developed a tetrameric peptide (P5779 (SEQ ID NO: 1)) that is a disulfide HMGB1-specific inhibitor. P5779 (SEQ ID NO: 1) has been shown to prevent MD-2-HMGB1 interaction and subsequent TLR4 signaling, effectively binding to MD-2 with relatively potent affinity (Kd=0.65 µM) (and without binding to HMGB1 or TLR4 in the absence of MD-2), to inhibit HMGB1-induced TNF release from macrophages in a concentration-dependent manner and to not suppress TNF release in macrophages stimulated by lipopolysaccharide (LPS, TLR4 agonist), peptidoglycan (PGN, TLR2), Poly I:C (TLR3), CpG DNA (TLR9) or S100 A12 (RAGE). (Yang H., *MD-2 is required for disulfide HMGB1-dependent TLR4 signaling*, J Exp Med., 2015; 212(1): 5-14). It is protective in a diverse array of in vivo models, reducing mortality in models of ischemia/ reperfusion injury, acetaminophen toxicity, and sepsis, underscoring the importance of HMGB1/MD-2/TLR4 as the major pro-inflammatory signaling axis in these models. (Id.). Significantly, in a mouse model of influenza-induced ALI and lethality, P5779 (SEQ ID NO: 1) reduces mortality approximately 9-fold in mice when given daily for five days beginning two days after influenza infection (see FIG. 11 which shows P5779 (SEQ ID NO: 1) rescues survival after lethal influenza infection with strain PR8), and it lowers clinical scores in survivors. (Shirey K A, *Novel strategies for targeting innate immune responses to influenza*, Mucosal Immunol., 2016; 9(5):1173-82).

As a result, P5779 (SEQ ID NO: 1) is a potent TLR4/ MD-2 inhibitor that selectively blocks disulfide HMGB1-mediated inflammation without causing immune-suppression as it does not inhibit LPS-TLR4 signaling. (Yang H., *MD-2 is required for disulfide HMGB1—dependent TLR4 signaling*, J Exp Med, 2015:jem. 20141318). Although P5779 (SEQ ID NO: 1) diminished cytokine release from macrophages exposed to recombinant HMGB1, it did not inhibit LPS-stimulated cytokine release in vitro or in vivo. This is not attributable to low in vivo activity, however, since repeat doses of the peptide reduced mortality in models of ischemia/reperfusion injury, acetaminophen toxicity, cecal ligation and puncture-induced sepsis (Id.) and acute lung injury (Shirey, K. A., et al., *Novel strategies for targeting innate immune responses to influenza*, Mucosal Immunol, 2016, 9(5): p. 1173-82). Thus, P5779 (SEQ ID NO: 1) allows TLR4/MD-2/HMGB1-driven inflammation to be attenuated without impairing the immune response to microbes. Thus, in one instance P5779 (SEQ ID NO: 1) administration blunts HMGB1-mediated activation of the TLR4/MD-2 signaling pathway and diminishes HMGB1-induced release of pro-inflammatory cytokines from macrophages.

The potential to attenuate HMGB1-driven inflammation without impairing the immune response to microbes, and the wide therapeutic window HMGB1 has shown in other indications, make HMGB1 antagonists superb candidates for treating a broad range of inflammatory syndromes, including sepsis, ALI and DPN. Yet P5779 (SEQ ID NO: 1) is a poor therapeutic candidate due to the minimal plasma stability and short in vivo half-life, which likely would necessitate unfeasible dosing and frequency in the clinical setting.

The present invention is directed, in part, to peptidomimetic small molecules which overcome the clinical deficiencies of P5779 (SEQ ID NO: 1). More particularly, the present invention is directed to a method of treating and/or preventing and/or inhibiting severe sepsis in a mammal comprising administering to a mammal a therapeutically effective amount of a peptidomimetic small molecule modeled after an HMGB1 antagonist tetramer peptide, P5779 (SEQ ID NO: 1). In certain preferred embodiments, the peptidomimetic small molecule is an HMGB1 antagonist tetramer peptide which has been stabilized with at least one azapeptide linkage. In certain preferred embodiments of the invention, the peptidomimetic small molecule is a modified P5779 (SEQ ID NO: 1) wherein at least one terminal peptide bond has been replaced with an azapeptide linkage and in other further preferred embodiments, both of the terminal peptide bonds have been replaced with azapeptide linkages.

The present invention is also directed to a method for reducing mortality and pathology associated with ALI, and a method of restraining the unchecked inflammation that precipitates ALI. HMGB1 is a therapeutic target for sterile inflammation and infection. Annual Review Immunol, 2011; 29:139-62. It is released by injured or infected cells and specifically activates immunocompetent cells to release pro-inflammatory cytokines that recruit additional innate immune cells. As a late mediator of inflammation, inhibiting HMGB1 activity has a more amenable therapeutic window than other pro-inflammatory signals.

The present invention is directed in part to peptidomimetic small molecules which overcome the clinical deficiencies of P5779 (SEQ ID NO: 1). More particularly, the present invention is directed to a method of treating and/or preventing and/or inhibiting acute lung injury in a mammal comprising administering a therapeutically effective amount of a peptidomimetic small molecule modeled after an HMGB1 antagonist tetramer peptide. In certain preferred embodiments, the peptidomimetic small molecule is an HMGB1 antagonist tetramer peptide which has been stabilized with at least one azatide linkage. In further preferred embodiments, the peptidomimetic small molecule is a modified P5779 (SEQ ID NO: 1) wherein at least one terminal peptide bond has been replaced with an azatide linkage and in other preferred embodiments, both of the terminal peptide bonds have been replaced with azatide linkages.

The present invention is also directed, in part, to small molecules that are structural mimics of peptides that interfere with pro-inflammatory signaling initiated by HGMB1, an alarmin and a primary late mediator of inflammation. (Andersson U, *HMGB1 is a therapeutic target for sterile inflammation and infection*, Annu. Rev. Immunol, 2011; 29:139-62; Harris H E, *HMGB1: a multifunctional alarmin driving autoimmune and inflammatory disease*, Nat. Rev. Rheumatol., 2012; 8(4):195-202; Lotze M T, *High-mobility group box 1 protein (HMGB1): nuclear weapon in the immune arsenal*, Nat Rev Immunol., 2005; 5(4):331-42; Yang H, *Targeting HMGB1 in inflammation*, Biochim Biophys Acta., 2010; 1799(1-2):149-56). Certain preferred embodiments of the invention are directed to a small molecule that is a structural mimic of a previously described peptide that interferes with pro-inflammatory signaling initiated by HGMB1. HMGB1 activates the inflammatory response through the TLR4 receptor after binding to the TLR4 co-receptor, MD2. TLR4/MD2 has been implicated in ALI. (Imai Y, *Identification of oxidative stress and Toll-like receptor 4 signaling as a key pathway of acute lung injury*, Cell, 2008; 133(2):235-49; Martin T R, *A TRIFfic perspective on acute lung injury*, Cell, 2008; 133(2):208-10; Shirey K A, *Novel strategies for targeting innate immune responses to influenza*, Mucosal Immunol., 2016; 9(5):1173-82; Shirey K A, *The TLR4 antagonist Eritoran protects mice from lethal influenza infection*, Nature, 2013; 497(7450):498-502). Notably, by antagonizing the inflammatory cascade that drives ALI, this novel new small molecule inhibitor has the potential to be an effective therapy for ALI irrespective of the triggering insult.

The present invention is also directed, in part, to peptidomimetic small molecules which overcome the clinical deficiencies of P5779 (SEQ ID NO: 1). More particularly, the present invention is directed to a method of treating and/or preventing and/or inhibiting neuropathic pain, and in particular DPN in a mammal comprising administering to a mammal a therapeutically effective amount of a peptidomimetic small molecule modeled after an HMGB1 antagonist tetramer peptide. In certain preferred embodiments, the peptidomimetic small molecule is an HMGB1 antagonist tetramer peptide which has been stabilized with at least one azatide linkage. In certain preferred embodiments of the invention, the peptidomimetic small molecule is a modified P5779 (SEQ ID NO: 1) wherein at least one terminal peptide bond has been replaced with an azatide linkage and in other further preferred embodiments both of the terminal peptide bonds have been replaced with azatide linkages.

The present invention is also directed to a pharmaceutical composition comprising a therapeutically effective amount of a peptidomimetic molecule having the chemical structure:

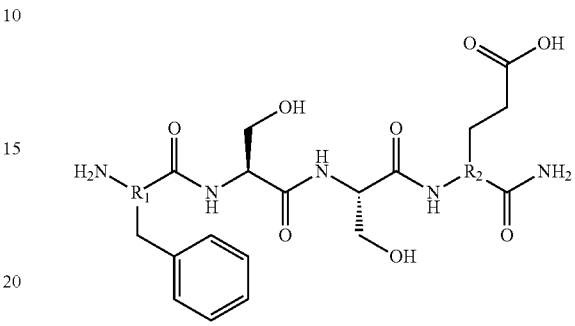

wherein R is C or N; and at least one of $R_1$ and $R_2$ is N to provide an azatide linkage, such that the peptidomimetic molecule is stabilized relative to a peptidomimetic molecule wherein both $R_1$ and $R_2$=C, and at least one pharmaceutically acceptable excipient. In certain further embodiments, both terminal peptide bonds have been replaced with azatide linkages such that both $R_1$ and $R_2$=N and the peptidomimetic molecule has the structure:

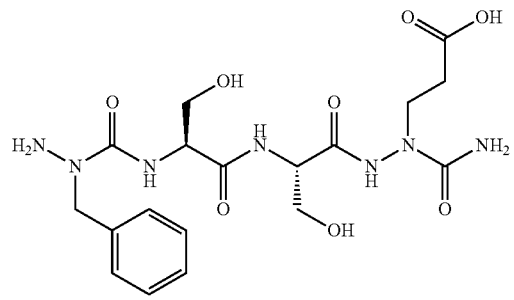

In certain preferred embodiments, the invention is directed to a peptidomimetic small molecule, referred to herein as "K883". Similar to P5779 (SEQ ID NO: 1), K883 was shown to bind to MD-2 and also the TLR4:MD-2 complex (data not shown) and to inhibit HMGB1 binding using surface plasmon resonance (SPR) technology. The SPR (Biacore T200) analysis of (A) P5779 (SEQ ID NO: 1) and (B) K883 inhibition of HMGB1-MD-2 binding can be seen in FIG. 12. Also, K883 docking and molecular dynamic simulations were revealed to be similar to P5779 (SEQ ID NO: 1) (data not shown).

The compounds of the present invention can be prepared by the methods described in Applicant's co-pending U.S. application Ser. No. 16/869,692, filed May 8, 2020 hereby incorporated by reference in its entirety.

To create K883, the terminal peptide bonds of P5779 (SEQ ID NO: 1) were replaced with azapeptide linkages. The structures of P5779 (SEQ ID NO: 1) and of K883 can be seen below, with the azapeptide linkages which distinguish K883 in bold.

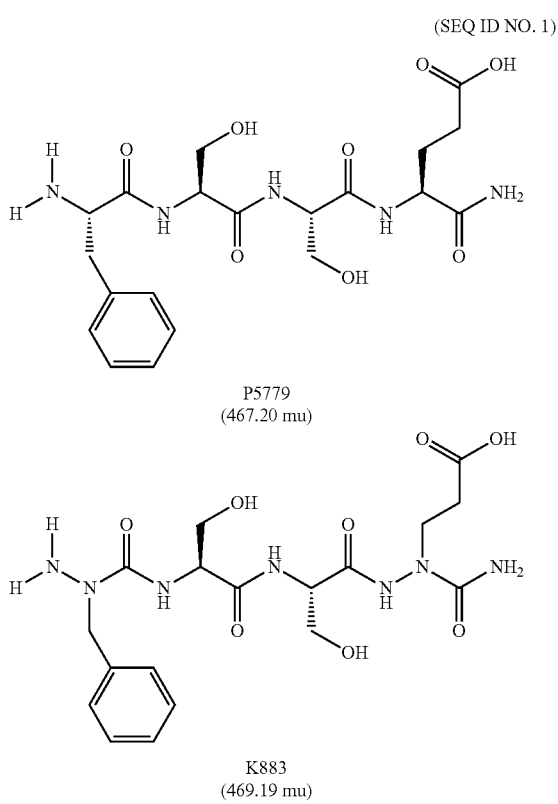

P5779
(SEQ ID NO: 1)
(467.20 mu)

K883
(469.19 mu)

K883 has shown increased potency to prevent MD-2 binding to disulfide HMGB1 ($IC_{50}$=90 nM) and also has extended in vivo half-life (T½>60 min). K883 also effectively reduces peripheral neuropathy in a rat chronic constriction injury of the sciatic nerve (CCI) model.

K883 shows significantly higher in vitro and in vivo stability than P5779 (SEQ ID NO: 1). In rat plasma and whole blood, the half-life for degradation of P5779 (SEQ ID NO: 1) was 12 and 13 minutes, respectively. In contrast, K883 was not degraded after incubating 120 minutes in rat plasma and blood. Following IV administration to rats, the plasma half-life of P5779 (SEQ ID NO: 1) was <5 minutes while for K883 it was 1.2+/−0.2 hours (n=3 animals/experiment). K883 and P5779 (SEQ ID NO: 1) have similar MD-2-binding affinity. The experiments discussed below test K883's activity to protect mice following cecal ligation and puncture. K883 mimics the well-characterized peptide P5779 (SEQ ID NO: 1) to antagonize HMGB1 signaling through the TLR4/MD-2 receptor, but with significantly longer in vivo half-life than the peptide.

Figure 13:
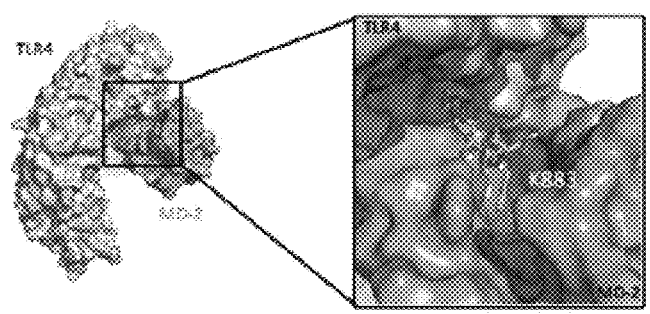
FIG. 13 is a modeling depiction of the azapeptide K883 binding in a pocket between the TLR4 receptor and the adaptor protein MD-2. TLR4 and MD-2 protein surfaces are represented in gray and orange, respectively and K883 carbon atoms are shown in blue.

FIG. 13 is a modeling depiction of azapeptide K883 binding in a pocket between the TLR4 receptor and the adaptor protein MD-2. The K883 binds at the interface area of TLR4/MD-2 complex with the N-terminal (Phenylalanine residue) anchoring in the MD-2 hydrophobic pocket and the C-terminal (glutamic acid residue) binding to TLR4. The C-terminal carboxylic acid groups can form salt bridges with the Lys362 and Arg264 on the TLR4. Other hydrogen bonds involve Asn339 on TLR4 and Glu92, Val93, Tyr102, Ser118 on MD-2. The phenyl side chain on the P5779 (SEQ ID NO: 1) N-terminal stabilized the molecule into the MD-2 by forming Pi-pi interaction with Phe76 inside the hydrophobic pocket. FIG. 8A, FIG. 8B and FIG. 11 show a tetrameric peptide antagonist of HMGB1 rescues survival following cecal ligation and puncture.

K883 binds MD-2 and is functionally active in vitro similar to P5779 (SEQ ID NO: 1) and exhibits a serum half-life>1 hour. This improvement allows for lower/less frequent dosing to achieve comparable or superior outcomes to those achieved with P5779 (SEQ ID NO: 1).

K883 represents an unprecedented opportunity to prevent/treat/inhibit the pathogenic inflammation that leads to mortality or other sequelae (eg. ALI) in sepsis survivors through targeted immunosuppression. HMGB1 is a central mediator in the inflammatory cascade. HMGB1-mediated signaling is central for precipitating the pathogenic inflammation that leads to mortality or other sequelae in sepsis survivors. Furthermore, K883 antagonizes HMGB1 pro-inflammatory signaling specifically through the TLR4/MD-2 receptor, which has long been implicated in ALI. (Imai Y, *Identification of oxidative stress and Toll-like receptor 4 signaling as a key pathway of acute lung injury*, Cell, 2008; 133(2):235-49; Shirey K A, *The TLR4 antagonist Eritoran protects mice from lethal influenza infection*, Nature, 2013; 497(7450): 498-502; PMCID: PMC3725830). By diminishing HMGB1 signaling rather than abolishing it, K883 has the ability to dampen the inflammatory response to avoid immunopathology without blocking the body's ability to clear pathogens.

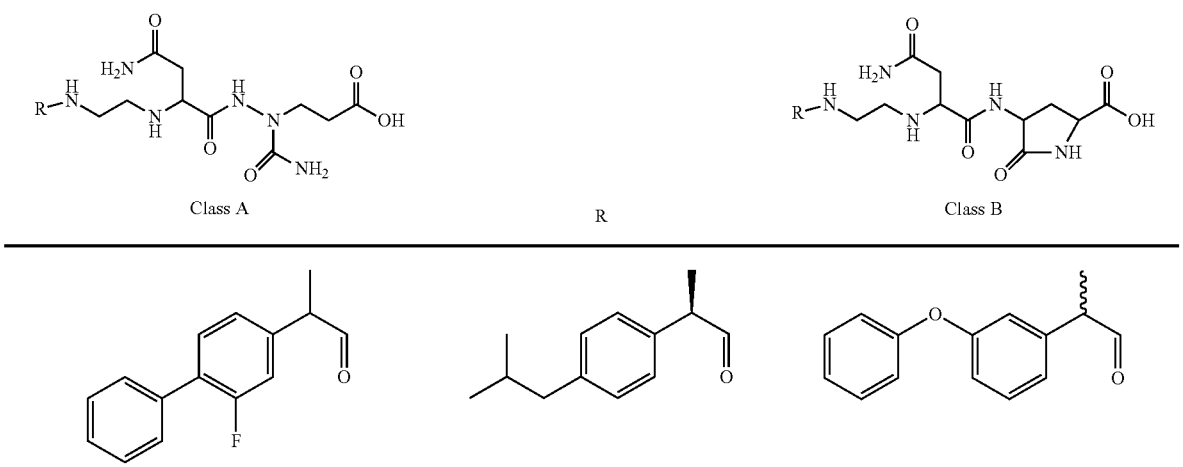

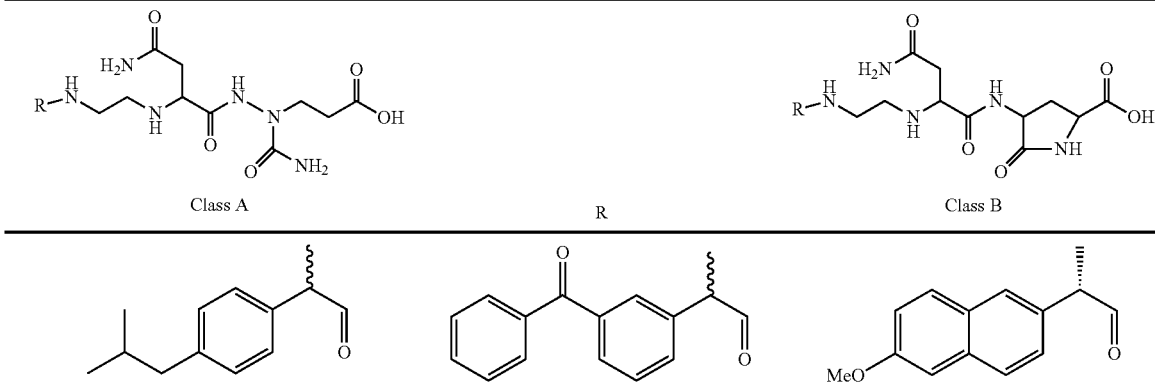

By virtue of the understanding of the present invention, it is now known that now known that HMGB1-dependent TLR4 signaling is the key and dominant mechanism underlying the generation of cytokines (Yang H, et al., *Redox modification of cysteine residues regulates the cytokine activity of high mobility group box*-1, (*HMGB*1), Molecular Medicine, 2012; 18(1):250; Yang H., et al., *The many faces of HMGB*1: *molecular structure functional activity in inflammation, apoptosis, and chemotaxis*, Journal of Leukocyte Biology, 2013; 93(6):865-873); 2) dorsal root ganglia (DRG) sensory neurons are selectively activated by HMGB1-induced Ca2+ influx; 3) potent MD-2 ligands (K883) have been synthesized; 4) the novel HMGB1-TLR4/MD2 inhibitor (K883) selectively blocks HMGB1-mediated inflammation without causing immune-suppression as it does not inhibit LPS-TLR4 signaling (Yang H, et al., *MD-2 is required for disulfide HMGB*1—*dependent TLR*4 *signaling*, J Exp Med, 2015:jem, 20141318; 5) K883 exhibits increased potency to prevent MD-2 binding to disulfide HMGB1 (IC50=90 nM) and extended in vivo half-life (T½=1.5 hr); 6) K883 effectively reduces peripheral neuropathy in a rat chronic constriction injury (CCI) model.

K883 represents a promising treatment for e.g. sepsis, ALI, bacterial and viral respiratory infections such as influenza and SARS-CoV-2 and peripheral neuropathy that is independent of the instigating pathogen, insult, or injury.

Additional Clinical Applications

Furthermore, given the central role HMGB1 plays in inflammation and innate immune activation, it is likely that the HMGB1 antagonist tetramer peptide which has been stabilized with at least one azapeptide linkage will find clinical application for a much wider range of indications beyond ALI resulting from acute respiratory infection caused by influenza and ALI triggers such as sepsis, non-influenza pulmonary infections, smoke or toxic gas inhalation, gastric acid aspiration and treatments for ALI such as transfusion reactions and mechanical ventilation which can cause additional airway injury that exacerbates the condition. For example, HMGB1 has been directly implicated in regulating innate and adaptive immunity in health and during arthritis, colitis, sterile ischemia, traumatic injury, cancer and infection. (Ulf Andersson, *HMGB*1 *is a Therapeutic Target for Sterile Inflammation and Infection*, Annu. Rev. Immunol., 2011, 29:139-62). Further possible indications could include treatment of hemorrhagic shock, endotoxemia, gastrointestinal disorders including gastrointestinal inflammation, inflammatory bowel disease such as cecal perforation, intraperitoneal LPS injection, and IBD based on chemically induced colitis, respiratory disorders including sepsis, inflammatory lung injury, acute lung injury, patients subjected to long-term ventilator therapy and cystic fibrosis, autoimmune diseases such as arthritis, dermatomyositis, multiple sclerosis, systemic lupus erythematosus (SLE), celiac disease, chronic fatigue syndrome, Crohn's disease, type 1 diabetes, Graves disease, juvenile arthritis, chronic Lyme disease, myocarditis, myositis, polymyositis, post-myocardial infarction syndrome, psoriasis, psoriatic arthritis, reactive arthritis, rheumatic fever, scleroderma, Sjogren's syndrome, thrombocytopenia, ulcerative colitis; neurodegenerative diseases including Alzheimer's, mild cognitive impairment (pre-Alzheimer's), Parkinson's disease, amyotrophic lateral sclerosis (ALS); arthritis including osteoarthritis (OA), arthritic joint inflammation, juvenile idiopathic arthritis (JIA) and serum rheumatoid arthritis (RA); asthma; cancer, including pancreatic cancer, colorectal cancer, skin cancers including melanoma; cardiac and vessel disease including coronary artery disease (CAD), coronary heart disease, acute coronary, and atherosclerosis, heart failure; metabolic disorders including type 2 diabetes; β-cell transplantation in diabetes; lung injury and lung related diseases including COPD, pulmonary hypertension, pulmonary fibrosis and pneumonia; Intensive care unit patients being treated for various conditions including sepsis, systemic inflammatory response syndrome, severe trauma, blunt chest trauma, hemorrhagic shock/trauma, traumatic brain injury, stroke, spinal cord injury, influenza, chemical toxicity, severe viral or bacterial infections; post sepsis impairments including cognitive impairments, persistent splenomegaly, post sepsis anemia; post-surgery neurocognitive disorders; drug induced liver injury including acetaminophen-induced liver injury, ethanol-induced liver diseases, cryopyrin-associated autoinflammatory syndrome, bleomycin induced lung fibrosis and paracetamol intoxication; nociceptive pain; ischemia (with or without reperfusion), including cardiac ischemia, cerebral ischemia and skeletal muscle ischemia; inflammatory bowel disease; kidney and liver related disease including kidney failure and liver failure, hepatic ischemia/reperfusion injury, acute kidney injury (CHD), chronic kidney disease (CKD), acute liver failure (ALF) including ALF-SIRS and ALF-systemic, liver fibrosis and alcoholic liver disease; trauma/ischemia caused by transplant and graft-versus-host disease; obesity/metabolic syndrome; pancreatitis; pregnancy complication such as preeclampsia; epilepsy; pulmonary arterial hypertension (PAH); chronic pain; chronic inflammation; chronic inflammatory diseases including chronic obstructive pulmonary disease (COPD), atherosclerosis and arthritic joint inflammation; and other diseases causing moderate to severe pain but not limited to post-surgical pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, and injuries, peptic ulcers, gastritis, regional enteritis, ulcerative colitis, diverticulitis or with a recurrent history of gastrointestinal lesions; GI bleeding, coagulation disorders including anemia such as hypoprothrombinemia, hemophilia or other bleeding problems; kidney disease; chronic fatigue syndrome, traumatic brain injury, concussion and migraines; those prior to surgery or taking anticoagulants. (Id.; Sonya VanPatten, *High Mobility Group Box-1 (HMGb1): Current Wisdom and Advancement as a Potential Drug Target Miniperspective*, J. Med. Chem, Dec. 21, 2017, pp. 3-4; Damien Bertheloot, *HMGB1, IL-1α, IL-33 and S100 proteins: dual-function alarmins*, Cellular & Molecular Immunology (2016), 13, 1-22; A. Tsung, *High-mobility group box-1 in sterile inflammation*, Journal of Internal Medicine, 2014, 276, 425-443; Ulf Andersson, *Extracellular HMGB1 as a therapeutic target in inflammatory diseases*, Expert Opin Ther Targets, 2018 March; 22(3), 263-277; Ulf Andersson, *High-mobility group box 1 protein (HMGB1) operates as an alarmin outside as well as inside cells*, Semin Immunol, 2018 Mar. 9, pii: S1044-5323(17) 30076-3; Sangeeta S Chavan, *HMGB1 Mediates Cognitive Impairment in Sepsis Survivors*, Molecular Medicine, 18: 930-937 (2012); Li Fu, *Therapeutic effects of anti-HMGB1 monoclonal antibody on pilocarpine-induced status epilepticus in mice*, Scientific Reports, 7: 1179 (2017); Peter Lundback, *A Novel High Mobility Group Box 1 Neutralizing Chimeric Antibody Attenuates Drug-Induced Liver Injury and Postinjury Inflammation in Mice*, Hepatology, Vol. 64, No. 5 (2016); Taylor M Parker, *The Danger Zone: Systematic Review Of The Role Of Hmgb1 Danger Signaling In Traumatic Brain Injury*, Brain Inj., 31(1): 2-8 (2017); Matteo Santoro, *In-vivo evidence that high mobility group box 1 exerts deleterious effects in the 1-methyl-4-phenyl-1,2,3,6-tetrahydropyridine model and Parkinson's disease which can be attenuated by glycyrrhizin*, Neurobiology of Disease, 91, pp. 59-68 (2016); Karatas H, et al. *Spreading depression triggers headache by activating neuronal Panx1 channels*, Science, 2013, 339(6123):1092-5) has implicated HMGB1 and migraine aura and headache; TBI/concussion: A recent review in Neuron has implicated HMGb1 and its receptor RAGE in this condition. (Jassam, Y, et al. *Neuroimmunology of Traumatic Brain Injury: Time for a Paradigm Shift*, Neuron, 2017, 95(6):1246-1265)

The therapeutically effective amount of a peptidomimetic small molecule modeled after an HMGB1 antagonist tetramer peptide (e.g. a modified P5779 (SEQ ID NO: 1)) is administered to a mammal (e.g. a human) in a suitable dosage form. The suitable dosage form may be administered, e.g. via oral delivery, parenteral delivery, buccal delivery, sublingual delivery, nasal delivery, inhalation delivery, nebulization delivery, topical delivery, transdermal delivery and suppository delivery. In certain embodiments, the oral dosage form is a suitable controlled or sustained release formulation. In certain embodiments, the dosage form is an oral liquid dosage form. In certain preferred formulations, the release of the peptidomimetic small molecule occurs in the intestinal tract.

In certain dosage forms, the active agent will be a modified P5779 (SEQ ID NO: 1) having a terminal peptide bonds replaced with azatide linkages and preferably the composition is K883. In certain embodiments, the active agent (e.g. K883) is combined with an excipient selected from the group consisting of 1) phosphate buffered saline, 2) PEG, 3) propylene glycol and 4) polysorbate 80 and 5) combinations thereof. In certain embodiments, the active agent (e.g. K883) is combined with an excipient comprising PBS:PEG 300:propylene glycol:polysorbate 80 at 50:40:5:5. In preferred formulations, the aqueous solubility of the modified P5779 used as the active ingredient is greater than about 1 mg/ml. In other preferred formulations, the aqueous solubility of the modified P5779 used as the active ingredient is greater than about 5 mg/ml. In further preferred formulations, the modified P5779 used as the active ingredient is stable for greater than 60 minutes in plasma or simulated stomach acid.

A therapeutically effective amount of the active agent will be administered in a suitable pharmaceutical composition for the treatment and/or prevention and/or inhibition of an autoimmune or inflammatory disease or condition. The pharmaceutical composition can be administered to a patient in need of treatment for e.g. severe sepsis, acute lung injury, neuropathic pain, including DPN in a mammal (e.g. a human). The pharmaceutical composition can also be administered for the treatment and/or prevention and/or inhibition of the effects of bacterial and viral respiratory infections such as influenza and SARS-CoV-2. The pharmaceutical composition can also be administered for the treatment and/or prevention and/or inhibition of adverse conditions relating to surgery or the administration of anticoagulants.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The composition of the invention may consist of the active ingredient alone, in a form suitable for administration to a (human) subject or patient, or the composition may comprise at least one active ingredient and one or more pharmaceutically acceptable excipients.

In one embodiment, the compositions of the invention are formulated using one or more pharmaceutically acceptable carriers. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey). The carrier may be a solvent or dispersion medium containing, for example, water, ethanol, polyol (for example, glycerol, propylene glycol, and liquid polyethylene glycol, and the like), suitable mixtures thereof, and vegetable oils.

Formulations may be employed in admixtures with conventional excipients, i.e., pharmaceutically acceptable organic or inorganic carrier substances suitable for oral, vaginal, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof.

The composition may include an anti-oxidant and a chelating agent that inhibits the degradation of the compound. Examples of antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

Controlled- or sustained-release formulations of a composition of the invention may be made using conventional technology, in addition to the disclosure set forth elsewhere herein. In some cases, the dosage forms to be used can be provided as slow or controlled-release of one or more active ingredients therein using, for example, hydropropylmethylcellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the compositions of the invention.

For oral administration, particularly suitable are tablets, dragees, liquids, drops, capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more inert, non-toxic pharmaceutically excipients. Such excipients include, for example an inert diluent such as lactose; granulating and disintegrating agents such as cornstarch; binding agents such as starch; and lubricating agents such as magnesium stearate. The oral compositions of the invention in the form of tablets or capsules prepared by conventional means with pharmaceutically acceptable excipients such as binding agents; fillers; lubricants; disintegrates; or wetting agents.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation. For oral administration, If desired, the tablets may be coated using suitable methods and coating materials such as OPADRY® film coating systems available from Colorcon, West Point, Pa. (e.g., OPADRY® OY Type, OYC Type, Organic Enteric OY-P Type, Aqueous Enteric OY-A Type, OY-PM Type and OPADRY® White, 32K18400).

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin. Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen free water) prior to parenteral administration of the reconstituted composition.

A pharmaceutical composition of the invention may be prepared, packaged, or sold in a formulation suitable for topical administration. There are several advantages to delivering compounds, including drugs or other therapeutic agents, into the skin (dermal drug delivery) or into the body through the skin (transdermal drug delivery). Transdermal compound delivery offers an attractive alternative to injections and oral medications.

Additional dosage forms of this invention include dosage forms as described in U.S. Pat. Nos. 6,340,475; 6,488,962; 6,451,808; 5,972,389; 5,582,837 and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Additional diseases that may be treated and/or prevented and/or inhibited using the pharmaceutical composition of the present invention include autoimmune diseases such as non-influenza pulmonary infections, smoke or toxic gas inhalation, gastric acid aspiration, transfusion reactions, reactions and injuries caused by mechanical ventilation, arthritis, colitis, sterile ischemia, traumatic injury, cancer and infection, hemorrhagic shock, endotoxemia, gastrointestinal disorders including gastrointestinal inflammation, inflammatory bowel disease such as cecal perforation, intraperitoneal LPS injection, and IBD based on chemically induced colitis, respiratory disorders including sepsis, inflammatory lung injury, acute lung injury, patients subjected to long-term ventilator therapy and cystic fibrosis, autoimmune diseases such as arthritis, dermatomyositis, multiple sclerosis, systemic lupus erythematosus (SLE), celiac disease, chronic fatigue syndrome, Crohn's disease, type 1 diabetes, Graves disease, juvenile arthritis, chronic Lyme disease, myocarditis, myositis, polymyositis, post-myocardial infarction syndrome, psoriasis, psoriatic arthritis, reactive arthritis, rheumatic fever, scleroderma, Sjogren's syndrome, thrombocytopenia, ulcerative colitis; neurodegenerative diseases including Alzheimer's, mild cognitive impairment (pre-Alzheimer's), Parkinson's disease, amyotrophic lateral sclerosis (ALS); arthritis including osteoarthritis (OA), arthritic joint inflammation, juvenile idiopathic arthritis (JIA) and serum rheumatoid arthritis (RA); asthma; cancer, including pancreatic cancer, colorectal cancer, skin cancers including melanoma; cardiac and vessel disease including coronary artery disease (CAD), coronary heart disease, acute coronary, and atherosclerosis, heart failure; metabolic disorders including type 2 diabetes; β-cell transplantation in diabetes; lung injury and lung related diseases including COPD, pulmonary hypertension, pulmonary fibrosis and pneumonia; Intensive care unit patients being treated for various conditions including sepsis, systemic inflammatory response syndrome, severe trauma, blunt chest trauma, hemorrhagic shock/trauma, traumatic brain injury, stroke, spinal cord injury, influenza, chemical toxicity, severe viral or bacterial infections; post-sepsis impairments including cognitive impairments, persistent splenomegaly, post sepsis anemia; post-surgery neurocognitive disorders; drug induced liver injury including acetaminophen-induced liver injury, ethanol-induced liver diseases, cryopyrin-associated autoinflammatory syndrome, bleomycin induced lung fibrosis and paracetamol intoxication; nociceptive pain; ischemia (with or without reperfusion), including cardiac ischemia, cerebral ischemia and skeletal muscle ischemia; inflammatory bowel disease; kidney and liver related disease including kidney failure and liver failure, hepatic ischemia/reperfusion injury, acute kidney injury (CHD), chronic kidney disease (CKD), acute liver failure (ALF) including ALF-SIRS and ALF-systemic, liver fibrosis and alcoholic liver disease; trauma/ischemia caused by transplant and graft-versus-host disease; obesity/metabolic syndrome; pancreatitis; pregnancy complication such as preeclampsia; epilepsy; pulmonary arterial hypertension (PAH); chronic pain; chronic inflammation; chronic inflammatory diseases including chronic obstructive pulmonary disease (COPD), atherosclerosis and arthritic joint inflammation; and other diseases causing moderate to severe pain but not limited to post-surgical pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, and injuries, peptic ulcers, gastritis, regional enteritis, ulcerative colitis, diverticulitis or with a recurrent history of gastrointestinal lesions; GI bleeding, coagulation disorders including anemia such as hypoprothrombinemia, hemophilia or other bleeding problems; kidney disease, chronic fatigue syndrome, traumatic brain injury, concussion and migraines wherein the treatment comprises administering to the mammal a therapeutically effective amount of a peptidomimetic small molecule modeled after an HMGB1 antagonist tetramer peptide.

DETAILED DESCRIPTION OF THE PREFERRED EMBODIMENTS

The following examples are not meant to be limiting and represent certain embodiments of the present invention.

The experimental testing was designed for robust and unbiased results, with the testing is controlled for the sex, age, and strain of mice. (Yang, H., et al., *MD-2 is required for disulfide HMGB1-dependent TLR4 signaling*, J Exp Med, 2015, 212(1): p. 5-14) Statistical power analyses guided the experiment planning and when possible, commercial reagents (e.g.) that were verified by the supplier were used and the authenticity and purity of specialty reagents made in-house or obtained from other laboratories were confirmed through appropriate positive controls and analytical testing.

More than 2500 publications have used the cecal ligation and puncture model of sepsis since its introduction in 1954 (Fojanini, G. and I. Novi, *Histological picture of peritonitis due to ligature of the ceco-appendicular segment of the artificially hibernated animal*, Arch. Italian Chir., 1954, 78: p. 240-248). The experiments use 20-25 g male Balb/c mice from Charles River, Wilmington, Mass. (Valdés-Ferrer, S. I., et al., *High-mobility group box 1 mediates persistent splenocyte priming in sepsis survivors: evidence from a murine model*, Shock, 2013, 40(6): p. 492-495). Mice are acclimated for seven days before experiments and observed for any symptoms or deficiencies that might confound experiments.

Assuming a reduction in mortality of 50% compared to control, four animals in each cohort provides 90% statistical power; assuming a reduction of mortality of 25%, 15 animals in each group provides 90% statistical power. Male animals are used; these studies are not powered to include two sexes.

Example 1—Synthesis of K883

In Example 1, K883 ($C_{18}H_{27}N_7O_8$, having an exact mass of 469.19) was synthesized in 13 steps; the product of each step was purified, followed by LC-MS to confirm the purity. After purification, compounds were characterized by high resolution MS and NMR methods (1H, and 13C). The synthetic procedure was as follows:

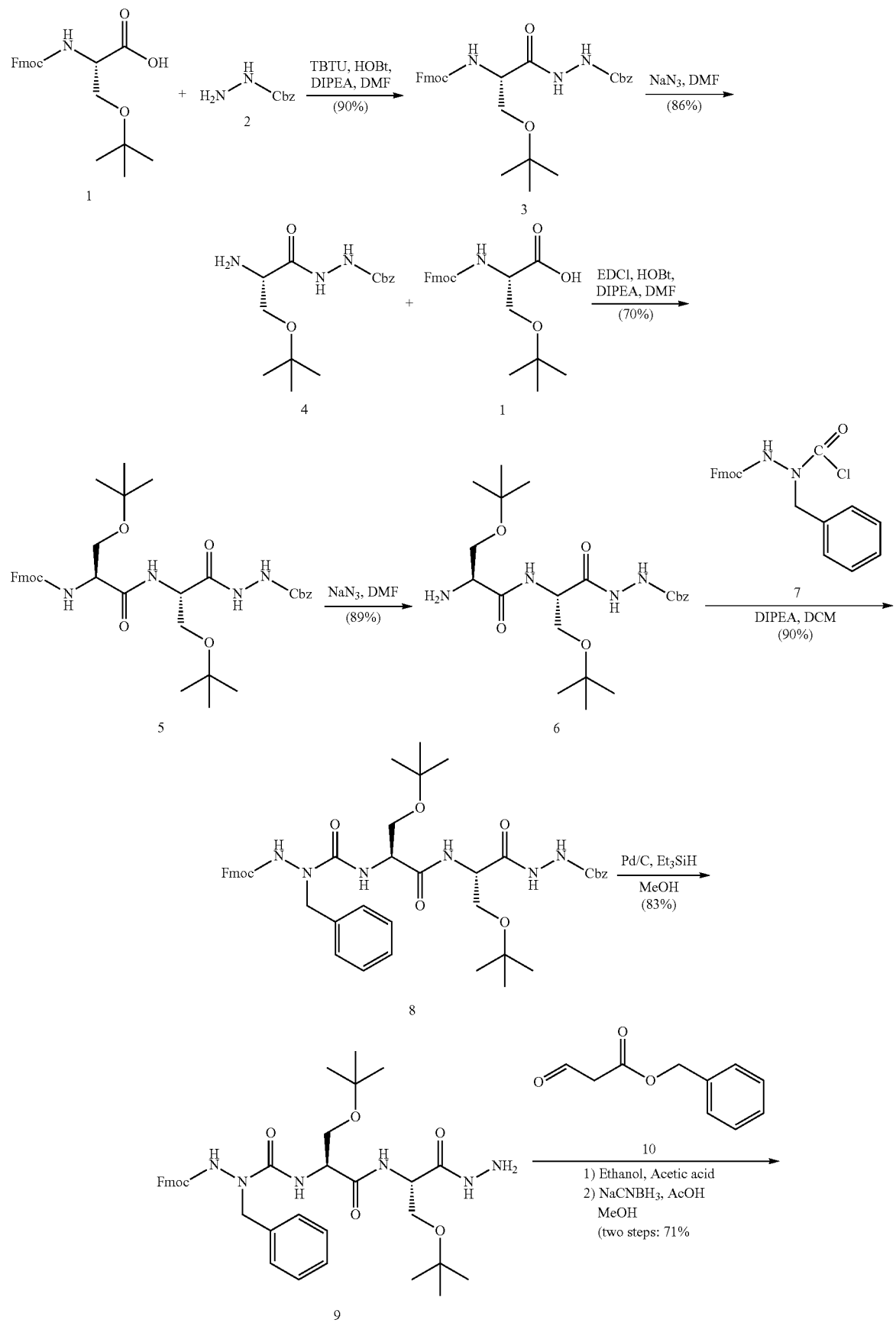

-continued

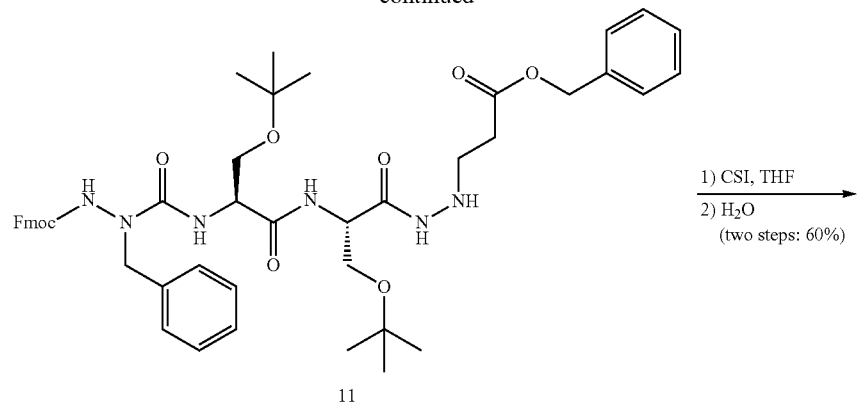

11

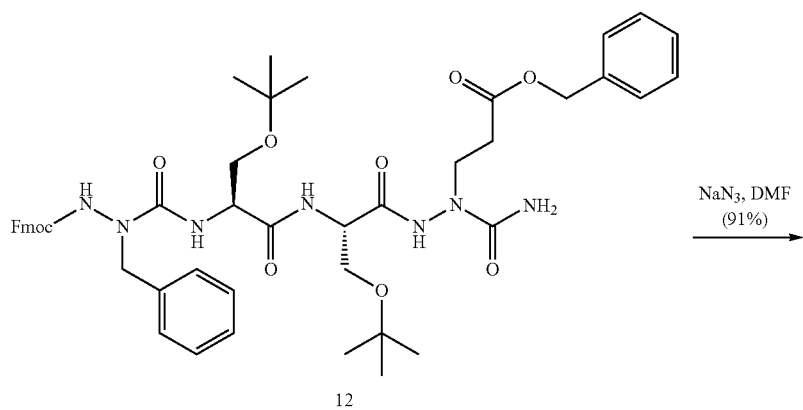

12

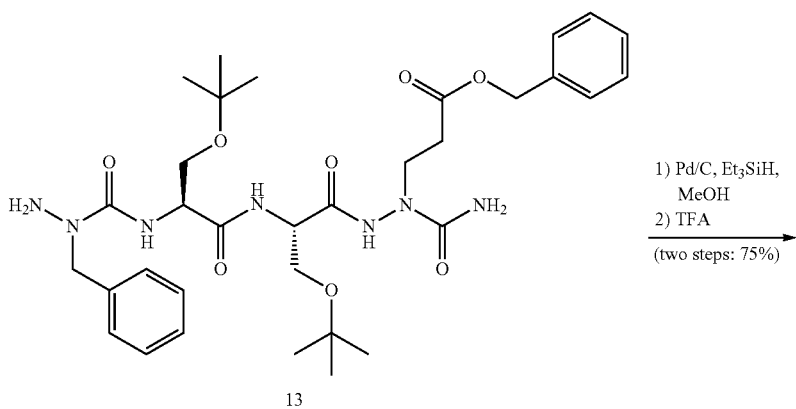

13

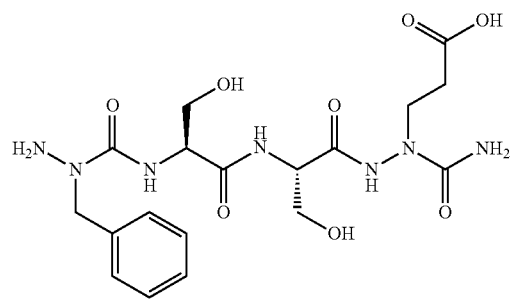

K883
13 steps; total yield = 10%

Commercially available Fmoc-O-tert-butyl-L-serine (1) and Cbz-hydrazine (2) were coupled in the presence of TBTU, HOBt and DIPEA in DMF to form the Cbz-protected semicarbazide (3) with 90% yield. Fmoc is 9-fluorenyl- methoxycarbonyl. The Fmoc group of the semicarbazide (3) was removed by sodium azide in DMF to yield the free amine (4) (86% yield), which was further elongated with another Fmoc-O-tert-butyl-L-serine (1) in the presence of EDCI, HOBt and DIPEA in DCM to di-Serine Cbz-protected semicarbazide (5) (70% yield). After removal of the Fmoc group with sodium azide in DMF (89% yield), the free amine (6) was coupled with N-Fmoc-phenyl hydrazine acid chloride (7) in present of DIPEA in DCM to form the azapeptide (8) in 90% yield. Then the Cbz group was de-protected with Pd/C and Et$_3$SiH in methanol to get the semicarbazide (9) in 83% yield. Condensations of Fmoc-protected semicarbazide (9) with 3-Benzylpropionate aldehyde (10) (Dess Martine oxidation of Benzyl 3-Hydroxypropinonate) to an acyl hydrazone which was reduced by the catalytic hydrogenation and hydride addition to the protected aza-tetrapeptide (11) (two steps, 71% yield). CSI then converted the amine (11) into the corresponding amide (12) (two steps, 60% yield). The Fmoc group was removed with sodium azide in DMF to yield the tetra azapeptide (13) (91% yield). De-protection of O-tert-butyl-L-serine with TFA and O-benzyl with Pd/C and Et$_3$SiH in methanol to get the Aza-P5779 (SEQ ID NO: 1) (K883) (two steps, 75% yield). There are thirteen reaction steps to the final molecule with the total yield of 10%.

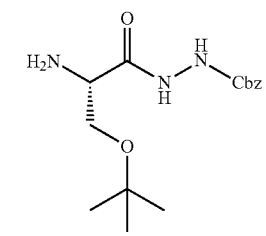

(4)

N-(2-Amino-3-tert-butoxy-propionyl)-hydrazinecarboxylic acid benzyl ester

To a solution of Cbz-protected semicarbazide (3) (5.65 mmol) in anhydrous DMF (30 mL) was added NaN$_3$ (6.78 mmol). The mixture was stirred at 50° C. under nitrogen for 3 hrs then concentrated to dryness and partitioned between water (50 mL) and EtOAc (50 mL). The aqueous layer was extracted with EtOAc (2×50 mL) and the combined organic phases were washed with brine (50 mL), dried over Na$_2$SO4, filtered and concentrated to afford the crude product which was purified by flash silica gel column chromatography eluting with hexane/EtOAc/MeOH mixtures to afford the products as a white solids in 86% yield. $^1$H NMR (500 MHz, CDCl$_3$) δ 7.36-7.28 (m, 5H), 6.87 (br, 1H), 5.03 (s, 2H), 3.51-3.48 (m, 3H), 1.23 (s, 9H) ppm. $^{13}$C NMR (125 MHz, CDCl$_3$) δ172.83, 156.13, 135.80, 128.72, 128.51, 128.35, 73.86, 667.87, 67.35, 63.66, 54.87, 27.62 ppm. Mass Spectrum: (ESI) m/z 310.20 (M+H)$^+$, m/z 332.20 (M+Na)$^+$.

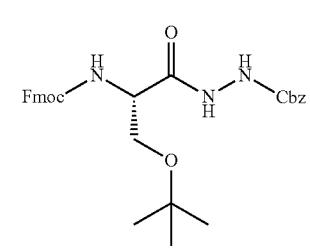

(3)

N-[3-tert-Butoxy-2-(9H-fluoren-9-ylmethoxycarbonylamino)-propionyl]-hydrazinecarboxylic acid benzyl ester To a solution of Cbz-hydrazine (2) (3.0 mmol) and Fmoc-O-tert-butyl-L-serine (1) (3.0 mmol) in anhydrous DMF (30 mL) was add TBTU (3.6 mmol), HOBt (3.0 mmol) and DIPEA (3.0 mmol). The solution was stirred at 25° C. under nitrogen for 15 hrs then concentrated to dryness and partitioned between 0.5N HCl (50 mL) and EtOAc (50 mL). The aqueous layer was extracted with EtOAc (2×50 mL) and the combined organic phase were washed with brine (50 mL), dried over Na2SO4, filtered and concentrated to afford the crude product which was purified by flash silica gel column chromatography eluting with hexane/EtOAc mixtures to afford the products as a white solids in 90% yield. 1H NMR (500 MHz, CDCl3) δ 8.56 (br, 1H), 7.78 (d, 2H), 7.61 (m, 2H), 7.44-7.28 (m, 9H), 6.87 (br, 1H), 5.78 (br, 1H), 5.19 (s, 2H), 4.43-4.37 (m, 3H), 4.24 (t, 1H), 3.81 (m, 1H), 3.47 (m, 1H), 1.27 (s, 9H) ppm. 13C NMR (125 MHz, CDCl3) δ170.59, 156.32, 156.12, 144.03, 143.81, 141.46, 135.62, 128.73, 128.65, 128.58, 128.37, 127.90, 127.24, 125.26, 120.02, 74.85, 68.04, 67.35, 61.42, 53.71, 47.24, 27.53 ppm. Mass Spectrum: (ESI) m/z 532.40 (M+H)+, m/z 554.40 (M+Na)+.

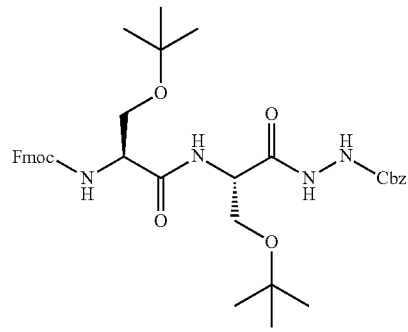

(5)

N-{3-tert-Butoxy-2-[3-tert-butoxy-2-(9H-fluoren-9-ylmethoxycarbonylamino)-propionylamino]-propionyl}-hydrazinecarboxylic acid benzyl ester To a solution of Cbz-semicarbazide amine (4) (2.9 mmol) and Fmoc-O-tert-butyl-L-serine (1) (3.2 mmol) in anhydrous DCM (50 mL) was add EDCI (4.3 mmol), HOBt (0.58 mmol) and DIPEA (2.9 mmol). The solution was stirred at 25° C. under nitrogen for 5 hrs then concentrated to dryness and partitioned between water (50 mL) and EtOAc (50 mL). The aqueous layer was extracted with EtOAc (2×50 mL) and the combined organic phases were washed with brine (50 mL), dried over Na$_2$SO$_4$, filtered and concentrated to afford the crude product which was purified by flash silica gel column chromatography eluting with hexane/EtOAc mixtures to afford the products as a white solids in 70% yield. $^1$H NMR (500 MHz, CDCl$_3$) δ 8.82 (br, 1H), 7.80 (d, 2H), 7.63 (d, 2H), 7.44-7.28 (m, 9H), 7.18 (br, 1H), 6.71 (br, 1H), 5.83 (br, 1H), 5.17 (s, 2H), 4.62 (br, 1H) 4.42 (d, 2H), 4.28-4.23 (m, 2H), 3.93 (m, 1H), 3.82 (m, 1H), 3.48 (m, 2H), 1.24 (s, 18H) ppm. $^{13}$C NMR (125 MHz, CDCl$_3$) δ170.17, 170.02, 156.21, 155.95, 144.00, 143.81, 141.47, 141.44, 135.74, 128.68, 128.50, 128.35, 127.91, 127.25, 125.28, 120.18, 75.30, 74.42, 67.90, 67.41, 62.08, 60.80, 60.58, 54.95, 53.03, 47.24, 27.52 ppm. Mass Spectrum: (ESI) m/z 675.13 (M+H)+, m/z 692.07 (M+Na)+.

(6)

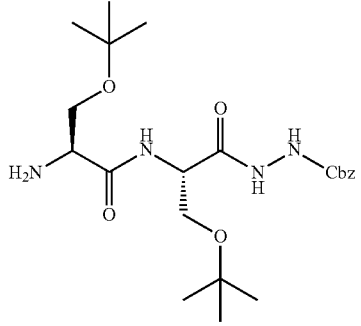

N-[2-(2-Amino-3-tert-butoxy-propionylamino)-3-tert-butoxy-propionyl]-hydrazinecarboxylic acid benzyl ester To a solution of Cbz-protected di-serine semicarbazide (5) (2.49 mmol) in anhydrous DMF (10 mL) was added NaN3 (3.02 mmol). The mixture was stirred at 50° C. under nitrogen for 3 hrs then concentrated to dryness and partitioned between water (25 mL) and EtOAc (25 mL). The aqueous layer was extracted with EtOAc (2×25 mL) and the combined organic phases were washed with brine (25 mL), dried over Na2SO4, filtered and concentrated to afford the crude product which was purified by flash silica gel column chromatography eluting with hexane/EtOAc mixtures to afford the products as a white solids in 89% yield. Mass Spectrum: (ESI) m/z 453.20 (M+H)+, m/z 475.33 (M+Na)+.

(8)

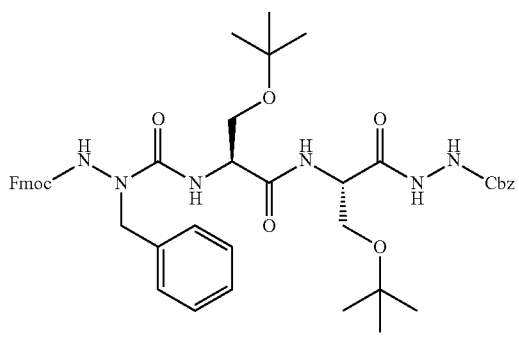

To a solution of Cbz-protected di-serine semicarbazide amine (6) (2.44 mmol) and N-Fmoc-phenyl hydrazine acid chloride (7) (2.44 mmol) in anhydrous DCM (24 mL) at 0° C. was added DIPEA (2.44 mmol). The solution was stirred and warmed to 25° C. under nitrogen for 5 hrs then concentrated to dryness and partitioned between water (50 mL) and EtOAc (50 mL). The aqueous layer was extracted with EtOAc (2×50 mL) and the combined organic phases were washed with brine (50 mL), dried over Na2SO4, filtered and concentrated to afford the crude product which was purified by flash silica gel column chromatography eluting with hexane/EtOAc mixtures to afford the products as a white solids in 90% yield. 1H NMR (500 MHz, CDCl3) δ 8.93 (br, 1H), 7.80 (d, 2H), 7.54 (d, 2H), 7.44 (t, 2H), 7.35-7.31 (m, 12H), 7.18 (br, 2H), 6.63 (br, 1H), 6.48 (br, 1H) 6.32 (br, 1H), 5.16 (s, 2H), 4.62 (m, 1H) 4.53 (m, 2H), 4.36 (m, 1H), 4.20 (m, 1H), 3.91 (m, 1H), 3.80 (m, 1H), 3.49 (m, 2H), 1.20 (s, 18H) ppm. 13C NMR (125 MHz, CDCl3) δ170.65, 169.92, 157.26, 155.90, 155.88, 155.21, 143.27, 143.18, 141.37, 135.62, 135.53, 129.00, 128.51, 128.29, 128.14, 128.06, 127.95, 127.20, 124.93, 120.12, 74.94, 74.12, 67.70, 61.97, 60.70, 54.76, 52.92, 50.77, 46.96, 27.38 ppm.

(9)

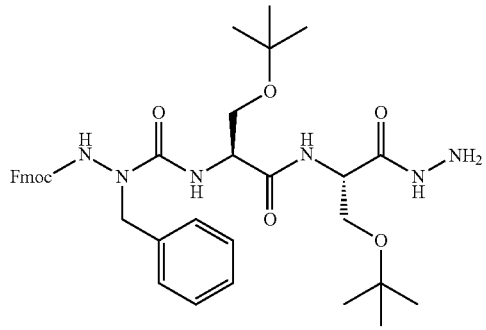

To a solution of Cbz-protected di-serine semicarbazide (8) (2.05 mmol) in anhydrous MeOH (10 mL) was added 10% Pd/C (340 mg) followed by Et3SiH (20.5 mmol). The mixture was stirred at 25° C. under nitrogen for 20 mins then filtered through a pad of celite and concentrated to dryness and partitioned between water (50 mL) and EtOAc (50 mL). The aqueous layer was extracted with EtOAc (2×50 mL) and the combined organic phases were washed with brine (50 mL), dried over Na2SO4, filtered and concentrated to afford the crude product which was purified by flash silica gel column chromatography eluting with hexane/EtOAc mixtures to afford the products as a white solids in 83% yield. 1H NMR (500 MHz, CDCl3) δ 8.26 (br, 1H), 7.79 (d, 2H), 7.54 (d, 2H), 7.44 (t, 2H), 7.35-7.28 (m, 5H), 7.18 (m, 2H), 6.99 (br, 1H), 6.39 (br, 1H), 6.48 (br, 1H) 6.30 (d, 1H), 4.50 (m, 3H), 4.37 (m, 1H), 4.20 (m, 1H), 3.91 (m, 1H), 3.82 (m, 1H), 3.49-3.39 (m, 2H), 1.26 (s, 9H), 1.18 (s, 9H) ppm. 13C NMR (125 MHz, CDCl3) δ170.73, 170.64, 157.26, 155.34, 143.44, 143.38, 141.59, 135.75, 129.14, 129.08, 128.27, 128.15, 127.39, 125.09, 120.31, 75.18, 73.99, 67.95, 62.34, 61.11, 54.80, 53.18, 50.77, 47.21, 27.61, 27.58 ppm.

(11)

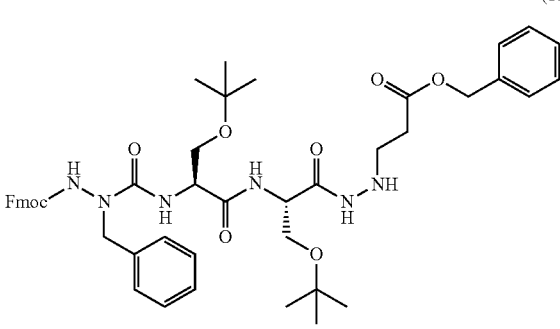

To a solution of protected di-serine semicarbazide (9) (0.87 mmol) and 3-Benzylpropionate aldehyde (10) (2.62 mmol) in anhydrous ethanol (6 mL) was added acetic acid (24 uL). The solution was stirred at 25° C. under nitrogen for 2 hrs then concentrated to dryness. The crude product re-dissolved in anhydrous MeOH (20 mL) and added NaCNBH₃ (4.35 mmol) followed by acetic acid (4.35 mmol). The mixture was stirred at 55° C. under nitrogen for 15 hrs then concentrated to dryness and partitioned between water (50 mL) and EtOAc (50 mL). The aqueous layer was extracted with EtOAc (2×25 mL) and the combined organic phases were washed with brine (25 mL), dried over Na₂SO₄, filtered and concentrated to afford the crude product which was purified by flash silica gel column chromatography eluting with hexane/EtOAc mixtures to afford the products as a white solids in 71% yield (two steps). ¹H NMR (500 MHz, CDCl₃) δ 8.43 (br, 1H), 7.80 (d, 2H), 7.54 (d, 2H), 7.44 (t, 2H), 7.36-7.31 (m, 10H), 7.17 (br, 2H), 7.01 (br, 1H), 6.30 (br, 2H), 5.12 (s, 2H), 4.52 (m, 3H), 4.33 (m, 1H), 4.21 (t, 1H), 3.91 (m, 1H), 3.81 (m, 1H), 3.42 (m, 2H), 3.14 (t, 2H), 2.56 (t, 2H), 1.22 (s, 9H), 1.17 (s, 9H) ppm. ¹³C NMR (125 MHz, CDCl₃) δ172.08, 170.59, 169.75, 157.38, 143.40, 143.35, 141.56, 136.00, 135.64, 129.13, 129.09, 128.69, 128.41, 128.37, 128.27, 128.13, 127.37, 125.08, 125.07, 120.30, 75.10, 73.96, 67.91, 66.54, 62.20, 61.11, 60.60, 54.94, 53.23, 50.78, 47.34, 47.15, 32.82, 27.58 ppm. Mass Spectrum: (ESI) m/z 851.33 (M+H)⁺, m/z 873.40 (M+Na)⁺.

(12)

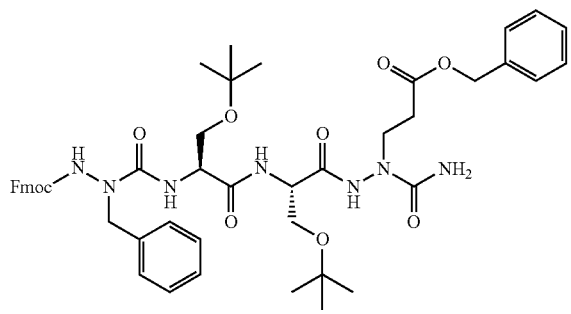

To a solution of the protected aza-tetrapeptide amine (11) (0.70 mmol) in anhydrous THF (5 mL) at 0° C. was added chlorosulfonyl (CSI) (0.84 mmol) rapidly. The solution was stirred at 0° C. under nitrogen for 1 hr then water added (5 mL). The solution was warmed to room temperature then concentrated and partitioned between water (25 mL) and EtOAc (25 mL). The aqueous layer was extracted with EtOAc (2×15 mL) and the combined organic phases were washed with brine (25 mL), dried over Na₂SO₄, filtered and concentrated to afford the crude product which was purified by flash silica gel column chromatography eluting with hexane/EtOAc mixtures afford the products as a white solids in 60% yield (two steps). ¹H NMR (500 MHz, CDCl₃) δ 9.05 (br, 1H), 7.70 (d, 2H), 7.43 (d, 2H), 7.34 (t, 2H), 7.24-7.21 (m, 10H), 7.06 (m, 4H), 6.68 (br, 1H), 6.30 (br, 1H), 5.14 (br, 2H), 4.47 (m, 1H), 4.34 9m, 2H), 4.13 (m, 1H), 4.09 (m, 2H), 3.82 (m, 2H), 3.76 (m, 2H), 3.63 (m, 2H), 3.51 (m, 1H), 3.45 (m, 2H), 3.23 (t, 2H), 1.08 (s, 18H) ppm. ¹³C NMR (125 MHz, CDCl₃) δ 172.10, 170.56, 169.75, 157.36, 157.34, 143.40, 143.35, 141.57, 136.03, 136.65, 129.14, 129.09, 128.70, 128.41, 128.37, 128.28, 128.14, 127.38, 125.08, 120.31, 75.12, 73.96, 69.94, 66.52, 62.23, 61.13, 54.86, 53.24, 50.78, 47.36, 47.10, 32.92, 27.47 ppm. Mass Spectrum: (ESI) m/z 894.40 (M+H)⁺, m/z 916.47 (M+Na)⁺.

(13)

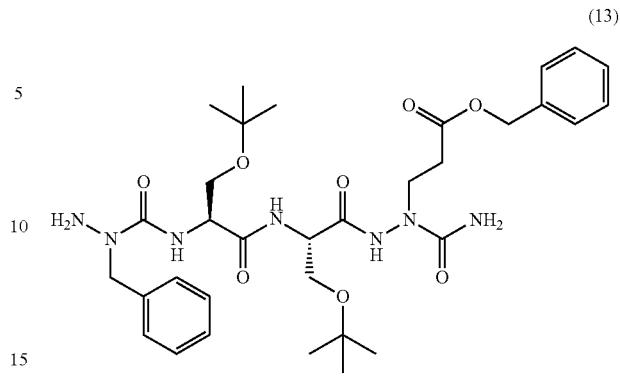

To a solution of protected aza-tetrapeptide amide (12) (0.48 mmol) in anhydrous DMF (5 mL) was added NaN₃ (0.72 mmol). The mixture was stirred at 50° C. under nitrogen for 2 hrs then concentrated to dryness for and partitioned between water (5 mL) and EtOAc (5 mL). The aqueous layer was extracted with EtOAc (2×5 mL) and the combined organic phases were washed with brine (5 mL), dried over Na₂SO₄, filtered and concentrated to afford the crude product which was purified by flash silica gel column chromatography eluting with hexane/EtOAc/MeOH mixtures to afford the products as a white solids in 91% yield. Mass Spectrum: (ESI) m/z 672.47 (M+H)⁺, m/z 694.33 (M+Na)⁺.

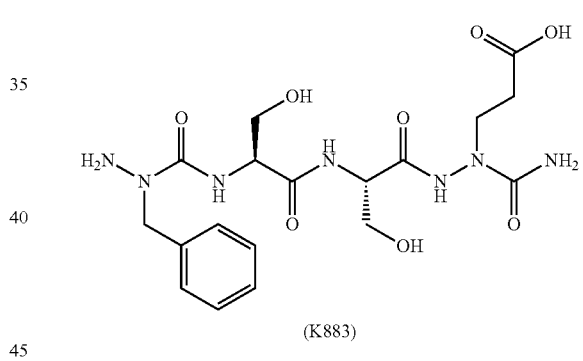

(K883)

To a solution of aza-tetrapeptide amide (13) (0.43 mmol) in anhydrous MeOH (5 mL) was added 10% Pd/C (58 mg) followed by Et₃SiH (4.3 mmol). The mixture was stirred at 25° C. under nitrogen for 20 mins then filtered through a pad of celite and concentrated to dryness. The acid was used directly for next step. Mass Spectrum: (ESI) m/z 582.20 (M+H)⁺, m/z 604.27 (M+Na)⁺.

The crude acid (0.43 mmol) was dissolved in 10 mL TFA at 0° C. then was stirred and warmed to 25° C. under nitrogen for 1 hr. After concentrated to dryness, the crude product was purified by flash silica gel column chromatography eluting with CHCl3/MeOH (4:1 v/v) mixture to afford the Aza-P5779 (SEQ ID NO: 1) (K883) as a white solids in 75% yield (two steps). ¹H NMR (600 MHz, CDCl₃) δ 7.3-7.30 (m, 5H), 4.69 (s, 2H), 4.40 (t, 1H), 4.36 (t, 1H), 3.98 (dd, 1H), 3.95 (dd, 1H), 3.85 (dd, 1H), 3.82 (dd, 1H), 3.80 (br, 2H), 2.48 (t, 2H) ppm. ¹³C NMR (125 MHz, CDCl3) δ 178.10, 173.33, 170.83, 160.27, 159.81, 136.77, 128.67, 128.07, 127.52, 62.31, 61.21, 56.63, 55.42, 52.80, 44.88, 34.91 ppm. Mass Spectrum: (ESI) m/z 470.00 (M+H)+, m/z 492.07 (M+Na)+.

Example 2—Stability of K883

Figure 14A:
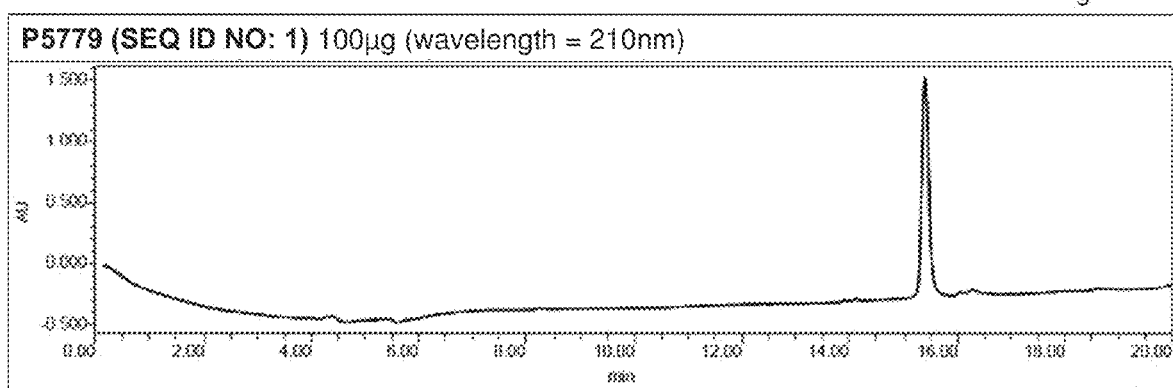
FIGS. 14A-14C are graphical depictions showing relative stability measured by HPLC of the peptide P5779 (SEQ ID NO: 1) at time 0 (FIG. 14A) versus 3 hours (FIG. 14B) and 6 hours (FIG. 14C) after in vitro incubation with mouse serum.
Figure 14B:
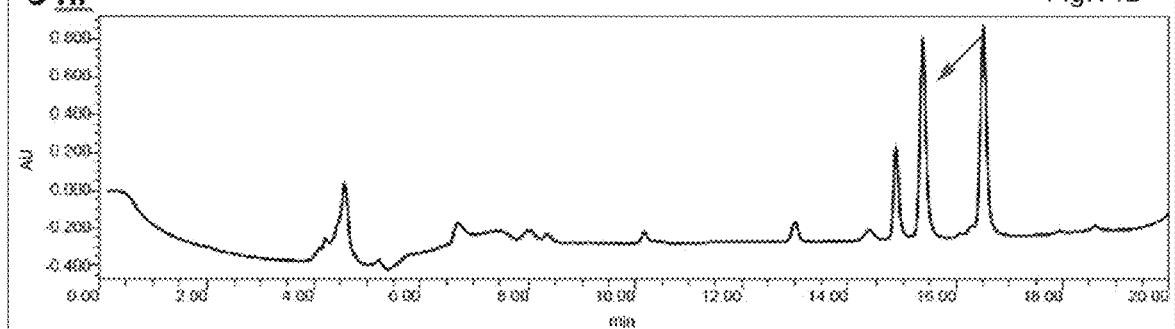
Figure 14C:
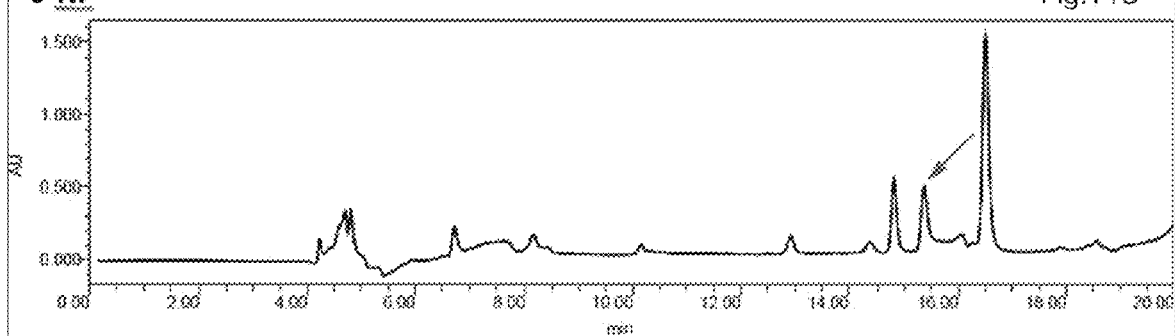

In Example 2, the stability of K883 is compared to that of the peptide P5779 (SEQ ID NO: 1). P5779 (SEQ ID NO: 1) is the peptide that corresponds to K883 prior to replacement of α-carbon atoms with α-nitrogen atoms. The in vitro stability of P5779 (SEQ ID NO: 1) and K883 were tested in mouse serum; residual compound was monitored at a wavelength of 210 nm and sampled at 0 hours, 3 hours and 6 hours. The initial concentration of the P5779 (SEQ ID NO: 1) and K883 were both 100 µg. The results are depicted in FIG. 14, with FIGS. 14A-14F showing the relative stability measured by HPLC of the peptide P5779 (SEQ ID NO: 1) and the enhanced stability of K883 versus P5779 (SEQ ID NO: 1) as tested in mouse serum. Thus, K883 displayed a significant stability profile and 95% of the material survived upon incubation in mouse sera compared to 25% of compound P5779 (SEQ ID NO: 1) (FIGS. 14A-14F).

Example 3—Bioavailability and Administration

In Example 3, the bioavailability and optimal route of administration for K883 is determined. K883 is poorly soluble in water (<100 µg/ml) and has, to date, been dissolved in dimethyl sulfoxide (DMSO), which has been associated with cytotoxicity even at low concentrations (de Menorval M A., *Effects of dimethyl sulfoxide in cholesterol-containing lipid membranes: a comparative study of experiments in silico and with cells*, PLoS One, 2012; 7(7):e41733; Galvao J, *Unexpected low-dose toxicity of the universal solvent DMSO*, FASEB J, 2014; 28(3):1317-30; Hanslick J L, *Dimethyl sulfoxide (DMSO) produces widespread apoptosis in the developing central nervous system*, Neurobiol Dis., 2009; 34(1):1-10; Notman R, *Molecular basis for dimethylsulfoxide (DMSO) action on lipid membranes*, J Am Chem Soc., 2006; 128(43):13982-3). Preliminary evidence suggests that K883 is soluble to >5 mg/ml in a mixture containing PBS:PEG 300:propylene glycol:polysorbate 80 at 50:40:5:5, which are acceptable excipients to the FDA. This provides the basis for developing intravenous (IV) formulation that will serve as a benchmark for developing oral (PO) formulations.

The testing is controlled for the sex, age, and strain of mice. Statistical power analyses guide experiment planning. When possible, commercial reagents (e.g. antibodies and synthesized peptides) that are verified by the supplier are used and the authenticity and purity of specialty reagents made in-house or obtained from other laboratories by including appropriate positive controls and analytical testing.

Numerous published studies from major influenza labs have failed to reveal a sex difference in lethality following influenza infection, consistent with statistical analysis of the inventors of WT male vs. female responses to PR8 infection. Female mice are typically used as males are more aggressive and fight, leading to inflammation that can confound interpretations. Power analysis indicates that five mice/treatment, (two experimental replicates=10 mice in total), is sufficient to detect a 40% difference for 2 samples with repeated measures with α=0.05 and power=0.88.

In Example 3, an acceptable oral formulation for animal and human dosing is developed and is assessed for solubility using a standard flocculation assay in blood; PO formulations are tested by incubation with simulated stomach acid. K883 stability is confirmed by LC-MS. Formulations exhibiting>1 mg/ml solubility will be advanced to bioavailability testing.

For each formulation, at least two cohorts of rats are dosed with K883 either intravenously (IV) or with one of the oral (PO) formulations. For the IV cohort, rats are administered 1 mg/kg K883; for the first PO cohort of each new formulation, rats are administered 10 mg/kg to enable detection of as low as 10% bioavailability. For all cohorts, blood samples are collected at baseline (immediately prior to K883 administration) and at 15, 30, 60, 90, 120, 180, 240, 360 and 480 minutes post-administration; PO cohorts have an additional sample collected at 600 minutes post-administration. Plasma concentrations of K883 are determined by LC-MS/MS; the detection threshold using this method is 0.5 ng/ml. Next, bioavailability is estimated for each formulation. If the bioavailability for any of the PO formulations is estimated at >25%, the experiment is repeated using a PO dose of 1 mg/kg, equivalent to the IV dose. Pharmacokinetics parameters are derived using WinNonlin (v6.4) software using a non-compartmental model. The maximum plasma concentrations (CO) after IV dosing and the plasma half-life (t½) are estimated. The area under the time-concentration curve (AUC) is computed using the linear trapezoidal rule with calculation to the last quantifiable data point. Clearance (CL) is calculated from dose/AUC. Steady state volume of distribution (Vss) is calculated from CL*MRT (mean residence time). Samples below the limit of quantitation (0.5 ng/mL) are treated as zero for pharmacokinetic data analysis.

In the event that none of the oral formulations show adequate bioavailability for use in subsequent in vivo testing, in vivo tests described in Example 2 using only intravenously administered K883 are conducted.

Example 4—Efficacy of K883

In Example 4 and in Example 17 (below), the efficacy of K883 for rescuing survival in a mouse model of sepsis and for mitigating the persistent anemia observed in sepsis survivors is evaluated. The HMGB1 antagonists are synthesized and purified according to Examples 1 and 2. K883 will be evaluated for rescuing mortality and reducing anemia following cecal ligation and puncture. Inhibiting the interaction between HMGB1 and MD-2 with the peptide antagonist P5779 (SEQ ID NO: 1) rescued cecal ligation and puncture-associated mortality compared to an inactive control peptide. (Yang, H., et al., *MD-2 is required for disulfide HMGB1-dependent TLR4 signaling*, J Exp Med, 2015, 212 (1): p. 5-14). These experiments test the efficacy of K883, which persists in circulation>12-fold longer than P5779 (SEQ ID NO: 1), for enhancing survival following cecal ligation and puncture. (See Example 17 and FIG. 25 discussed below)

In survival studies, wild-type mice are randomly assigned to one of six groups to undergo either sham surgery (n=10) or cecal ligation and puncture to induce sepsis. One cecal ligation and puncture cohort (n=30) receives no treatment and serves as the negative control; the remaining four cecal ligation and puncture cohorts (30 mice each) receive one of the following interventions: K883 (500 µm/mouse) or vehicle is delivered by tail vein injection, or K883 (500 µm/mouse) or vehicle delivered by oral gavage. Doses are administered daily for four days starting 24 hr post-surgery. Doses and timing are based on previous studies with the peptide antagonist. (Yang, H., et al., *MD-2 is required for disulfide HMGB1-dependent TLR4 signaling*, J Exp Med, 2015, 212(1): p. 5-14); the interval may be adjusted upon evaluation of pharmacokinetics data for K883. Mice are observed for seven days to determine survival rates for each group.

In anemia studies, wildtype mice are randomly assigned to one of three groups to undergo either sham surgery (120 mice) or cecal ligation and puncture to induce sepsis. The "negative control" cecal ligation and puncture cohort (120 mice) receive no treatment; the remaining cecal ligation and puncture cohort (120 mice) are given K883 (500 μm/mouse) on days 2-5 via the more effective route identified above. Starting at day 9, survivors from the cecal ligation and puncture+treatment cohort are evenly divided and randomly assigned to two groups. The first receive K883 (500 μm/mouse) on days 9-11; the second receive daily doses of K883 (500 μm/mouse) on days 9-28. Dosing interval may be modified once pharmacokinetics data are available. For each group, at 5-day intervals starting on day 11, 6 survivors are sacrificed and blood collected by cardiac puncture for CBC analysis to measure hematocrit (Hct) and hemoglobin (Hgb) levels. Interferon (IFN) signatures and HMGB1 levels are also determined. (Valdes-Ferrer, S. I., et al., *HMGB1 mediates anemia of inflammation in murine sepsis survivors*, Mol Med, 2015). At day 31, all remaining survivors are sacrificed for blood collection.

Example 5—K883 Inhibition of MD-2 Binding to HMGB1

In Example 5, the ability of K883 to inhibit HMGb1 binding to MD-2 is evaluated in an in vitro protein/protein interaction assay using human proteins.

Figure 12A:
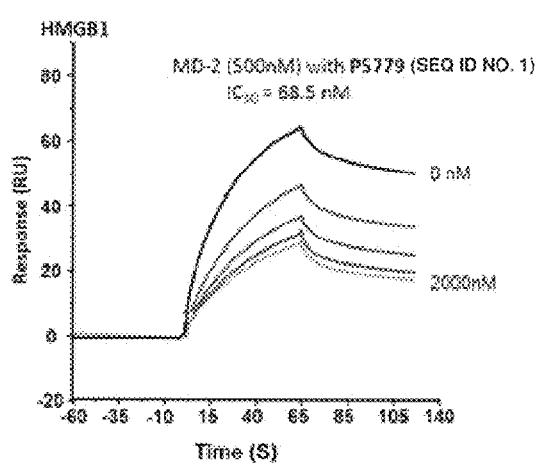
FIGS. 12A and 12B are graphical depictions of inhibition of MD-2 binding to HMGB1 as measured by SPR binding studies using a Biacore T200® instrument.
Figure 12B:
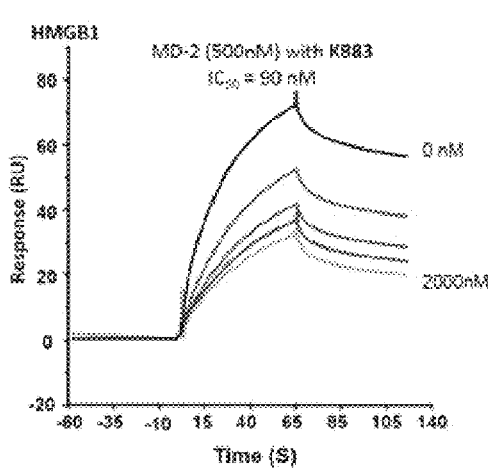

FIGS. 12A and 12B show the inhibition of MD-2 binding to HMGB1 as measured by SPR binding the inhibition of MD-2 binding to HMGB1 as measured by SPR binding studies using a Biacore T200® instrument with the inhibition achieved with P5779 (SEQ ID NO: 1) shown in FIG. 12A and the dose-responsive inhibition achieved with increasing concentrations of K883 (1-2000 nM) shown in FIG. 12B. In FIG. 12A, MD-2 held constant throughout assay at 500 nM, concentration of P5779 (SEQ ID NO: 1) varied (2×) from 2000 nM to 0 nM, IC50 is around 68.5 nM inhibition of HMGB1 binding to MD2. In FIG. 12B, MD-2 is held constant throughout assay at 500 nM, concentration of K883 varied (2×) from 2000 to 0 nM and IC50 is around 90 nM. Both compounds were very comparable in inhibiting HMGb1: MD2 complex formation which is a critical step for HMGb1 proinflammatory signaling pathway.

Inhibiting HMGb1 and MD2 is a critical step in HMGb1 proinflammatory signaling pathway. P5779 (SEQ ID NO: 1) has been previously identified first as an inhibitor of HMGb1:MD2 complex formation in Surface Plasmon Resonance (SPR) binding studies and consequently was examined in multiple meurine models of inflammation and has been shown to be protective (Yang, H., et al., *MD-2 is required for disulfide HMGB1-dependent TLR4 signaling*, J Exp Med, 2015, 212(1): p. 5-14; Both compounds are shown in Example 5 to be very comparable in inhibiting HMGb1: MD2 complex formation. This is a first step in validating that the modification in the sequence of P5779 (SEQ ID NO: 1) to azapeptide does not alter the affinity toward MD2 and inhibition of the HMGb1:MD2 complex formation.

Example 6—K883 Inhibition of HMGB1-Induced TNF Release

In Example 6, the ability of K883 to inhibit HMGB1-induced TNF release in human and mouse macrophages was evaluated. As discussed above, TNF is an early effector of inflammation. Drugs intended to antagonize early effectors of inflammation, such as TNFα (tumor necrosis factor), were ineffective due to the early and short therapeutic window (Anti-tumor necrosis factor therapy in sepsis: update on clinical trials and lessons learned, Crit Care Med, 2001, 29(7 Suppl): p. S121-5) and possibly harmful. HMGB1, however, is a late mediator of inflammation.

Figure 15A:
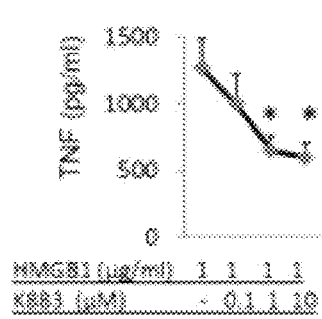
FIGS. 15A-15C are graphical depictions of the inhibition of HMGB1-induced tumor necrosis factor (TNF) secretion in both human and mouse macrophages.
Figure 15B:
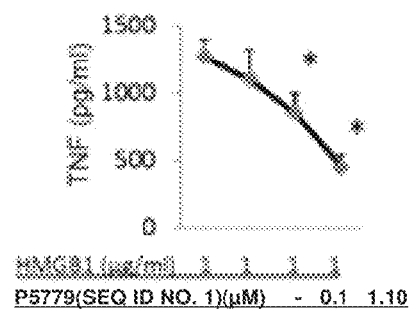
Figure 15C:
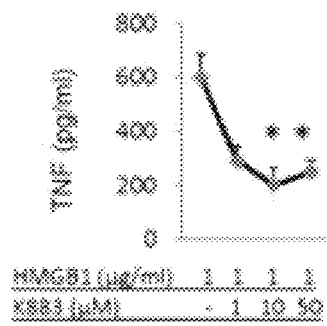
Figure 16A:
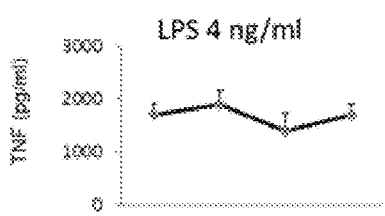
FIGS. 16A to 16D are graphical depictions showing PAMP-induced TNF release in human macrophages is not inhibited by various concentrations of K883.
Figure 16B:
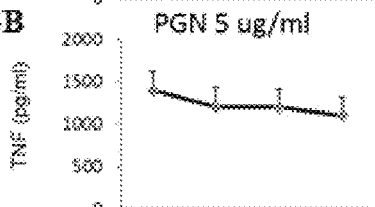
Figure 16C:
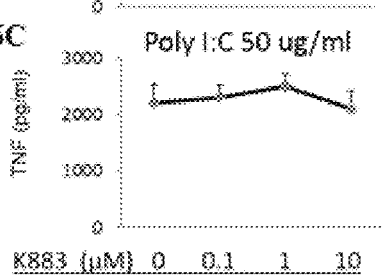
Figure 16D:
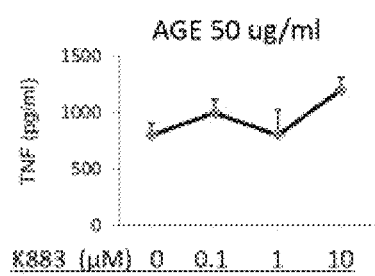
Figure 17A:
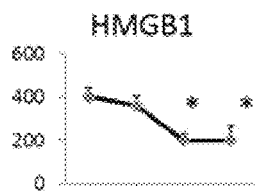
FIGS. 17A-17G display graphs showing TNF secretion induced by various DAMPs in human macrophages. K883 causes inhibition of HMGB1-induced TNF secretion (FIG.
Figure 17B:
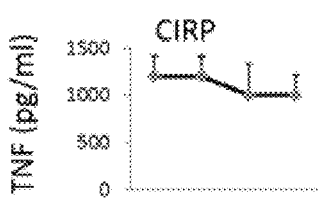
Figure 17C:
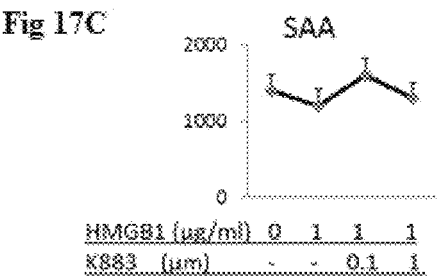
Figure 17D:
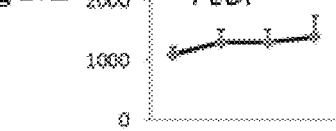
Figure 17E:
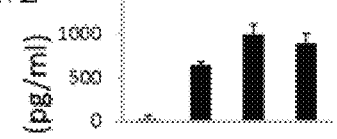
Figure 17F:
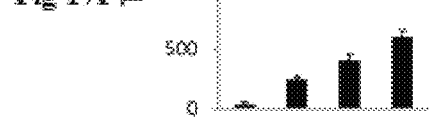
Figure 17G:
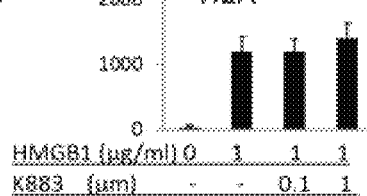

FIGS. 15A-15C are graphical depictions of the inhibition of HMB1-induced tumor necrosis factor (TNF) secretion in both human and mouse macrophages. In the studies of FIGS. 15A and 15B, mouse primary macrophages in 96 well plate were stimulated with HMGB1 (1 μg/ml), plus increasing amounts of P5779 (SEQ ID NO: 1) or K883 (0.1, 1 and 10 uM) for 16 hours. In the study of FIG. 15C, human primary macrophages in 96 well plate were stimulated with HMGB1 (1 μg/ml), plus increasing amounts of K883 (0.1, 1 and 10 uM) for 16 hours. For all of these studies, TNF released was measured using an ELISA. The data shown in the Figures are means+SEM (n=4-5). *: P<0.05 vs. HMGB1.

FIG. 15A shows the inhibition achieved with increasing concentrations of K883 (0-10 μM) in human primary macrophages and FIG. 15B shows the inhibition achieved with P5779 (SEQ ID NO: 1) (0-10 μM) in human primary macrophages. FIG. 15C shows the inhibition achieved with increasing concentrations of K883 (0-50 μM) of HMGB1-induced TNF secretion from mouse macrophages. In both human and mouse macrophages, K883 significantly inhibits TNF release with an $IC_{50}$ of 1 uM while similar inhibition with P5779 (SEQ ID NO: 1) was achieved at 10 uM. The potency of K883 over P5779 (SEQ ID NO: 1) is due in part to stability as described above.

Example 7—K883 does not Inhibit PAMPs-Induced TNF Release in Human Macrophages

In Example 7, K883 is evaluated for inhibition of PAMPs-induced TNF release in human macrophages. The selectivity of K883 toward HMGb1 and not other PAMPs such as LPS, PGN, AGE and Poly I:C was assessed by measuring the TNF release in human macrophages after exposure to the above PAMPS in the presence of compound K883. In the studies of FIG. 15, human primary macrophages in 96 well plate were stimulated with HMGB1 (1 μg/ml), TLR4-agonist LPS at 4 ng/ml, TLR3 agonist poly I:C at 50 μg/ml, TLR2 agonist peptidoglycan (PGN) at 5 μg/ml and RAGE agonist S100A12 at 50 μg/ml plus increasing amounts of K883 for 16 hours. TNF released was measured. Data shown in the Figures are means+SEM (n=4-5). *: P<0.05 vs. HMGB1.

The results demonstrate the selectivity of compound K883 toward HMGB1 (FIGS. 15A-C) since it failed to inhibit other PAMPS (FIG. 16A-D).

Example 8—K883 does not Inhibit DAMPs-Induced TNF Release in Human Macrophages

In Example 8, the ability of K883 to inhibit DAMPs-induced TNF release in human macrophages was evaluated. As discussed above, compound K883 was selective toward HMGB1 in inhibiting TNF release. In the studies of FIGS. 16A-D, human primary macrophages in 96 well plate were stimulated with HMGB1 (1 μg/ml), TLR4-agonist LPS at 4 ng/ml, TLR3 agonist poly I:C at 50 μg/ml, TLR2 agonist peptidoglycan (PGN) at 5 μg/ml and RAGE agonist S100A12 at 50 μg/ml plus increasing amounts of K883 for 16 hours. TNF released was measured. Data shown are means+SEM (n=4-5). *: P<0.05 vs. HMGB1. The data of FIGS. 16A-D demonstrate that K883 does not inhibit other PAMPs (LPS, PGN, AGE and Poly I:C).

Example 9—K883 does not Inhibit DAMPs-Induced TNF Secretion

The experiments of FIGS. 17A-G test ability of K883 to inhibit DAMPs-induced TNF secretion. TNF is an early effector of inflammation. Drugs intended to antagonize early effectors of inflammation, such as TNFα (tumor necrosis factor), were ineffective due to the early and short therapeutic window (*Anti-tumor necrosis factor therapy in sepsis: update on clinical trials and lessons learned*, Crit Care Med, 2001, 29(7 Suppl): p. S121-5) and possibly harmful. HMGB1, however, is a late mediator of inflammation.

In the experiments of FIGS. 17A-G, human primary macrophages on 96-well culture plates (105 cell/well) were stimulated with HMGB1 (1 µg/ml), CIRP (cold-induced RNA binding protein, 1 µg/ml), SAA (serum amyloid A, 5 µg/ml), PEDF (pigment epithelial derived factor, 5 µg/ml), HSP 70 (heat shock protein 70, 1 µg/ml), HSP90 (heat shock protein 90, 1 µg/ml) or H2A (histone 2A, 5 µg/ml) plus increasing amounts of K883 as indicated for 16 hours. TNF released was measured by ELISA. *: P<0.05 vs. HMGB1 alone. N=5 experiments.

FIGS. 17A-G show that K883 causes inhibition of HMGB1-induced TNF secretion (FIG. 17A) but TNF secretion induced by other DAMPs (FIG. 17B-G) is not inhibited by various concentrations of K883 in human macrophages.

Example 10—P5779 (SEQ ID NO:1) Peptide Enhances Survival in Cecal Ligation and Puncture-Sepsis and Reduces Liver Injury in Ischemia/Reperfusion Model The proinflammatory role of HMGb1 has been well established in multiple animal models and in this application, we examined the efficacy of inhibiting circulating HMGb1 by K883 in two mouse models (sepsis (no data) and liver injury). Previously, Yang H, *MD-2 is required for disulfide HMGB1-dependent TLR4 signaling*, J Exp Med., 2015; 212(1):5-14) showed that P5779 (SEQ ID NO: 1) was protective in these two models as seen below.

FIGS. 18, 19 and 20A are all directed to comparative data for compound P5779 (SEQ ID NO: 1). P5779 (SEQ ID NO: 1) protects against sepsis lethality induced by cecal ligation and puncture (CLP) in male C57BL/6 mice. In the comparative experiment of Example 11, P5779 (SEQ ID NO: 1) (at 50 or 500 µg/mouse) or scrambled control peptide (500 µg/mouse) was given IP once a day for 4 days starting at 24 hours post CLP surgery. Survival was monitored for 2 weeks. *: P<0.05 vs. control peptide group. n=20 mice/group. FIG. 18 shows that P5779 (SEQ ID NO: 1) peptide enhanced percentage survival in cecal ligation and puncture-sepsis.

Example 11—Treatment with HMGB1 Inhibitor P5779 (SEQ ID NO: 1) Ameliorates APAP-Mediated Toxicity FIGS. 19A to 19F show effects of treatment with P5779 (SEQ ID NO: 1) on ameliorating APAP-mediated toxicity such as inflammation, lethality, and tissue damage in a mouse model of APAP-induced liver injury. FIGS. 19A-D depict the serum inflammatory markers, AST (FIG. 19A), ALT (FIG. 19B, TNF (FIG. 19C), and HMGB1 (FIG. 19D) after P5779 (SEQ ID NO: 1) treatment.

In the comparative experiment of FIG. 19A, after overnight fasting, male C57BL/6 mice received APAP injection (IP, 350 mg/kg) plus P5779 (SEQ ID NO: 1) (at 50 or 500 µg/mouse) or scrambled control peptide (500 µg/mouse, IP injected at 2 and 7 hours post-APAP) and mice were euthanized at 24 hours post-APAP. n=6-10 mice per group. Besides serum measurements, H&E images of livers from APAP-injected mice showed reduced liver necrosis (arrow) in mice received P5779 (SEQ ID NO: 1) compared to scrambled control peptide-treated group. Clinical scores were assessed based on the amount of necrosis and inflammation (Methods). Percent survival (2 weeks) post-APAP (400 mg/kg) was significantly improved in mice received treatment of P5779 (SEQ ID NO: 1) (500 µg/mouse, IP once a day for 5 days starting at 2 hours post-APAP injection) n=30 mice in each group. *: P<0.05 vs. control peptide group.

In the comparative experiment of FIG. 19B, administration of P5779 (SEQ ID NO: 1) ameliorates tissue damage in warm liver ischemia and reperfusion (I/R) in male C57BL/6 mice. P5779 (SEQ ID NO: 1) (or vehicle control) was administered intraperitoneally at 500 µg/mouse at the time of I/R surgery and euthanized 6 hours later. Serum levels of ALT and AST were reduced in P5779 (SEQ ID NO: 1)-treated group vs. vehicle controls. *: P<0.05 vs. I/R group. n=5-7 mice/group.

Images of liver H&E staining (6 hours after reperfusion) showed reduced inflammation in P5779 (SEQ ID NO: 1)-treated mice as compared to vehicle control (neutrophil infiltration, arrow). n=3-5 mice per group. FIG. 19E shows increased survival after treatment with P5779 but not control scramble peptide, while FIG. 19F depicts histology images showing treatment with HMGB1 inhibitor P5779 (SEQ ID NO: 1) reduced APAP-mediated liver injury.

Example 12—K883 Reduces APAP-Induced Liver Injury: Histology

HMGb1 has been implicated in sterile injury and blocking HMGb1 by either anti-HMGb1 or P5779 (SEQ ID NO: 1) has been shown to be efficacious as evident by improving survival, reducing elevated liver enzymes due to injury and reducing liver damage/necrosis as evident by histology. (Yang, H., et al., MD-2 is required for disulfide HMGB1-dependent TLR4 signaling, J Exp Med, 2015, 212(1): p. 5-14).

FIGS. 21A to 21C show histology images demonstrating that K883 reduces APAP-Induced liver injury in the mouse model. In the experiment of FIGS. 21A-C, after overnight fasting, male C57BL/6 mice received APAP injection (IP, 350 mg/kg) plus K883 (at 50 µg/mouse, IP injected at 2 and 7 hours post-APAP) and mice were euthanized at 24 hours post-APAP. n=6-10 mice per group. Besides serum measurements, H&E images of livers from APAP-injected mice showed reduced liver necrosis (arrow) in mice received K883 compared to vehicle treated group. Clinical scores were assessed based on the amount of necrosis and inflammation. FIG. 21A is a histology obtain from a control mouse (not treated with APAP). In FIG. 21B, necrosis is evident in the histology in response to APAP. Necrosis was resolved in APAP-treated mouse upon administration of K883.

Example 13—K883 Improved APAP-Induced Survival in Mice

In the experiment of FIG. 22, mice (n=15 in each group) were treated with APAP (400 mg/kg) to induce liver damage and lethality. The group that received K883 showed significant improvement measured by percent survival (2 weeks) post-APAP over the control group with 14 mice out of 15 surviving the toxicity of APAP when treated with K883. (50 μg/mouse, IP once-a-day for 5 days starting at 2 hours post-APAP injection) compared to 8 in the control group. *: P<0.05 vs. control peptide group.

Thus, FIG. 22 shows improved survival outcome in mice that have been administered K883 in the APAP-induced liver injury model.

Example 14—PK/PD, Dosing and Formulation

FIGS. 20A and 20B shows that K883 is effective at a lower dose than P5779 (SEQ ID NO: 1) in APAP model. FIG. 20A shows serum inflammatory markers after P5779 (SEQ ID NO: 1) treatment in the APAP-liver toxicity model, 500 ugs/mouse led to significant reductions in ALT and FIG. 20B is a graphical depiction showing that treatment with 50 ugs/mouse of K883 reduced serum ALT in the liver APAP-toxicity model when compared to vehicle controls. P<0.05 vs. I/R group. n=5-7 mice/group.

Images of liver H&E staining (6 hours after reperfusion) showed reduced inflammation in K883-treated mice as compared to vehicle control (neutrophil infiltration, arrow). n=3-5 mice per group are seen in FIGS. 21A-C.

Example 15—Stability of P5779 (SEQ ID NO 1) in Mice Serum

In FIG. 23, the pharmacokinetics of K883 and P5779 (SEQ ID NO: 1) was assessed by LC-MS upon intravenous administration of 1 mg/kg of each compound. Both compounds were dissolved in 100 mM of PBS. Following IV administration to rats, the plasma half-life of P5779 (SEQ ID NO: 1) was <1 minute while for K883 it was 1.2+/−0.2 hours (n=3 animals/experiment).

Where Example 2 shows that P5779 (SEQ ID NO: 1) inhibits HMGB binding to MD2 using Surface Plasmon Resonance (SPR), in the present Example, it can be seen that K883 also has a similar inhibitory effect. The in-vitro and in-vivo half-lives of K883 and P5779 (SEQ ID NO: 1) were measured. The in-vitro half-life of K883 was greater than 15 hours (FIG. 14A-F), while the in-vitro half-life of the native peptide P5779 (SEQ ID NO: 1) was 60 minutes. The in-vivo half-life of K883 was greater than 69 min, while the in-vivo half-life of the native peptide P5779 (SEQ ID NO: 1) was less than 1 min. The results are provided in Tables 2 and 3 below. The data of Tables 2 and 3 are also plotted in FIG. 23.

TABLE 2

Individual and Average Plasma Concentrations (ng/ml) for FSSE after Intravenous Administration at 1 mg/KG in Male Sprague-Dawley rats Intravenous (1 mg/kg)

| | Rat # | | | | |
|---|---|---|---|---|---|
| Time (hr) | 970 | 971 | 972 | Mean | SD |
| 0 (pre-dose) | BLOQ | BLOQ | BLOQ | ND | ND |
| 0.017 | BLOQ | BLOQ | BLOQ | ND | ND |
| 0.033 | BLOQ | BLOQ | BLOQ | ND | ND |
| 0.083 | BLOQ | BLOQ | BLOQ | ND | ND |
| 0.167 | BLOQ | BLOQ | BLOQ | ND | ND |
| 0.25 | BLOQ | BLOQ | BLOQ | ND | ND |
| 0.33 | BLOQ | BLOQ | BLOQ | ND | ND |
| 0.50 | BLOQ | BLOQ | BLOQ | ND | ND |
| Animal Weight (kg) | 0.284 | 0.271 | 0.281 | 0.279 | 0.007 |
| Volume Dosed (mL) | 0.28 | 0.27 | 0.28 | 0.28 | 0.01 |
| $C_0$ (ng/mL)[1] | ND | ND | ND | ND | ND |
| $t_{max}$ (hr)[1] | ND | ND | ND | ND | ND |
| $t_{1/2}$ (hr) | ND | ND | ND | ND | ND |
| $MRT_{last}$ (hr) | ND | ND | ND | ND | ND |
| CL (L/hr/kg) | ND | ND | ND | ND | ND |
| $V_{ss}$ (L/kg) | ND | ND | ND | ND | ND |
| $AUC_{last}$ (hr · ng/mL) | ND | ND | ND | ND | ND |
| $AUC_\infty$ (hr · ng/mL) | ND | ND | ND | ND | ND |

TABLE 3

Individual and Average Plasma Concentrations (ng/ml) for K883 after Intravenous Administration at 1 mg/KG in Male Sprague-Dawley Rats Intravenous (1 mg/kg)

| | Rat # | | | | |
|---|---|---|---|---|---|
| Time (hr) | 973 | 974 | 975 | Mean | SD |
| 0 (pre-dose) | BLOQ | BLOQ | BLOQ | ND | ND |
| 0.25 | 4360 | 4240 | 3830 | 4143 | 278 |
| 0.50 | 3020 | 2500 | 3220 | 2913 | 372 |
| 1.0 | 814 | 1160 | 1300 | 1091 | 250 |
| 1.5 | 281 | 258 | 280 | 273 | 13.0 |
| 2.0 | 133 | 130 | 142 | 135 | 6.24 |
| 4.0 | 17.0 | 15.1 | 17.7 | 16.6 | 1.35 |
| 6.0 | 6.49 | 4.04 | 4.77 | 5.10 | 1.26 |
| 8.0 | 2.01 | 0.871 | 1.68 | 1.52 | 0.586 |
| Animal Weight (kg) | 0.288 | 0.282 | 0.281 | 0.284 | 0.004 |
| Volume Dosed (mL) | 0.29 | 0.28 | 0.28 | 0.28 | 0.01 |
| $C_0$ (ng/mL)[1] | 6295 | 7191 | 4556 | 6014 | 1340 |
| $t_{max}$ (hr)[1] | 0 | 0 | 0 | 0 | 0 |
| $t_{1/2}$ (hr) | 1.30 | 0.972 | 1.18 | 1.15 | 0.165 |
| $MRT_{last}$ (hr) | 0.535 | 0.528 | 0.606 | 0.556 | 0.0430 |
| CL (L/hr/kg) | 0.265 | 0.263 | 0.267 | 0.265 | 0.00200 |

TABLE 3-continued

Individual and Average Plasma Concentrations (ng/ml) for K883 after
Intravenous Administration at 1 mg/KG in Male Sprague-Dawley Rats
Intravenous (1 mg/kg)

| | Rat # | | | | |
|---|---|---|---|---|---|
| Time (hr) | 973 | 974 | 975 | Mean | SD |
| $V_{ss}$ (L/kg) | 0.144 | 0.139 | 0.163 | 0.149 | 0.0127 |
| $AUC_{last}$ (hr · ng/mL) | 3772 | 3807 | 3749 | 3776 | 29.4 |
| $AUC_\infty$ (hr · ng/mL) | 3776 | 3808 | 3751 | 3778 | 28.5 |

Example 16—K883 Increases the Survival of Flu Virus Infected Mice Compared with P5779 (SEQ ID NO: 1) Peptide Mice were infected with mouse-adapted influenza virus, strains A/PR/8/34 intranasally (i.n.) (PR8; ~7500 $TCID_{50}$, 25 µl/nares) or maCa.04 (~2200 $TCID_{50}$, i.n.). K883 is a small molecule inhibitor of HMGB1 that was shown recently to prevent MD-2/HMGB1 interaction and block HMGB1-induced TLR4 signaling, while not interfering with LPS-induced cytokine/chemokine induction. K883 protected mice against hepatic ischemia/reperfusion injury, APAP chemical toxicity, and sepsis. To assess the efficacy of K883 in influenza infection, WT C57BL/6J mice were infected with PR8 and, two days later mice were treated intraperitoneally with either vehicle or with K883 (100 ug/mouse) for 5 consecutive days. Survival and clinical scores were monitored daily for 14 days. (5-10 mice/treatment group/experiment). K883 treated mice showed significant survival and lowered clinical scores, while mice treated with the vehicle showed higher clinical scores and succumbed to infection (FIG. 24). As shown in FIG. 24, K883, an HMGB1 antagonist, blocks influenza-mediated lethality.

Example 17—K883 Enhances Survival in Cecal Ligation and Puncture-Sepsis

The proinflammatory role of HMGb1 was examined by evaluating the efficacy of inhibition of circulating HMGb1 by K883 in a sepsis. As discussed above (see e.g. Example 10), Yang H, *MD-2 is required for disulfide HMGB1-dependent TLR4 signaling*, J Exp Med., 2015; 212(1):5-14) showed that P5779 (SEQ ID NO: 1) was protective in these two models.

As seen in FIG. 25, K883 protects against sepsis lethality induced by cecal ligation and puncture (CLP) in male C57BL/6 mice. In the comparative experiment of Example 18, K883 (at 500 µg/mouse) or vehicle (control) was given IP once a day for 3 days starting at 24 hours post CLP surgery. Survival was monitored for 2 weeks. *: P<0.05 vs. control peptide group. n=15 mice/group. FIG. 25 shows that K883 enhanced percentage survival in cecal ligation and puncture-sepsis.

Example 18—Evaluation of Therapeutic Potential of K883 for Reducing Influenza-Induced ALI in Mice When administered daily for five days, starting two days post-infection, the peptide P5779 (SEQ ID NO: 1) rescues lethality in a mouse model of influenza-induced ALI. (Shirey K A, Novel strategies for targeting innate immune responses to influenza, Mucosal Immunol, 2016; 9(5):1173-82). Example 5 ascertains the efficacy of K883 for the same indication, using P5779 (SEQ ID NO: 1) as a positive control.

Three in vivo studies are conducted, each comprising two independent replicate experiments. For each experiment, cohorts of mice are treated with K883, the peptide P5779 (SEQ ID NO: 1), or vehicle following intranasal infection with a lethal dose of influenza, strain A/PR/8/34. Previous experiments have shown that experimental cohorts of five mice (i.e., 10 mice/cohort/study) yield sufficient statistical power to infer treatment effects. (Shirey K A, *Novel strategies for targeting innate immune responses to influenza*, Mucosal Immunol., 2016; 9(5):1173-82; Shirey K A, *The TLR4 antagonist Eritoran protects mice from lethal influenza infection*, Nature, 2013; 497(7450):498-502). For the survival and histology/serology studies, the cohorts are the following: 1-P5779 (SEQ ID NO: 1), 500 µg in IV vehicle delivered intraperitoneally on days 2-6 post-infection (positive control); 2-IV vehicle (no treatment); 3-Gavage vehicle (no treatment); 4-K883, dose 1 delivered intravenously on days 2-6 post-infection; 5-K883, 5× (dose 1) delivered intravenously on days 2-6 post-infection; 6-K883, dose 1 delivered by oral gavage on days 2-6 post-infection; 7-K883, 5× (dose 1) delivered by oral gavage on days 2-6 post-infection. "Dose 1" will be determined based on bioavailability and PK.

As a survival study, six- to eight-week old wildtype C57BL/6J mice are infected with the mouse-adapted influenza strain PR8 intranasally as previously described. (Shirey K A, *Novel strategies for targeting innate immune responses to influenza*, Mucosal Immunol., 2016; 9(5):1173-82; Shirey K A, *The TLR4 antagonist Eritoran protects mice from lethal influenza infection*, Nature, 2013; 497(7450):498-502). Starting on the second day post-infection and continuing through day 6, mice are treated according to their cohort. Mice are monitored daily for survival, weight loss, and clinical signs of illness (e.g., lethargy, piloerection, ruffled fur, hunched posture, rapid shallow breathing, and audible crackling). Mice receive a clinical score ranging from 0 (no symptoms) to 5 (moribund) daily; mice scoring a 5 on two consecutive days will be euthanized. Mice are observed for 14 days, at which point survivors are euthanized.

For study of histology/serology, infection and treatment are performed as in the survival study. On day 7 post-infection, all surviving mice are euthanized to collect serum by cardiac puncture, bronchoalveolar lavage fluid (BALF, from one lung), and tissue samples for histological and serological analysis (from the contralateral lung). Samples are collected and then analyzed. Levels of HMGB1 in serum and BALF are determined using a commercially available ELISA test. In addition, the levels of the pro-inflammatory signals TNFα (tumor necrosis factor) and soluble RAGE in BALF are measured. (37-40). (Raucci A, *A soluble form of the receptor for advanced glycation endproducts (RAGE) is* produced by proteolytic cleavage of the membrane-bound form by the sheddase a disintegrin and metalloprotease 10 (ADAM10), FASEB J., 2008; 22(10):3716-27; Uchida T, *Receptor for advanced glycation end products is a marker of type I cell injury in acute lung injury*, Am J Respir Crit Care Med., 2006; 173(9):1008-15; van Zoelen M A, *Receptor for advanced glycation end products is detrimental during influenza A virus pneumonia*, Virology, 2009; 391(2):265-73; Zhang L, *Receptor for advanced glycation end products is subjected to protein ectodomain shedding by metalloproteinases*, J Biol Chem., 2008; 283(51):35507-16). For histopathology, fixed sections of paraffin-embedded lungs are stained with hematoxylin and eosin. Slides are randomized and blinded, then scored for tissue damage and inflammation, necrosis, apoptosis, and innate immune cell infiltration.

Assuming K883 rescues lethality in the survival studies, the therapeutic window is studied by defining the time interval post-infection when K883 offers protection. For this study, the optimal K883 dose (IV or PO) determined by the survival studies is administered to the experimental cohorts on subsequent days following infection. The control cohort are treated with vehicle starting on the third day post-infection; experimental cohorts are treated with K883 on days 3-6, days 4-6, days 5 and 6, or only day 6 post-infection. Mice are monitored daily for survival and scored as described above for clinical illness.

High-resolution structural studies and molecular docking modelling are conducted to visualize binding between K883 and MD-2/TLR4, as previously reported for P5779 (SEQ ID NO: 1). (Yang H, *MD-2 is required for disulfide HMGB1-dependent TLR4 signaling*, J Exp Med., 2015; 212(1):5-14). A secondary risk is that mice will react adversely to repeated dosing with K883. This concern is substantially mitigated by the observation that K883 has been well-tolerated in single-dose studies with rats. Furthermore, the survival study features high- and low-dose treatment with K883 by two routes of administration. It is expected that at least one of these four configurations will indicate a regimen conducive to treating with K883. If mice even in the low-dose cohorts have an adverse reaction, however, the survival study with low-dose K883 treatment will first be repeated only on alternate days rather than daily. In case this strategy does not resolve the problem, the dose of K883 will be halved and the survival study will be repeated.

Example 19—the Effect of HMGB1 in Sciatic Nerve (CCI) Model

In Example 19, the effect of HMGB1 in sciatic nerve (CCI) model is evaluated in rats that have undergone CCI compared to untreated rats.

As seen in FIG. 26, disulfide HMGB1 levels in spinal cord are elevated in CCI model in rats. Disulfide HMGB1 induces neuropathic pain (mechanical allodynia) in rat paws in a time dependent manner (data not shown). As shown in FIG. 26, this effect can be partially reversed by neutralizing anti-HMGB1 antibody (mAb) 2g7 which ameliorates HMGB1-induced mechanical allodynia. (N=6-8 rats/group. *, **: p<0.05) These results indicated that selective HMGB1 isoforms are critical for the development of mechanical hypersensitivity. Furthermore, in the CCI-induced chronic pain model. (Bennett G. J., *A peripheral mononeuropathy in rat that produces disorders of pain sensation like those seen in man*, Pain, 1988; 33(1): 87-107), elevated HMGB1 levels in spinal cord were reported. (Wan W., *The emerging role of HMGB1 in neuropathic pain: a potential therapeutic target for neuroinflammation*, Journal of Immunology research, (2016); He Z., *Intrathecal lentivirus-mediated transfer of interleukin-10 attenuates chronic constriction injury-induced neuropathic pain through modulation of spinal high-mobility group box 1 in rats*, Pain Physician, 2012; 16(5): E615-625). Administration of K883 ameliorated both mechanical and thermal hypersensitivity.

Example 20—Effect of Selective HMGB1-TLR4/MID-2 Inhibition on Neuropathic Pain

Example 20 determines the effect of selective HMGB1-TLR4/MD-2 inhibition on reduction of neuropathic pain in sciatic nerve (CCI) model rats.

Twenty-four male Wistar rats were separated into four groups (n=6/group) for treatment as follows [please give details concerning each of the four groups regarding procedure and treatment:

Group I: CCI
Group II: Normal
Group III CCI+PBS (phosphate-buffered saline) vehicle control (PBS)
Group IV CCI+=K883 (800 µg/rat) or vehicle control (PBS) was administered after CCI as an IP injection once daily for three days.

The CCI rats each received surgery. The K883 and were evaluated for 2 weeks afterward. In FIGS. 27A and 27B, the groups are listed as CC K883 (800 µg/rat) or vehicle control was given as IP injection once daily for three days. Mechanical and thermal sensitivity tests were also performed over time. Hargreaves Thermal Hypersensitivity test was administered to the rats as well as Von Frey mechanical hypersensitivity test. The results of this testing can be seen in FIGS. 27A and 27B which show the effects of the repeated K883 administration on CCI-induced neuropathic pain (*: P<0.05 vs. CCI PBS group N=6 rats/group). These results indicate that rats did not develop tolerance to repeated treatment of K883 during the short period of time.

Example 21—Effect of Selective HMGB1-TLR4/MD-2 Inhibition in STZ-Induced Diabetes In Example 21, the effect of selective HMGB1-TLR4/MD-2 inhibition in STZ-induced diabetes was evaluated. Increased levels of HMGB1 have been reported in both diabetic patients and animal models. For example, elevated expression of HMGB1 is found in the retinas of diabetic patients and rat models with retinopathy. (Pachydaki S. I., *Upregulation of RAGE and its ligands in proliferative retinal disease*, Experimental Eye Research, 2006; 82(5): 807-815; Yu Y., *The role of high mobility group box 1 (HMGB-1) in the diabetic retinopathy inflammation and apoptosis*, International Journal of Clinical and Experimental Pathology, 2015; 8(6): 6807). Moreover, elevated serum HMGB1 levels were seen in diabetic patients. (Dasu M. R., *Increased toll-like receptor (TLR) activation and TLR ligands in recently diagnosed type 2 diabetic subjects*, Diabetes Care, 2010; 33(4): 861-868) and rats with hyperglycemia. (Hagiwara S., *Effects of hyperglycemia and insulin therapy on high mobility group box 1 in endotoxin-induced acute lung injury in a rat model*, Critical Care Medicine, 2008; 36(8): 2407-2413; Škrha Jr J, *Relationship of soluble RAGE and RAGE ligands HMGB1 and EN-RAGE to endothelial dysfunction in type 1 and type 2 diabetes mellitus*, Experimental and Clinical Endocrinology & Diabetes, 2012; 120(05): 277-281). Based on this literature, tests were conducted on the effects of P5779 (SEQ ID NO: 1) and K883 on STZ-induced diabetes in mice.

Mice were administered repetitive administration of K883 (500 μg/mouse). The results of the testing is seen in FIGS. 28A-C, which show that K883 is beneficial in STZ-induced diabetes. Repetitive administration of K883 was therefore shown to be beneficial in STZ-induced diabetes. Compared to AI5779 or PBS controls, treatment with K883 delays hyperglycemia and improves weight gain, and reduces insulitis in STZ-diabetic mice. (*: P<0.05 vs. PBS group. N=6-8 mice per group).

Example 22—Design of K883 Derivatives to Improve Oral Bioavailability

Rationale: Although K883 has a better pharmacokinetic profile compared to P5779 (SEQ ID NO: 1) (t½>60 min versus <5 min), it has low oral bioavailability. It was initially hypothesized that the poor bioavailability might be due to the acid liability of the amide bond between the two serine residues upon exposure to the gastric fluid. To address this concern, K883 was incubated under acidic conditions (pH=2) for two hours and the stability was monitored over time by LC-MS. The conclusion of this stability testing was that K883 was resistant to acid hydrolysis. In order to improve the oral bioavailability K883, different formulations of K883 will be tested for improved absorption, followed by new PK studies of the most attractive oral formulations. In parallel to this testing, K883 will be further optimized in order to generate multiple derivatives to improve its absorption followed by new PK studies of the most attractive derivative to determine the oral bioavailability.

Binding (SPR) and computational studies were conducted with an initial lead peptide. Based on this testing, it was learned that: 1) the glutamate of the P5779 (SEQ ID NO: 1) peptide is required to form hydrogen bonds with MD-2 and TLR4 residues (H bonds and salt bridges are formed between the glutamate residue and Arg264, Asp339 (TLR4) and Tyr102, Glu92 (MD-2)); 2) the phenyl moiety of the phenylalanine is anchored in the hydrophobic pocket of MD-2 and substitution of the phenyl moiety by fluorobiphenyl binds better due to multiple pi-pi stacking; 3) replacing serine by asparagine generates an elegant set of hydrogen bonds with the backbone of MD-2 (Tyr102, Glu92 and Val93; and 4) optimization of a linker (—CH2CH2-) that fits well between the biphenyl moiety and the azapeptide of asparagine-glutamate. These findings will be used to synthesize a specific, potent and orally bioavailable inhibitor of HMGB1:MD-2: TLR4 complex formation by translating and integrating the known chemical information concerning P5779 (SEQ ID NO: 1) and K883 into a new class with more attractive pharmacokinetics due to the improve stability of the serine-serine amide bond in P5779 (SEQ ID NO: 1) and K883.

Building the Class of Compounds:

Compounds were identified using binding and computational and synthesis methods. Based on the results, the aryl system was identified as an attractive moiety to anchor in the hydrophobic pocket of MD-2. Shown below is the proposed synthesis of Class A compounds, with the R pharmacores discussed above. As seen below, the aryl systems are propionic acid-based derivatives that can be coupled in the final stage to the fully protected moiety of Asp-Glu(aza) peptide.

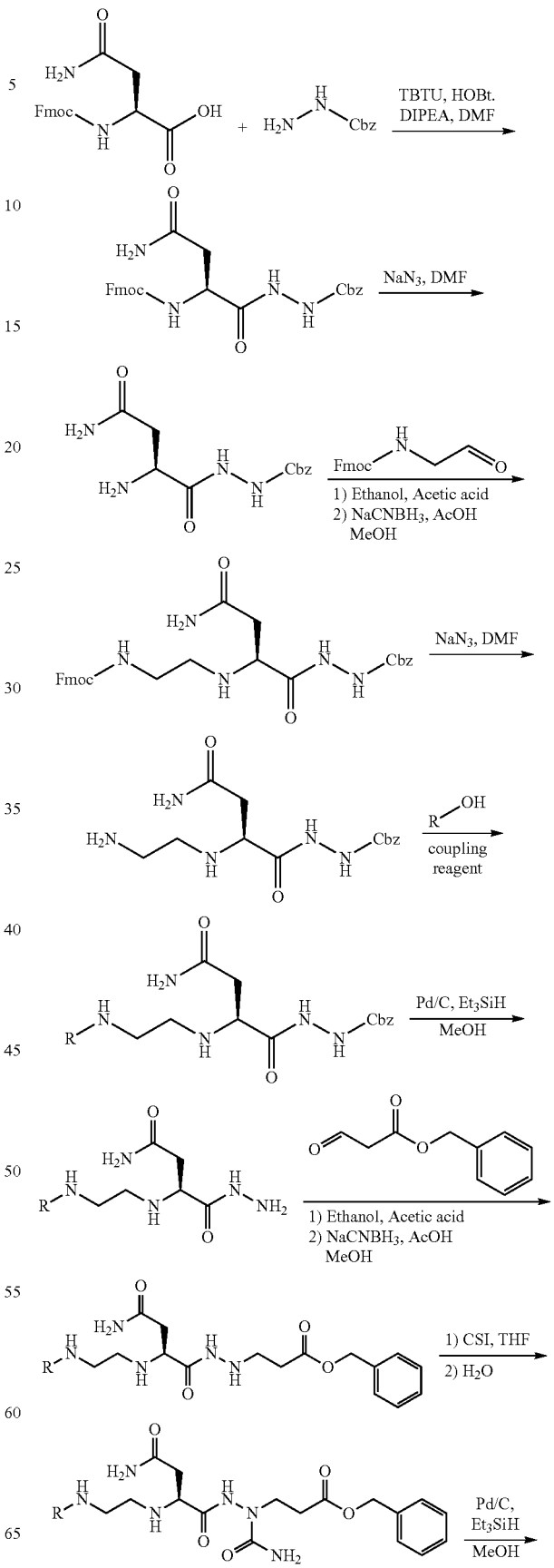

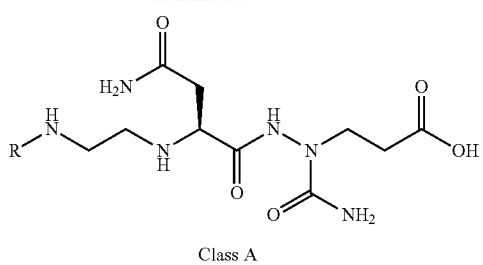

Class A

The next objective was to restrict the flexibility of glutamic acid while preserving the selectivity and binding affinity toward MD-2. To address this objective, Class B were identified based on substituting the glutamic acid residue with pyrrolidin-2-ones (g-lactams), aka as L-proline, 4-amino-5-oxo. Shown below is the proposed synthesis of Class B compounds, with the R pharmacores shown above.

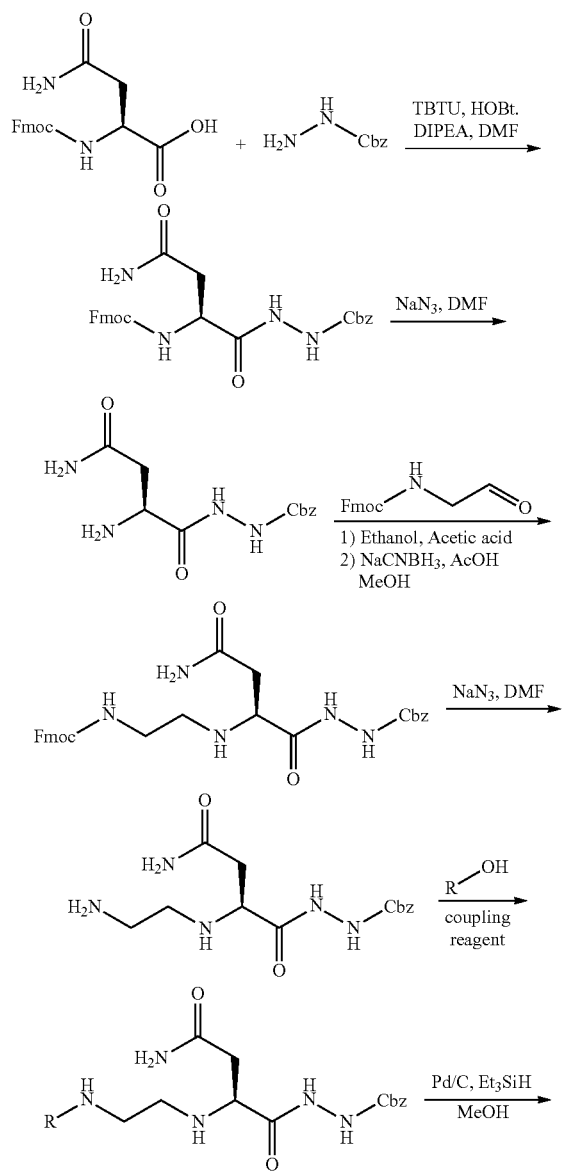

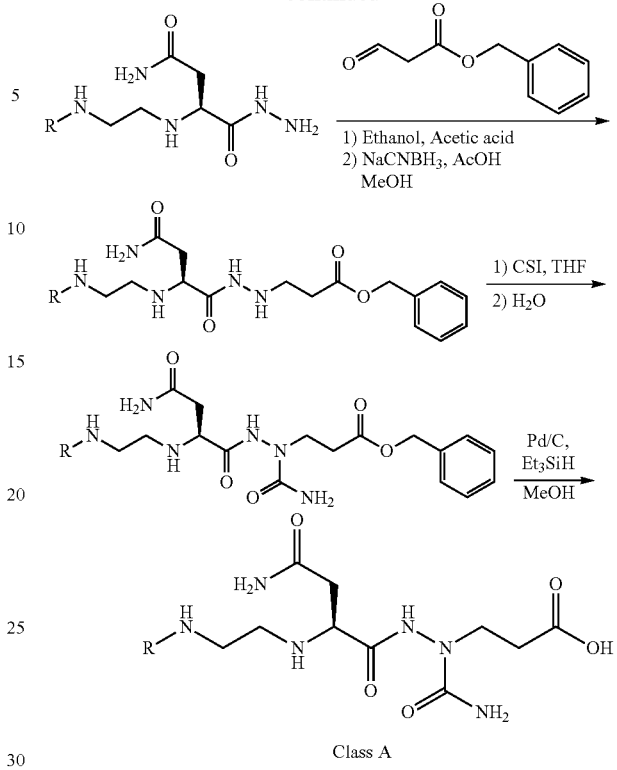

Class A

This building block can serve as an isostere of aspartic and glutamic acid. Previously, it has been shown that incorporation of such units is advantageous and improved the stability and bioavailability compared to parent peptides. (Abell A., *Advances in amino acid mimetics and peptidomimetics*, Elsevier; Vol. 2, 1999), and the stereoselective synthesis of these isomers has been well documented and they are commercially available. The computational study demonstrated that these units should provide the expected interaction with TLR4 and MD-2, but to a lesser extent compared to class A.

In vitro permeability (Caco2 cells) and human microsomal stability studies will next be conducted to predict the oral bioavailability of these K883 derivatives. The outcome of these studies will support continued development of an oral formulation of K883 derivative or may indicate that an alternative route of administration (e.g. subcutaneous) may be preferable. It is expected that the docking and molecular dynamic simulations of the newly developed K883 derivatives will be similar to K883. In vitro permeability and microsomal stability data will be obtained for both parent K883 and K883 derivatives. The outcome of these studies will support continued development of an oral formulation of K883 derivative. However, the therapeutic effects of K883 derivatives are likely dependent on the tissue distribution. Thus, future studies will evaluate the oral bioavailability and tissue distribution of the most promising K883 derivative.

Example 23—Pharmacokinetics of K883 Following Subcutaneous Administration

Rationale: Subcutaneous administration route is often used for management of diabetes treatment. To determine whether subcutaneous administration route is suitable for K883, K883 will be subcutaneously administered into healthy minipigs, after which the PK parameters will be defined.

Design: K883 will be subcutaneously administered into healthy minipigs, after which the PK parameters will be defined. Plasma samples will be collected for analysis immediately prior to dosing and at 15, 30, 60 and 90 minutes and 2, 4, 8, 12, and 24 hr after the dose and analyzed to determine the concentration of K883 using LC-MS.

Expected outcomes and alternative approaches: The outcome of these studies will support the decision to continue development of an SC formulation of K883, along with the results of the oral bioavailability studies of the molecules to be synthesized in.

Example 24—Efficacy of Selective HMGB1-TLR4/MD-2 Inhibition in a Rodent Model of DPN Rationale: Recent research on diabetic neuropathy has been focused on the changes in the interactions between the nervous system and the immune system that occur in parallel with glial cell activation. Several animal models have been used to study the underlying mechanisms for this complication. Some commonly used animal models include STZ-induced rat and mouse models. Even though the manifestations of diabetic neuropathic pain vary, impaired neurotrophism and proinflammatory responses have been identified in the development of diabetic neuropathic pain. Thus, as a proof-of-concept study in this Phase I project, the efficacy of selective HMGB1-TLR4/MD-2 inhibition in a rat (male and female) model of STZ-induced diabetic neuropathy will be tested.

In Example 24, the efficacy of intravenously administered K883 in rat (male and female) model of streptozotocin (STZ)-induced diabetic neuropathy will be tested. Pain behavior tests, weight change and blood glucose levels will be recorded. At the end of experiment, the rats will be euthanized so that their pancreas, DRG, spine and blood can be assessed for histological changes, chemokine and cytokines levels, immune and physiological responses.

Design: A well-established rodent model of diabetes and DPN80, the STZ-DPN model, will be used to evaluate efficacy. This STZ-DPN model mirrors clinical type 1 diabetes in humans. (Kitada M., *Rodent models of diabetic nephropathy: their utility and limitations*, International Journal of Nephrology and Renovascular Disease, 2016; 9: 279). After evaluation of the results of this testing, a positive result were lead to further evaluation of other types of diabetes DPN models (i.e. type 2 diabetes). Rats (Sprague-Dawley, 150-180 gm, male and female) will subject to low dose of STZ (50 mg/kg) IP injection once a day for 5 days to induce diabetes and DPN. The regimen of multiple injection of low dose STZ is chosen to minimize the non-specific toxicity of STZ to other organs besides pancreas (Id.), and is also based on observations that it will induce diabetes (see FIG. 29) and will induce DPN. (Zhao X., *Inhibition of CaMKIV relieves streptozotocin-induced diabetic neuropathic pain through regulation of HMGB1*, BMC Anesthesiology, 2016; 16(1): 27; Kitada M., *Rodent models of diabetic nephropathy: their utility and limitations*, International Journal of Nephrology and Renovascular Disease, 2016; 9: 279; Akbar S., *6-Methoxyflavanone attenuates mechanical allodynia and vulvodynia in the streptozotocin-induced diabetic neuropathic pain*, Biomedicine & Pharmacotherapy, 2016; 84: 962-971). Animals will receive K883 or control peptide injected daily intravenously (via implanted jugular vein catheter) for 2 weeks starting at 2 weeks after STZ administration. K883 treatment in this STZ model in mice was beneficial as revealed by diabetic parameters (preliminary data, FIG. 29). This time frame was chosen as DPN was observed starting 2 weeks after STZ administration and last till 8 weeks in rodents. (Id.) Three logarithmic doses of K883 or control peptide (0, 8, 80 or 800 µg/rat/day) will be included to cover both effective and non-effective doses of K883 based on previous results achieved with STZ and CCI pain models (FIGS. 28 and 29). Pain behavior tests, weight change and blood glucose levels will be recorded during that time.

At the end of the 2-week treatment, animals (10 per group) will be euthanized so that pancreas, DRG (dorsal root ganglion), spine and blood can be assessed for histological changes, chemokine and cytokines levels, immune and physiological responses. The following are the list of animal groups and tests/assays that will be performed in this study.

Animal groups: The study will use eight groups of rats per sex, with each group having 10 rats. (80 female rats and 80 male rats) as follows:
Group 1: normal rats.
Groups 2-4: STZ rats with K883 treatment (doses of 8, 80 and 800 ug/rat/day).
Groups 5-7: STZ rats with control peptide treatment.
Group 8: STZ rats with PBS (vehicle) treatment.
Total=8 groups per sex (male or female).

In previous studies of K883 in the CCI rat model, it was observed that in vehicle-treated control rats with neuropathic pain, paw withdrawal occurred at 3.73+/−0.58 (SD) seconds compared to 5.45+/−0.98 seconds in rats treated with K883. Assuming in the STZ model that a similar difference (1.6 seconds) is found, with SD of 1.0, then to achieve 90% power at the alpha=0.05 level, 5 animals per group are required. As this will be the first study of the effects of K883 in the STZ diabetes model, 10 animals per group will be used to account for lesser difference between groups or larger SD.

Tests/Assays:
1. Body weight and blood glucose levels (via tail vein) over time.
2. Allodynia assessment: mechanical, thermal hypersensitivity (both heat and cold) assessment over time.
3. Histology of pancreas: insulitis score.
4. Serum measurements: insulin, glucagon (diabetes parameters), HMGB1, CXCL1, TNF, IL-6 and IL-1β (inflammation markers)
5. DRG and spine: HMGB1, CXCL1, TNF, IL-6 and IL-1l3 (inflammation markers). Could be squeezed to save room.

Expected Outcomes and Alternative Approaches:
Previous studies demonstrated that K883 specifically blocks disulfide (cytokine-inducing) HMGB1-mediated inflammation and does not block the immune integrity to PAMPs. It is therefore expected that intravenous administration of K883 will dose-dependently reduce mechanical and thermal hypersensitivity in rats with STZ-induced DPN. Intravenous administration route was chosen for a proof-of-concept study to avoid issues concerning the low oral bioavailability of K883. As the only known selective HMGB1-TLR4/MD-2 inhibitor, using K883 will provide vital information about the effects of selective HMGB1-TLR4/MD-2 inhibition on painful DPN. As preferred administration routes for diabetic patients are oral and subcutaneous routes, future studies will expand these findings by using novel K883 derivatives with improved oral bioavailability or a preferred subcutaneous formulation of parent K883.

Example 25—Disulfide HMGB1-Induced Calcium Influx in F11 Cells

K883 is shown to inhibit disulfide hmgb1-induced calcium influx in F11 cells in FIGS. 30A-30E. These studies all measured relative fluorescent intensity with FIG. 30C which included the largest amount of K883 (50 µg/ml) having the most inhibition of disulfide HMGB1.

Example 26—CCI-Induced Thermal and Mechanical Hypersensitivity

The effect of K883 on CCI-induced thermal and mechanical hypersensitivity over time in rats was assessed. Rats (male Wistar, 150-180 gm, n=6/group) had CCI surgery. K883 (800 µg/rat) or vehicle control (PBS) was given as IP injection once a day for 3 days. Two weeks after surgery, thermal (Hargreaves) or mechanical (von Frey) hypersensitivity was assessed. *: P<0.05 vs. PBS group. As seen in FIGS. 31A and 31B, K883 improved CCI-induced thermal and mechanical hypersensitivity over time in rats.

Example 27—CCI-Induced CXCL1 and TNF Expression (DRGs)

K883 is shown to reduce CCI-induced CSCL1 and TNF expression (DRGs) FIGS. 32A-32C.

Example 28—CCI-Induced CXCL1. TNF and IL-1β Expression (Spine)

K883 is shown to reduce CCI-induced CSCL1, TNF and IL-1β expression (Spine) in FIGS. 33A-33D.

Example 29—Novel HMGB1-Mediated Neurobiological Mechanism

Dorsal root ganglia (DRG) sensory neurons are selectively activated by disulfide HMGB1-induced Ca2+ influx as seen from FIG. 34. Calcium is an essential intracellular mediator in neurons, and Ca2+ influx increases 10-100 fold when neuron is activated 57-60. Preliminary studies have shown that exposure to disulfide HMGB1 in rat primary DRGs (cell body of sensory nociceptors) stimulated calcium influx, and HMGB1 mAb 2g7 reverses the effects in vitro. This novel mechanism may be another untapped target for therapeutic intervention of DPN.

Example 30—Selective HMGB1-TLR-4/MD2 Inhibition Reduces Neuropathic Pain in CCI Rats HMGB1 (disulfide and fully reduced) induces neuropathic pain (mechanical allodynia) in rat paws (FIG. 35A) in a time dependent manner (data not shown). This effect can be partially reversed by anti-HMGB1 mAb 2g7 treatment (FIG. 35B). These results indicated that selective HMGB1 isoforms are critical for the development of mechanical hypersensitivity. Furthermore, in the CCI-induced chronic pain model (Bennett G J, Xie Y-K, *A peripheral mononeuropathy in rat that produces disorders of pain sensation like those seen in man*, Pain, 1988; 33(1):87-107,71), elevated HMGB1 levels in spinal cord have been reported. (Wan W, et al., *The emerging role of HMGB1 in neuropathic pain: a potential therapeutic target for neuroinflammation*, Journal of Immunology Research. 2016; 2016. 27,72; He Z, et al., *Intrathecal lentivirus-mediated transfer of interleukin*-10 *attenuates chronic constriction injury-induced neuropathic pain through modulation of spinal high-mobility group box 1 in rats*, Pain Physician, 2012; 16(5):E615-625) Administration of HMGB1 mAb 2g7 or HMGB1 specific inhibitor K883 ameliorated the thermal hypersensitivity (Table 4).

TABLE 4

| | Paw Withdrawal Latency (sec) | | | | |
|---|---|---|---|---|---|
| | | CCI (Hours post treatment) | | | |
| Treatment | NO CCI | 0 | 2 | 6 | 24 |
| mAb2g7 | 9.5 ± 1.0 | 4.1 ± 1.0 | 7.1 ± 1.0* | 6.4 ± 0.6* | 5.6 ± 0.4 |
| K883 | 9.5 ± 1.0 | 4.1 ± 1.0 | 4.3 ± 1.2 | 6.0 ± 0.6* | 5.0 ± 0.5 |
| Vehicle | 9.5 ± 1.0 | 4.1 ± 1.0 | 4.0 ± 0.5 | 3.7 ± 0.2 | 4.6 ± 0.7 |

*P < 0.05 vs. 0 hr.

In this experiment, male Wistar rats (n=6/group) had CCI surgery. K883 (800 µg/rat) or 2g7 (300 µg/rat) or vehicle control was given as IP injection 30 minutes prior to disulfide HMGB1 injection to the hindpaw. Mechanical allodynia was assessed 5 hours later. N=6-8 rats/group. *: p<0.05) vs. HMGB1 alone. Mechanical and thermal sensitivity tests were also performed over time. In these experiments, K883 (800 µg/rat) or vehicle control was given as IP injection once daily for three days. After 2 weeks, the results indicated that rats did not develop tolerance to repeated treatment of K883 during the short period of time. FIG. 35A show that HMGB1 induces mechanical allodynia in rats. *: p<0.05) vs. PBS and FIG. 35B mAb 2g7 ameliorates HMGB1-induced mechanical allodynia in rats.

CONCLUSION

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

What is claimed is:

1. A pharmaceutical composition comprising a peptidomimetic small molecule of the formula:

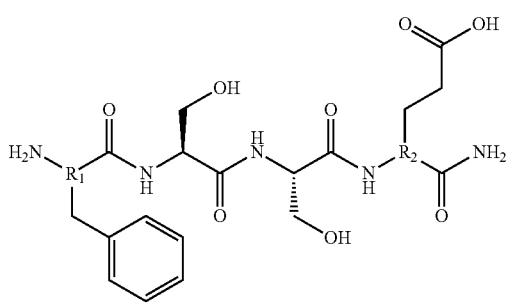

wherein:

$R_1$ is CH or N; and
$R_2$ is CH or N,
provided that at least one of $R_1$ or $R_2$ is N,
and at least one pharmaceutically acceptable excipient.

2. The pharmaceutical composition of claim 1, wherein $R_1$ is CH and $R_2$ is N.

3. The pharmaceutical composition of claim 1, wherein $R_1$ is N and $R_2$ is CH.

4. The pharmaceutical composition of claim 1, wherein the peptidomimetic small molecule is of the formula:

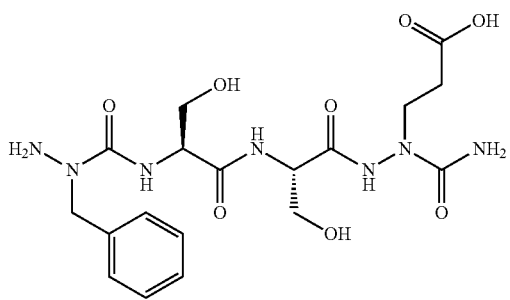 [SMILES: NC(=O)N(CCC(=O)O)NC(=O)[C@H](CO)NC(=O)[C@H](CO)NC(=O)N(N)Cc1ccccc1]

5. The pharmaceutical composition of claim 1, which is a dosage form selected from the group consisting of an oral dosage form, a parenteral dosage form, a buccal dosage form, a sublingual dosage form, a nasal dosage form, an inhaler, a nebulizer, a topical dosage form, a transdermal dosage form and a suppository.

6. The pharmaceutical composition of claim 1, wherein the pharmaceutical excipient comprises PBS:PEG 300:propylene glycol:polysorbate 80.

7. The pharmaceutical composition of claim 1, wherein the pharmaceutical excipient comprising PBS:PEG 300:propylene glycol:polysorbate 80 in a ratio of about 50:40:5:5.

8. The pharmaceutical composition of claim 6, wherein the composition is an oral liquid dosage form or a parenteral dosage form.

9. The pharmaceutical composition of claim 1, wherein the pharmaceutical excipient is selected from the group consisting of 1) phosphate buffered saline, 2) polyethylene glycol, 3) propylene glycol and 4) polysorbate 80 and 5) combinations thereof.

10. The pharmaceutical composition of claim 9, wherein the polyethylene glycol is PEG 300.

11. The pharmaceutical composition of claim 1, wherein the pharmaceutical composition is an oral dosage form.

12. The pharmaceutical composition of claim 1, wherein the pharmaceutical composition is a parenteral dosage form.

13. The pharmaceutical composition of claim 1, wherein the aqueous solubility of the peptidomimetic molecule is greater than 1 mg/ml.

14. The pharmaceutical composition of claim 1, wherein the peptidomimetic molecule stable for greater than 60 minutes in plasma or simulated stomach acid.

15. The pharmaceutical composition of claim 4, wherein the peptidomimetic molecule stable for greater than 60 minutes in plasma or simulated stomach acid.

16. The pharmaceutical composition of claim 4, which is a dosage form selected from the group consisting of an oral dosage form, a parenteral dosage form, a buccal dosage form, a sublingual dosage form, a nasal dosage form, an inhaler, a nebulizer, a topical dosage form, a transdermal dosage form and a suppository.

17. The pharmaceutical composition of claim 4, wherein the pharmaceutical excipient comprises PBS:PEG 300:propylene glycol:polysorbate 80.

18. The pharmaceutical composition of claim 4, wherein the pharmaceutical excipient comprising PBS:PEG 300:propylene glycol:polysorbate 80 in a ratio of about 50:40:5:5.

19. The pharmaceutical composition of claim 17, wherein the composition is an oral liquid dosage form or a parenteral dosage form.

20. The pharmaceutical composition of claim 4, wherein the pharmaceutical composition is an oral dosage form or a parenteral dosage form.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
```

```
<220> FEATURE:
<223> OTHER INFORMATION: FSSE P5779

<400> SEQUENCE: 1

Phe Ser Ser Glu
1
```